US011548923B2

(12) United States Patent
Olson et al.

(10) Patent No.: US 11,548,923 B2
(45) Date of Patent: Jan. 10, 2023

(54) PEPTIDE COMPOSITIONS AND METHODS OF USE THEREOF FOR DISRUPTING TEAD INTERACTIONS

(71) Applicant: Fred Hutchinson Cancer Center, Seattle, WA (US)

(72) Inventors: James M. Olson, Seattle, WA (US); Zachary Crook, Bothell, WA (US); Philip H. Bradley, Seattle, WA (US)

(73) Assignee: FRED HUTCHINSON CANCER CENTER, Seattle, WA (US)

( * ) Notice: Subject to any disclaimer, the term of this patent is extended or adjusted under 35 U.S.C. 154(b) by 0 days.

(21) Appl. No.: 16/478,672

(22) PCT Filed: Jan. 18, 2018

(86) PCT No.: PCT/US2018/014203
§ 371 (c)(1),
(2) Date: Jul. 17, 2019

(87) PCT Pub. No.: WO2018/136614
PCT Pub. Date: Jul. 26, 2018

(65) Prior Publication Data
US 2019/0345211 A1     Nov. 14, 2019

Related U.S. Application Data

(60) Provisional application No. 62/510,719, filed on May 24, 2017, provisional application No. 62/447,864, filed on Jan. 18, 2017.

(51) Int. Cl.
| | |
|---|---|
| *A61K 38/00* | (2006.01) |
| *C07K 14/47* | (2006.01) |
| *G16B 15/20* | (2019.01) |
| *G16B 15/30* | (2019.01) |

(52) U.S. Cl.
CPC .......... *C07K 14/4703* (2013.01); *G16B 15/20* (2019.02); *G16B 15/30* (2019.02); *A61K 38/00* (2013.01); *C07K 2319/10* (2013.01)

(58) Field of Classification Search
None
See application file for complete search history.

(56) References Cited

U.S. PATENT DOCUMENTS

| | | | |
|---|---|---|---|
| 7,507,413 B2 * | 3/2009 | Rosen | A61P 15/00 424/192.1 |
| 9,944,683 B2 | 4/2018 | Olson | |
| 2003/0031669 A1 | 2/2003 | Goldenberg | |
| 2006/0088899 A1 | 4/2006 | Alvarez et al. | |
| 2009/0142266 A1 | 6/2009 | Ronjat et al. | |
| 2010/0215575 A1 | 8/2010 | O'Neill et al. | |
| 2013/0028836 A1 | 1/2013 | Sentissi et al. | |
| 2013/0164220 A1 | 6/2013 | Yu et al. | |
| 2013/0280281 A1 | 10/2013 | Castaigne et al. | |
| 2014/0179560 A1 | 6/2014 | Olson et al. | |
| 2016/0264636 A1 | 9/2016 | Rebollo et al. | |
| 2016/0272690 A1 | 9/2016 | Li et al. | |
| 2019/0117728 A1 | 4/2019 | Olson et al. | |

FOREIGN PATENT DOCUMENTS

| | | |
|---|---|---|
| CA | 2993891 A1 | 1/2017 |
| CN | 101583370 A | 11/2009 |
| CN | 106589064 A | 4/2017 |
| JP | 2013224283 A | 10/2013 |
| WO | WO-03082196 A2 | 10/2003 |
| WO | WO-2008063291 A2 | 5/2008 |
| WO | WO-2012064658 A1 | 5/2012 |
| WO | WO-2013078250 A2 | 5/2013 |
| WO | WO-2014063012 A1 | 4/2014 |
| WO | WO-2014093406 A1 | 6/2014 |
| WO | WO-2014180534 A1 | 11/2014 |
| WO | WO-2015022283 | 2/2015 |
| WO | WO-2015022283 A1 | 2/2015 |
| WO | WO-2015179635 A2 | 11/2015 |
| WO | WO-2016112208 A2 | 7/2016 |
| WO | WO-2016118859 A1 | 7/2016 |
| WO | 2016196560 A1 | 12/2016 |
| WO | WO-2016210376 A2 | 12/2016 |
| WO | WO-2017044894 A2 | 3/2017 |
| WO | WO-2017064277 A1 | 4/2017 |
| WO | WO-2017100700 A2 | 6/2017 |
| WO | WO-2017143259 A1 | 8/2017 |
| WO | WO-2018049285 A1 | 3/2018 |
| WO | WO-2018119001 A1 | 6/2018 |

(Continued)

OTHER PUBLICATIONS

Akhmedov, D., et al. Knock-in luciferase reporter mice for in vivo monitoring of CREB activity. PLoS One 11, 1-13 (2016).

Almagro et al.: Progress and Challenges in the Design and Clinical Development of Antibodies for Cancer Therapy. Frontiers in immunology; 8, 1751 (2018) doi:10.3389/fimmu.2017.01751 https://www.frontiersin.org/articles/10.3389/fimmu.2017.01751/full.

Altschul, et al. Optimal sequence alignment using affine gap costs. Bulletin of Mathematical Biology. 1986; 48(5-6):603-16.

Baik, et al. Fluorescence Identification of Head and Neck Squamous Cell Carcinoma and High-Risk Oral Dysplasia With BLZ-100, a Chlorotoxin-Indocyanine Green Conjugate. JAMA Otolaryngol Head Neck Surg. Published on line Feb. 18, 2016. doi: 10.1001/jamaoto. 2015.3617; JAMA Otolaryngol Head Neck Surg. Apr. 1, 2016; 142(4): 330-338.

(Continued)

*Primary Examiner* — Thomas S Heard
(74) *Attorney, Agent, or Firm* — DLA Piper LLP

(57) ABSTRACT

Described herein are peptides and variants and mutants thereof capable of interacting with TEAD, disrupting the HIPPO pathway, or modulating the activity or function of TEAD interactions in a cell. Pharmaceutical compositions and uses of peptides, as well as methods of designing and manufacturing such peptides, to treat cancer, tumor, or any other disease/condition associated with a dysregulated HIPPO pathway or uncontrolled cell growth are also described herein.

39 Claims, 40 Drawing Sheets

Specification includes a Sequence Listing.

(56) References Cited

FOREIGN PATENT DOCUMENTS

| WO | WO-2018136614 A1 | 7/2018 |
|----|------------------|--------|
| WO | WO-2018170480 A1 | 9/2018 |

OTHER PUBLICATIONS

Baker et al. Electrostatics of nanosystems: application to microtubules and the ribosome. Proc Natl Acad Sci U S A. Aug. 28, 2001;98(18):10037-41.

Bao, et al. The tripeptide phenylalanine-(D) glutamate-(D) glycine modulates leukocyte infiltration and oxidative damage in rat injured spinal cord. Neuroscience. Jul. 7, 2006;140(3):1011-22. Epub Apr. 3, 2006.

Barchetta et al. Neurotensin Is a Lipid-Induced Gastrointestinal Peptide Associated with Visceral Adipose Tissue Inflammation in Obesity. Nutrients 10, 526 (2018).

Barton, Geoffrey J. Protein secondary structure prediction. Curr Opin Struct Biol. Jun. 1995;5(3):372-6.

Bendtsen, et al. Improved prediction of signal peptides: SignalP 3.0. Journal of molecular biology 340.4 (2004): 783-795.

Berman, et al. The protein data bank. Nucleic acids research 28.1 (2000): 235-242.

Bernard et al. Identification of an interleukin-15alpha receptor-binding site on human interleukin-15. J Biol Chem. Jun. 4, 2004;279(23):24313-22.

Bjellqvist et al. Reference points for comparisons of two-dimensional maps of proteins from different human cell types defined in a pH scale where isoelectric points correlate with polypeptide compositions. Electrophoresis. Mar.-Apr. 1994;15(3-4):529-39.

Bjellqvist et al. The focusing positions of polypeptides in immobilized pH gradients can be predicted from their amino acid sequences. Electrophoresis. Oct. 1993;14(10):1023-31.

Bodenhofer, et al. msa: an R package for multiple sequence alignment. Bioinformatics 31.24 (2015): 3997-3999.

Boswell, C. A. et al. Comparative Physiology of Mice and Rats: Radiometric Measurement of Vascular Parameters in Rodent Tissues. (2014).

Bouchaud et al. The exon-3-encoded domain of IL-15ralpha contributes to IL-15 high-affinity binding and is crucial for the IL-15 antagonistic effect of soluble IL-15Ralpha. J Mol Biol. Sep. 26, 2008;382(1):1-12.

Boules, et el, Diverse roles of neurotensin agonists in the central nervous system; Front Endocrinol (Lausanne). 2013; 4: 36.

Brüggemann, M. et al. Human Antibody Production in Transgenic Animals. Arch. Immunol. Ther. Exp. (Warsz). 63, 101-8 (2015).

Bruno, et al. Basics and recent advances in peptide and protein drug delivery. Ther Deliv. Nov. 2013;4(11):1443-67.

Carver, et al. The design of Jemboss: a graphical user interface to EMBOSS. Bioinformatics. Sep. 22, 2003;19(14):1837-43.

Chen, et al., A targeted IL-15 fusion protein with potent anti-tumor activity. Cancer biology & therapy. Sep. 2015. vol. 16 No. 8, pp. 1415-1421; abstract; p. 1416, 1st column, 1st paragraph; p. 1416.

Chen, et al. The application of aptamer in apoptosis. Biochimie. vol. 132, Jan. 2017, pp. 1-8. Available online Oct. 14, 2016.

Chen, et al. Toxin acidic residue evolutionary function-guided design of de novo peptide drugs for the immunotherapeutic target, the Kv1. 3 channel. Scientific reports 5 (2015): 9881.

Chen, et al. Unusual binding mode of scorpion toxin BmKTX onto potassium channels relies on its distribution of acidic residues. Biochemical and biophysical research communications 447.1 (2014): 70-76.

Chen, J. et al., Protein-protein interactions: General trends in the relationship between binding affinity and interfacial buried surface area. Protein Sci. 22, 510-515 (2013).

Collaborative computational Project, No. 4. The CCP4 suite: programs for protein crystallography. Acta Crystallogr. D Biol. Crystallogr. 50:760-763 (1994).

Cordes, et al. Sequence space, folding and protein design. Curr Opin Struct Biol. Feb. 1996;6(1):3-10.

Correnti, et al. Screening, large-scale production, and structure-based classification for cystine-dense peptides. Nat Struct Mol Biol. Mar. 2018; 25(3): 270-278.

Craik et al., Potential therapeutic applications of the cyclotides and related cystine knot mini-proteins. Expert Opin. Investig. Drugs 16, 595-604 (2007).

Crook, Z. R. et al. Mammalian display screening of diverse cystine-dense peptides for difficult to drug targets. Nat. Commun. 8, 2244 (2017).

Daly, et al. Bioactive cystine knot proteins. Curr Opin Chem Biol. Jun. 2011;15(3):362-8. doi: 10.1016/j.cbpa.2011.02.008. Epub Feb. 27, 2011.

Daniels, T. R. et al. The transferrin receptor and the targeted delivery of therapeutic agents against cancer. Biochim. Biophys. Acta-Gen. Subj. 1820, 291-317 (2012).

Davis, et al. MolProbity: all-atom contacts and structure validation for proteins and nucleic acids. Nucleic acids research 35.suppl_2 (2007): W375-W383.

Derakhshankhah H et al.; Cell penetrating peptides: A concise review with emphasis on biomedical applications; Biomed Pharmacother. Dec. 2018;108:1090-1096. doi: 10.1016/j.biopha.2018.09.097. Epub Sep. 28, 2018.

Dolinsky et al. PDB2PQR: expanding and upgrading automated preparation of biomolecular structures for molecular simulations. Nucleic Acids Res. Jul. 2007;35(Web Server issue):W522-5.

Dou, et al. Overview of proteasome inhibitor-based anti-cancer therapies: perspective on bortezomib and second generation proteasome inhibitors versus future generation inhibitors of ubiquitin-proteasome system. Curr Cancer Drug Targets. 2014;14(6):517-36.

Elmallah, et al. Marine Drugs Regulating Apoptosis Induced by Tumor Necrosis Factor-Related Apoptosis-Inducing Ligand (TRAIL). Mar Drugs. Nov. 13, 2015;13(11):6884-909. doi: 10.3390/md13116884.

EMBOSS iep. Available at http://emboss.sourceforge.net/apps/release/6.6/emboss/apps/iep.html. Accessed on Dec. 26, 2018.

Emsley et al. Coot: model-building tools for molecular graphics. Acta crystallographica Section D, Biological crystallography 60:2126-2132 (2004).

EP16815459.9 Extended European Search Report dated Nov. 28, 2018.

EP16845226.6 The Extended European Search Report dated Mar. 28, 2019.

EP16874006.6 The Extended European Search Report dated Jul. 30, 2019.

EP16874006.6 The partial Supplemental European Search Report dated Apr. 24, 2019.

EP17849695.6 The Extended European Search Report dated Apr. 1, 2020.

Everts, S. Can we hit the snooze button on aging?. Chemical & Engineering News 95.10 (Mar. 6, 2017): 31-35.

Fidel et al. Preclinical Validation of the Utility of BLZ-100 in Providing Fluorescence Contrast for Imaging Spontaneous Solid Tumors. Cancer Res. Oct. 15, 2015;75(20):4283-91.

Fischer, et al. Apoptosis-based therapies and drug targets. Cell Death Differ. Aug. 2005;12 Suppl 1:942-61.

Gasteiger, et al. Protein Identification and Analysis Tools on the ExPASy Server. Excerpt, available at: http://web.expasy.org/compute_pi/pi_tool-doc.html. Accessed Nov. 7, 2018.

Gasteiger, et al. Protein Identification and Analysis Tools on the ExPASy Server. (In) John M. Walker (ed): The Proteomics Protocols Handbook, Humana Press (2005; pp. 571-607).

Gelly, et al. The KNOTTIN website and database: a new information system dedicated to the knottin scaffold. Nucleic acids research 32.suppl_1 (2004): D156-D159.

Gibson, et al. BCL-2 Antagonism to Target the Intrinsic Mitochondrial Pathway of Apoptosis. Clin Cancer Res. Nov. 15, 2015;21(22):5021-9. doi: 10.1158/1078-0432.CCR-15-0364.

Gould, et al. Cyclotides, a novel ultrastable polypeptide scaffold for drug discovery. Current pharmaceutical design 17.38 (2011): 4294-4307.

(56) References Cited

OTHER PUBLICATIONS

Hamman, et al. Oral delivery of peptide drugs: barriers and developments. BioDrugs. 2005;19(3):165-77.
Han, et al. Structural basis of a potent peptide inhibitor designed for Kv1.3 channel, a therapeutic target of autoimmune disease. Journal of Biological Chemistry 283.27 (2008): 19058-19065.
Henikoff et al. Amino acid substitution matrices from protein blocks. PNAS USA 89(22):10915-10919 (1992).
Hermans et al., Phospholipase C activation by neurotensin and neuromedin N in Chinese hamster ovary cells expressing the rat neurotensin receptor. Molecular Brain Research, 1992; 15: 332-338.
Herzig, et al. The Cystine Knot Is Responsible for the Exceptional Stability of the Insecticidal Spider Toxin ω-Hexatoxin-Hv1a. Toxins (Basel). Oct. 2015; 7(10): 4366-4380.
Hockaday, et al., Imaging Glioma Extent with 131I-TM-601, J. Nuc. Med. 46(4): 580-586 (2005).
IUPHAR/BPS. Guide to Pharmacology—Tumour necrosis factor (TNF) receptor family. Available at: http://www.guidetopharmacology.org/GRAC/FamilyDisplayForward?familyId=334. Accessed Nov. 7, 2018.
Iyer, et al. Tying the knot: The cystine signature and molecular-recognition processes of the vascular endothelial growth factor family of angiogenic cytokines. The FEBS journal278.22 (2011): 4304-4322.
Janzer, et al. Drug conjugation affects pharmacokinetics and specificity of kidney-targeted peptide carriers, Bioconjugate chemistry 27.10 (2016):2441-2449.
Karlsson, R., et al., Analyzing a kinetic titration series using affinity biosensors. Anal. Biochem. 349, 136-147 (2006).
Kikuchi, et al., High proteolytic resistance of spider-derived inhibitor cystine knots. Int. J. Pept. 2015, (2015).
Kintizing, et al. Engineered knottin peptides as diagnostics, therapeutics, and drug delivery vehicles. Current opinion in chemical biology 34 (2016): 143-150.
Kirkland, et al. Clinical strategies and animal models for developing senolytic agents. Exp Gerontol. Aug. 2015;68:19-25. doi: 10.1016/j.exger.2014.10.012. Epub Oct. 28, 2014.
Kirkland, James L. Translating Advances from the Basic Biology of Aging into Clinical Application. Exp Gerontol. Jan. 2013; 48(1): 1-5. Published online Dec. 10, 2012. doi: 10.1016/j.exger.2012.11.014.
Kolmar, H. Biological diversity and therapeutic potential of natural and engineered cystine knot miniproteins. Current opinion in pharmacology 9.5 (2009): 608-614.
Kolmar, H. Natural and engineered cystine knot miniproteins for diagnostic and therapeutic applications. Current pharmaceutical design 17.38 (2011): 4329-4336.
Kozminsky-Atias, et al. Isolation of the first toxin from the scorpion Buthus occitanus israelis showing preference for Shaker potassium channels. FEBS letters 581.13 (2007): 2478-2484.
Krezel, et al. Solution structure of the potassium channel inhibitor agitoxin 2: caliper for probing channel geometry. Protein Science 4.8 (1995): 1478-1489.
Kumari, et al. Cysteine-Rich Peptide Family with Unusual Disulfide Connectivity from Jasminum sambac. J Nat Prod. Nov. 25, 2015;78(11):2791-9. doi: 10.1021/acs.jnatprod.5b00762. Epub Nov. 10, 2015.
Larking, et al. Clustal W and Clustal X version 2.0. Bioinformatics applications note. 2007. 2947-2948; 23(21).
Li, et al. Mitochondria and apoptosis: emerging concepts. F1000Prime Rep. 2015; 7: 42. Published online Apr. 1, 2015. doi: 10.12703/P7-42.
Li, Z. et al. Influence of molecular size on tissue distribution of antibody fragments. MAbs 8, 113-9 (2016).
Ling et al., Molecular mechanism of the sea anemone toxin ShK recognizing the Kv1.3 channel explored by docking and molecular dynamic simulations. J. Chem. Inf. Model. 47, 1967-1972 (2007).
Liu, et al., Dual receptor recognizing cell penetrating peptide for selective targeting, efficient intratumoral diffusion and synthesized anti-glioma therapy. Theranostics. Jan. 1, 2016. vol. 6, No. 2, pp. 177-191.
Liu, et al. Robust structural analysis of native biological macromolecules from multi-crystal anomalous diffraction data. Acta Crystallographica Section D: Biological Crystallography 69.7 (2013): 1314-1332.
Ma, et al. Engineered nanoparticles induce cell apoptosis: potential for cancer therapy. Oncotarget. Jun. 28, 2016;7(26):40882-40903. doi: 10.18632/oncotarget.8553.
Maillere, et al. Immunogenicity of a disulphide-containing neurotoxin: presentation to T-cells requires a reduction step. Toxicon, 1995; 33(4): 475-482.
Mamelak, et al. Phase I single-dose study of intracavitary-administered iodine-131-TM-601 in adults with recurrent high-grade glioma. J Clin Oncol. Aug. 1, 2006;24(22):3644-50.
McCoy, et al. Phaser crystallographic software. J Appl Crystallogr. Aug. 1, 2007;40(Pt 4):658-674. Epub Jul. 13, 2007.
Mitragotri, et al. Overcoming the challenges in administering biopharmaceuticals: formulation and delivery strategies. Nat Rev Drug Discov. Sep. 2014;13(9):655-72.
Moore, et al. Knottins: disulfide-bonded therapeutic and diagnostic peptides. Drug Discovery Today: Technologiesvol. 9, Issue 1, Spring 2012, pp. e3-e11.
Moroz, et al. Oral delivery of macromolecular drugs: Where we are after almost 100years of attempts. Adv Drug Deliv Rev. Jun. 1, 2016;101:108-121.
Mortier, et al. Soluble interleukin-15 receptor alpha (IL-15R alpha)-sushi as a selective and potent agonist of IL-15 action through IL-15R beta/gamma. Hyperagonist IL-15 × IL-15R alpha fusion proteins.J Biol Chem. Jan. 20, 2006;281(3):1612-9. Epub Nov. 11, 2005.
Moura, et al. Relative amino acid composition signatures of organisms and environments. PloS one 8.10 (2013): e77319.
Moyse, E. et al. Distribution of neurotensin binding sites in rat brain: A light microscopic radioautographic study using monoiodo [125I]Tyr3-neurotensin. Neuroscience 22, 525-536 (1987).
Murshudov et al. Refinement of macromolecular structures by the maximum-likelihood method. Acta Cryst D53:240-255 (1997).
Mustain, et al., The role of neurotensin in physiologic and pathologic processes. Curr. Opin. Endocrinol. Diabetes Obes. 18, 75-82 (2011).
Myszka, D. G. Improving biosensor analysis. J. Mol. Recognit. 12, 279-284 (1999).
Nagase et al.: Substrate specificity of MMPs; Matrix Metalloproteinase Inhibitors in Cancer Therapy; Clendeninn & Appelt Eds., Springer Science Media New York; 39-66 (2001).
Needleman et al. A general method applicable to the search for similarities in the amino acid sequence of two proteins. J. Mol. Biol. 48:443-453 (1970).
Nielsen et al. NN-align. An artificial neural network-based alignment algorithm for MHC class II peptide binding prediction. BMC Bioinformatics.Sep. 18, 2009;10:296.
Nielsen, et al., Prediction of MHC class II bindingaffinity using SMM-align, a novel stabilization matrix alignment method. BMCBioinformatics, vol. 8, Article No. 238 (2007): 1-12.
Njiojob et al. Tailored near-infrared contrast agents for image guided surgery. J Med Chem. Mar. 26, 2015;58(6):2845-54 . . . .
Ojeda et al. (Review: Chlorotoxin: Structure, Activity, and Potential Uses in Cancer Therapy; PeptideScience vol. 106, No. 1; Sep. 29, 2015).
Otwinowski et al. Processing of X-ray diffraction data collected in oscillation mode. Method Enzymol 276:307-326 (1997).
PCT/US16/66007 International Search Report and Written Opinion dated May 24, 2017.
PCT/US2016/039431 International Search Report and Written Opinion dated Jan. 13, 2017.
PCT/US2016/051166 International Preliminary Report on Patentability dated Mar. 22, 2018.
PCT/US2016/051166 International Search Report dated Mar. 23, 2017.
PCT/US2018/023006 International Search Report and Written Opinion dated Jul. 27, 2018.

(56) References Cited

OTHER PUBLICATIONS

PCT/US2018/037544 International Search Report and Written Opinion dated Oct. 26, 2018.
PCT/US2018/066337 International Search Report and Written Opinion dated Apr. 30, 2019.
PCT/US2019/022630 International Search Report and Written Opinion dated Jul. 5, 2019.
Pearson et al. Improved Tools for Biological Sequence Comparison. PNAS USA 85:2444-48 (1988).
Pearson. Rapid and sensitive sequence comparison with FASTP and FASTA. Meth. Enzymol. 183:63-98 (1990).
Potterton et al., A graphical user interface to the CCP4 program suite. Acta Crystallogr.-Sect. D Biol. Crystallogr. (2003). doi:10.1107/S0907444903008126.
Rashid, M. H. et al. A potent andKv1.3-selective analogue of the scorpion toxin HsTX1 as a potential therapeuticfor autoimmune diseases. Scientific Reports, Mar. 2014; 4(4509): 1-9.
Reinwarth, et al. Chemical synthesis, backbone cyclization and oxidative folding of cystine-knot peptides—promising scaffolds for applications in drug design. Molecules 17.11 (2012): 12533-12552.
Renisio, et al. Solution structure of BmKTX, a K+ blocker toxin from the Chinese scorpion *Buthus martensi*. Proteins: Structure, Function, and Bioinformatics 38.1 (2000): 70-78.
Ricci, et al. Chemotherapeutic approaches for targeting cell death pathways. Oncologist. Apr. 2006;11(4):342-57.
Rice, et al. EMBOSS: the European Molecular Biology Open Software Suite. Trends Genet. Jun. 2000;16(6):276-7.
Sellers, Peter H. On the theory and computation of evolutionary distances. SIAM Journal on Applied Mathematics. 1974;26:787.
Shire, et al. Challenges in the development of high protein concentration formulations. Journal of pharmaceutical sciences 93.6 (2004): 1390-1402.
Sillero et al. Isoelectric point determination of proteins and other macromolecules: oscillating method. Comput Biol Med. Feb. 2006;36(2):157-66. Epub Jan. 1, 2005.
Sillero et al. Isoelectric points of proteins: theoretical determination. Anal Biochem. Jun. 1989;179(2):319-25.
Simeon, Rudo et al., In vitro-engineered non-antibody protein therapeutics, Protein Cell 218, 9(1);3-14.
Singh, et al. Antibody-Drug Conjugates: Design, Formulation and Physicochemical Stability. Pharm Res. Nov. 2015;32(11):3541-71.
Sinha, et al. Oral colon-specific drug delivery of protein and peptide drugs. Crit Rev Ther Drug Carrier Syst. 2007;24(1):63-92.
Sinniah, R. et al., Serum iron, total iron-binding capacity, and percentage saturation in normal subjects. J. Clin. Pathol. 21, 603-10 (1968).
Solon, E.G. Autoradiography techniques and quantification of drug distribution. 2015 Cell Tiss. Res. 360(1): 87-107.
Soroceanu, et al. Use of chlorotoxin for targeting of primary brain tumors. Cancer Res. Nov. 1, 1998;58(21):4871-9.
Sottero et al. Pacifastin-derived Peptides Target Tumors for Use in In Vivo Imaging. Anticancer Res. Jan. 2018;38(1):51-60.
Stern, et al. Alternative non-antibody protein scaffolds for molecular imaging of cancer. Current opinion in chemical engineering 2.4 (2013): 425-432.
Sutherland, R. et al. Ubiquitous cell-surface glycoprotein on tumor cells is proliferation-associated receptor for transferrin. Proc. Natl. Acad. Sci. U. S. A. 78, 4515-9 (1981).
Tabrizi, et al., Biodistribution mechanisms of therapeutic monoclonal antibodies in health and disease. AAPS J. 12, 33-43 (2010).
Tait, et al. Die another way—non-apoptotic mechanisms of cell death. J Cell Sci. May 15, 2014;127(Pt 10):2135-44. doi: 10.1242/jcs.093575.
Tam, et al., Antimicrobial peptides from plants. Pharmaceuticals 8, 711-757 (2015).
Tesmer, J. J., et al. The structure, catalytic mechanism and regulation of adenylyl cyclase. Curr. Opin. Struct. Biol. 8, 713-719 (1998).
The UniProt Consortium. UniProt: The Universal Protein Knowledgebase. Nucleic Acids Research, 2017, 45, D158-D169. Published online Nov. 11, 2016.
Trenevska, I., et al., Therapeutic Antibodies against Intracellular Tumor Antigens. Front. Immunol. 8, 1001 (2017).
Trudeau, L. E. Neurotensin regulates intracellular calcium in ventral tegmental area astrocytes: Evidence for the involvement of multiple receptors. Neuroscience 97, 293-302 (2000).
Tundo, et al. Effect of cisplatin on proteasome activity. J Inorg Biochem. Dec. 2015;153:253-258. doi: 10.1016/j.jinorgbio.2015.08.027. Epub Sep. 4, 2015.
U.S. Appl. No. 15/739,669 Office Action dated May 14, 2020.
U.S. Appl. No. 15/758,320 Office Action dated Apr. 15, 2020.
U.S. Appl. No. 15/739,669 Office Action dated Nov. 27, 2019.
U.S. Appl. No. 15/758,320 Office Action dated Feb. 26, 2019.
U.S. Appl. No. 15/758,320 Office Action dated Jul. 25, 2019.
Vincent et al., Neurotensin and neurotensin receptors. Trends Pharmacol. Sci. 20, 302-309 (1999).
Vitt, et al. Evolution and classification of cystine knot-containing hormones and related extracellular signaling molecules. Molecular endocrinology15.5 (2001): 681-694.
Vordenbaumen, et al. Defensins potential effectors autoimmune rheumatic disorders. Polymers. 2011; 3:1268-1281.
Wakankar, et al. Formulation considerations for proteins susceptible to asparagine deamidation and aspartate isomerization. Journal of pharmaceutical sciences 95.11 (2006): 2321-2336.
Wang, X. et al. Characterization of promoter elements regulating the expression of the human neurotensin/neuromedin N gene. J. Biol. Chem. 286, 542-554 (2011).
Weatherall, et al. Small conductance calcium-activated potassium channels: from structure to function. Prog Neurobiol. Jul. 2010;91(3):242-55. doi: 10.1016/j.pneurobio.2010.03.002. Epub Mar. 30, 2010.
Werle, et al. The potential of cystine-knot microproteins as novel pharmacophoric scaffolds in oral peptide drug delivery. J. Drug Targeting 2006; 14:137-146.
Winn, et al. Overview of the CCP4 suite and current developments. Acta Crystallographica Section D 67.4 (2011): 235-242.
Wiranowska, et al. Clathrin-mediated entry and cellular localization of chlorotoxin in human glioma. Cancer Cell Int. Aug. 12, 2011;11:27.
Wischnjow, et al. Renal Targeting: Peptide-Based Drug Delivery to Proximal Tubule Cells. Bioconjug Chem. Apr. 20, 2016;27(4):1050-7. doi: 10.1021/acs.bioconjchem.6b00057. Epub Mar. 30, 2016.
Yang, J. et al. The I-TASSER Suite: protein structure and function prediction. Nat. Methods 12, 7-8 (2015).
Ye, et al. The scorpion toxin analogue BmKTX-D33H as a potential Kv1. 3 channel-selective immunomodulator for autoimmune diseases. Toxins 8.4 (2016): 115.
Yurkovetskiy, et al. A Polymer-Based Antibody-Vinca Drug Conjugate Platform: Characterization and Preclinical Efficacy. Cancer Res. Aug. 15, 2015;75(16):3365-72.
Zhou, et al. Kidney-targeted drug delivery systems. Acta Pharm Sin B. Feb. 2014; 4(1): 37-42. Published online Jan. 23, 2014. doi: 10.1016/j.apsb.2013.12.005.
Zhu et al. Precursor nucleotide sequence and genomic organization of BmTXKS1, a new scorpion toxin-like peptide from *Buthus martensii* Karsch. Toxicon. Sep. 2001;39(9):1291-6.
"Supplementary European Search Report Patent Application No. 18741953.6," dated Dec. 1, 2020, pp. 10.
Crook Z.R., et al., "Abstract 2971: Optides (optimized knottin peptides) Computationally Designed to Target the Oncogenic HIPPO Pathway," Cancer Research, Jul. 2016, vol. 76, No. 14, 4 pages.
Akdag, et al. The Uptake Mechanism of the Cell-Penetrating pVEC Peptide. J. Chem. 2013, 1-9 (2013).
Appelbaum, et al. Arginine Topology Controls Escape of Minimally Cationic Proteins from Early Endosomes to the Cytoplasm. Chem. Biol. 19, 819-830 (2012).
Baar, et al. Targeted apoptosis of senescent cells restores tissue homeostasis in response to chemotoxicity and aging. Cell 169.1 (2017): 132-147.
Balayssac, et al. Comparison of Penetratin and Other Homeodomain-Derived Cell-Penetrating Peptides: Interaction in a Membrane-Mimicking Environment and Cellular Uptake Efficiency. Biochemistry 45, 1408-1420 (2006).
Bandaranayake, et al. Daedalus: a robust, turnkey platform for rapid production of decigram quantities of active recombinant proteins in

(56) References Cited

OTHER PUBLICATIONS human cell lines using novel lentiviral vectors. Nucleic Acids Res. Nov. 2011;39(21):e143. doi: 10.1093/nar/gkr706. Epub Sep. 12, 2011.
Berger, et al. Computationally designed high specificity inhibitors delineate the roles of BCL2 family proteins in cancer. Elife 5, (2016).
Bhardwaj, et al. Accurate de novo design of hyperstable constrained peptides. Nature 538, 329-335 (2016).
Bohlen, et al. A bivalent tarantula toxin activates the capsaicin receptor, TRPV1, by targeting the outer pore domain. Cell 141, 834-845 (2010).
Boisseau, et al. Cell penetration properties of maurocalcine, a natural venom peptide active on the intracellular ryanodine receptor. Biochim. Biophys. Acta—Biomembr. 1758, 308-319 (2006).
Butte, et al. Near-infrared imaging of brain tumors using the Tumor Paint BLZ-100 to achieve near-complete resection of brain tumors. Neurosurg Focus. Feb. 2014;36(2):E1.
Choi, et al. A general strategy for generating intact, full-length IgG antibodies that penetrate into the cytosol of living cells. MAbs 6, 1402-1414 (2014).
Corbi-Verge, et al. Strategies to Develop Inhibitors of Motif-Mediated Protein-Protein Interactions as Drug Leads. Annu. Rev. Pharmacol. Toxicol. 57, 39-60 (2017).
Cordenonsi, et al. The Hippo transducer TAZ confers cancer stem cell-related traits on breast cancer cells. Cell 147, 759-72 (2011).
De Coupade, et al. Novel human-derived cell-penetrating peptides for specific subcellular delivery of therapeutic biomolecules. Biochem. J. 390, 407-418 (2005).
Dohmen, et al. Multifunctional CPP polymer system for tumor-targeted pDNA and siRNA delivery. Methods Mol Biol. 2011;683:453-63. doi: 10.1007/978-1-60761-919-2_32.
Drin, et al. Physico-chemical requirements for cellular uptake of pAntp peptide: Role of lipid-binding affinity. Eur. J. Biochem. 268, 1304-1314 (2001).
D'Souza, et al. Structural parameters modulating the cellular uptake of disulfide-rich cyclic cell-penetrating peptides: MCoTI-II and SFTI-1. Eur. J. Med. Chem. 88, 10-18 (2014).
Duchardt, et al. A cell-penetrating peptide derived from human lactoferrin with conformation-dependent uptake efficiency. J. Biol .Chem. 284, 36099-108 (2009).
Dulhunty, et al. Multiple actions of imperatoxin A on ryanodine receptors: Interactions with the II-III loop 'A' fragment. J. Biol. Chem. 279, 11853-11862 (2004).
Erazo-Oliveras, et al. Protein delivery into live cells by incubation with an endosomolytic agent. Nat. Methods 11, 861-867 (2014).
Esteve, et al. Critical amino acid residues determine the binding affinity and the Ca 2+ release efficacy of maurocalcine in skeletal muscle cells. J. Biol. Chem. 278, 37822-37831 (2003).
Fernandez-L, et al. Oncogenic YAP promotes radioresistance and genomic instability in medulloblastoma through IGF2-mediated Akt activation. Oncogene 31, 1923-37 (2012).
Fidel, et al. Preclinical Validation of the Utility of BLZ-100 in Providing Fluorescence Contrast for Imaging Spontaneous Solid Tumors. Cancer Res. 75, 4283-4291 (2015).
Finton, et al. Autoreactivity and Exceptional CDR Plasticity (but Not Unusual Polyspecificity) Hinder Elicitation of the Anti-HIV Antibody 4E10. PLoS Pathog. 9, e1003639 (2013).
Furtek, et al. Strategies and Approaches of Targeting STAT3 for Cancer Treatment. ACS Chem. Biol. 11, 308-318 (2016).
Garcia, et al. Constitutive activation of Stat3 by the Src and JAK tyrosine kinases participates in growth regulation of human breast carcinoma cells. Oncogene 20, 2499-2513 (2001).
Gautam, et al. Topical Delivery of Protein and Peptide Using Novel Cell Penetrating Peptide IMT-P8. Sci. Rep. 6, 26278 (2016).
Gilbert, H. Molecular and cellular aspects of thiol-disulfide exchange. Adv. Enzymol. Relat. Areas Mol. Biol. 63, 69-172 (1990).
Gujral, et al. Hippo pathway mediates resistance to cytotoxic drugs. Proc. Natl. Acad. Sci. 2017, 201703096 (2017).

Gump, et al. TAT transduction: the molecular mechanism and therapeutic prospects. Trends Mol Med. Oct. 2007;13(10):443-8.
Gurrola, et al. Imperatoxin A, a Cell-Penetrating Peptide from Scorpion Venom, as a Probe of Ca-Release Channels/Ryanodine Receptors. Pharmaceuticals (Basel). 3, 1093-1107 (2010).
Harada, et al. Antitumor protein therapy; application of the protein transduction domain to the development of a protein drug for cancer treatment. Breast Cancer. 2006;13(1):16-26.
Harvey, et al. The Hippo pathway and human cancer. Nat Rev Cancer. Apr. 2013;13(4):246-57. doi: 10.1038/nrc3458. Epub Mar. 7, 2013.
Hong, et al. The YAP and TAZ transcription coactivators: key downstream effectors of the mammalian Hippo pathway. Semin Cell Dev Biol. Sep. 2012; 23(7): 785-793.
Jang, et al. A nucleic acid-hydrolyzing antibody penetrates into cells via caveolae-mediated endocytosis, localizes in the cytosol and exhibits cytotoxicity. Cell. Mol. Life Sci. 66, 1985-1997 (2009).
Kern, et al. Enzyme-Cleavable Polymeric Micelles for the Intracellular De-livery of Pro-Apoptotic Peptides. Mol Pharm. May 1, 2017;14(5):1450-1459. doi: 10.1021/acs.molpharmaceut.6b01178. Epub Mar. 30, 2017.
Kimura, et al. Engineered cystine knot peptides that bind $\alpha v\beta 3$, $\alpha v\beta 5$, and $\alpha 5\beta 1$ integrins with low-nanomolar affinity. Proteins Struct. Funct. Bioinforma. 77, 359-369 (2009).
Knight, et al. TEAD1 and c-Cbl are novel prostate basal cell markers that correlate with poor clinical outcome in prostate cancer. Br J Cancer. Dec. 2, 2008;99(11):1849-58.
Lange, et al. Classical Nuclear Localization Signals: Definition, Function, and Interaction with Importin $\alpha$*,s. J Biol Chem. Feb. 23, 2007; 282(8): 5101-5105.
Li, et al. Structural insights into the YAP and TEAD complex. Genes Dev. 24, 235-240 (2010).
Lim, et al. A Cancer Specific Cell-Penetrating Peptide, BR2, for the Efficient Delivery of an scFv into Cancer Cells. PLoS One 8, (2013).
Liu-Chittenden, et al. Genetic and pharmacological disruption of the TEAD-YAP complex suppresses the oncogenic activity of YAP. Genes Dev. 26, 1300-5 (2012).
Mitchell, et al. Polyarginine enters cells more efficiently than other polycationic homopolymers. J. Pept. Res. 56, 318-25 (2000).
Montagne, et al. The max b-HLH-LZ can transduce into cells and inhibit c-Myc transcriptional activities. PLoS One 7, 2-10 (2012).
Moore, et al. Engineering knottins as novel binding agents. Methods Enzymol. 2012;503:223-51.
Mouhat, et al. Diversity of folds in animal toxins acting on ion channels. Biochem. J. 378, 717-26 (2004).
Nelson, et al. Myristoyl-based transport of peptides into living cells. Biochemistry 46, 14771-14781 (2007).
Ojeda, et al. Lysine to arginine mutagenesis of chlorotoxin enhances its cellular uptake. Biopolymers 1-76 (2017). doi:10.1002/bip.23025.
PCT/US18/14203 International Search Report and Written Opinion dated May 23, 2018.
Poillot, et al. Small efficient cell-penetrating peptides derived from scorpion toxin maurocalcine. J. Biol. Chem. 287, 17331-17342 (2012).
Pooga, et al. Cell penetration by transportan. FASEB J. 12, 67-77 (1998).
Procko, et al. A computationally designed inhibitor of an Epstein-Barr viral Bcl-2 protein induces apoptosis in infected cells. Cell 157, 1644-56 (2014).
Qian, et al. Early endosomal escape of a cyclic cell-penetrating peptide allows effective cytosolic cargo delivery. Biochemistry. Jun. 24, 2014;53(24):4034-46.
Quintas-Cardama, et al. Molecular pathways: JAK/STAT pathway: Mutations, inhibitors, and resistance. Clin. Cancer Res. 19, 1933-1940 (2013).
Rees, et al. Refined crystal structure of the potato inhibitor complex of carboxypeptidase A at 2.5 A resolution. J. Mol. Biol. 160, 475-98 (1982).
Rhee, et al. Mechanism of uptake of C105Y, a novel cell-penetrating peptide. J. Biol. Chem. 281, 1233-1240 (2006).
Rohl, et al. Protein structure prediction using Rosetta. Methods Enzymol. 2004;383:66-93.

(56) References Cited

OTHER PUBLICATIONS

Said, et al. The anti-HIV cytokine midkine binds the cell surface-expressed nucleolin as a low affinity receptor. J Biol Chem. Oct. 4, 2002;277(40):37492-502. Epub Jul. 29, 2002.
Samy, et al. Animal venoms as antimicrobial agents. Biochem Pharmacol. Jun. 15, 2017;134:127-138. doi: 10.1016/j.bcp.2017.03.005. Epub Mar. 10, 2017.
Sangphukieo, et al. Computational Design of Hypothetical New Peptides Based on a Cyclotide Scaffold as HIV gp120 Inhibitor. PLoS One 10, e0139562 (2015).
Sansone, et al. Targeting the interleukin-6/jak/stat pathway in human malignancies. J. Clin. Oncol. 30, 1005-1014 (2012).
Santos, et al. Thermofluor-based optimization strategy for the stabilization and crystallization of Campylobacter jejuni desulforubrerythrin. Protein Expr. Purif. 81, 193-200 (2012).
Santucci, et al. The Hippo Pathway and YAP/TAZ-TEAD Protein-Protein Interaction as Targets for Regenerative Medicine and Cancer Treatment. J Med Chem. Jun. 25, 2015;58(12):4857-73.
Schwartz, et al. Characterization of hadrucalcin, a peptide from *Hadrurus gertschi* scorpion venom with pharmacological activity on ryanodine receptors. Br J Pharmacol. Jun. 2009; 157(3): 392-403.
Shahbazzadeh, et al. Hemicalcin, a new toxin from the Iranian scorpion *Hemiscorpius tepturus* which is active on ryanodine-sensitive Ca2+ channels. Biochem. J. 404, 89-96 (2007).
Shaji, et al. Protein and Peptide drug delivery: oral approaches. Indian J Pharm Sci. May-Jun. 2008;70(3):269-77.
Stalmans, et al. Cell-penetrating peptides selectively cross the blood-brain barrier in vivo. PLoS One 10, 1-22 (2015).
Steinhardt, et al. Expression of Yes-associated protein in common solid tumors. Hum. Pathol. 39, 1582-9 (2008).
Sudo, et al. Human-derived fusogenic peptides for the intracellular delivery of proteins. J. Control. Release 255, 1-11 (2017).
Takayama, et al. Enhanced intracellular delivery using arginine-rich peptides by the addition of penetration accelerating sequences (Pas). J. Control. Release 138, 128-133 (2009).
Tangri, et al. Rationally engineered proteins or antibodies with absent or reduced immunogenicity. Curr. Med. Chem. 9, 2191-9 (2002).
Trussel, et al. New strategy for the extension of the serum half-life of antibody fragments. Bioconjug Chem. Dec. 2009;20(12):2286-92. doi: 10.1021/bc9002772.
Tsunemi, et al. Crystallization of a complex between an elastase-specific inhibitor elafin and porcine pancreatic elastase. J. Mol. Biol. 232, 310-1 (1993).
Vasalou, et al. A Mechanistic Tumor Penetration Model to Guide Antibody Drug Conjugate Design. PLoS One 10, (2015).
Veiseh, et al. Tumor paint: a chlorotoxin:Cy5.5 bioconjugate for intraoperative visualization of cancer foci. Cancer Res. Jul. 15, 2007;67(14):6882-8.
Vives, et al. A Truncated HIV-1 Tat Protein Basic Domain Rapidly Translocates Through the Plasma Membrane and Accumulates in the Cell Nucleus. J. Biol. Chem. 1997 272(25):16010-16017.
Winnard, et al. Development of novel chimeric transmembrane proteins for multimodality imaging of cancer cells. Cancer Biol. Ther. 6, 1889-99 (2007).
Xia, et al. YAP/TEAD Co-Activator regulated pluripotency and chemoresistance in ovarian cancer Initiated Cells. PLoS One 9, (2014).
Xu, et al. Challenges and Opportunities in Absorption, Distribution, Metabolism, and Excretion Studies of Therapeutic Biologies. AAPS J. 14, 781-791 (2012).
Xu, et al. Yes-associated protein is an independent prognostic marker in hepatocellular carcinoma. Cancer 115, 4576-85 (2009).
Yamada, et al. Internalization of bacterial redox protein azurin in mammalian cells: Entry domain and specificity. Cell. Microbiol. 7, 1418-1431 (2005).
Yang, et al. Protein-peptide interactions analyzed with the yeast two-hybrid system. Nucleic Acids Res. 23, 1152-1156 (1995).
Yu, et al. The Hippo pathway: Regulators and regulations. Genes Dev. 27, 355-371 (2013).
Zanconato, et al. YAP/TAZ as therapeutic targets in cancer. Curr. Opin. Pharmacol. 29, 26-33 (2016).
Zhang, et al. Tumor-selective proteotoxicity of verteporfin inhibits colon cancer progression independently of YAP1. Sci. Signal. 8, ra98 (2015).
Zhao, et al. Chemical engineering of cell penetrating antibodies. J. Immunol. Methods 254, 137-145 (2001).
Zhou, et al. TAZ is a novel oncogene in non-small cell lung cancer. Oncogene. May 5, 2011;30(18):2181-6.
Zhu, et al. Evolutionary origin of inhibitor cystine knot peptides. FASEB J. 17, 1765-1767 (2003).

\* cited by examiner

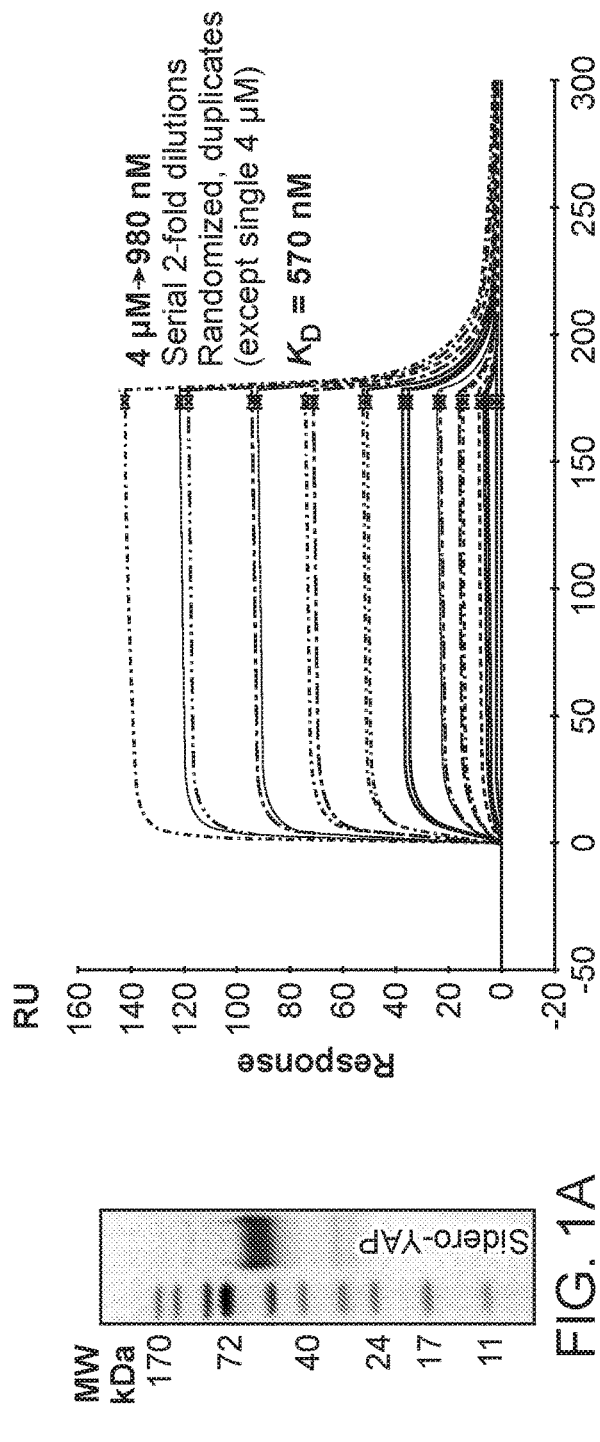
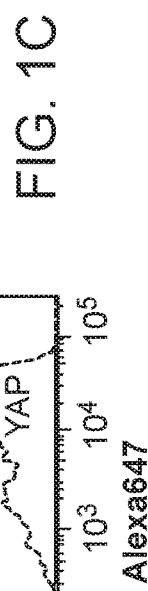
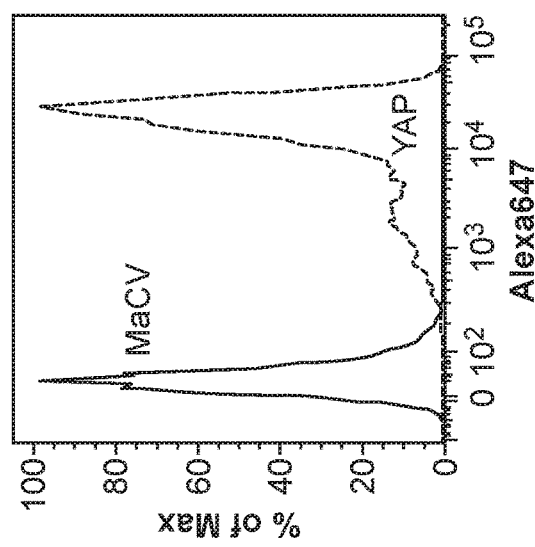
FIG. 1A
FIG. 1B
FIG. 1C

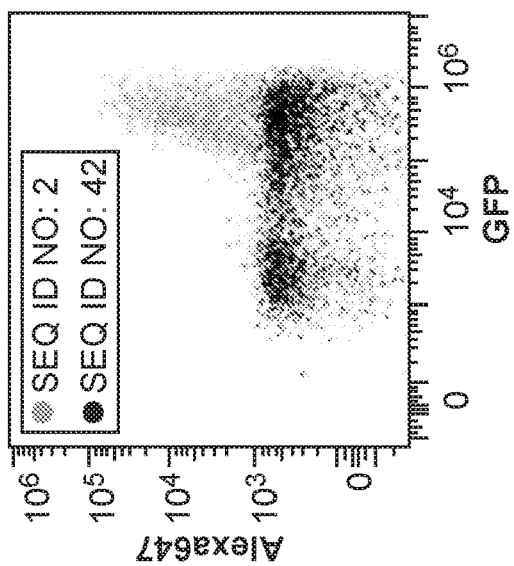
FIG. 4B
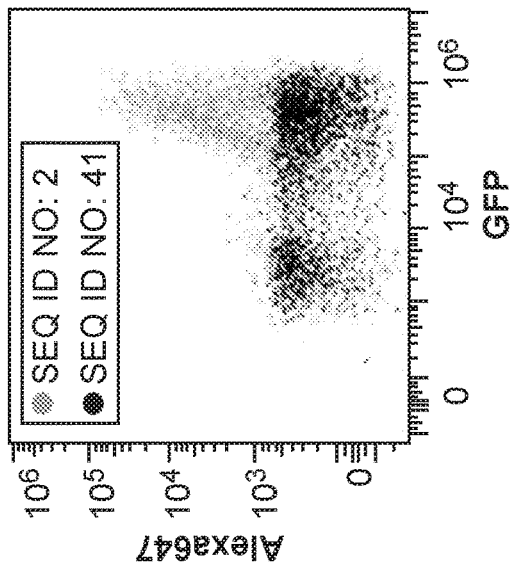
FIG. 4E
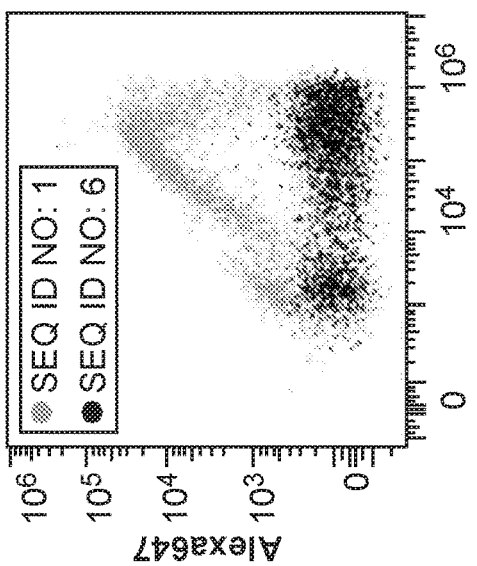
FIG. 4C
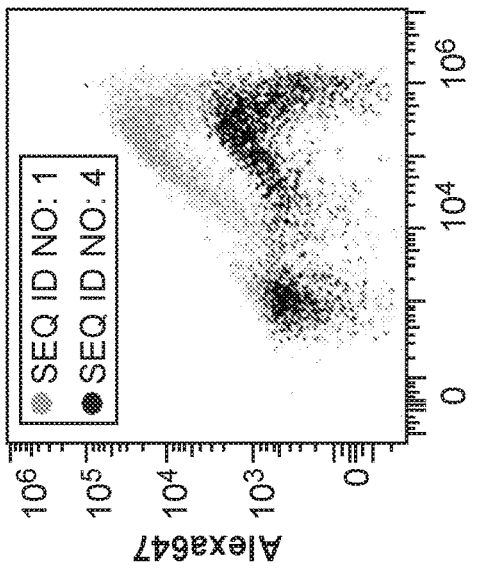
FIG. 4F
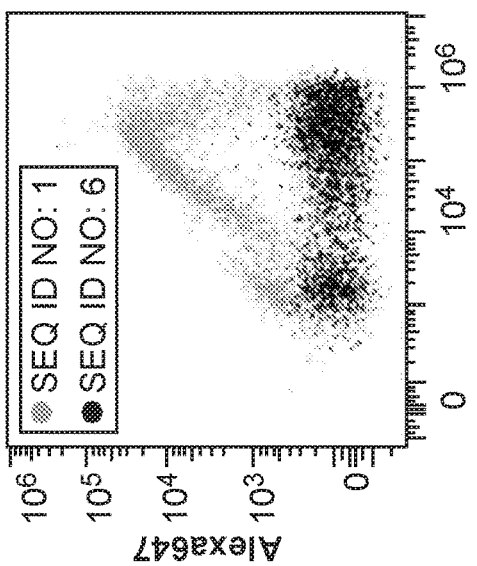
FIG. 4D
FIG. 4G

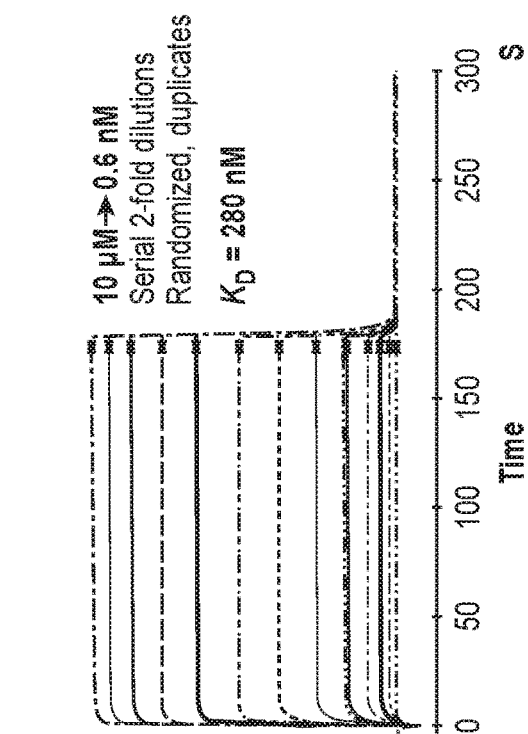
FIG. 5C
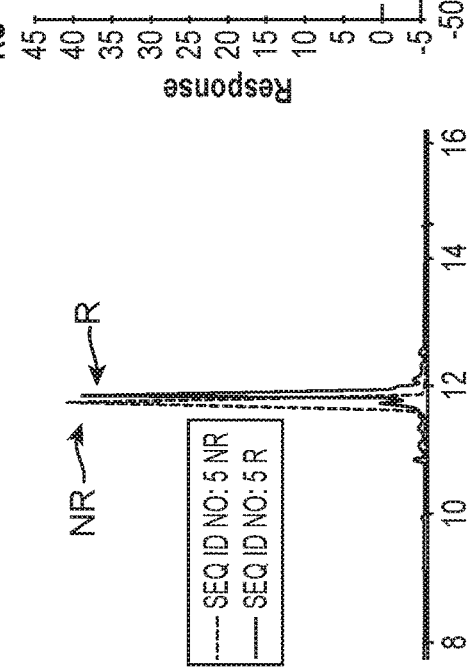
FIG. 5F
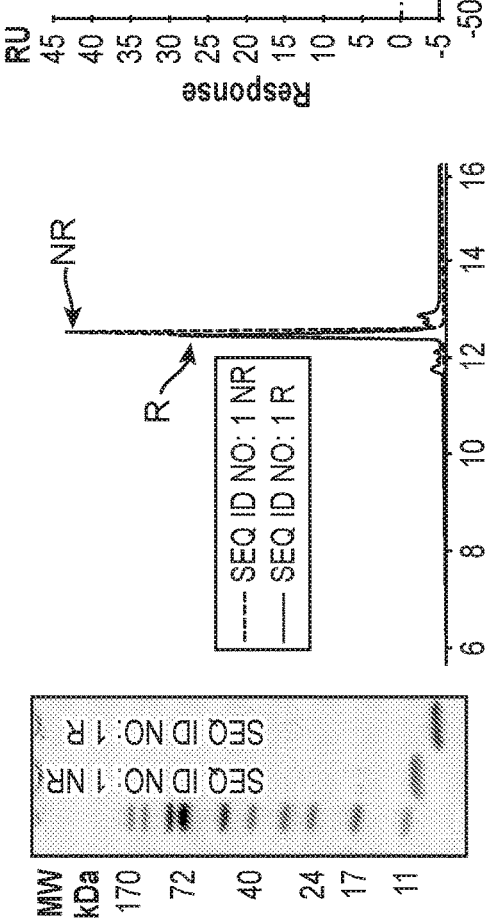
FIG. 5A
FIG. 5B
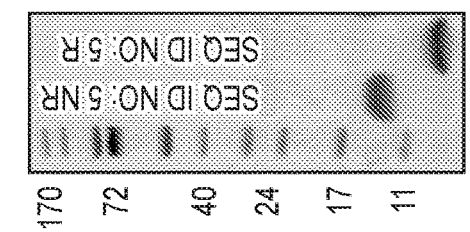
FIG. 5D
FIG. 5E

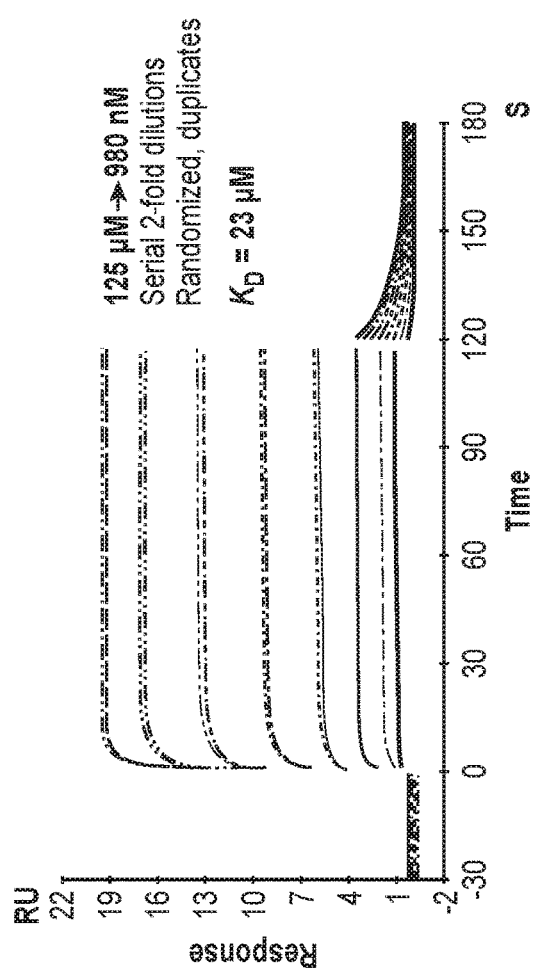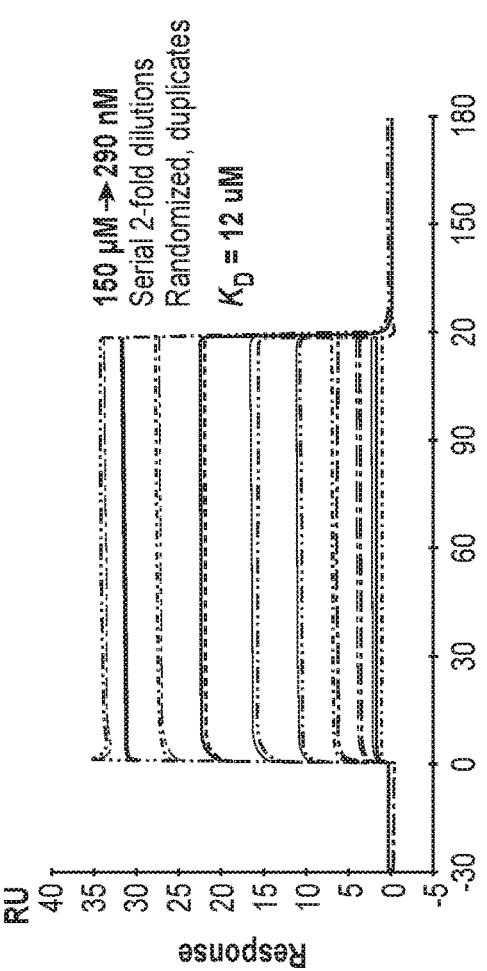
FIG. 5G  FIG. 5H  FIG. 5I
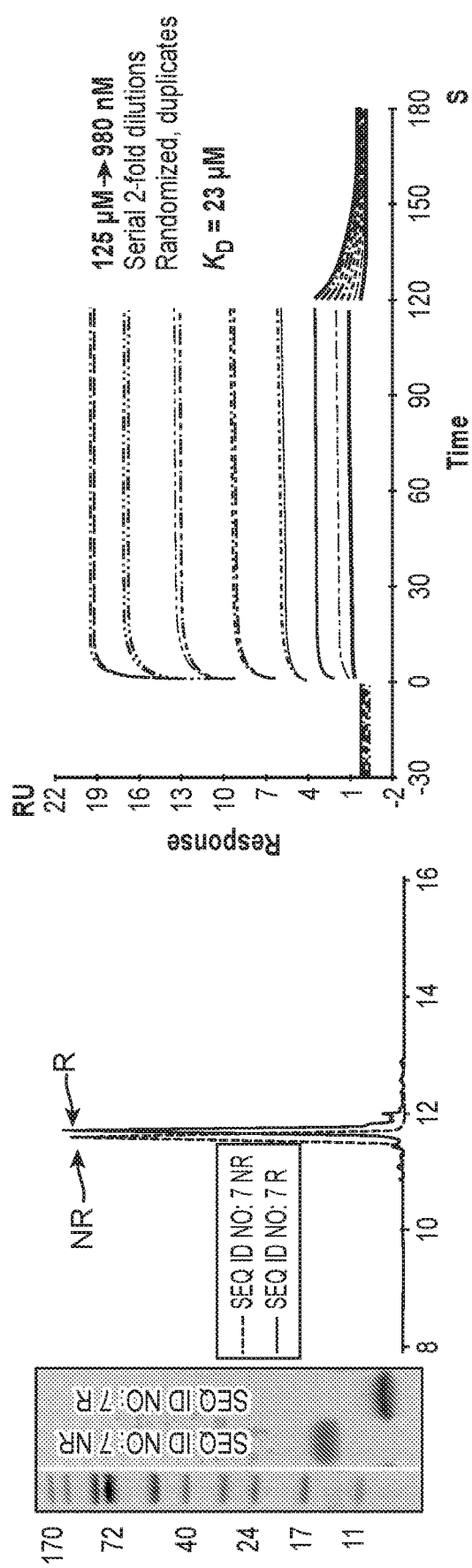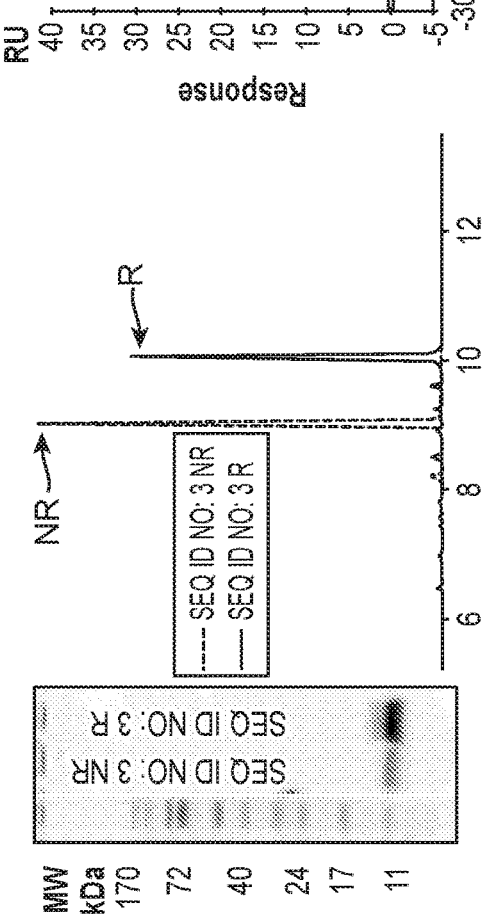
FIG. 5J  FIG. 5K  FIG. 5L

FIG. 8A

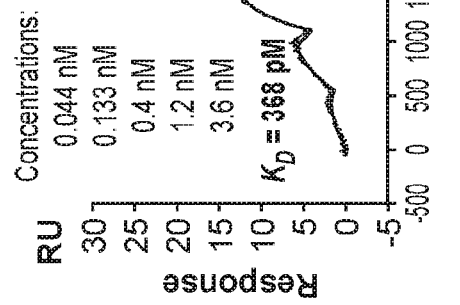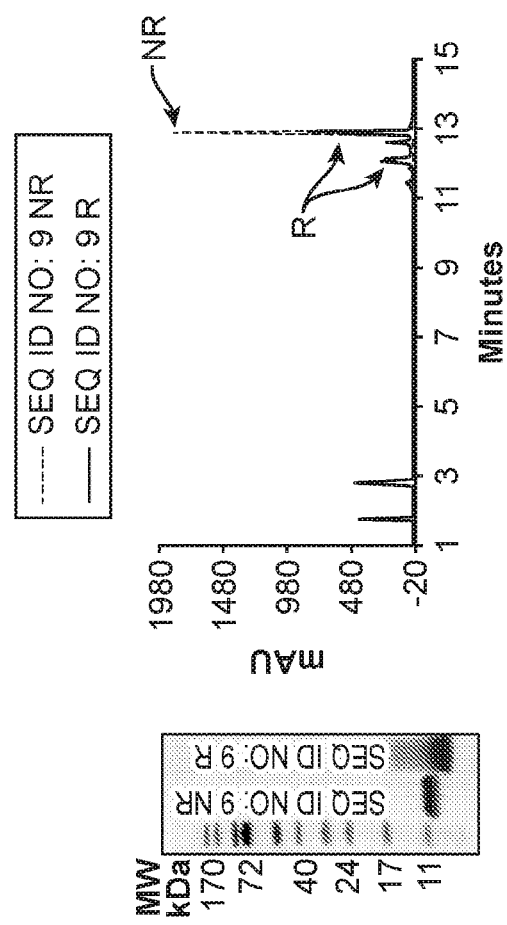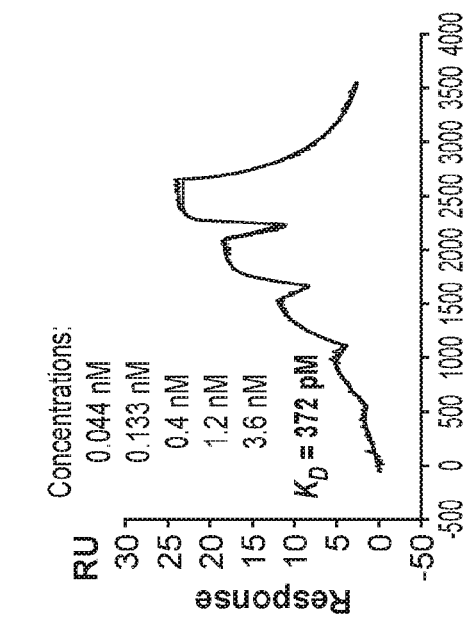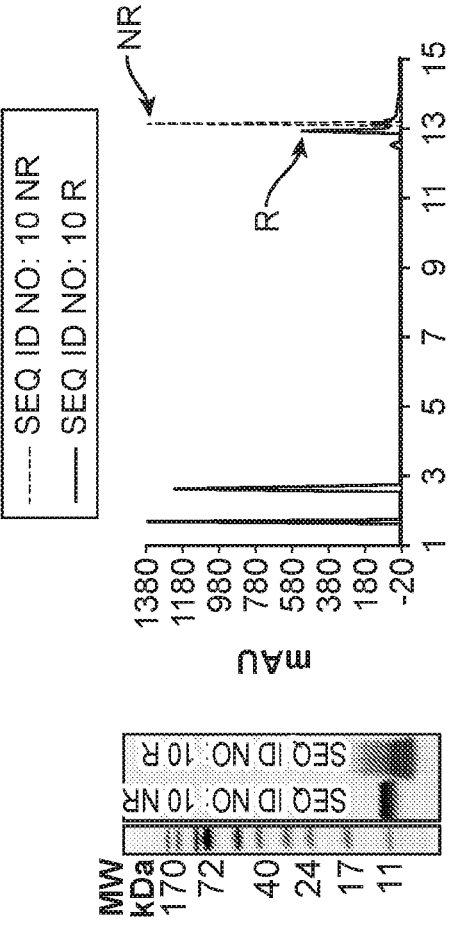
FIG. 10A  FIG. 10B  FIG. 10C
FIG. 10D  FIG. 10E  FIG. 10F YAP-TEAD Binding with TEAD Binders

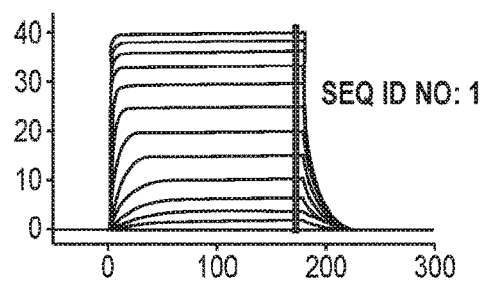 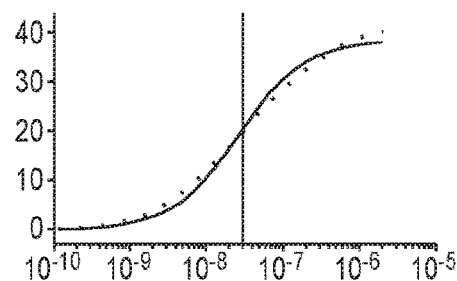
FIG. 15A  FIG. 15B
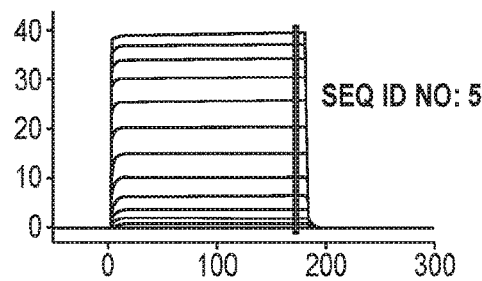 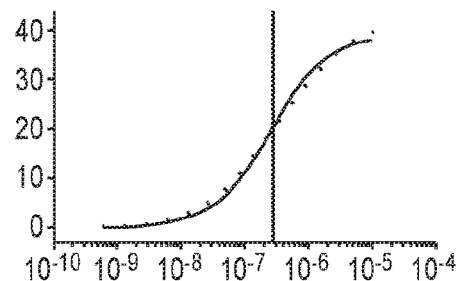
FIG. 15C  FIG. 15D
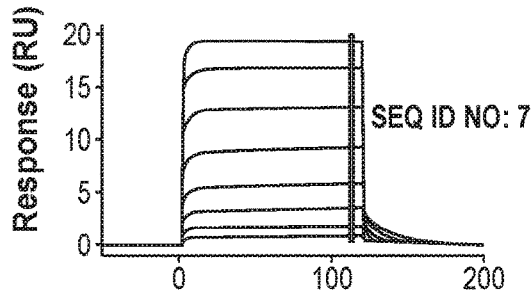 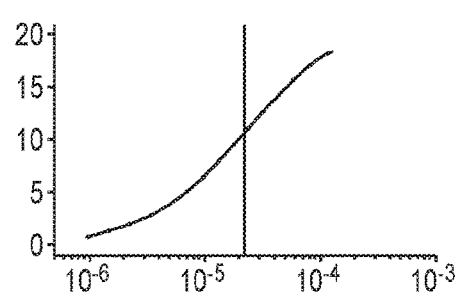
FIG. 15E  FIG. 15F
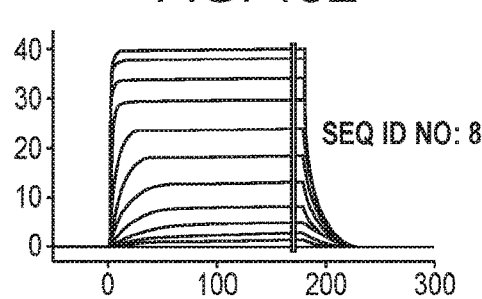 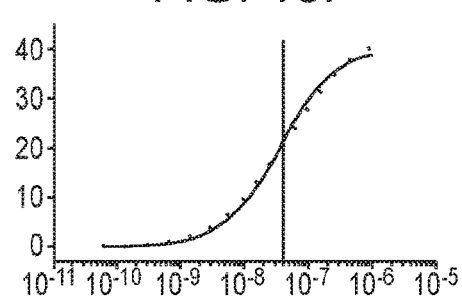
FIG. 15G  FIG. 15H
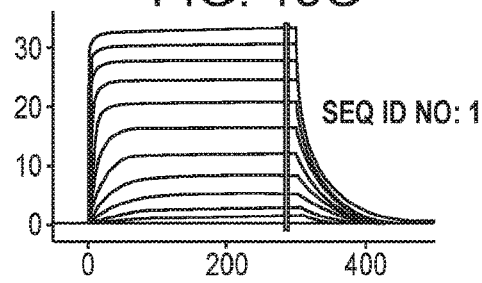 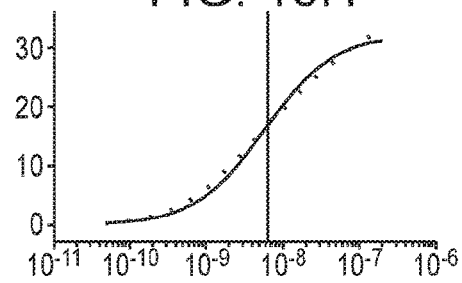
FIG. 15I  FIG. 15J

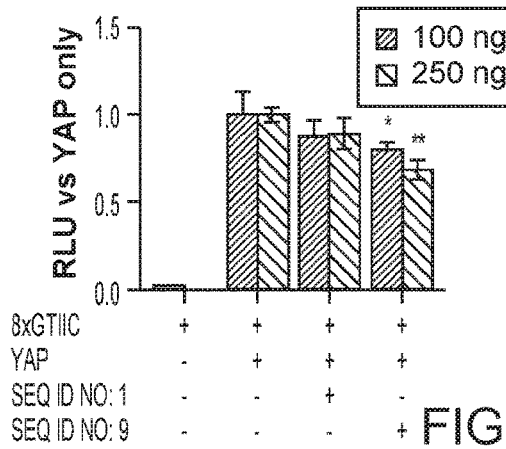
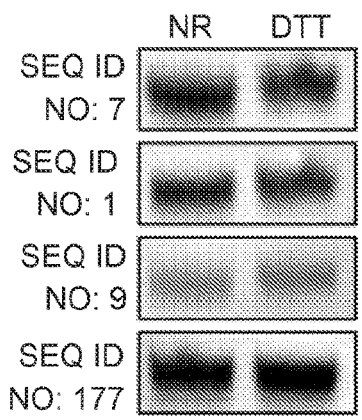
FIG. 18A  FIG. 18B
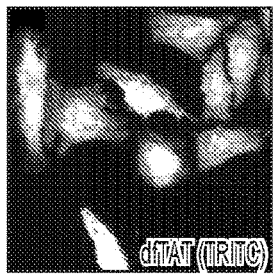
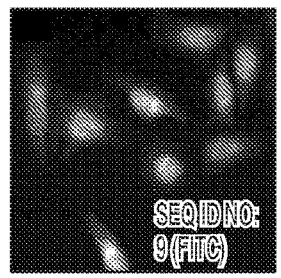
FIG. 18C  FIG. 18D  FIG. 18E
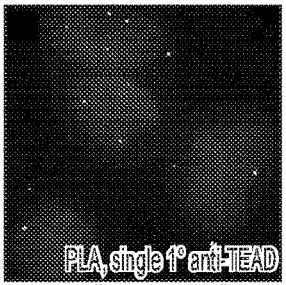
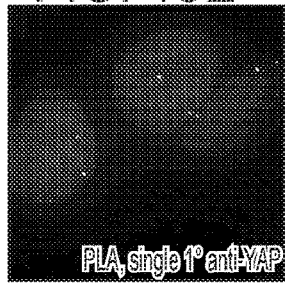
FIG. 18F  FIG. 18G  FIG. 18H
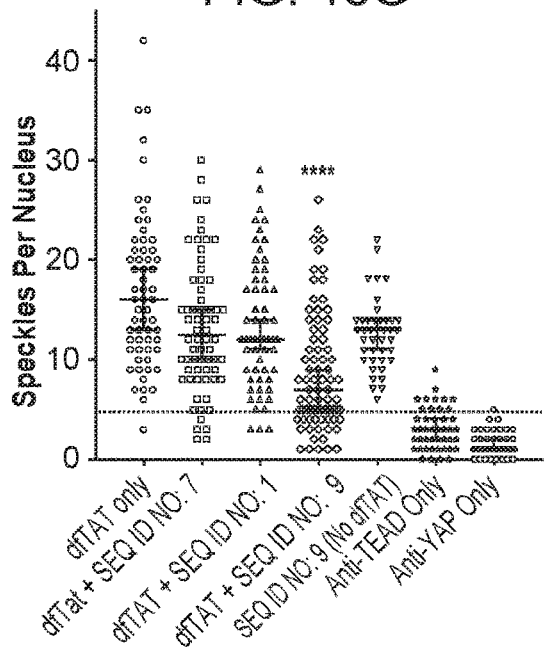
FIG. 18I

FIG. 25 (Cont.)

TABLE 4 – SSM Screen of Positions 1-20 of SEQ ID NO: 1

| | P01 | D02 | E03 | Y04 | I05 | E06 | R07 | A08 | K09 | E10 | C11 | C12 | K13 | K14 | G15 | D16 | I17 | Q18 | C19 | C20 |
|---|---|---|---|---|---|---|---|---|---|---|---|---|---|---|---|---|---|---|---|---|
| G | 1.70 | -0.32 | -0.62 | -2.21 | -3.97 | -1.15 | 1.31 | -4.11 | -0.48 | -0.44 | | | 0.70 | 1.11 | | -9.54 | -5.40 | -2.03 | | |
| D | -0.65 | | 0.80 | -1.79 | -3.47 | -0.60 | -2.25 | -4.17 | -0.58 | -0.89 | | | 0.43 | 1.27 | -0.26 | | -9.42 | -0.19 | | |
| E | 1.12 | 1.16 | | -6.52 | -1.23 | | -0.16 | -2.66 | 3.95 | | | | -0.10 | 1.00 | 1.99 | -3.60 | -0.30 | -0.84 | | |
| H | -0.88 | -1.05 | -0.31 | -1.90 | -2.99 | -1.57 | -0.32 | -7.27 | -1.50 | -1.97 | | | -0.44 | 0.53 | 3.18 | -4.55 | -3.33 | -4.39 | | |
| K | -0.29 | -1.07 | -0.50 | -1.58 | -1.50 | -1.13 | 0.47 | -4.73 | | -2.30 | | | | 4.43 | -6.95 | -4.53 | -1.54 | | | |
| R | -2.10 | -7.12 | -1.81 | -0.94 | -3.27 | -1.78 | | -5.84 | -1.30 | -2.84 | | | -0.81 | -1.06 | 0.91 | -5.59 | 0.46 | -3.67 | | |
| M | -1.02 | -1.86 | 2.57 | -0.68 | -1.87 | -2.04 | -1.06 | -10.14 | -3.56 | -0.34 | | | -0.40 | -0.92 | 1.64 | -4.12 | -2.95 | -9.52 | | |
| N | -0.49 | -0.16 | 0.58 | 0.04 | -1.34 | -0.82 | 0.34 | -9.20 | 3.31 | -0.45 | | | 0.60 | 1.51 | 3.06 | -2.70 | 0.47 | -0.16 | | |
| Q | -0.84 | -0.20 | -1.35 | 0.29 | -1.23 | -2.41 | -0.48 | -6.00 | 1.10 | -1.94 | | | 2.23 | 0.17 | 2.50 | -3.47 | -3.10 | | | |
| S | 0.13 | -1.01 | -0.41 | -0.74 | -2.04 | -1.09 | 0.31 | -2.79 | -0.91 | -2.47 | | | 1.43 | 1.61 | 2.37 | -2.71 | -2.10 | -1.25 | | |
| T | -0.57 | -0.52 | 1.19 | -0.87 | -1.77 | -0.92 | -4.07 | -3.84 | 2.68 | -1.57 | | | 1.49 | 3.18 | 2.65 | -10.01 | 2.21 | -2.28 | | |
| A | 0.36 | -1.43 | -2.02 | 0.26 | -1.20 | -0.68 | 0.28 | | -1.27 | -0.24 | | | 1.94 | -0.22 | 1.89 | -5.23 | -4.36 | -1.53 | | |
| I | -2.27 | -0.70 | -0.26 | -0.41 | | -1.56 | -3.98 | -8.31 | -3.03 | -0.65 | | | -1.54 | -0.99 | -1.96 | -6.42 | | -11.42 | | |
| L | -2.90 | -3.53 | 0.32 | -1.81 | -0.38 | -0.40 | -0.39 | -9.93 | -11.17 | -1.83 | | | -1.37 | -0.89 | -0.59 | -8.99 | 1.28 | -4.91 | | |
| V | -0.59 | -2.34 | -1.39 | -0.75 | -0.27 | -1.55 | -2.31 | -4.43 | -8.88 | -1.77 | | | -1.65 | 0.08 | 0.99 | -7.81 | 4.17 | -0.77 | | |
| F | -1.30 | -3.41 | 0.32 | 0.67 | -8.36 | -1.96 | -1.04 | -4.33 | -3.52 | -1.60 | | | -1.14 | -0.50 | -1.98 | -1.86 | -3.50 | -4.21 | | |
| W | -9.10 | -2.95 | -1.40 | -2.47 | -7.46 | -1.53 | -1.28 | -5.46 | -4.41 | -1.58 | | | -2.99 | -2.64 | -4.75 | -2.30 | -10.45 | -11.11 | | |
| Y | -3.33 | -1.63 | -0.36 | | -10.86 | -2.33 | -1.01 | -3.35 | -4.96 | -5.61 | | | -1.29 | -0.68 | -1.14 | -3.84 | -9.48 | -8.35 | | |
| P | | -2.11 | -0.40 | 1.02 | -0.43 | -2.84 | -2.49 | -4.70 | -4.50 | -3.72 | | | -10.43 | -10.61 | -1.25 | -4.62 | -2.41 | 0.69 | | |
| X | -1.28 | -1.68 | -0.28 | -1.13 | -2.98 | -1.46 | -1.01 | -5.63 | -2.17 | -1.79 | | | -0.74 | -0.45 | 0.76 | -5.24 | -2.93 | -3.75 | | |

FIG. 29

TABLE 5 – SSM Screen of Positions 21-40 of SEQ ID NO: 1

| | L21 | R22 | Y23 | F24 | E25 | E26 | S27 | G28 | D29 | P30 | N31 | V32 | M33 | L34 | I35 | C36 | L37 | F38 | C39 | P40 |
|---|---|---|---|---|---|---|---|---|---|---|---|---|---|---|---|---|---|---|---|---|
| G | -6.04 | 0.72 | -1.35 | -11.45 | -10.71 | -3.06 | -1.27 |  | -3.23 | -10.38 | -4.80 | -7.60 | -11.71 | -9.49 | -4.09 |  | -1.96 | -10.92 |  | 3.87 |
| D | -4.87 | 1.03 | 1.00 | -10.21 | 5.78 | -0.94 | -3.00 | 1.32 |  | -6.54 | -0.20 | -11.61 | -10.83 | -12.01 | -7.62 |  | -4.30 | -5.37 |  | 4.44 |
| E | -5.16 | -0.55 | 2.72 | -11.11 |  |  | -10.80 | 3.12 | -3.44 | -0.10 | -2.46 | -8.12 | -3.64 | -11.48 | -0.21 |  | -6.21 | -6.43 |  | 5.48 |
| H | -2.71 | 0.40 | -0.37 | -2.83 | -9.49 | -0.94 | -1.68 | 3.83 | -4.07 | -4.72 | -1.85 | -8.47 | -6.40 | -10.33 | -5.99 |  | 0.32 | -8.33 |  | 4.09 |
| K | -11.54 | 1.23 | 0.76 | -5.89 | -9.40 | 1.62 | -2.37 | 6.22 | -8.65 | -9.22 | -3.93 | -7.31 | -5.62 | -9.75 | -7.49 |  | -10.57 | -11.79 |  | 5.91 |
| R | -3.83 |  | 1.66 | -10.68 | -10.77 | -1.95 | -3.49 | -1.11 | -11.33 | -8.66 | -10.78 | -11.16 | -3.96 | -9.48 | -11.49 |  | -7.75 | -4.30 |  | 4.09 |
| M | -2.66 | -0.86 | 3.09 | -6.01 | -10.47 | 2.48 | -2.36 | -2.46 | -9.80 | -8.62 | -7.50 | -2.51 |  | -3.58 | -1.06 |  | -1.77 | -10.63 |  | 3.56 |
| N | -8.42 | 1.24 | 2.61 | -8.70 | -2.44 | -0.22 | -3.25 | 4.02 | -1.65 | -9.89 |  | -10.56 | -9.95 | -1.67 | -6.55 |  | -3.48 | -11.59 |  | 5.11 |
| Q | -5.92 | 0.67 | 4.09 | -6.77 | -5.86 | -0.68 | -5.40 | 4.51 | -2.48 | -3.42 | -1.74 | -11.11 | -4.00 | -7.26 | -3.15 |  | -1.02 | -2.36 |  | 5.32 |
| S | -10.77 | -1.07 | 3.56 | -3.57 | -5.06 | -0.37 |  | 2.13 | -3.79 | -3.21 | -2.24 | -3.67 | -10.55 | -11.06 | -10.07 |  | -4.45 | -5.70 |  | 5.70 |
| T | -3.23 | -1.35 | 4.48 | -10.48 | -4.88 | -1.77 | -0.14 | -0.15 | -6.20 | -5.80 | -5.82 | -6.67 | -10.18 | -6.24 | -5.66 |  | -9.84 | -10.82 |  | 4.96 |
| A | -9.76 | -0.15 | 4.15 | -4.74 | -9.29 | -1.38 | -4.71 | 0.21 | -10.78 | -4.30 | -8.06 | -6.43 | -9.17 | -10.71 | -9.78 |  | -2.56 | -7.69 |  | 4.30 |
| I | -0.71 | -5.68 | 4.38 | -11.76 | -10.99 | -0.29 | -4.20 | -4.03 | -6.90 | -10.47 | -5.43 | -0.08 | -3.16 | -1.19 |  |  | -8.87 | -10.17 |  | 4.96 |
| L |  | -8.23 | -1.38 | -4.46 | -8.91 | -1.15 | -10.71 | -2.53 | -1.03 | -11.39 | -6.98 | -5.60 | -10.20 |  | -5.22 |  |  | -10.27 |  | 2.46 |
| V | -2.18 | -3.73 | 4.92 | -9.81 | -6.97 | -1.52 | -3.78 | -2.57 | -10.45 | -4.69 | -10.99 |  | -4.70 | -2.09 | 0.30 |  | -3.80 | -8.31 |  | 4.10 |
| F | -8.97 | -4.07 | -0.40 |  | -8.76 | -3.85 | -3.57 | -5.70 | -8.95 | -6.69 | -11.40 | -6.92 | -11.51 | -7.21 | -1.52 |  | -6.98 |  |  | 4.42 |
| W | -10.86 | -4.72 | -0.77 | -3.21 | -10.07 | -10.26 | -6.16 | -6.69 | -7.27 | -8.91 | -12.78 | -12.64 | -11.42 | -10.92 | -11.53 |  | -10.52 | -9.40 |  | 5.56 |
| Y | -9.22 | -2.70 |  | -0.95 | -11.33 | -6.03 | -4.30 | -3.28 | -10.93 | -9.27 | -6.41 | -8.77 | -10.21 | -10.36 | -5.39 |  | -5.54 | -5.12 |  | 2.50 |
| P | -4.12 | -4.67 | -4.23 | -1.77 | -9.08 | -8.38 | -11.47 | -4.98 | -6.75 |  | -8.99 | -10.01 | -11.25 | -7.30 | -10.21 |  | -12.22 | -5.33 |  |  |
| X | -6.16 | -1.81 | 1.61 | -6.91 | -7.71 | -2.15 | -4.59 | -0.45 | -6.54 | -7.02 | -6.24 | -7.74 | -8.25 | -7.90 | -5.93 |  | -5.64 | -8.03 |  | 4.49 |

FIG. 30

SEQUENCE LISTING

<160> NUMBER OF SEQ ID NOS: 304

<210> SEQ ID NO 1
<211> LENGTH: 42
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 1

Gly Ser Pro Asp Glu Tyr Ile Glu Arg Ala Lys Glu Cys Cys Lys Lys
1               5                   10                  15

Gly Asp Ile Gln Cys Cys Leu Arg Tyr Phe Glu Ser Gly Asp Pro
            20                  25                  30

Asn Val Met Leu Ile Cys Leu Phe Cys Pro
        35                  40

<210> SEQ ID NO 2
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gly Ser Leu Glu Arg Leu Lys Lys Cys Cys Asn Gln Gly Leu Asp Cys
1               5                   10                  15

Glu Glu Ala Arg Trp Lys Cys Glu Leu Glu Ala Leu Phe Gln Gly Lys
            20                  25                  30

Asn Arg Glu Thr Cys Leu Glu Glu Cys
        35                  40

<210> SEQ ID NO 3
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gly Ser Phe Gly Leu Tyr Asp Asn Gln Cys Ala Thr Ser Asp Ala Cys
1               5                   10                  15

Ser Ala Ile Cys Lys Tyr Trp Thr Gly Ser Gly Gln Gly Lys Cys Gln
            20                  25                  30

Asn Asn Gln Cys Arg Cys Tyr
        35

<210> SEQ ID NO 4
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gly Ser Pro Asp Glu Tyr Ile Glu Arg Ala Lys Glu Cys Cys Lys Lys
1               5                   10                  15

Gly Asp Ile Gln Cys Cys Leu Arg Tyr Phe Ala Glu Ser Gly Asp Pro
            20                  25                  30

Asn Val Met Leu Ile Cys Leu Phe Cys Pro
        35                  40

<210> SEQ ID NO 5
<211> LENGTH: 42
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 5

Gly Ser Pro Asp Glu Tyr Ile Glu Arg Ala Lys Glu Cys Cys Lys Lys
1               5                   10                  15

Gly Asp Ile Gln Cys Cys Leu Arg Tyr Phe Glu Glu Ser Gly Asp Pro
            20                  25                  30

Asn Val Met Leu Ile Cys Ala Phe Cys Pro
        35                  40

<210> SEQ ID NO 6
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gly Ser Pro Asp Glu Tyr Ile Glu Arg Ala Lys Glu Cys Cys Lys Lys
1               5                   10                  15

Gly Asp Ile Gln Cys Cys Leu Arg Tyr Phe Glu Glu Ser Gly Asp Pro
            20                  25                  30

Asn Val Ala Leu Ile Cys Leu Phe Cys Pro
        35                  40

<210> SEQ ID NO 7
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gly Ser Pro Asp Glu Tyr Ile Glu Arg Ala Lys Glu Cys Cys Lys Lys
1               5                   10                  15

Gly Asp Ile Gln Cys Cys Leu Arg Tyr Phe Glu Glu Ser Gly Asp Pro
            20                  25                  30

Asn Val Met Leu Ile Cys Leu Ala Cys Pro
        35                  40

<210> SEQ ID NO 8
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gly Ser Pro Asp Glu Tyr Ile Glu Arg Ala Arg Arg Cys Cys Arg Arg
1               5                   10                  15

Gly Asp Ile Gln Cys Cys Leu Arg Tyr Phe Glu Glu Ser Gly Asp Pro
            20                  25                  30

Asn Val Met Leu Ile Cys Leu Phe Cys Pro
        35                  40

<210> SEQ ID NO 9
<211> LENGTH: 42

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gly Ser Pro Asp Glu Tyr Ile Glu Arg Ala Lys Glu Cys Cys Lys Lys
1               5                   10                  15

Gln Asp Ile Gln Cys Cys Leu Arg Ile Phe Asp Glu Ser Lys Asp Pro
            20                  25                  30

Asn Val Met Leu Ile Cys Leu Phe Cys Trp
        35                  40

<210> SEQ ID NO 10
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gly Ser Pro Asp Glu Tyr Ile Glu Arg Ala Lys Glu Cys Cys Lys Lys
1               5                   10                  15

Gln Asp Ile Gln Cys Cys Leu Arg Ile Phe Asp Glu Ser Gly Asp Pro
            20                  25                  30

Asn Val Met Leu Ile Cys Leu Phe Cys Trp
        35                  40

<210> SEQ ID NO 11
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gly Ser Pro Asp Glu Tyr Ile Glu Arg Ala Lys Glu Cys Cys Lys Lys
1               5                   10                  15

Gln Asp Ile Gln Cys Cys Leu Arg Ile Phe Asp Glu Ser Lys Asp Pro
            20                  25                  30

Asn Val Met Leu Ile Cys Leu Phe Cys Pro
        35                  40

<210> SEQ ID NO 12
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gly Ser Pro Asp Glu Tyr Ile Glu Arg Ala Lys Glu Cys Cys Lys Lys
1               5                   10                  15

Gly Asp Ile Gln Cys Cys Leu Arg Ile Phe Asp Glu Ser Lys Asp Pro
            20                  25                  30

Asn Val Met Leu Ile Cys Leu Phe Cys Trp
        35                  40

<210> SEQ ID NO 13
```

```
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gly Ser Pro Asp Glu Tyr Ile Glu Arg Ala Lys Glu Cys Cys Lys Lys
1               5                   10                  15

Gln Asp Ile Gln Cys Cys Leu Arg Tyr Phe Asp Glu Ser Lys Asp Pro
            20                  25                  30

Asn Val Met Leu Ile Cys Leu Phe Cys Trp
        35                  40

<210> SEQ ID NO 14
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gly Ser Pro Asp Glu Tyr Ile Glu Arg Ala Lys Glu Cys Cys Lys Lys
1               5                   10                  15

Gln Asp Ile Gln Cys Cys Leu Arg Ile Phe Glu Glu Ser Lys Asp Pro
            20                  25                  30

Asn Val Met Leu Ile Cys Leu Phe Cys Trp
        35                  40

<210> SEQ ID NO 15
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gly Ser Pro Asp Glu Tyr Ile Glu Arg Ala Lys Glu Cys Cys Lys Lys
1               5                   10                  15

Gly Asp Ile Gln Cys Cys Leu Arg Tyr Phe Asp Glu Ser Lys Asp Pro
            20                  25                  30

Asn Val Met Leu Ile Cys Leu Phe Cys Trp
        35                  40

<210> SEQ ID NO 16
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gly Ser Pro Asp Glu Tyr Ile Glu Arg Ala Lys Glu Cys Cys Lys Lys
1               5                   10                  15

Gly Asp Ile Gln Cys Cys Leu Arg Ile Phe Glu Glu Ser Lys Asp Pro
            20                  25                  30

Asn Val Met Leu Ile Cys Leu Phe Cys Trp
        35                  40
```

-continued

```
<210> SEQ ID NO 17
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gly Ser Pro Asp Glu Tyr Ile Glu Arg Ala Lys Glu Cys Cys Lys Lys
1               5                   10                  15

Gly Asp Ile Gln Cys Cys Leu Arg Ile Phe Asp Glu Ser Gly Asp Pro
            20                  25                  30

Asn Val Met Leu Ile Cys Leu Phe Cys Trp
        35                  40

<210> SEQ ID NO 18
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gly Ser Pro Asp Glu Tyr Ile Glu Arg Ala Lys Glu Cys Cys Lys Lys
1               5                   10                  15

Gly Asp Ile Gln Cys Cys Leu Arg Ile Phe Asp Glu Ser Lys Asp Pro
            20                  25                  30

Asn Val Met Leu Ile Cys Leu Phe Cys Pro
        35                  40

<210> SEQ ID NO 19
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gly Ser Pro Asp Glu Tyr Ile Glu Arg Ala Lys Glu Cys Cys Lys Lys
1               5                   10                  15

Gln Asp Ile Gln Cys Cys Leu Arg Tyr Phe Glu Glu Ser Lys Asp Pro
            20                  25                  30

Asn Val Met Leu Ile Cys Leu Phe Cys Trp
        35                  40

<210> SEQ ID NO 20
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gly Ser Pro Asp Glu Tyr Ile Glu Arg Ala Lys Glu Cys Cys Lys Lys
1               5                   10                  15

Gln Asp Ile Gln Cys Cys Leu Arg Tyr Phe Asp Glu Ser Gly Asp Pro
            20                  25                  30

Asn Val Met Leu Ile Cys Leu Phe Cys Trp
        35                  40
```

<210> SEQ ID NO 21
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gly Ser Pro Asp Glu Tyr Ile Glu Arg Ala Lys Glu Cys Cys Lys Lys
1               5                   10                  15

Gln Asp Ile Gln Cys Cys Leu Arg Tyr Phe Asp Glu Ser Lys Asp Pro
            20                  25                  30

Asn Val Met Leu Ile Cys Leu Phe Cys Pro
        35                  40

<210> SEQ ID NO 22
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gly Ser Pro Asp Glu Tyr Ile Glu Arg Ala Lys Glu Cys Cys Lys Lys
1               5                   10                  15

Gln Asp Ile Gln Cys Cys Leu Arg Ile Phe Glu Glu Ser Gly Asp Pro
            20                  25                  30

Asn Val Met Leu Ile Cys Leu Phe Cys Trp
        35                  40

<210> SEQ ID NO 23
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gly Ser Pro Asp Glu Tyr Ile Glu Arg Ala Lys Glu Cys Cys Lys Lys
1               5                   10                  15

Gln Asp Ile Gln Cys Cys Leu Arg Ile Phe Glu Glu Ser Lys Asp Pro
            20                  25                  30

Asn Val Met Leu Ile Cys Leu Phe Cys Pro
        35                  40

<210> SEQ ID NO 24
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gly Ser Pro Asp Glu Tyr Ile Glu Arg Ala Lys Glu Cys Cys Lys Lys
1               5                   10                  15

Gln Asp Ile Gln Cys Cys Leu Arg Ile Phe Asp Glu Ser Gly Asp Pro
            20                  25                  30

Asn Val Met Leu Ile Cys Leu Phe Cys Pro
        35                  40

```
<210> SEQ ID NO 25
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gly Ser Pro Asp Arg Tyr Ile Glu Arg Ala Lys Arg Cys Cys Lys Arg
1               5                   10                  15

Gln Asp Ile Gln Cys Cys Leu Arg Ile Phe Asp Glu Ser Lys Asp Pro
            20                  25                  30

Asn Val Met Leu Ile Cys Leu Phe Cys Trp
        35                  40

<210> SEQ ID NO 26
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gly Ser Pro Asp Arg Tyr Ile Arg Glu Ala Lys Arg Cys Cys Arg Lys
1               5                   10                  15

Gln Asp Ile Gln Cys Cys Leu Arg Ile Phe Asp Glu Ser Lys Asp Pro
            20                  25                  30

Asn Val Met Leu Ile Cys Leu Phe Cys Trp
        35                  40

<210> SEQ ID NO 27
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gly Ser Pro Asp Arg Tyr Ile Glu Arg Ala Lys Arg Cys Cys Arg Arg
1               5                   10                  15

Gln Asp Ile Gln Cys Cys Leu Arg Ile Phe Asp Glu Ser Lys Asp Pro
            20                  25                  30

Asn Val Met Leu Ile Cys Leu Phe Cys Trp
        35                  40

<210> SEQ ID NO 28
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gly Ser Pro Asp Arg Tyr Ile Arg Glu Ala Arg Arg Cys Cys Arg Lys
1               5                   10                  15

Gln Asp Ile Gln Cys Cys Leu Arg Ile Phe Asp Glu Ser Lys Asp Pro
            20                  25                  30

Asn Val Met Leu Ile Cys Leu Phe Cys Trp
```

<210> SEQ ID NO 29
<211> LENGTH: 42
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

Gly Ser Pro Asp Arg Tyr Ile Arg Arg Ala Lys Arg Cys Cys Arg Lys
1               5                   10                  15

Gln Asp Ile Gln Cys Cys Leu Arg Ile Phe Asp Glu Ser Lys Asp Pro
            20                  25                  30

Asn Val Met Leu Ile Cys Leu Phe Cys Trp
        35                  40

<210> SEQ ID NO 30
<211> LENGTH: 42
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

Gly Ser Pro Asp Arg Tyr Ile Arg Arg Ala Lys Arg Cys Cys Lys Arg
1               5                   10                  15

Gln Asp Ile Gln Cys Cys Leu Arg Ile Phe Asp Glu Ser Lys Asp Pro
            20                  25                  30

Asn Val Met Leu Ile Cys Leu Phe Cys Trp
        35                  40

<210> SEQ ID NO 31
<211> LENGTH: 42
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

Gly Ser Pro Asp Arg Tyr Ile Arg Arg Ala Lys Arg Cys Cys Arg Arg
1               5                   10                  15

Gln Asp Ile Gln Cys Cys Leu Arg Ile Phe Asp Glu Ser Lys Asp Pro
            20                  25                  30

Asn Val Met Leu Ile Cys Leu Phe Cys Trp
        35                  40

<210> SEQ ID NO 32
<211> LENGTH: 42
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

Gly Ser Pro Asp Arg Tyr Ile Glu Arg Ala Lys Arg Cys Cys Lys Arg
1               5                   10                  15

Gln Asp Ile Gln Cys Cys Leu Arg Ile Phe Asp Glu Ser Gly Asp Pro
            20                  25                  30

Asn Val Met Leu Ile Cys Leu Phe Cys Trp
            35                  40

<210> SEQ ID NO 33
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gly Ser Pro Asp Arg Tyr Ile Arg Glu Ala Lys Arg Cys Cys Arg Lys
1               5                   10                  15

Gln Asp Ile Gln Cys Cys Leu Arg Ile Phe Asp Glu Ser Gly Asp Pro
            20                  25                  30

Asn Val Met Leu Ile Cys Leu Phe Cys Trp
            35                  40

<210> SEQ ID NO 34
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gly Ser Pro Asp Arg Tyr Ile Glu Arg Ala Lys Arg Cys Cys Arg Arg
1               5                   10                  15

Gln Asp Ile Gln Cys Cys Leu Arg Ile Phe Asp Glu Ser Gly Asp Pro
            20                  25                  30

Asn Val Met Leu Ile Cys Leu Phe Cys Trp
            35                  40

<210> SEQ ID NO 35
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gly Ser Pro Asp Arg Tyr Ile Arg Glu Ala Arg Arg Cys Cys Arg Lys
1               5                   10                  15

Gln Asp Ile Gln Cys Cys Leu Arg Ile Phe Asp Glu Ser Gly Asp Pro
            20                  25                  30

Asn Val Met Leu Ile Cys Leu Phe Cys Trp
            35                  40

<210> SEQ ID NO 36
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gly Ser Pro Asp Arg Tyr Ile Arg Arg Ala Lys Arg Cys Cys Arg Lys
1               5                   10                  15

Gln Asp Ile Gln Cys Cys Leu Arg Ile Phe Asp Glu Ser Gly Asp Pro
            20                  25                  30

Asn Val Met Leu Ile Cys Leu Phe Cys Trp
          35                  40

<210> SEQ ID NO 37
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gly Ser Pro Asp Arg Tyr Ile Arg Arg Ala Lys Arg Cys Cys Lys Arg
1               5                   10                  15

Gln Asp Ile Gln Cys Cys Leu Arg Ile Phe Asp Glu Ser Gly Asp Pro
            20                  25                  30

Asn Val Met Leu Ile Cys Leu Phe Cys Trp
          35                  40

<210> SEQ ID NO 38
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gly Ser Pro Asp Arg Tyr Ile Arg Arg Ala Lys Arg Cys Cys Arg Arg
1               5                   10                  15

Gln Asp Ile Gln Cys Cys Leu Arg Ile Phe Asp Glu Ser Gly Asp Pro
            20                  25                  30

Asn Val Met Leu Ile Cys Leu Phe Cys Trp
          35                  40

<210> SEQ ID NO 39
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gly Ser Leu Glu Arg Leu Lys Lys Cys Cys Asn Gln Gly Leu Asp Cys
1               5                   10                  15

Glu Glu Ala Arg Ala Lys Cys Glu Leu Glu Ala Leu Phe Gln Gly Lys
            20                  25                  30

Asn Arg Glu Thr Cys Leu Glu Glu Cys
          35                  40

<210> SEQ ID NO 40
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gly Ser Leu Glu Arg Leu Lys Lys Cys Cys Asn Gln Gly Leu Asp Cys
1               5                   10                  15

Glu Glu Ala Arg Trp Lys Cys Glu Ala Glu Ala Leu Phe Gln Gly Lys
            20                  25                  30

20                  25                  30

Asn Arg Glu Thr Cys Leu Glu Glu Cys
        35                  40

<210> SEQ ID NO 41
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gly Ser Leu Glu Arg Leu Lys Lys Cys Cys Asn Gln Gly Leu Asp Cys
1               5                   10                  15

Glu Glu Ala Arg Trp Lys Cys Glu Leu Glu Ala Ala Phe Gln Gly Lys
                20                  25                  30

Asn Arg Glu Thr Cys Leu Glu Glu Cys
        35                  40

<210> SEQ ID NO 42
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gly Ser Leu Glu Arg Leu Lys Lys Cys Cys Asn Gln Gly Leu Asp Cys
1               5                   10                  15

Glu Glu Ala Arg Trp Lys Cys Glu Leu Glu Ala Leu Ala Gln Gly Lys
                20                  25                  30

Asn Arg Glu Thr Cys Leu Glu Glu Cys
        35                  40

<210> SEQ ID NO 43
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Pro Asp Glu Tyr Ile Glu Arg Ala Lys Glu Cys Cys Lys Lys Gly Asp
1               5                   10                  15

Ile Gln Cys Cys Leu Arg Tyr Phe Glu Glu Ser Gly Asp Pro Asn Val
                20                  25                  30

Met Leu Ile Cys Leu Phe Cys Pro
        35                  40

<210> SEQ ID NO 44
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Leu Glu Arg Leu Lys Lys Cys Cys Asn Gln Gly Leu Asp Cys Glu Glu
1               5                   10                  15

Ala Arg Trp Lys Cys Glu Leu Glu Ala Leu Phe Gln Gly Lys Asn Arg
            20                  25                  30

Glu Thr Cys Leu Glu Glu Cys
        35

<210> SEQ ID NO 45
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Phe Gly Leu Tyr Asp Asn Gln Cys Ala Thr Ser Asp Ala Cys Ser Ala
1               5                   10                  15

Ile Cys Lys Tyr Trp Thr Gly Ser Gly Gln Gly Lys Cys Gln Asn Asn
            20                  25                  30

Gln Cys Arg Cys Tyr
        35

<210> SEQ ID NO 46
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Pro Asp Glu Tyr Ile Glu Arg Ala Lys Glu Cys Cys Lys Lys Gly Asp
1               5                   10                  15

Ile Gln Cys Cys Leu Arg Tyr Phe Ala Glu Ser Gly Asp Pro Asn Val
            20                  25                  30

Met Leu Ile Cys Leu Phe Cys Pro
        35                  40

<210> SEQ ID NO 47
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Pro Asp Glu Tyr Ile Glu Arg Ala Lys Glu Cys Cys Lys Lys Gly Asp
1               5                   10                  15

Ile Gln Cys Cys Leu Arg Tyr Phe Glu Glu Ser Gly Asp Pro Asn Val
            20                  25                  30

Met Leu Ile Cys Ala Phe Cys Pro
        35                  40

<210> SEQ ID NO 48
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Pro Asp Glu Tyr Ile Glu Arg Ala Lys Glu Cys Cys Lys Lys Gly Asp
1               5                   10                  15

```
Ile Gln Cys Cys Leu Arg Tyr Phe Glu Glu Ser Gly Asp Pro Asn Val
            20                  25                  30

Ala Leu Ile Cys Leu Phe Cys Pro
            35                  40

<210> SEQ ID NO 49
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Pro Asp Glu Tyr Ile Glu Arg Ala Lys Glu Cys Cys Lys Lys Gly Asp
1               5                   10                  15

Ile Gln Cys Cys Leu Arg Tyr Phe Glu Glu Ser Gly Asp Pro Asn Val
            20                  25                  30

Met Leu Ile Cys Leu Ala Cys Pro
            35                  40

<210> SEQ ID NO 50
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Pro Asp Glu Tyr Ile Glu Arg Ala Arg Arg Cys Cys Arg Arg Gly Asp
1               5                   10                  15

Ile Gln Cys Cys Leu Arg Tyr Phe Glu Glu Ser Gly Asp Pro Asn Val
            20                  25                  30

Met Leu Ile Cys Leu Phe Cys Pro
            35                  40

<210> SEQ ID NO 51
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Pro Asp Glu Tyr Ile Glu Arg Ala Lys Glu Cys Cys Lys Lys Gln Asp
1               5                   10                  15

Ile Gln Cys Cys Leu Arg Ile Phe Asp Glu Ser Lys Asp Pro Asn Val
            20                  25                  30

Met Leu Ile Cys Leu Phe Cys Trp
            35                  40

<210> SEQ ID NO 52
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Pro Asp Glu Tyr Ile Glu Arg Ala Lys Glu Cys Cys Lys Lys Gln Asp
```

```
                1               5                   10                  15
Ile Gln Cys Cys Leu Arg Ile Phe Asp Glu Ser Gly Asp Pro Asn Val
                    20                  25                  30

Met Leu Ile Cys Leu Phe Cys Trp
            35                  40
```

<210> SEQ ID NO 53
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

```
Pro Asp Glu Tyr Ile Glu Arg Ala Lys Glu Cys Cys Lys Lys Gln Asp
1               5                   10                  15

Ile Gln Cys Cys Leu Arg Ile Phe Asp Glu Ser Lys Asp Pro Asn Val
                    20                  25                  30

Met Leu Ile Cys Leu Phe Cys Pro
            35                  40
```

<210> SEQ ID NO 54
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Pro Asp Glu Tyr Ile Glu Arg Ala Lys Glu Cys Cys Lys Lys Gly Asp
1               5                   10                  15

Ile Gln Cys Cys Leu Arg Ile Phe Asp Glu Ser Lys Asp Pro Asn Val
                    20                  25                  30

Met Leu Ile Cys Leu Phe Cys Trp
            35                  40
```

<210> SEQ ID NO 55
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

```
Pro Asp Glu Tyr Ile Glu Arg Ala Lys Glu Cys Cys Lys Lys Gln Asp
1               5                   10                  15

Ile Gln Cys Cys Leu Arg Tyr Phe Asp Glu Ser Lys Asp Pro Asn Val
                    20                  25                  30

Met Leu Ile Cys Leu Phe Cys Trp
            35                  40
```

<210> SEQ ID NO 56
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Pro Asp Glu Tyr Ile Glu Arg Ala Lys Glu Cys Cys Lys Lys Gln Asp
1               5                   10                  15

Ile Gln Cys Cys Leu Arg Ile Phe Glu Glu Ser Lys Asp Pro Asn Val
                20                  25                  30

Met Leu Ile Cys Leu Phe Cys Trp
            35                  40

<210> SEQ ID NO 57
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Pro Asp Glu Tyr Ile Glu Arg Ala Lys Glu Cys Cys Lys Lys Gly Asp
1               5                   10                  15

Ile Gln Cys Cys Leu Arg Tyr Phe Asp Glu Ser Lys Asp Pro Asn Val
                20                  25                  30

Met Leu Ile Cys Leu Phe Cys Trp
            35                  40

<210> SEQ ID NO 58
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Pro Asp Glu Tyr Ile Glu Arg Ala Lys Glu Cys Cys Lys Lys Gly Asp
1               5                   10                  15

Ile Gln Cys Cys Leu Arg Ile Phe Glu Glu Ser Lys Asp Pro Asn Val
                20                  25                  30

Met Leu Ile Cys Leu Phe Cys Trp
            35                  40

<210> SEQ ID NO 59
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Pro Asp Glu Tyr Ile Glu Arg Ala Lys Glu Cys Cys Lys Lys Gly Asp
1               5                   10                  15

Ile Gln Cys Cys Leu Arg Ile Phe Asp Glu Ser Gly Asp Pro Asn Val
                20                  25                  30

Met Leu Ile Cys Leu Phe Cys Trp
            35                  40

<210> SEQ ID NO 60
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Pro Asp Glu Tyr Ile Glu Arg Ala Lys Glu Cys Cys Lys Lys Gly Asp
1               5                   10                  15

Ile Gln Cys Cys Leu Arg Ile Phe Asp Glu Ser Lys Asp Pro Asn Val
            20                  25                  30

Met Leu Ile Cys Leu Phe Cys Pro
        35                  40

<210> SEQ ID NO 61
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Pro Asp Glu Tyr Ile Glu Arg Ala Lys Glu Cys Cys Lys Lys Gln Asp
1               5                   10                  15

Ile Gln Cys Cys Leu Arg Tyr Phe Glu Glu Ser Lys Asp Pro Asn Val
            20                  25                  30

Met Leu Ile Cys Leu Phe Cys Trp
        35                  40

<210> SEQ ID NO 62
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Pro Asp Glu Tyr Ile Glu Arg Ala Lys Glu Cys Cys Lys Lys Gln Asp
1               5                   10                  15

Ile Gln Cys Cys Leu Arg Tyr Phe Asp Glu Ser Gly Asp Pro Asn Val
            20                  25                  30

Met Leu Ile Cys Leu Phe Cys Trp
        35                  40

<210> SEQ ID NO 63
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Pro Asp Glu Tyr Ile Glu Arg Ala Lys Glu Cys Cys Lys Lys Gln Asp
1               5                   10                  15

Ile Gln Cys Cys Leu Arg Tyr Phe Asp Glu Ser Lys Asp Pro Asn Val
            20                  25                  30

Met Leu Ile Cys Leu Phe Cys Pro
        35                  40

<210> SEQ ID NO 64
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 64

Pro Asp Glu Tyr Ile Glu Arg Ala Lys Glu Cys Cys Lys Lys Gln Asp
1               5                   10                  15

Ile Gln Cys Cys Leu Arg Ile Phe Glu Glu Ser Gly Asp Pro Asn Val
            20                  25                  30

Met Leu Ile Cys Leu Phe Cys Trp
            35                  40

<210> SEQ ID NO 65
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Pro Asp Glu Tyr Ile Glu Arg Ala Lys Glu Cys Cys Lys Lys Gln Asp
1               5                   10                  15

Ile Gln Cys Cys Leu Arg Ile Phe Glu Glu Ser Lys Asp Pro Asn Val
            20                  25                  30

Met Leu Ile Cys Leu Phe Cys Pro
            35                  40

<210> SEQ ID NO 66
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Pro Asp Glu Tyr Ile Glu Arg Ala Lys Glu Cys Cys Lys Lys Gln Asp
1               5                   10                  15

Ile Gln Cys Cys Leu Arg Ile Phe Asp Glu Ser Gly Asp Pro Asn Val
            20                  25                  30

Met Leu Ile Cys Leu Phe Cys Pro
            35                  40

<210> SEQ ID NO 67
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Pro Asp Arg Tyr Ile Glu Arg Ala Lys Arg Cys Cys Lys Arg Gln Asp
1               5                   10                  15

Ile Gln Cys Cys Leu Arg Ile Phe Asp Glu Ser Lys Asp Pro Asn Val
            20                  25                  30

Met Leu Ile Cys Leu Phe Cys Trp
            35                  40

<210> SEQ ID NO 68
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 68

Pro Asp Arg Tyr Ile Arg Glu Ala Lys Arg Cys Cys Arg Lys Gln Asp
1               5                   10                  15

Ile Gln Cys Cys Leu Arg Ile Phe Asp Glu Ser Lys Asp Pro Asn Val
            20                  25                  30

Met Leu Ile Cys Leu Phe Cys Trp
            35                  40

<210> SEQ ID NO 69
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Pro Asp Arg Tyr Ile Glu Arg Ala Lys Arg Cys Cys Arg Arg Gln Asp
1               5                   10                  15

Ile Gln Cys Cys Leu Arg Ile Phe Asp Glu Ser Lys Asp Pro Asn Val
            20                  25                  30

Met Leu Ile Cys Leu Phe Cys Trp
            35                  40

<210> SEQ ID NO 70
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Pro Asp Arg Tyr Ile Arg Glu Ala Arg Arg Cys Cys Arg Lys Gln Asp
1               5                   10                  15

Ile Gln Cys Cys Leu Arg Ile Phe Asp Glu Ser Lys Asp Pro Asn Val
            20                  25                  30

Met Leu Ile Cys Leu Phe Cys Trp
            35                  40

<210> SEQ ID NO 71
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Pro Asp Arg Tyr Ile Arg Arg Ala Lys Arg Cys Cys Arg Lys Gln Asp
1               5                   10                  15

Ile Gln Cys Cys Leu Arg Ile Phe Asp Glu Ser Lys Asp Pro Asn Val
            20                  25                  30

Met Leu Ile Cys Leu Phe Cys Trp
            35                  40

<210> SEQ ID NO 72
<211> LENGTH: 40
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 72

Pro Asp Arg Tyr Ile Arg Arg Ala Lys Arg Cys Cys Lys Arg Gln Asp
1               5                   10                  15

Ile Gln Cys Cys Leu Arg Ile Phe Asp Glu Ser Lys Asp Pro Asn Val
            20                  25                  30

Met Leu Ile Cys Leu Phe Cys Trp
        35                  40

<210> SEQ ID NO 73
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Pro Asp Arg Tyr Ile Arg Arg Ala Lys Arg Cys Cys Arg Arg Gln Asp
1               5                   10                  15

Ile Gln Cys Cys Leu Arg Ile Phe Asp Glu Ser Lys Asp Pro Asn Val
            20                  25                  30

Met Leu Ile Cys Leu Phe Cys Trp
        35                  40

<210> SEQ ID NO 74
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Pro Asp Arg Tyr Ile Glu Arg Ala Lys Arg Cys Cys Lys Arg Gln Asp
1               5                   10                  15

Ile Gln Cys Cys Leu Arg Ile Phe Asp Glu Ser Gly Asp Pro Asn Val
            20                  25                  30

Met Leu Ile Cys Leu Phe Cys Trp
        35                  40

<210> SEQ ID NO 75
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Pro Asp Arg Tyr Ile Arg Glu Ala Lys Arg Cys Cys Arg Lys Gln Asp
1               5                   10                  15

Ile Gln Cys Cys Leu Arg Ile Phe Asp Glu Ser Gly Asp Pro Asn Val
            20                  25                  30

Met Leu Ile Cys Leu Phe Cys Trp
        35                  40

<210> SEQ ID NO 76
<211> LENGTH: 40
<212> TYPE: PRT
<213> ORGANISM: Artificial Sequence
<220> FEATURE:

```
<223> OTHER INFORMATION: Description of Artificial Sequence: Synthetic
      polypeptide

<400> SEQUENCE: 76

Pro Asp Arg Tyr Ile Glu Arg Ala Lys Arg Cys Cys Arg Arg Gln Asp
1               5                   10                  15

Ile Gln Cys Cys Leu Arg Ile Phe Asp Glu Ser Gly Asp Pro Asn Val
            20                  25                  30

Met Leu Ile Cys Leu Phe Cys Trp
            35                  40

<210> SEQ ID NO 77
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Pro Asp Arg Tyr Ile Arg Glu Ala Arg Arg Cys Cys Arg Lys Gln Asp
1               5                   10                  15

Ile Gln Cys Cys Leu Arg Ile Phe Asp Glu Ser Gly Asp Pro Asn Val
            20                  25                  30

Met Leu Ile Cys Leu Phe Cys Trp
            35                  40

<210> SEQ ID NO 78
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Pro Asp Arg Tyr Ile Arg Arg Ala Lys Arg Cys Cys Arg Lys Gln Asp
1               5                   10                  15

Ile Gln Cys Cys Leu Arg Ile Phe Asp Glu Ser Gly Asp Pro Asn Val
            20                  25                  30

Met Leu Ile Cys Leu Phe Cys Trp
            35                  40

<210> SEQ ID NO 79
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Pro Asp Arg Tyr Ile Arg Arg Ala Lys Arg Cys Cys Lys Arg Gln Asp
1               5                   10                  15

Ile Gln Cys Cys Leu Arg Ile Phe Asp Glu Ser Gly Asp Pro Asn Val
            20                  25                  30

Met Leu Ile Cys Leu Phe Cys Trp
            35                  40

<210> SEQ ID NO 80
<211> LENGTH: 40
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 80

Pro Asp Arg Tyr Ile Arg Arg Ala Lys Arg Cys Cys Arg Arg Gln Asp
1               5                   10                  15

Ile Gln Cys Cys Leu Arg Ile Phe Asp Glu Ser Gly Asp Pro Asn Val
            20                  25                  30

Met Leu Ile Cys Leu Phe Cys Trp
        35                  40

<210> SEQ ID NO 81
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Leu Glu Arg Leu Lys Lys Cys Cys Asn Gln Gly Leu Asp Cys Glu Glu
1               5                   10                  15

Ala Arg Ala Lys Cys Glu Leu Glu Ala Leu Phe Gln Gly Lys Asn Arg
            20                  25                  30

Glu Thr Cys Leu Glu Glu Cys
        35

<210> SEQ ID NO 82
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Leu Glu Arg Leu Lys Lys Cys Cys Asn Gln Gly Leu Asp Cys Glu Glu
1               5                   10                  15

Ala Arg Trp Lys Cys Glu Ala Glu Ala Leu Phe Gln Gly Lys Asn Arg
            20                  25                  30

Glu Thr Cys Leu Glu Glu Cys
        35

<210> SEQ ID NO 83
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Leu Glu Arg Leu Lys Lys Cys Cys Asn Gln Gly Leu Asp Cys Glu Glu
1               5                   10                  15

Ala Arg Trp Lys Cys Glu Leu Glu Ala Ala Phe Gln Gly Lys Asn Arg
            20                  25                  30

Glu Thr Cys Leu Glu Glu Cys
        35

<210> SEQ ID NO 84
<211> LENGTH: 39
<212> TYPE: PRT
```

-continued

```
<213> ORGANISM: Artificial Sequence
<220> FEATURE:
<223> OTHER INFORMATION: Description of Artificial Sequence: Synthetic
      polypeptide

<400> SEQUENCE: 84

Leu Glu Arg Leu Lys Lys Cys Cys Asn Gln Gly Leu Asp Cys Glu Glu
1               5                   10                  15

Ala Arg Trp Lys Cys Glu Leu Glu Ala Leu Ala Gln Gly Lys Asn Arg
            20                  25                  30

Glu Thr Cys Leu Glu Glu Cys
        35

<210> SEQ ID NO 85
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Gly Ser Gly Arg Lys Lys Arg Arg Gln Arg Arg Gly Gly Ser Pro
1               5                   10                  15

Asp Glu Tyr Ile Glu Arg Ala Lys Glu Cys Cys Lys Lys Gln Asp Ile
            20                  25                  30

Gln Cys Cys Leu Arg Ile Phe Asp Glu Ser Lys Asp Pro Asn Val Met
        35                  40                  45

Leu Ile Cys Leu Phe Cys Trp
    50                  55

<210> SEQ ID NO 86
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Gly Ser Cys Tyr Arg Lys Lys Arg Arg Gln Arg Arg Arg Gly Gly Ser
1               5                   10                  15

Pro Asp Glu Tyr Ile Glu Arg Ala Lys Glu Cys Cys Lys Lys Gln Asp
            20                  25                  30

Ile Gln Cys Cys Leu Arg Ile Phe Asp Glu Ser Lys Asp Pro Asn Val
        35                  40                  45

Met Leu Ile Cys Leu Phe Cys Trp
    50                  55

<210> SEQ ID NO 87
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Gly Ser Pro Phe Val Ile Gly Ala Gly Val Leu Gly Ala Leu Gly Thr
1               5                   10                  15

Gly Ile Gly Gly Ile Gly Arg Lys Lys Arg Arg Gln Arg Arg Arg Gly
            20                  25                  30
```

```
Gly Ser Pro Asp Glu Tyr Ile Glu Arg Ala Lys Glu Cys Cys Lys Lys
                35                  40                  45

Gln Asp Ile Gln Cys Cys Leu Arg Ile Phe Asp Glu Ser Lys Asp Pro
        50                  55                  60

Asn Val Met Leu Ile Cys Leu Phe Cys Trp
65                  70

<210> SEQ ID NO 88
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Gly Ser Phe Phe Leu Ile Pro Lys Gly Gly Arg Lys Lys Arg Arg Gln
1               5                   10                  15

Arg Arg Arg Gly Gly Ser Pro Asp Glu Tyr Ile Glu Arg Ala Lys Glu
                20                  25                  30

Cys Cys Lys Lys Gln Asp Ile Gln Cys Cys Leu Arg Ile Phe Asp Glu
            35                  40                  45

Ser Lys Asp Pro Asn Val Met Leu Ile Cys Leu Phe Cys Trp
        50                  55                  60

<210> SEQ ID NO 89
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Gly Ser Arg Arg Arg Arg Arg Arg Arg Gly Gly Ser Pro Asp Glu
1               5                   10                  15

Tyr Ile Glu Arg Ala Lys Glu Cys Cys Lys Lys Gln Asp Ile Gln Cys
                20                  25                  30

Cys Leu Arg Ile Phe Asp Glu Ser Lys Asp Pro Asn Val Met Leu Ile
            35                  40                  45

Cys Leu Phe Cys Trp
        50

<210> SEQ ID NO 90
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Gly Ser Phe Phe Leu Ile Pro Lys Gly Arg Arg Arg Arg Arg Arg Arg
1               5                   10                  15

Arg Gly Gly Ser Pro Asp Glu Tyr Ile Glu Arg Ala Lys Glu Cys Cys
                20                  25                  30

Lys Lys Gln Asp Ile Gln Cys Cys Leu Arg Ile Phe Asp Glu Ser Lys
            35                  40                  45

Asp Pro Asn Val Met Leu Ile Cys Leu Phe Cys Trp
        50                  55                  60
```

<210> SEQ ID NO 91
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Gly Ser Arg Gln Ile Lys Ile Trp Phe Gln Asn Arg Arg Met Lys Trp
1               5                   10                  15

Lys Lys Gly Gly Ser Pro Asp Glu Tyr Ile Glu Arg Ala Lys Glu Cys
            20                  25                  30

Cys Lys Lys Gln Asp Ile Gln Cys Cys Leu Arg Ile Phe Asp Glu Ser
        35                  40                  45

Lys Asp Pro Asn Val Met Leu Ile Cys Leu Phe Cys Trp
    50                  55                  60

<210> SEQ ID NO 92
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Gly Ser Phe Phe Leu Ile Pro Lys Gly Arg Gln Ile Lys Ile Trp Phe
1               5                   10                  15

Gln Asn Arg Arg Met Lys Trp Lys Lys Gly Gly Ser Pro Asp Glu Tyr
            20                  25                  30

Ile Glu Arg Ala Lys Glu Cys Cys Lys Lys Gln Asp Ile Gln Cys Cys
        35                  40                  45

Leu Arg Ile Phe Asp Glu Ser Lys Asp Pro Asn Val Met Leu Ile Cys
    50                  55                  60

Leu Phe Cys Trp
65

<210> SEQ ID NO 93
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Gly Ser Phe Phe Leu Ile Pro Lys Gly Arg Arg Arg Asn Arg Thr
1               5                   10                  15

Arg Arg Asn Arg Arg Val Arg Gly Gly Ser Pro Asp Glu Tyr Ile
            20                  25                  30

Glu Arg Ala Lys Glu Cys Cys Lys Lys Gln Asp Ile Gln Cys Cys Leu
        35                  40                  45

Arg Ile Phe Asp Glu Ser Lys Asp Pro Asn Val Met Leu Ile Cys Leu
    50                  55                  60

Phe Cys Trp
65

<210> SEQ ID NO 94
<211> LENGTH: 54
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 94

Gly Ser Gly Asp Ala Leu Pro His Leu Lys Leu Gly Gly Ser Pro Asp
1               5                   10                  15

Glu Tyr Ile Glu Arg Ala Lys Glu Cys Cys Lys Lys Gln Asp Ile Gln
            20                  25                  30

Cys Cys Leu Arg Ile Phe Asp Glu Ser Lys Asp Pro Asn Val Met Leu
        35                  40                  45

Ile Cys Leu Phe Cys Trp
    50

<210> SEQ ID NO 95
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Gly Ser Gly Asp Ala Leu Pro His Leu Lys Arg Gly Gly Ser Pro Asp
1               5                   10                  15

Glu Tyr Ile Glu Arg Ala Lys Glu Cys Cys Lys Lys Gln Asp Ile Gln
            20                  25                  30

Cys Cys Leu Arg Ile Phe Asp Glu Ser Lys Asp Pro Asn Val Met Leu
        35                  40                  45

Ile Cys Leu Phe Cys Trp
    50

<210> SEQ ID NO 96
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Gly Ser Ser Glu Lys Asp Ala Ile Lys His Leu Gln Arg Gly Gly Ser
1               5                   10                  15

Pro Asp Glu Tyr Ile Glu Arg Ala Lys Glu Cys Cys Lys Lys Gln Asp
            20                  25                  30

Ile Gln Cys Cys Leu Arg Ile Phe Asp Glu Ser Lys Asp Pro Asn Val
        35                  40                  45

Met Leu Ile Cys Leu Phe Cys Trp
    50                  55

<210> SEQ ID NO 97
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Gly Ser Lys Asp Ala Ile Lys His Leu Gln Arg Gly Gly Ser Pro Asp
1               5                   10                  15

Glu Tyr Ile Glu Arg Ala Lys Glu Cys Cys Lys Lys Gln Asp Ile Gln
```

```
                 20                  25                  30

Cys Cys Leu Arg Ile Phe Asp Glu Ser Lys Asp Pro Asn Val Met Leu
            35                  40                  45

Ile Cys Leu Phe Cys Trp
         50
```

<210> SEQ ID NO 98
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

```
Gly Ser Val Leu Asp Ser Leu Glu Phe Ile Ala Ser Lys Leu Gly Gly
1               5                   10                  15

Ser Pro Asp Glu Tyr Ile Glu Arg Ala Lys Glu Cys Cys Lys Lys Gln
            20                  25                  30

Asp Ile Gln Cys Cys Leu Arg Ile Phe Asp Glu Ser Lys Asp Pro Asn
        35                  40                  45

Val Met Leu Ile Cys Leu Phe Cys Trp
    50                  55
```

<210> SEQ ID NO 99
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

```
Gly Ser Pro Asp Glu Tyr Ile Glu Arg Ala Lys Glu Cys Cys Lys Lys
1               5                   10                  15

Phe Phe Arg Arg Arg Arg Asp Ile Gln Cys Cys Leu Arg Ile Phe Asp
            20                  25                  30

Glu Ser Lys Asp Pro Asn Val Met Leu Ile Cys Leu Phe Cys Trp
        35                  40                  45
```

<210> SEQ ID NO 100
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

```
Gly Ser Lys Ala Val Leu Gly Ala Thr Lys Ile Asp Leu Pro Val Asp
1               5                   10                  15

Ile Asn Asp Pro Tyr Asp Leu Gly Leu Leu Arg His Leu Arg His
            20                  25                  30

His Ser Asn Leu Leu Ala Asn Ile Gly Asp Pro Ala Val Arg Glu Gln
        35                  40                  45

Val Leu Ser Ala Met Gln Glu Glu Gly Gly Ser Pro Asp Glu Tyr
    50                  55                  60

Ile Glu Arg Ala Lys Glu Cys Cys Lys Lys Gln Asp Ile Gln Cys Cys
65                  70                  75                  80

Leu Arg Ile Phe Asp Glu Ser Lys Asp Pro Asn Val Met Leu Ile Cys
                85                  90                  95
```

```
Leu Phe Cys Trp
         100

<210> SEQ ID NO 101
<211> LENGTH: 73
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Gly Ser Leu Ser Thr Ala Ala Asp Met Gln Gly Val Val Thr Asp Gly
1               5                  10                  15

Met Ala Ser Gly Leu Asp Lys Asp Tyr Leu Lys Pro Asp Asp Gly Gly
            20                  25                  30

Ser Pro Asp Glu Tyr Ile Glu Arg Ala Lys Glu Cys Cys Lys Lys Gln
        35                  40                  45

Asp Ile Gln Cys Cys Leu Arg Ile Phe Asp Glu Ser Lys Asp Pro Asn
    50                  55                  60

Val Met Leu Ile Cys Leu Phe Cys Trp
65                  70

<210> SEQ ID NO 102
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Gly Ser Arg Arg Trp Arg Arg Trp Asn Arg Phe Asn Arg Arg Arg Cys
1               5                  10                  15

Arg Gly Gly Ser Pro Asp Glu Tyr Ile Glu Arg Ala Lys Glu Cys Cys
            20                  25                  30

Lys Lys Gln Asp Ile Gln Cys Cys Leu Arg Ile Phe Asp Glu Ser Lys
        35                  40                  45

Asp Pro Asn Val Met Leu Ile Cys Leu Phe Cys Trp
    50                  55                  60

<210> SEQ ID NO 103
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gly Ser Arg Ala Gly Leu Gln Phe Pro Val Gly Arg Leu Leu Arg Arg
1               5                  10                  15

Leu Leu Arg Gly Gly Ser Pro Asp Glu Tyr Ile Glu Arg Ala Lys Glu
            20                  25                  30

Cys Cys Lys Lys Gln Asp Ile Gln Cys Cys Leu Arg Ile Phe Asp Glu
        35                  40                  45

Ser Lys Asp Pro Asn Val Met Leu Ile Cys Leu Phe Cys Trp
    50                  55                  60

<210> SEQ ID NO 104
<211> LENGTH: 58
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Gly Ser Lys Arg Ala His His Asn Ala Leu Glu Arg Lys Arg Arg Gly
1               5                   10                  15

Gly Ser Pro Asp Glu Tyr Ile Glu Arg Ala Lys Glu Cys Cys Lys Lys
                20                  25                  30

Gln Asp Ile Gln Cys Cys Leu Arg Ile Phe Asp Glu Ser Lys Asp Pro
            35                  40                  45

Asn Val Met Leu Ile Cys Leu Phe Cys Trp
        50                  55

<210> SEQ ID NO 105
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Gly Ser Arg Arg Met Lys Ala Asn Ala Arg Glu Arg Asn Arg Met Gly
1               5                   10                  15

Gly Ser Pro Asp Glu Tyr Ile Glu Arg Ala Lys Glu Cys Cys Lys Lys
                20                  25                  30

Gln Asp Ile Gln Cys Cys Leu Arg Ile Phe Asp Glu Ser Lys Asp Pro
            35                  40                  45

Asn Val Met Leu Ile Cys Leu Phe Cys Trp
        50                  55

<210> SEQ ID NO 106
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Gly Ser Leu Leu Ile Ile Leu Arg Arg Arg Ile Arg Lys Gln Ala His
1               5                   10                  15

Ala His Ser Lys Gly Gly Ser Pro Asp Glu Tyr Ile Glu Arg Ala Lys
                20                  25                  30

Glu Cys Cys Lys Lys Gln Asp Ile Gln Cys Cys Leu Arg Ile Phe Asp
            35                  40                  45

Glu Ser Lys Asp Pro Asn Val Met Leu Ile Cys Leu Phe Cys Trp
        50                  55                  60

<210> SEQ ID NO 107
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Gly Ser Arg Arg Leu Ser Tyr Ser Arg Arg Arg Phe Gly Gly Ser Pro
1               5                   10                  15
```

```
Asp Glu Tyr Ile Glu Arg Ala Lys Glu Cys Cys Lys Lys Gln Asp Ile
            20                  25                  30

Gln Cys Cys Leu Arg Ile Phe Asp Glu Ser Lys Asp Pro Asn Val Met
        35                  40                  45

Leu Ile Cys Leu Phe Cys Trp
    50                  55

<210> SEQ ID NO 108
<211> LENGTH: 64
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Gly Ser Val Lys Arg Gly Leu Lys Leu Arg His Val Arg Pro Arg Val
1               5                   10                  15

Thr Arg Met Asp Val Gly Gly Ser Pro Asp Glu Tyr Ile Glu Arg Ala
            20                  25                  30

Lys Glu Cys Cys Lys Lys Gln Asp Ile Gln Cys Cys Leu Arg Ile Phe
        35                  40                  45

Asp Glu Ser Lys Asp Pro Asn Val Met Leu Ile Cys Leu Phe Cys Trp
    50                  55                  60

<210> SEQ ID NO 109
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Gly Ser Cys Ser Ile Pro Pro Glu Val Lys Phe Asn Lys Pro Phe Val
1               5                   10                  15

Tyr Leu Ile Gly Gly Ser Pro Asp Glu Tyr Ile Glu Arg Ala Lys Glu
            20                  25                  30

Cys Cys Lys Lys Gln Asp Ile Gln Cys Cys Leu Arg Ile Phe Asp Glu
        35                  40                  45

Ser Lys Asp Pro Asn Val Met Leu Ile Cys Leu Phe Cys Trp
    50                  55                  60

<210> SEQ ID NO 110
<211> LENGTH: 72
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Gly Ser Gly Trp Thr Leu Asn Ser Ala Gly Tyr Leu Leu Gly Lys Ile
1               5                   10                  15

Asn Leu Lys Ala Leu Ala Ala Leu Ala Lys Lys Ile Leu Gly Gly Ser
            20                  25                  30

Pro Asp Glu Tyr Ile Glu Arg Ala Lys Glu Cys Cys Lys Lys Gln Asp
        35                  40                  45

Ile Gln Cys Cys Leu Arg Ile Phe Asp Glu Ser Lys Asp Pro Asn Val
    50                  55                  60
```

```
Met Leu Ile Cys Leu Phe Cys Trp
 65                  70
```

<210> SEQ ID NO 111
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

```
Gly Ser Lys Gly Glu Gly Ala Ala Val Leu Leu Pro Val Leu Leu Ala
1               5                   10                  15

Ala Pro Gly Gly Gly Ser Pro Asp Glu Tyr Ile Glu Arg Ala Lys Glu
            20                  25                  30

Cys Cys Lys Lys Gln Asp Ile Gln Cys Leu Arg Ile Phe Asp Glu
        35                  40                  45

Ser Lys Asp Pro Asn Val Met Leu Ile Cys Leu Phe Cys Trp
    50                  55                  60
```

<210> SEQ ID NO 112
<211> LENGTH: 67
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

```
Gly Ser Lys Cys Phe Gln Trp Gln Arg Asn Met Arg Lys Val Arg Gly
1               5                   10                  15

Pro Pro Val Ser Cys Ile Lys Arg Gly Gly Ser Pro Asp Glu Tyr Ile
            20                  25                  30

Glu Arg Ala Lys Glu Cys Cys Lys Lys Gln Asp Ile Gln Cys Cys Leu
        35                  40                  45

Arg Ile Phe Asp Glu Ser Lys Asp Pro Asn Val Met Leu Ile Cys Leu
    50                  55                  60

Phe Cys Trp
65
```

<210> SEQ ID NO 113
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

```
Gly Ser Pro Phe Val Tyr Leu Ile Gly Gly Ser Pro Asp Glu Tyr Ile
1               5                   10                  15

Glu Arg Ala Lys Glu Cys Cys Lys Lys Gln Asp Ile Gln Cys Cys Leu
            20                  25                  30

Arg Ile Phe Asp Glu Ser Lys Asp Pro Asn Val Met Leu Ile Cys Leu
        35                  40                  45

Phe Cys Trp
    50
```

<210> SEQ ID NO 114
<211> LENGTH: 54
<212> TYPE: PRT

<213> ORGANISM: Artificial Sequence
<220> FEATURE:
<223> OTHER INFORMATION: Description of Artificial Sequence: Synthetic
     polypeptide

<400> SEQUENCE: 114

Gly Ser Arg Arg Arg Arg Arg Arg Arg Gly Gly Gly Ser Pro Asp
1               5                   10                  15

Glu Tyr Ile Glu Arg Ala Lys Glu Cys Cys Lys Lys Gly Asp Ile Gln
            20                  25                  30

Cys Cys Leu Arg Tyr Phe Glu Glu Ser Gly Asp Pro Asn Val Met Leu
        35                  40                  45

Ile Cys Leu Phe Cys Pro
        50

<210> SEQ ID NO 115
<211> LENGTH: 57
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 115

Gly Ser Tyr Gly Arg Lys Lys Arg Arg Gln Arg Arg Arg Gly Gly Gly
1               5                   10                  15

Ser Pro Asp Glu Tyr Ile Glu Arg Ala Lys Glu Cys Cys Lys Lys Gly
            20                  25                  30

Asp Ile Gln Cys Cys Leu Arg Tyr Phe Glu Glu Ser Gly Asp Pro Asn
        35                  40                  45

Val Met Leu Ile Cys Leu Phe Cys Pro
        50                  55

<210> SEQ ID NO 116
<211> LENGTH: 90
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 116

Gly Ser Met Cys Met Pro Cys Phe Thr Thr Asp His Gln Met Ala Arg
1               5                   10                  15

Lys Cys Asp Asp Cys Cys Gly Gly Lys Gly Arg Gly Lys Cys Tyr Gly
            20                  25                  30

Pro Gln Cys Leu Cys Arg Gly Gly Ser Gly Gly Ser Gly Gly
        35                  40                  45

Gly Ser Pro Asp Glu Tyr Ile Glu Arg Ala Lys Glu Cys Cys Lys Lys
    50                  55                  60

Gln Asp Ile Gln Cys Cys Leu Arg Ile Phe Asp Glu Ser Lys Asp Pro
65                  70                  75                  80

Asn Val Met Leu Ile Cys Leu Phe Cys Trp
                85                  90

<210> SEQ ID NO 117
<211> LENGTH: 90
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 117

Gly Ser Met Cys Met Pro Cys Phe Thr Thr Asp His Gln Met Ala Arg
1               5                   10                  15

Lys Cys Asp Asp Cys Cys Gly Gly Lys Gly Arg Gly Lys Cys Tyr Gly
            20                  25                  30

Pro Gln Cys Leu Cys Arg Lys Lys Tyr Lys Pro Tyr Val Pro Val Thr
        35                  40                  45

Thr Asn Pro Asp Glu Tyr Ile Glu Arg Ala Lys Glu Cys Cys Lys Lys
    50                  55                  60

Gln Asp Ile Gln Cys Cys Leu Arg Ile Phe Asp Glu Ser Lys Asp Pro
65                  70                  75                  80

Asn Val Met Leu Ile Cys Leu Phe Cys Trp
                85                  90

<210> SEQ ID NO 118
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Gly Ser Met Cys Met Pro Cys Phe Thr Thr Asp His Gln Met Ala Arg
1               5                   10                  15

Lys Cys Asp Asp Cys Cys Gly Gly Lys Gly Arg Gly Lys Cys Tyr Gly
            20                  25                  30

Pro Gln Cys Leu Cys Arg Glu Pro Lys Ser Ser Asp Lys Thr His Thr
        35                  40                  45

Pro Asp Glu Tyr Ile Glu Arg Ala Lys Glu Cys Cys Lys Lys Gln Asp
    50                  55                  60

Ile Gln Cys Cys Leu Arg Ile Phe Asp Glu Ser Lys Asp Pro Asn Val
65                  70                  75                  80

Met Leu Ile Cys Leu Phe Cys Trp
                85

<210> SEQ ID NO 119
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Gly Ser Gly Asp Cys Leu Pro His Leu Lys Leu Cys Lys Glu Asn Lys
1               5                   10                  15

Asp Cys Cys Ser Lys Lys Cys Lys Arg Arg Gly Thr Asn Ile Glu Lys
            20                  25                  30

Arg Cys Arg Gly Gly Gly Ser Gly Gly Ser Gly Gly Ser Pro
        35                  40                  45

Asp Glu Tyr Ile Glu Arg Ala Lys Glu Cys Cys Lys Lys Gln Asp Ile
    50                  55                  60

Gln Cys Cys Leu Arg Ile Phe Asp Glu Ser Lys Asp Pro Asn Val Met
65                  70                  75                  80

Leu Ile Cys Leu Phe Cys Trp
                85

<210> SEQ ID NO 120
<211> LENGTH: 87
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 120

Gly Ser Gly Asp Cys Leu Pro His Leu Lys Leu Cys Lys Glu Asn Lys
1               5                   10                  15

Asp Cys Cys Ser Lys Lys Cys Lys Arg Arg Gly Thr Asn Ile Glu Lys
                20                  25                  30

Arg Cys Arg Lys Lys Tyr Lys Pro Tyr Val Pro Val Thr Thr Asn Pro
            35                  40                  45

Asp Glu Tyr Ile Glu Arg Ala Lys Glu Cys Cys Lys Lys Gln Asp Ile
        50                  55                  60

Gln Cys Cys Leu Arg Ile Phe Asp Glu Ser Lys Asp Pro Asn Val Met
65                  70                  75                  80

Leu Ile Cys Leu Phe Cys Trp
                85

<210> SEQ ID NO 121
<211> LENGTH: 85
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 121

Gly Ser Gly Asp Cys Leu Pro His Leu Lys Leu Cys Lys Glu Asn Lys
1               5                   10                  15

Asp Cys Cys Ser Lys Lys Cys Lys Arg Arg Gly Thr Asn Ile Glu Lys
                20                  25                  30

Arg Cys Arg Glu Pro Lys Ser Ser Asp Lys Thr His Thr Pro Asp Glu
            35                  40                  45

Tyr Ile Glu Arg Ala Lys Glu Cys Cys Lys Lys Gln Asp Ile Gln Cys
        50                  55                  60

Cys Leu Arg Ile Phe Asp Glu Ser Lys Asp Pro Asn Val Met Leu Ile
65                  70                  75                  80

Cys Leu Phe Cys Trp
                85

<210> SEQ ID NO 122
<211> LENGTH: 87
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 122

Gly Ser Gly Asp Cys Leu Pro His Leu Lys Arg Cys Lys Ala Asp Asn
1               5                   10                  15

Asp Cys Cys Gly Lys Lys Cys Lys Arg Arg Gly Thr Asn Ala Glu Lys
                20                  25                  30

Arg Cys Arg Gly Gly Ser Gly Gly Ser Gly Gly Ser Pro
            35                  40                  45

Asp Glu Tyr Ile Glu Arg Ala Lys Glu Cys Cys Lys Lys Gln Asp Ile

```
            50                  55                  60
Gln Cys Cys Leu Arg Ile Phe Asp Glu Ser Lys Asp Pro Asn Val Met
 65                  70                  75                  80

Leu Ile Cys Leu Phe Cys Trp
                85

<210> SEQ ID NO 123
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Gly Ser Gly Asp Cys Leu Pro His Leu Lys Arg Cys Lys Ala Asp Asn
 1               5                  10                  15

Asp Cys Cys Gly Lys Lys Cys Lys Arg Arg Gly Thr Asn Ala Glu Lys
                20                  25                  30

Arg Cys Arg Lys Lys Tyr Lys Pro Tyr Val Pro Val Thr Thr Asn Pro
            35                  40                  45

Asp Glu Tyr Ile Glu Arg Ala Lys Glu Cys Cys Lys Lys Gln Asp Ile
        50                  55                  60

Gln Cys Cys Leu Arg Ile Phe Asp Glu Ser Lys Asp Pro Asn Val Met
 65                  70                  75                  80

Leu Ile Cys Leu Phe Cys Trp
                85

<210> SEQ ID NO 124
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Gly Ser Gly Asp Cys Leu Pro His Leu Lys Arg Cys Lys Ala Asp Asn
 1               5                  10                  15

Asp Cys Cys Gly Lys Lys Cys Lys Arg Arg Gly Thr Asn Ala Glu Lys
                20                  25                  30

Arg Cys Arg Glu Pro Lys Ser Ser Asp Lys Thr His Thr Pro Asp Glu
            35                  40                  45

Tyr Ile Glu Arg Ala Lys Glu Cys Cys Lys Lys Gln Asp Ile Gln Cys
        50                  55                  60

Cys Leu Arg Ile Phe Asp Glu Ser Lys Asp Pro Asn Val Met Leu Ile
 65                  70                  75                  80

Cys Leu Phe Cys Trp
                85

<210> SEQ ID NO 125
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Gly Ser Gly Asp Cys Leu Pro His Leu Lys Leu Cys Lys Ala Asp Lys
 1               5                  10                  15
```

Asp Cys Cys Ser Lys Lys Cys Lys Arg Arg Gly Thr Asn Pro Glu Lys
            20                  25                  30

Arg Cys Arg Gly Gly Ser Gly Gly Ser Gly Gly Ser Pro
        35                  40                  45

Asp Glu Tyr Ile Glu Arg Ala Lys Glu Cys Cys Lys Lys Gln Asp Ile
50                  55                  60

Gln Cys Cys Leu Arg Ile Phe Asp Glu Ser Lys Asp Pro Asn Val Met
65                  70                  75                  80

Leu Ile Cys Leu Phe Cys Trp
                85

<210> SEQ ID NO 126
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Gly Ser Gly Asp Cys Leu Pro His Leu Lys Leu Cys Lys Ala Asp Lys
1               5                   10                  15

Asp Cys Cys Ser Lys Lys Cys Lys Arg Arg Gly Thr Asn Pro Glu Lys
            20                  25                  30

Arg Cys Arg Lys Lys Tyr Lys Pro Tyr Val Pro Val Thr Thr Asn Pro
        35                  40                  45

Asp Glu Tyr Ile Glu Arg Ala Lys Glu Cys Cys Lys Lys Gln Asp Ile
50                  55                  60

Gln Cys Cys Leu Arg Ile Phe Asp Glu Ser Lys Asp Pro Asn Val Met
65                  70                  75                  80

Leu Ile Cys Leu Phe Cys Trp
                85

<210> SEQ ID NO 127
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Gly Ser Gly Asp Cys Leu Pro His Leu Lys Leu Cys Lys Ala Asp Lys
1               5                   10                  15

Asp Cys Cys Ser Lys Lys Cys Lys Arg Arg Gly Thr Asn Pro Glu Lys
            20                  25                  30

Arg Cys Arg Glu Pro Lys Ser Ser Asp Lys Thr His Thr Pro Asp Glu
        35                  40                  45

Tyr Ile Glu Arg Ala Lys Glu Cys Cys Lys Lys Gln Asp Ile Gln Cys
    50                  55                  60

Cys Leu Arg Ile Phe Asp Glu Ser Lys Asp Pro Asn Val Met Leu Ile
65                  70                  75                  80

Cys Leu Phe Cys Trp
                85

<210> SEQ ID NO 128
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Gly Ser Gly Asp Cys Leu Pro His Leu Lys Arg Cys Lys Glu Asn Asn
1               5                   10                  15

Asp Cys Cys Ser Lys Lys Cys Lys Arg Arg Gly Thr Asn Pro Glu Lys
                20                  25                  30

Arg Cys Arg Gly Gly Gly Ser Gly Gly Gly Ser Gly Gly Gly Ser Pro
            35                  40                  45

Asp Glu Tyr Ile Glu Arg Ala Lys Glu Cys Cys Lys Lys Gln Asp Ile
50                  55                  60

Gln Cys Cys Leu Arg Ile Phe Asp Glu Ser Lys Asp Pro Asn Val Met
65                  70                  75                  80

Leu Ile Cys Leu Phe Cys Trp
                85

<210> SEQ ID NO 129
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Gly Ser Gly Asp Cys Leu Pro His Leu Lys Arg Cys Lys Glu Asn Asn
1               5                   10                  15

Asp Cys Cys Ser Lys Lys Cys Lys Arg Arg Gly Thr Asn Pro Glu Lys
                20                  25                  30

Arg Cys Arg Lys Lys Tyr Lys Pro Tyr Val Pro Val Thr Thr Asn Pro
            35                  40                  45

Asp Glu Tyr Ile Glu Arg Ala Lys Glu Cys Cys Lys Lys Gln Asp Ile
50                  55                  60

Gln Cys Cys Leu Arg Ile Phe Asp Glu Ser Lys Asp Pro Asn Val Met
65                  70                  75                  80

Leu Ile Cys Leu Phe Cys Trp
                85

<210> SEQ ID NO 130
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Gly Ser Gly Asp Cys Leu Pro His Leu Lys Arg Cys Lys Glu Asn Asn
1               5                   10                  15

Asp Cys Cys Ser Lys Lys Cys Lys Arg Arg Gly Thr Asn Pro Glu Lys
                20                  25                  30

Arg Cys Arg Glu Pro Lys Ser Ser Asp Lys Thr His Thr Pro Asp Glu
            35                  40                  45

Tyr Ile Glu Arg Ala Lys Glu Cys Cys Lys Lys Gln Asp Ile Gln Cys
    50                  55                  60

Cys Leu Arg Ile Phe Asp Glu Ser Lys Asp Pro Asn Val Met Leu Ile
65                  70                  75                  80

```
Cys Leu Phe Cys Trp
            85

<210> SEQ ID NO 131
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Gly Ser Gly Asp Cys Leu Pro His Leu Lys Arg Cys Lys Glu Asn Asn
1               5                   10                  15

Asp Cys Cys Ser Lys Lys Cys Lys Arg Arg Gly Ala Asn Pro Glu Lys
                20                  25                  30

Arg Cys Arg Gly Gly Ser Gly Gly Ser Gly Gly Ser Pro
            35                  40                  45

Asp Glu Tyr Ile Glu Arg Ala Lys Glu Cys Cys Lys Lys Gln Asp Ile
        50                  55                  60

Gln Cys Cys Leu Arg Ile Phe Asp Glu Ser Lys Asp Pro Asn Val Met
65                  70                  75                  80

Leu Ile Cys Leu Phe Cys Trp
                85

<210> SEQ ID NO 132
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Gly Ser Gly Asp Cys Leu Pro His Leu Lys Arg Cys Lys Glu Asn Asn
1               5                   10                  15

Asp Cys Cys Ser Lys Lys Cys Lys Arg Arg Gly Ala Asn Pro Glu Lys
                20                  25                  30

Arg Cys Arg Lys Lys Tyr Lys Pro Tyr Val Pro Val Thr Thr Asn Pro
            35                  40                  45

Asp Glu Tyr Ile Glu Arg Ala Lys Glu Cys Cys Lys Lys Gln Asp Ile
        50                  55                  60

Gln Cys Cys Leu Arg Ile Phe Asp Glu Ser Lys Asp Pro Asn Val Met
65                  70                  75                  80

Leu Ile Cys Leu Phe Cys Trp
                85

<210> SEQ ID NO 133
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Gly Ser Gly Asp Cys Leu Pro His Leu Lys Arg Cys Lys Glu Asn Asn
1               5                   10                  15

Asp Cys Cys Ser Lys Lys Cys Lys Arg Arg Gly Ala Asn Pro Glu Lys
                20                  25                  30

Arg Cys Arg Glu Pro Lys Ser Ser Asp Lys Thr His Thr Pro Asp Glu
```

```
                35                  40                  45

Tyr Ile Glu Arg Ala Lys Glu Cys Cys Lys Lys Gln Asp Ile Gln Cys
             50                  55                  60

Cys Leu Arg Ile Phe Asp Glu Ser Lys Asp Pro Asn Val Met Leu Ile
 65                  70                  75                  80

Cys Leu Phe Cys Trp
                 85

<210> SEQ ID NO 134
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Gly Ser Ser Glu Lys Asp Cys Ile Lys His Leu Gln Arg Cys Arg Glu
1               5                  10                  15

Asn Lys Asp Cys Cys Ser Lys Lys Cys Ser Arg Arg Gly Thr Asn Pro
                 20                  25                  30

Glu Lys Arg Cys Arg Gly Gly Gly Ser Gly Gly Gly Ser Gly Gly Gly
             35                  40                  45

Ser Pro Asp Glu Tyr Ile Glu Arg Ala Lys Glu Cys Cys Lys Lys Gln
         50                  55                  60

Asp Ile Gln Cys Cys Leu Arg Ile Phe Asp Glu Ser Lys Asp Pro Asn
 65                  70                  75                  80

Val Met Leu Ile Cys Leu Phe Cys Trp
                 85

<210> SEQ ID NO 135
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Gly Ser Ser Glu Lys Asp Cys Ile Lys His Leu Gln Arg Cys Arg Glu
1               5                  10                  15

Asn Lys Asp Cys Cys Ser Lys Lys Cys Ser Arg Arg Gly Thr Asn Pro
                 20                  25                  30

Glu Lys Arg Cys Arg Lys Lys Tyr Lys Pro Tyr Val Pro Val Thr Thr
             35                  40                  45

Asn Pro Asp Glu Tyr Ile Glu Arg Ala Lys Glu Cys Cys Lys Lys Gln
         50                  55                  60

Asp Ile Gln Cys Cys Leu Arg Ile Phe Asp Glu Ser Lys Asp Pro Asn
 65                  70                  75                  80

Val Met Leu Ile Cys Leu Phe Cys Trp
                 85

<210> SEQ ID NO 136
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136
```

```
Gly Ser Ser Glu Lys Asp Cys Ile Lys His Leu Gln Arg Cys Arg Glu
1               5                   10                  15

Asn Lys Asp Cys Cys Ser Lys Lys Cys Ser Arg Arg Gly Thr Asn Pro
            20                  25                  30

Glu Lys Arg Cys Arg Glu Pro Lys Ser Ser Asp Lys Thr His Thr Pro
        35                  40                  45

Asp Glu Tyr Ile Glu Arg Ala Lys Glu Cys Cys Lys Lys Gln Asp Ile
    50                  55                  60

Gln Cys Cys Leu Arg Ile Phe Asp Glu Ser Lys Asp Pro Asn Val Met
65              70                  75                  80

Leu Ile Cys Leu Phe Cys Trp
                85
```

<210> SEQ ID NO 137
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

```
Gly Ser Cys Lys Tyr Lys Phe Glu Asn Trp Gly Ala Cys Asp Gly Gly
1               5                   10                  15

Thr Gly Thr Lys Val Arg Gln Gly Thr Leu Lys Lys Ala Arg Tyr Asn
            20                  25                  30

Ala Gln Cys Gln Glu Thr Ile Arg Val Thr Lys Pro Cys Gly Gly Gly
        35                  40                  45

Ser Gly Gly Gly Ser Gly Gly Gly Ser Pro Asp Glu Tyr Ile Glu Arg
    50                  55                  60

Ala Lys Glu Cys Cys Lys Lys Gln Asp Ile Gln Cys Cys Leu Arg Ile
65              70                  75                  80

Phe Asp Glu Ser Lys Asp Pro Asn Val Met Leu Ile Cys Leu Phe Cys
                85                  90                  95

Trp
```

<210> SEQ ID NO 138
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

```
Gly Ser Cys Lys Tyr Lys Phe Glu Asn Trp Gly Ala Cys Asp Gly Gly
1               5                   10                  15

Thr Gly Thr Lys Val Arg Gln Gly Thr Leu Lys Lys Ala Arg Tyr Asn
            20                  25                  30

Ala Gln Cys Gln Glu Thr Ile Arg Val Thr Lys Pro Cys Lys Lys Tyr
        35                  40                  45

Lys Pro Tyr Val Pro Val Thr Thr Asn Pro Asp Glu Tyr Ile Glu Arg
    50                  55                  60

Ala Lys Glu Cys Cys Lys Lys Gln Asp Ile Gln Cys Cys Leu Arg Ile
65              70                  75                  80

Phe Asp Glu Ser Lys Asp Pro Asn Val Met Leu Ile Cys Leu Phe Cys
                85                  90                  95
```

Trp

<210> SEQ ID NO 139
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Gly Ser Cys Lys Tyr Lys Phe Glu Asn Trp Gly Ala Cys Asp Gly Gly
1               5                   10                  15

Thr Gly Thr Lys Val Arg Gln Gly Thr Leu Lys Lys Ala Arg Tyr Asn
            20                  25                  30

Ala Gln Cys Gln Glu Thr Ile Arg Val Thr Lys Pro Cys Glu Pro Lys
        35                  40                  45

Ser Ser Asp Lys Thr His Thr Pro Asp Glu Tyr Ile Glu Arg Ala Lys
    50                  55                  60

Glu Cys Cys Lys Lys Gln Asp Ile Gln Cys Cys Leu Arg Ile Phe Asp
65                  70                  75                  80

Glu Ser Lys Asp Pro Asn Val Met Leu Ile Cys Leu Phe Cys Trp
                85                  90                  95

<210> SEQ ID NO 140
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Gly Ser Ser Gly Ser Asp Gly Val Cys Pro Lys Ile Leu Lys Lys
1               5                   10                  15

Cys Arg Arg Asp Ser Asp Cys Pro Gly Ala Cys Ile Cys Arg Gly Asn
            20                  25                  30

Gly Tyr Cys Gly Gly Gly Ser Gly Gly Ser Gly Gly Ser
        35                  40                  45

Pro Asp Glu Tyr Ile Glu Arg Ala Lys Glu Cys Cys Lys Lys Gln Asp
    50                  55                  60

Ile Gln Cys Cys Leu Arg Ile Phe Asp Glu Ser Lys Asp Pro Asn Val
65                  70                  75                  80

Met Leu Ile Cys Leu Phe Cys Trp
                85

<210> SEQ ID NO 141
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Gly Ser Ser Gly Ser Asp Gly Val Cys Pro Lys Ile Leu Lys Lys
1               5                   10                  15

Cys Arg Arg Asp Ser Asp Cys Pro Gly Ala Cys Ile Cys Arg Gly Asn
            20                  25                  30

Gly Tyr Cys Gly Lys Lys Tyr Lys Pro Tyr Val Pro Val Thr Thr Asn
        35                  40                  45

Pro Asp Glu Tyr Ile Glu Arg Ala Lys Glu Cys Cys Lys Lys Gln Asp
    50                  55                  60

Ile Gln Cys Cys Leu Arg Ile Phe Asp Glu Ser Lys Asp Pro Asn Val
65                  70                  75                  80

Met Leu Ile Cys Leu Phe Cys Trp
                85

<210> SEQ ID NO 142
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Gly Ser Ser Gly Ser Asp Gly Val Cys Pro Lys Ile Leu Lys Lys
1               5                   10                  15

Cys Arg Arg Asp Ser Asp Cys Pro Gly Ala Cys Ile Cys Arg Gly Asn
                20                  25                  30

Gly Tyr Cys Gly Glu Pro Lys Ser Ser Asp Lys Thr His Thr Pro Asp
            35                  40                  45

Glu Tyr Ile Glu Arg Ala Lys Glu Cys Cys Lys Lys Gln Asp Ile Gln
    50                  55                  60

Cys Cys Leu Arg Ile Phe Asp Glu Ser Lys Asp Pro Asn Val Met Leu
65                  70                  75                  80

Ile Cys Leu Phe Cys Trp
                85

<210> SEQ ID NO 143
<211> LENGTH: 10
<212> TYPE: PRT
<213> ORGANISM: Human immunodeficiency virus

<400> SEQUENCE: 143

Gly Arg Lys Lys Arg Arg Gln Arg Arg Arg
1               5                   10

<210> SEQ ID NO 144
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Cys Tyr Arg Lys Lys Arg Arg Gln Arg Arg Arg
1               5                   10

<210> SEQ ID NO 145
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Pro Phe Val Ile Gly Ala Gly Val Leu Gly Ala Leu Gly Thr Gly Ile
1               5                   10                  15

Gly Gly Ile Gly Arg Lys Lys Arg Arg Gln Arg Arg Arg

```
                        20                  25

<210> SEQ ID NO 146
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Arg Arg Arg Arg Arg Arg Arg Arg
1               5

<210> SEQ ID NO 147
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Arg Gln Ile Lys Ile Trp Phe Gln Asn Arg Arg Met Lys Trp Lys Lys
1               5                   10                  15

<210> SEQ ID NO 148
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Phe Phe Leu Ile Pro Lys Gly Gly Arg Lys Lys Arg Arg Gln Arg Arg
1               5                   10                  15

Arg

<210> SEQ ID NO 149
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Phe Phe Leu Ile Pro Lys Gly Arg Arg Arg Arg Arg Arg Arg Arg
1               5                   10                  15

<210> SEQ ID NO 150
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Phe Phe Leu Ile Pro Lys Gly Arg Arg Arg Asn Arg Thr Arg Arg
1               5                   10                  15

Asn Arg Arg Arg Val Arg
                20

<210> SEQ ID NO 151
```

```
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Phe Phe Leu Ile Pro Lys Gly Arg Gln Ile Lys Ile Trp Phe Gln Asn
1               5                   10                  15

Arg Arg Met Lys Trp Lys Lys
            20

<210> SEQ ID NO 152
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Phe Phe Arg Arg Arg Arg
1               5

<210> SEQ ID NO 153
<211> LENGTH: 55
<212> TYPE: PRT
<213> ORGANISM: Unknown
<220> FEATURE:
<223> OTHER INFORMATION: Description of Unknown:
      B55 sequence

<400> SEQUENCE: 153

Lys Ala Val Leu Gly Ala Thr Lys Ile Asp Leu Pro Val Asp Ile Asn
1               5                   10                  15

Asp Pro Tyr Asp Leu Gly Leu Leu Arg His Leu Arg His His Ser
            20                  25                  30

Asn Leu Leu Ala Asn Ile Gly Asp Pro Ala Val Arg Glu Gln Val Leu
        35                  40                  45

Ser Ala Met Gln Glu Glu Glu
        50                  55

<210> SEQ ID NO 154
<211> LENGTH: 28
<212> TYPE: PRT
<213> ORGANISM: Pseudomonas aeruginosa

<400> SEQUENCE: 154

Leu Ser Thr Ala Ala Asp Met Gln Gly Val Val Thr Asp Gly Met Ala
1               5                   10                  15

Ser Gly Leu Asp Lys Asp Tyr Leu Lys Pro Asp Asp
            20                  25

<210> SEQ ID NO 155
<211> LENGTH: 15
<212> TYPE: PRT
<213> ORGANISM: Unknown
<220> FEATURE:
<223> OTHER INFORMATION: Description of Unknown:
      IMT-P8 sequence

<400> SEQUENCE: 155

Arg Arg Trp Arg Arg Trp Asn Arg Phe Asn Arg Arg Arg Cys Arg
1               5                   10                  15
```

-continued

```
<210> SEQ ID NO 156
<211> LENGTH: 17
<212> TYPE: PRT
<213> ORGANISM: Unknown
<220> FEATURE:
<223> OTHER INFORMATION: Description of Unknown:
      BR2 sequence

<400> SEQUENCE: 156

Arg Ala Gly Leu Gln Phe Pro Val Gly Arg Leu Leu Arg Arg Leu Leu
1               5                   10                  15

Arg

<210> SEQ ID NO 157
<211> LENGTH: 13
<212> TYPE: PRT
<213> ORGANISM: Unknown
<220> FEATURE:
<223> OTHER INFORMATION: Description of Unknown:
      OMOTAG1 sequence

<400> SEQUENCE: 157

Lys Arg Ala His His Asn Ala Leu Glu Arg Lys Arg Arg
1               5                   10

<210> SEQ ID NO 158
<211> LENGTH: 13
<212> TYPE: PRT
<213> ORGANISM: Unknown
<220> FEATURE:
<223> OTHER INFORMATION: Description of Unknown:
      OMOTAG2 sequence

<400> SEQUENCE: 158

Arg Arg Met Lys Ala Asn Ala Arg Glu Arg Asn Arg Met
1               5                   10

<210> SEQ ID NO 159
<211> LENGTH: 18
<212> TYPE: PRT
<213> ORGANISM: Unknown
<220> FEATURE:
<223> OTHER INFORMATION: Description of Unknown:
      pVEC sequence

<400> SEQUENCE: 159

Leu Leu Ile Ile Leu Arg Arg Arg Ile Arg Lys Gln Ala His Ala His
1               5                   10                  15

Ser Lys

<210> SEQ ID NO 160
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Arg Arg Leu Ser Tyr Ser Arg Arg Arg Phe
1               5                   10

<210> SEQ ID NO 161
<211> LENGTH: 19
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 161

Val Lys Arg Gly Leu Lys Leu Arg His Val Arg Pro Arg Val Thr Arg
1               5                   10                  15

Met Asp Val

<210> SEQ ID NO 162
<211> LENGTH: 17
<212> TYPE: PRT
<213> ORGANISM: Unknown
<220> FEATURE:
<223> OTHER INFORMATION: Description of Unknown:
      CY105Y sequence

<400> SEQUENCE: 162

Cys Ser Ile Pro Pro Glu Val Lys Phe Asn Lys Pro Phe Val Tyr Leu
1               5                   10                  15

Ile

<210> SEQ ID NO 163
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 164
<211> LENGTH: 17
<212> TYPE: PRT
<213> ORGANISM: Unknown
<220> FEATURE:
<223> OTHER INFORMATION: Description of Unknown:
      MTS sequence

<400> SEQUENCE: 164

Lys Gly Glu Gly Ala Ala Val Leu Leu Pro Val Leu Leu Ala Ala Pro
1               5                   10                  15

Gly

<210> SEQ ID NO 165
<211> LENGTH: 22
<212> TYPE: PRT
<213> ORGANISM: Homo sapiens

<400> SEQUENCE: 165

Lys Cys Phe Gln Trp Gln Arg Asn Met Arg Lys Val Arg Gly Pro Pro
1               5                   10                  15

Val Ser Cys Ile Lys Arg
            20

<210> SEQ ID NO 166
<211> LENGTH: 6
<212> TYPE: PRT
```

-continued

```
<213> ORGANISM: Unknown
<220> FEATURE:
<223> OTHER INFORMATION: Description of Unknown:
      PFVYLI sequence

<400> SEQUENCE: 166

Pro Phe Val Tyr Leu Ile
1               5

<210> SEQ ID NO 167
<211> LENGTH: 12
<212> TYPE: PRT
<213> ORGANISM: Unknown
<220> FEATURE:
<223> OTHER INFORMATION: Description of Unknown:
      yBBR sequence

<400> SEQUENCE: 167

Val Leu Asp Ser Leu Glu Phe Ile Ala Ser Lys Leu
1               5                  10

<210> SEQ ID NO 168
<211> LENGTH: 33
<212> TYPE: PRT
<213> ORGANISM: Maurus palmatus

<400> SEQUENCE: 168

Gly Asp Cys Leu Pro His Leu Lys Leu Cys Lys Glu Asn Lys Asp Cys
1               5                   10                  15

Cys Ser Lys Lys Cys Lys Arg Arg Gly Thr Asn Ile Glu Lys Arg Cys
            20                  25                  30

Arg

<210> SEQ ID NO 169
<211> LENGTH: 33
<212> TYPE: PRT
<213> ORGANISM: Pandinus imperator

<400> SEQUENCE: 169

Gly Asp Cys Leu Pro His Leu Lys Arg Cys Lys Ala Asp Asn Asp Cys
1               5                   10                  15

Cys Gly Lys Lys Cys Lys Arg Arg Gly Thr Asn Ala Glu Lys Arg Cys
            20                  25                  30

Arg

<210> SEQ ID NO 170
<211> LENGTH: 35
<212> TYPE: PRT
<213> ORGANISM: Hadrurus gertschi

<400> SEQUENCE: 170

Ser Glu Lys Asp Cys Ile Lys His Leu Gln Arg Cys Arg Glu Asn Lys
1               5                   10                  15

Asp Cys Cys Ser Lys Lys Cys Ser Arg Arg Gly Thr Asn Pro Glu Lys
            20                  25                  30

Arg Cys Arg
        35

<210> SEQ ID NO 171
<211> LENGTH: 33
<212> TYPE: PRT
<213> ORGANISM: Hemiscorpius lepturus
```

```
<400> SEQUENCE: 171

Gly Asp Cys Leu Pro His Leu Lys Leu Cys Lys Ala Asp Lys Asp Cys
1               5                   10                  15

Cys Ser Lys Lys Cys Lys Arg Arg Gly Thr Asn Pro Glu Lys Arg Cys
            20                  25                  30

Arg

<210> SEQ ID NO 172
<211> LENGTH: 33
<212> TYPE: PRT
<213> ORGANISM: Unknown
<220> FEATURE:
<223> OTHER INFORMATION: Description of Unknown:
      opicalcin-2 sequence

<400> SEQUENCE: 172

Gly Asp Cys Leu Pro His Leu Lys Arg Cys Lys Glu Asn Asn Asp Cys
1               5                   10                  15

Cys Ser Lys Lys Cys Lys Arg Arg Gly Thr Asn Pro Glu Lys Arg Cys
            20                  25                  30

Arg

<210> SEQ ID NO 173
<211> LENGTH: 33
<212> TYPE: PRT
<213> ORGANISM: Unknown
<220> FEATURE:
<223> OTHER INFORMATION: Description of Unknown:
      opicalcin-1 sequence

<400> SEQUENCE: 173

Gly Asp Cys Leu Pro His Leu Lys Arg Cys Lys Glu Asn Asn Asp Cys
1               5                   10                  15

Cys Ser Lys Lys Cys Lys Arg Arg Gly Ala Asn Pro Glu Lys Arg Cys
            20                  25                  30

Arg

<210> SEQ ID NO 174
<211> LENGTH: 43
<212> TYPE: PRT
<213> ORGANISM: Unknown
<220> FEATURE:
<223> OTHER INFORMATION: Description of Unknown:
      midkine sequence

<400> SEQUENCE: 174

Cys Lys Tyr Lys Phe Glu Asn Trp Gly Ala Cys Asp Gly Gly Thr Gly
1               5                   10                  15

Thr Lys Val Arg Gln Gly Thr Leu Lys Lys Ala Arg Tyr Asn Ala Gln
            20                  25                  30

Cys Gln Glu Thr Ile Arg Val Thr Lys Pro Cys
        35                  40

<210> SEQ ID NO 175
<211> LENGTH: 34
<212> TYPE: PRT
<213> ORGANISM: Momordica cochinchinensis

<400> SEQUENCE: 175

Ser Gly Ser Asp Gly Gly Val Cys Pro Lys Ile Leu Lys Lys Cys Arg
1               5                   10                  15
```

```
Arg Asp Ser Asp Cys Pro Gly Ala Cys Ile Cys Arg Gly Asn Gly Tyr
            20                  25                  30

Cys Gly

<210> SEQ ID NO 176
<211> LENGTH: 36
<212> TYPE: PRT
<213> ORGANISM: Leiurus quinquestriatus

<400> SEQUENCE: 176

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg
        35

<210> SEQ ID NO 177
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Gly Ser Pro Asp Glu Tyr Ile Glu Arg Ala Lys Glu Ser Ser Lys Lys
1               5                   10                  15

Gln Asp Ile Gln Ser Ser Leu Arg Ile Phe Asp Glu Ser Lys Asp Pro
            20                  25                  30

Asn Val Met Leu Ile Ser Leu Phe Ser Trp
        35                  40

<210> SEQ ID NO 178
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Gly Ser Pro Asp Glu Tyr Ile Glu Arg Ala Lys Glu Ser Cys Lys Lys
1               5                   10                  15

Gln Asp Ile Gln Ser Cys Leu Arg Ile Phe Asp Glu Ser Lys Asp Pro
            20                  25                  30

Asn Val Met Leu Ile Cys Leu Phe Cys Trp
        35                  40

<210> SEQ ID NO 179
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Gly Ser Pro Asp Glu Tyr Ile Glu Arg Ala Lys Glu Cys Ser Lys Lys
1               5                   10                  15

Gln Asp Ile Gln Cys Cys Leu Arg Ile Phe Asp Glu Ser Lys Asp Pro
            20                  25                  30
```

Asn Val Met Leu Ile Cys Leu Phe Ser Trp
            35                  40

<210> SEQ ID NO 180
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Gly Ser Pro Asp Glu Tyr Ile Glu Arg Ala Lys Glu Cys Cys Lys Lys
1               5                   10                  15

Gln Asp Ile Gln Cys Ser Leu Arg Ile Phe Asp Glu Ser Lys Asp Pro
            20                  25                  30

Asn Val Met Leu Ile Ser Leu Phe Cys Trp
            35                  40

<210> SEQ ID NO 181
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Gly Ser Pro Asp Glu Tyr Ile Glu Arg Ala Lys Glu Ser Ser Lys Lys
1               5                   10                  15

Gln Asp Ile Gln Ser Cys Leu Arg Ile Phe Asp Glu Ser Lys Asp Pro
            20                  25                  30

Asn Val Met Leu Ile Cys Leu Phe Ser Trp
            35                  40

<210> SEQ ID NO 182
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Gly Ser Pro Asp Glu Tyr Ile Glu Arg Ala Lys Glu Cys Ser Lys Lys
1               5                   10                  15

Gln Asp Ile Gln Cys Ser Leu Arg Ile Phe Asp Glu Ser Lys Asp Pro
            20                  25                  30

Asn Val Met Leu Ile Ser Leu Phe Ser Trp
            35                  40

<210> SEQ ID NO 183
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Gly Ser Pro Asp Glu Tyr Ile Glu Arg Ala Lys Glu Ser Cys Lys Lys
1               5                   10                  15

Gln Asp Ile Gln Ser Ser Leu Arg Ile Phe Asp Glu Ser Lys Asp Pro
            20                  25                  30

Asn Val Met Leu Ile Ser Leu Phe Cys Trp
        35                  40

<210> SEQ ID NO 184
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Gly Ser Pro Asp Glu Tyr Ile Glu Arg Ala Lys Glu Ser Ser Lys Lys
1               5                   10                  15

Gly Asp Ile Gln Ser Ser Leu Arg Tyr Phe Glu Glu Ser Gly Asp Pro
            20                  25                  30

Asn Val Met Leu Ile Ser Leu Phe Ser Pro
        35                  40

<210> SEQ ID NO 185
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Gly Ser Leu Glu Arg Leu Lys Lys Ser Ser Asn Gln Gly Leu Asp Ser
1               5                   10                  15

Glu Glu Ala Arg Trp Lys Ser Glu Leu Glu Ala Leu Phe Gln Gly Lys
            20                  25                  30

Asn Arg Glu Thr Ser Leu Glu Glu Ser
        35                  40

<210> SEQ ID NO 186
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Pro Asp Glu Tyr Ile Glu Arg Ala Lys Glu Ser Ser Lys Lys Gln Asp
1               5                   10                  15

Ile Gln Ser Ser Leu Arg Ile Phe Asp Glu Ser Lys Asp Pro Asn Val
            20                  25                  30

Met Leu Ile Ser Leu Phe Ser Trp
        35                  40

<210> SEQ ID NO 187
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Pro Asp Glu Tyr Ile Glu Arg Ala Lys Glu Ser Cys Lys Lys Gln Asp
1               5                   10                  15

Ile Gln Ser Cys Leu Arg Ile Phe Asp Glu Ser Lys Asp Pro Asn Val

```
                20                  25                  30

Met Leu Ile Cys Leu Phe Cys Trp
            35                  40

<210> SEQ ID NO 188
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Pro Asp Glu Tyr Ile Glu Arg Ala Lys Glu Cys Ser Lys Lys Gln Asp
1               5                   10                  15

Ile Gln Cys Cys Leu Arg Ile Phe Asp Glu Ser Lys Asp Pro Asn Val
            20                  25                  30

Met Leu Ile Cys Leu Phe Ser Trp
            35                  40

<210> SEQ ID NO 189
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Pro Asp Glu Tyr Ile Glu Arg Ala Lys Glu Cys Cys Lys Lys Gln Asp
1               5                   10                  15

Ile Gln Cys Ser Leu Arg Ile Phe Asp Glu Ser Lys Asp Pro Asn Val
            20                  25                  30

Met Leu Ile Ser Leu Phe Cys Trp
            35                  40

<210> SEQ ID NO 190
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Pro Asp Glu Tyr Ile Glu Arg Ala Lys Glu Ser Ser Lys Lys Gln Asp
1               5                   10                  15

Ile Gln Ser Cys Leu Arg Ile Phe Asp Glu Ser Lys Asp Pro Asn Val
            20                  25                  30

Met Leu Ile Cys Leu Phe Ser Trp
            35                  40

<210> SEQ ID NO 191
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Pro Asp Glu Tyr Ile Glu Arg Ala Lys Glu Cys Ser Lys Lys Gln Asp
1               5                   10                  15
```

Ile Gln Cys Ser Leu Arg Ile Phe Asp Glu Ser Lys Asp Pro Asn Val
            20                  25                  30

Met Leu Ile Ser Leu Phe Ser Trp
        35                  40

<210> SEQ ID NO 192
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Pro Asp Glu Tyr Ile Glu Arg Ala Lys Glu Ser Cys Lys Lys Gln Asp
1               5                   10                  15

Ile Gln Ser Ser Leu Arg Ile Phe Asp Glu Ser Lys Asp Pro Asn Val
            20                  25                  30

Met Leu Ile Ser Leu Phe Cys Trp
        35                  40

<210> SEQ ID NO 193
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Pro Asp Glu Tyr Ile Glu Arg Ala Lys Glu Ser Ser Lys Lys Gly Asp
1               5                   10                  15

Ile Gln Ser Ser Leu Arg Tyr Phe Glu Glu Ser Gly Asp Pro Asn Val
            20                  25                  30

Met Leu Ile Ser Leu Phe Ser Pro
        35                  40

<210> SEQ ID NO 194
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Leu Glu Arg Leu Lys Lys Ser Ser Asn Gln Gly Leu Asp Ser Glu Glu
1               5                   10                  15

Ala Arg Trp Lys Ser Glu Leu Glu Ala Leu Phe Gln Gly Lys Asn Arg
            20                  25                  30

Glu Thr Ser Leu Glu Glu Ser
        35

<210> SEQ ID NO 195
<211> LENGTH: 11
<212> TYPE: PRT
<213> ORGANISM: Human immunodeficiency virus

<400> SEQUENCE: 195

Tyr Gly Arg Lys Lys Arg Arg Gln Arg Arg Arg
1               5                   10

<210> SEQ ID NO 196

```
<211> LENGTH: 12
<212> TYPE: PRT
<213> ORGANISM: Human immunodeficiency virus

<400> SEQUENCE: 196

Gly Arg Lys Lys Arg Arg Gln Arg Arg Arg Pro Gln
1               5                   10

<210> SEQ ID NO 197
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Pro Lys Lys Lys Arg Arg Val
1               5

<210> SEQ ID NO 198
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Lys Arg Pro Ala Ala Thr Lys Lys Ala Gly Gln Ala Lys Lys Lys Lys
1               5                   10                  15

<210> SEQ ID NO 199
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Lys Lys Arg Arg
1

<210> SEQ ID NO 200
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Lys Lys Lys Arg Arg
1               5

<210> SEQ ID NO 201
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Lys Lys Lys Lys
1
```

<210> SEQ ID NO 202
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys or Arg
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Lys or Arg

<400> SEQUENCE: 202

Lys Xaa Xaa Xaa
1

<210> SEQ ID NO 203
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Gly Gly Gly Ser
1

<210> SEQ ID NO 204
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Gly Gly Ser Ser Gly
1               5

<210> SEQ ID NO 205
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Gly Gly Gly Gly Gly
1               5

<210> SEQ ID NO 206
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Gly Ser Gly Ser Gly Ser Gly Ser
1               5

<210> SEQ ID NO 207
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Gly Ser Gly Gly
1

<210> SEQ ID NO 208
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Gly Gly Gly Gly Ser
1               5

<210> SEQ ID NO 209
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Gly Gly Ser
1

<210> SEQ ID NO 210
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Gly Gly Gly Ser Gly Gly Gly Ser Gly Gly Gly Ser
1               5                   10

<210> SEQ ID NO 211
<211> LENGTH: 12
<212> TYPE: PRT
<213> ORGANISM: Haplopelma sp.

<400> SEQUENCE: 211

Lys Lys Tyr Lys Pro Tyr Val Pro Val Thr Thr Asn
1               5                   10

<210> SEQ ID NO 212
<211> LENGTH: 10
<212> TYPE: PRT
<213> ORGANISM: Homo sapiens

<400> SEQUENCE: 212

Glu Pro Lys Ser Ser Asp Lys Thr His Thr

<210> SEQ ID NO 213
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
tgtacttcca gggaggatcc                                                 20

<210> SEQ ID NO 214
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
aatggtgatg agcggcc                                                    17

<210> SEQ ID NO 215
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
ccagcaggag gtggaagcg                                                  19

<210> SEQ ID NO 216
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
atgatggtga tgatggtgag atcctc                                          26

<210> SEQ ID NO 217
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid
<220> FEATURE:
<223> OTHER INFORMATION: See specification as filed for detailed
      description of substitutions and preferred embodiments

<400> SEQUENCE: 217

Leu Xaa Xaa Leu Phe
1               5

<210> SEQ ID NO 218
<211> LENGTH: 7
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 218

Leu Xaa Xaa Phe Glu Xaa Ser
1               5

<210> SEQ ID NO 219
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid

<400> SEQUENCE: 219

Leu Xaa Xaa Phe Glu Xaa Ser Xaa Asp Pro Asn Val Met Leu
1               5                   10

<210> SEQ ID NO 220
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (14)..(15)
<223> OTHER INFORMATION: Any amino acid

<400> SEQUENCE: 220

Leu Xaa Xaa Phe Glu Xaa Ser Xaa Asp Pro Asn Val Met Xaa Xaa Leu
1               5                   10                  15
Phe

<210> SEQ ID NO 221
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Met Leu Ile Cys Leu Phe
1               5

<210> SEQ ID NO 222
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Gly Arg Lys Lys Arg Arg Gln Arg Arg Gly Gly Ser Pro Asp Glu
1               5                   10                  15

Tyr Ile Glu Arg Ala Lys Glu Cys Cys Lys Lys Gln Asp Ile Gln Cys
            20                  25                  30

Cys Leu Arg Ile Phe Asp Glu Ser Lys Asp Pro Asn Val Met Leu Ile
        35                  40                  45

Cys Leu Phe Cys Trp
    50

<210> SEQ ID NO 223
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Cys Tyr Arg Lys Lys Arg Arg Gln Arg Arg Gly Gly Ser Pro Asp
1               5                   10                  15

Glu Tyr Ile Glu Arg Ala Lys Glu Cys Cys Lys Lys Gln Asp Ile Gln
            20                  25                  30

Cys Cys Leu Arg Ile Phe Asp Glu Ser Lys Asp Pro Asn Val Met Leu
        35                  40                  45

Ile Cys Leu Phe Cys Trp
    50

<210> SEQ ID NO 224
<211> LENGTH: 72
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Pro Phe Val Ile Gly Ala Gly Val Leu Gly Ala Leu Gly Thr Gly Ile
1               5                   10                  15

Gly Gly Ile Gly Arg Lys Lys Arg Arg Gln Arg Arg Gly Gly Ser
            20                  25                  30

Pro Asp Glu Tyr Ile Glu Arg Ala Lys Glu Cys Cys Lys Lys Gln Asp
        35                  40                  45

Ile Gln Cys Cys Leu Arg Ile Phe Asp Glu Ser Lys Asp Pro Asn Val
    50                  55                  60
```

```
Met Leu Ile Cys Leu Phe Cys Trp
 65                  70
```

<210> SEQ ID NO 225
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

```
Phe Phe Leu Ile Pro Lys Gly Gly Arg Lys Arg Arg Gln Arg Arg
  1               5                  10                  15

Arg Gly Gly Ser Pro Asp Glu Tyr Ile Glu Arg Ala Lys Glu Cys Cys
                 20                  25                  30

Lys Lys Gln Asp Ile Gln Cys Cys Leu Arg Ile Phe Asp Glu Ser Lys
             35                  40                  45

Asp Pro Asn Val Met Leu Ile Cys Leu Phe Cys Trp
         50                  55                  60
```

<210> SEQ ID NO 226
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

```
Arg Arg Arg Arg Arg Arg Arg Gly Gly Ser Pro Asp Glu Tyr Ile
  1               5                  10                  15

Glu Arg Ala Lys Glu Cys Cys Lys Lys Gln Asp Ile Gln Cys Cys Leu
                 20                  25                  30

Arg Ile Phe Asp Glu Ser Lys Asp Pro Asn Val Met Leu Ile Cys Leu
             35                  40                  45

Phe Cys Trp
         50
```

<210> SEQ ID NO 227
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

```
Phe Phe Leu Ile Pro Lys Gly Arg Arg Arg Arg Arg Arg Arg Gly
  1               5                  10                  15

Gly Ser Pro Asp Glu Tyr Ile Glu Arg Ala Lys Glu Cys Cys Lys Lys
                 20                  25                  30

Gln Asp Ile Gln Cys Cys Leu Arg Ile Phe Asp Glu Ser Lys Asp Pro
             35                  40                  45

Asn Val Met Leu Ile Cys Leu Phe Cys Trp
         50                  55
```

<210> SEQ ID NO 228
<211> LENGTH: 59
<212> TYPE: PRT
<213> ORGANISM: Artificial Sequence
<220> FEATURE:

```
<223> OTHER INFORMATION: Description of Artificial Sequence: Synthetic
      polypeptide

<400> SEQUENCE: 228

Arg Gln Ile Lys Ile Trp Phe Gln Asn Arg Met Lys Trp Lys Lys
1               5                   10                  15

Gly Gly Ser Pro Asp Glu Tyr Ile Glu Arg Ala Lys Glu Cys Cys Lys
            20                  25                  30

Lys Gln Asp Ile Gln Cys Cys Leu Arg Ile Phe Asp Glu Ser Lys Asp
        35                  40                  45

Pro Asn Val Met Leu Ile Cys Leu Phe Cys Trp
    50                  55

<210> SEQ ID NO 229
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Gly Ser Phe Phe Leu Ile Pro Lys Gly Arg Gln Ile Lys Ile Trp Phe
1               5                   10                  15

Gln Asn Arg Arg Met Lys Trp Lys Lys Gly Gly Ser Pro Asp Glu Tyr
            20                  25                  30

Ile Glu Arg Ala Lys Glu Cys Cys Lys Lys Gln Asp Ile Gln Cys Cys
        35                  40                  45

Leu Arg Ile Phe Asp Glu Ser Lys Asp Pro Asn Val Met Leu Ile Cys
    50                  55                  60

Leu Phe Cys Trp
65

<210> SEQ ID NO 230
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Phe Phe Leu Ile Pro Lys Gly Arg Arg Arg Asn Arg Thr Arg Arg
1               5                   10                  15

Asn Arg Arg Val Arg Gly Gly Ser Pro Asp Glu Tyr Ile Glu Arg
            20                  25                  30

Ala Lys Glu Cys Cys Lys Lys Gln Asp Ile Gln Cys Cys Leu Arg Ile
        35                  40                  45

Phe Asp Glu Ser Lys Asp Pro Asn Val Met Leu Ile Cys Leu Phe Cys
    50                  55                  60

Trp
65

<210> SEQ ID NO 231
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231
```

Gly Asp Ala Leu Pro His Leu Lys Leu Gly Gly Ser Pro Asp Glu Tyr
1               5                   10                  15

Ile Glu Arg Ala Lys Glu Cys Cys Lys Lys Gln Asp Ile Gln Cys Cys
                20                  25                  30

Leu Arg Ile Phe Asp Glu Ser Lys Asp Pro Asn Val Met Leu Ile Cys
            35                  40                  45

Leu Phe Cys Trp
            50

<210> SEQ ID NO 232
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Gly Asp Ala Leu Pro His Leu Lys Arg Gly Gly Ser Pro Asp Glu Tyr
1               5                   10                  15

Ile Glu Arg Ala Lys Glu Cys Cys Lys Lys Gln Asp Ile Gln Cys Cys
                20                  25                  30

Leu Arg Ile Phe Asp Glu Ser Lys Asp Pro Asn Val Met Leu Ile Cys
            35                  40                  45

Leu Phe Cys Trp
            50

<210> SEQ ID NO 233
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Ser Glu Lys Asp Ala Ile Lys His Leu Gln Arg Gly Gly Ser Pro Asp
1               5                   10                  15

Glu Tyr Ile Glu Arg Ala Lys Glu Cys Cys Lys Lys Gln Asp Ile Gln
                20                  25                  30

Cys Cys Leu Arg Ile Phe Asp Glu Ser Lys Asp Pro Asn Val Met Leu
            35                  40                  45

Ile Cys Leu Phe Cys Trp
            50

<210> SEQ ID NO 234
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Lys Asp Ala Ile Lys His Leu Gln Arg Gly Gly Ser Pro Asp Glu Tyr
1               5                   10                  15

Ile Glu Arg Ala Lys Glu Cys Cys Lys Lys Gln Asp Ile Gln Cys Cys
                20                  25                  30

Leu Arg Ile Phe Asp Glu Ser Lys Asp Pro Asn Val Met Leu Ile Cys
            35                  40                  45

```
Leu Phe Cys Trp
    50

<210> SEQ ID NO 235
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Val Leu Asp Ser Leu Glu Phe Ile Ala Ser Lys Leu Gly Gly Ser Pro
1               5                   10                  15

Asp Glu Tyr Ile Glu Arg Ala Lys Glu Cys Cys Lys Lys Gln Asp Ile
            20                  25                  30

Gln Cys Cys Leu Arg Ile Phe Asp Glu Ser Lys Asp Pro Asn Val Met
        35                  40                  45

Leu Ile Cys Leu Phe Cys Trp
    50                  55

<210> SEQ ID NO 236
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Pro Asp Glu Tyr Ile Glu Arg Ala Lys Glu Cys Cys Lys Lys Phe Phe
1               5                   10                  15

Arg Arg Arg Arg Asp Ile Gln Cys Cys Leu Arg Ile Phe Asp Glu Ser
            20                  25                  30

Lys Asp Pro Asn Val Met Leu Ile Cys Leu Phe Cys Trp
        35                  40                  45

<210> SEQ ID NO 237
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Lys Ala Val Leu Gly Ala Thr Lys Ile Asp Leu Pro Val Asp Ile Asn
1               5                   10                  15

Asp Pro Tyr Asp Leu Gly Leu Leu Arg His Leu Arg His His Ser
            20                  25                  30

Asn Leu Leu Ala Asn Ile Gly Asp Pro Ala Val Arg Glu Gln Val Leu
        35                  40                  45

Ser Ala Met Gln Glu Glu Glu Gly Gly Ser Pro Asp Glu Tyr Ile Glu
    50                  55                  60

Arg Ala Lys Glu Cys Cys Lys Lys Gln Asp Ile Gln Cys Cys Leu Arg
65                  70                  75                  80

Ile Phe Asp Glu Ser Lys Asp Pro Asn Val Met Leu Ile Cys Leu Phe
                85                  90                  95

Cys Trp

<210> SEQ ID NO 238
```

<211> LENGTH: 71
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Leu Ser Thr Ala Ala Asp Met Gln Gly Val Val Thr Asp Gly Met Ala
1               5                   10                  15

Ser Gly Leu Asp Lys Asp Tyr Leu Lys Pro Asp Asp Gly Gly Ser Pro
            20                  25                  30

Asp Glu Tyr Ile Glu Arg Ala Lys Glu Cys Cys Lys Lys Gln Asp Ile
        35                  40                  45

Gln Cys Cys Leu Arg Ile Phe Asp Glu Ser Lys Asp Pro Asn Val Met
    50                  55                  60

Leu Ile Cys Leu Phe Cys Trp
65                  70

<210> SEQ ID NO 239
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Arg Arg Trp Arg Arg Trp Asn Arg Phe Asn Arg Arg Arg Cys Arg Gly
1               5                   10                  15

Gly Ser Pro Asp Glu Tyr Ile Glu Arg Ala Lys Glu Cys Cys Lys Lys
            20                  25                  30

Gln Asp Ile Gln Cys Cys Leu Arg Ile Phe Asp Glu Ser Lys Asp Pro
        35                  40                  45

Asn Val Met Leu Ile Cys Leu Phe Cys Trp
    50                  55

<210> SEQ ID NO 240
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Arg Ala Gly Leu Gln Phe Pro Val Gly Arg Leu Leu Arg Arg Leu Leu
1               5                   10                  15

Arg Gly Gly Ser Pro Asp Glu Tyr Ile Glu Arg Ala Lys Glu Cys Cys
            20                  25                  30

Lys Lys Gln Asp Ile Gln Cys Cys Leu Arg Ile Phe Asp Glu Ser Lys
        35                  40                  45

Asp Pro Asn Val Met Leu Ile Cys Leu Phe Cys Trp
    50                  55                  60

<210> SEQ ID NO 241
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Lys Arg Ala His His Asn Ala Leu Glu Arg Lys Arg Gly Gly Ser
1               5                   10                  15

Pro Asp Glu Tyr Ile Glu Arg Ala Lys Glu Cys Cys Lys Lys Gln Asp
                20                  25                  30

Ile Gln Cys Cys Leu Arg Ile Phe Asp Glu Ser Lys Asp Pro Asn Val
            35                  40                  45

Met Leu Ile Cys Leu Phe Cys Trp
    50                  55

<210> SEQ ID NO 242
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Arg Arg Met Lys Ala Asn Ala Arg Glu Arg Asn Arg Met Gly Gly Ser
1               5                   10                  15

Pro Asp Glu Tyr Ile Glu Arg Ala Lys Glu Cys Cys Lys Lys Gln Asp
                20                  25                  30

Ile Gln Cys Cys Leu Arg Ile Phe Asp Glu Ser Lys Asp Pro Asn Val
            35                  40                  45

Met Leu Ile Cys Leu Phe Cys Trp
    50                  55

<210> SEQ ID NO 243
<211> LENGTH: 61
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Leu Leu Ile Ile Leu Arg Arg Arg Ile Arg Lys Gln Ala His Ala His
1               5                   10                  15

Ser Lys Gly Gly Ser Pro Asp Glu Tyr Ile Glu Arg Ala Lys Glu Cys
                20                  25                  30

Cys Lys Lys Gln Asp Ile Gln Cys Cys Leu Arg Ile Phe Asp Glu Ser
            35                  40                  45

Lys Asp Pro Asn Val Met Leu Ile Cys Leu Phe Cys Trp
    50                  55                  60

<210> SEQ ID NO 244
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Arg Arg Leu Ser Tyr Ser Arg Arg Phe Gly Gly Ser Pro Asp Glu
1               5                   10              15

Tyr Ile Glu Arg Ala Lys Glu Cys Cys Lys Lys Gln Asp Ile Gln Cys
                20                  25                  30

Cys Leu Arg Ile Phe Asp Glu Ser Lys Asp Pro Asn Val Met Leu Ile
            35                  40                  45

Cys Leu Phe Cys Trp
    50

<210> SEQ ID NO 245
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Val Lys Arg Gly Leu Lys Leu Arg His Val Arg Pro Arg Val Thr Arg
1               5                   10                  15

Met Asp Val Gly Gly Ser Pro Asp Glu Tyr Ile Glu Arg Ala Lys Glu
            20                  25                  30

Cys Cys Lys Lys Gln Asp Ile Gln Cys Cys Leu Arg Ile Phe Asp Glu
        35                  40                  45

Ser Lys Asp Pro Asn Val Met Leu Ile Cys Leu Phe Cys Trp
    50                  55                  60

<210> SEQ ID NO 246
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Cys Ser Ile Pro Pro Glu Val Lys Phe Asn Lys Pro Phe Val Tyr Leu
1               5                   10                  15

Ile Gly Gly Ser Pro Asp Glu Tyr Ile Glu Arg Ala Lys Glu Cys Cys
            20                  25                  30

Lys Lys Gln Asp Ile Gln Cys Cys Leu Arg Ile Phe Asp Glu Ser Lys
        35                  40                  45

Asp Pro Asn Val Met Leu Ile Cys Leu Phe Cys Trp
    50                  55                  60

<210> SEQ ID NO 247
<211> LENGTH: 70
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu Gly Gly Ser Pro Asp
            20                  25                  30

Glu Tyr Ile Glu Arg Ala Lys Glu Cys Cys Lys Lys Gln Asp Ile Gln
            35                  40                  45

Cys Cys Leu Arg Ile Phe Asp Glu Ser Lys Asp Pro Asn Val Met Leu
        50                  55                  60

Ile Cys Leu Phe Cys Trp
65                  70

<210> SEQ ID NO 248
<211> LENGTH: 60

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Lys Gly Glu Gly Ala Ala Val Leu Leu Pro Val Leu Leu Ala Ala Pro
1               5                   10                  15

Gly Gly Gly Ser Pro Asp Glu Tyr Ile Glu Arg Ala Lys Glu Cys Cys
            20                  25                  30

Lys Lys Gln Asp Ile Gln Cys Cys Leu Arg Ile Phe Asp Glu Ser Lys
        35                  40                  45

Asp Pro Asn Val Met Leu Ile Cys Leu Phe Cys Trp
    50                  55                  60

<210> SEQ ID NO 249
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

Lys Cys Phe Gln Trp Gln Arg Asn Met Arg Lys Val Arg Gly Pro Pro
1               5                   10                  15

Val Ser Cys Ile Lys Arg Gly Gly Ser Pro Asp Glu Tyr Ile Glu Arg
            20                  25                  30

Ala Lys Glu Cys Cys Lys Lys Gln Asp Ile Gln Cys Cys Leu Arg Ile
        35                  40                  45

Phe Asp Glu Ser Lys Asp Pro Asn Val Met Leu Ile Cys Leu Phe Cys
    50                  55                  60

Trp
65

<210> SEQ ID NO 250
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Pro Phe Val Tyr Leu Ile Gly Gly Ser Pro Asp Glu Tyr Ile Glu Arg
1               5                   10                  15

Ala Lys Glu Cys Cys Lys Lys Gln Asp Ile Gln Cys Cys Leu Arg Ile
            20                  25                  30

Phe Asp Glu Ser Lys Asp Pro Asn Val Met Leu Ile Cys Leu Phe Cys
        35                  40                  45

Trp

<210> SEQ ID NO 251
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Arg Arg Arg Arg Arg Arg Arg Gly Gly Ser Pro Asp Glu Tyr
1               5                   10                  15

Ile Glu Arg Ala Lys Glu Cys Cys Lys Lys Gly Asp Ile Gln Cys Cys
            20                  25                  30

Leu Arg Tyr Phe Glu Glu Ser Gly Asp Pro Asn Val Met Leu Ile Cys
        35                  40                  45

Leu Phe Cys Pro
    50

<210> SEQ ID NO 252
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Tyr Gly Arg Lys Lys Arg Arg Gln Arg Arg Gly Gly Gly Ser Pro
1               5                   10                  15

Asp Glu Tyr Ile Glu Arg Ala Lys Glu Cys Cys Lys Lys Gly Asp Ile
            20                  25                  30

Gln Cys Cys Leu Arg Tyr Phe Glu Glu Ser Gly Asp Pro Asn Val Met
        35                  40                  45

Leu Ile Cys Leu Phe Cys Pro
    50                  55

<210> SEQ ID NO 253
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 253

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg Gly Gly Ser Gly Gly Gly Ser Gly Gly Ser
        35                  40                  45

Pro Asp Glu Tyr Ile Glu Arg Ala Lys Glu Cys Cys Lys Lys Gln Asp
    50                  55                  60

Ile Gln Cys Cys Leu Arg Ile Phe Asp Glu Ser Lys Asp Pro Asn Val
65                  70                  75                  80

Met Leu Ile Cys Leu Phe Cys Trp
                85

<210> SEQ ID NO 254
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln 20                  25                  30

Cys Leu Cys Arg Lys Lys Tyr Lys Pro Tyr Val Pro Val Thr Thr Asn
            35                  40                  45

Pro Asp Glu Tyr Ile Glu Arg Ala Lys Glu Cys Cys Lys Lys Gln Asp
        50                  55                  60

Ile Gln Cys Cys Leu Arg Ile Phe Asp Glu Ser Lys Asp Pro Asn Val
65                  70                  75                  80

Met Leu Ile Cys Leu Phe Cys Trp
                85

<210> SEQ ID NO 255
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg Glu Pro Lys Ser Ser Asp Lys Thr His Thr Pro Asp
        35                  40                  45

Glu Tyr Ile Glu Arg Ala Lys Glu Cys Cys Lys Lys Gln Asp Ile Gln
    50                  55                  60

Cys Cys Leu Arg Ile Phe Asp Glu Ser Lys Asp Pro Asn Val Met Leu
65                  70                  75                  80

Ile Cys Leu Phe Cys Trp
                85

<210> SEQ ID NO 256
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

Gly Asp Cys Leu Pro His Leu Lys Leu Cys Lys Glu Asn Lys Asp Cys
1               5                   10                  15

Cys Ser Lys Lys Cys Lys Arg Arg Gly Thr Asn Ile Glu Lys Arg Cys
            20                  25                  30

Arg Gly Gly Ser Gly Gly Gly Ser Gly Gly Gly Ser Pro Asp Glu
        35                  40                  45

Tyr Ile Glu Arg Ala Lys Glu Cys Cys Lys Lys Gln Asp Ile Gln Cys
    50                  55                  60

Cys Leu Arg Ile Phe Asp Glu Ser Lys Asp Pro Asn Val Met Leu Ile
65                  70                  75                  80

Cys Leu Phe Cys Trp
                85

<210> SEQ ID NO 257
<211> LENGTH: 85
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 257

Gly Asp Cys Leu Pro His Leu Lys Leu Cys Lys Glu Asn Lys Asp Cys
1               5                   10                  15

Cys Ser Lys Lys Cys Lys Arg Arg Gly Thr Asn Ile Glu Lys Arg Cys
            20                  25                  30

Arg Lys Lys Tyr Lys Pro Tyr Val Pro Val Thr Thr Asn Pro Asp Glu
        35                  40                  45

Tyr Ile Glu Arg Ala Lys Glu Cys Cys Lys Lys Gln Asp Ile Gln Cys
    50                  55                  60

Cys Leu Arg Ile Phe Asp Glu Ser Lys Asp Pro Asn Val Met Leu Ile
65                  70                  75                  80

Cys Leu Phe Cys Trp
                85

<210> SEQ ID NO 258
<211> LENGTH: 83
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Gly Asp Cys Leu Pro His Leu Lys Leu Cys Lys Glu Asn Lys Asp Cys
1               5                   10                  15

Cys Ser Lys Lys Cys Lys Arg Arg Gly Thr Asn Ile Glu Lys Arg Cys
            20                  25                  30

Arg Glu Pro Lys Ser Ser Asp Lys Thr His Thr Pro Asp Glu Tyr Ile
        35                  40                  45

Glu Arg Ala Lys Glu Cys Cys Lys Lys Gln Asp Ile Gln Cys Cys Leu
    50                  55                  60

Arg Ile Phe Asp Glu Ser Lys Asp Pro Asn Val Met Leu Ile Cys Leu
65                  70                  75                  80

Phe Cys Trp

<210> SEQ ID NO 259
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Gly Asp Cys Leu Pro His Leu Lys Arg Cys Lys Ala Asp Asn Asp Cys
1               5                   10                  15

Cys Gly Lys Lys Cys Lys Arg Arg Gly Thr Asn Ala Glu Lys Arg Cys
            20                  25                  30

Arg Gly Gly Gly Ser Gly Gly Ser Gly Gly Ser Pro Asp Glu
        35                  40                  45

Tyr Ile Glu Arg Ala Lys Glu Cys Cys Lys Lys Gln Asp Ile Gln Cys
    50                  55                  60

Cys Leu Arg Ile Phe Asp Glu Ser Lys Asp Pro Asn Val Met Leu Ile
65                  70                  75                  80

Cys Leu Phe Cys Trp
                85

<210> SEQ ID NO 260
<211> LENGTH: 85
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 260

Gly Asp Cys Leu Pro His Leu Lys Arg Cys Lys Ala Asp Asn Asp Cys
1               5                   10                  15

Cys Gly Lys Lys Cys Lys Arg Arg Gly Thr Asn Ala Glu Lys Arg Cys
            20                  25                  30

Arg Lys Lys Tyr Lys Pro Tyr Val Pro Val Thr Thr Asn Pro Asp Glu
        35                  40                  45

Tyr Ile Glu Arg Ala Lys Glu Cys Cys Lys Lys Gln Asp Ile Gln Cys
    50                  55                  60

Cys Leu Arg Ile Phe Asp Glu Ser Lys Asp Pro Asn Val Met Leu Ile
65                  70                  75                  80

Cys Leu Phe Cys Trp
            85

<210> SEQ ID NO 261
<211> LENGTH: 83
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 261

Gly Asp Cys Leu Pro His Leu Lys Arg Cys Lys Ala Asp Asn Asp Cys
1               5                   10                  15

Cys Gly Lys Lys Cys Lys Arg Arg Gly Thr Asn Ala Glu Lys Arg Cys
            20                  25                  30

Arg Glu Pro Lys Ser Ser Asp Lys Thr His Thr Pro Asp Glu Tyr Ile
        35                  40                  45

Glu Arg Ala Lys Glu Cys Cys Lys Lys Gln Asp Ile Gln Cys Cys Leu
    50                  55                  60

Arg Ile Phe Asp Glu Ser Lys Asp Pro Asn Val Met Leu Ile Cys Leu
65                  70                  75                  80

Phe Cys Trp

<210> SEQ ID NO 262
<211> LENGTH: 85
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 262

Gly Asp Cys Leu Pro His Leu Lys Leu Cys Lys Ala Asp Lys Asp Cys
1               5                   10                  15

Cys Ser Lys Cys Lys Arg Arg Gly Thr Asn Pro Glu Lys Arg Cys
            20                  25                  30

Arg Gly Gly Gly Ser Gly Gly Ser Gly Gly Ser Pro Asp Glu
        35                  40                  45

Tyr Ile Glu Arg Ala Lys Glu Cys Cys Lys Lys Gln Asp Ile Gln Cys
    50                  55                  60

```
Cys Leu Arg Ile Phe Asp Glu Ser Lys Asp Pro Asn Val Met Leu Ile
 65                  70                  75                  80

Cys Leu Phe Cys Trp
                 85

<210> SEQ ID NO 263
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 263

Gly Asp Cys Leu Pro His Leu Lys Leu Cys Lys Ala Asp Lys Asp Cys
1               5                   10                  15

Cys Ser Lys Lys Cys Lys Arg Arg Gly Thr Asn Pro Glu Lys Arg Cys
            20                  25                  30

Arg Lys Lys Tyr Lys Pro Tyr Val Pro Val Thr Thr Asn Pro Asp Glu
        35                  40                  45

Tyr Ile Glu Arg Ala Lys Glu Cys Cys Lys Lys Gln Asp Ile Gln Cys
 50                  55                  60

Cys Leu Arg Ile Phe Asp Glu Ser Lys Asp Pro Asn Val Met Leu Ile
 65                  70                  75                  80

Cys Leu Phe Cys Trp
                 85

<210> SEQ ID NO 264
<211> LENGTH: 83
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Gly Asp Cys Leu Pro His Leu Lys Leu Cys Lys Ala Asp Lys Asp Cys
1               5                   10                  15

Cys Ser Lys Lys Cys Lys Arg Arg Gly Thr Asn Pro Glu Lys Arg Cys
            20                  25                  30

Arg Glu Pro Lys Ser Ser Asp Lys Thr His Thr Pro Asp Glu Tyr Ile
        35                  40                  45

Glu Arg Ala Lys Glu Cys Cys Lys Lys Gln Asp Ile Gln Cys Cys Leu
 50                  55                  60

Arg Ile Phe Asp Glu Ser Lys Asp Pro Asn Val Met Leu Ile Cys Leu
 65                  70                  75                  80

Phe Cys Trp

<210> SEQ ID NO 265
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

Gly Asp Cys Leu Pro His Leu Lys Arg Cys Lys Glu Asn Asn Asp Cys
1               5                   10                  15

Cys Ser Lys Lys Cys Lys Arg Arg Gly Thr Asn Pro Glu Lys Arg Cys
```

-continued

```
                 20                  25                  30
Arg Gly Gly Gly Ser Gly Gly Ser Gly Gly Gly Ser Pro Asp Glu
             35                  40                  45

Tyr Ile Glu Arg Ala Lys Glu Cys Cys Lys Lys Gln Asp Ile Gln Cys
         50                  55                  60

Cys Leu Arg Ile Phe Asp Glu Ser Lys Asp Pro Asn Val Met Leu Ile
65                  70                  75                  80

Cys Leu Phe Cys Trp
                85

<210> SEQ ID NO 266
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Gly Asp Cys Leu Pro His Leu Lys Arg Cys Lys Glu Asn Asn Asp Cys
1               5                   10                  15

Cys Ser Lys Lys Cys Lys Arg Arg Gly Thr Asn Pro Glu Lys Arg Cys
            20                  25                  30

Arg Lys Lys Tyr Lys Pro Tyr Val Pro Val Thr Thr Asn Pro Asp Glu
         35                  40                  45

Tyr Ile Glu Arg Ala Lys Glu Cys Cys Lys Lys Gln Asp Ile Gln Cys
     50                  55                  60

Cys Leu Arg Ile Phe Asp Glu Ser Lys Asp Pro Asn Val Met Leu Ile
65                  70                  75                  80

Cys Leu Phe Cys Trp
                85

<210> SEQ ID NO 267
<211> LENGTH: 83
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

Gly Asp Cys Leu Pro His Leu Lys Arg Cys Lys Glu Asn Asn Asp Cys
1               5                   10                  15

Cys Ser Lys Lys Cys Lys Arg Arg Gly Thr Asn Pro Glu Lys Arg Cys
            20                  25                  30

Arg Glu Pro Lys Ser Ser Asp Lys Thr His Thr Pro Asp Glu Tyr Ile
         35                  40                  45

Glu Arg Ala Lys Glu Cys Cys Lys Lys Gln Asp Ile Gln Cys Cys Leu
     50                  55                  60

Arg Ile Phe Asp Glu Ser Lys Asp Pro Asn Val Met Leu Ile Cys Leu
65                  70                  75                  80

Phe Cys Trp

<210> SEQ ID NO 268
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 268

Gly Asp Cys Leu Pro His Leu Lys Arg Cys Lys Glu Asn Asn Asp Cys
1               5                   10                  15

Cys Ser Lys Lys Cys Lys Arg Arg Gly Ala Asn Pro Glu Lys Arg Cys
            20                  25                  30

Arg Gly Gly Gly Ser Gly Gly Gly Ser Gly Gly Gly Ser Pro Asp Glu
        35                  40                  45

Tyr Ile Glu Arg Ala Lys Glu Cys Cys Lys Lys Gln Asp Ile Gln Cys
50                  55                  60

Cys Leu Arg Ile Phe Asp Glu Ser Lys Asp Pro Asn Val Met Leu Ile
65                  70                  75                  80

Cys Leu Phe Cys Trp
                85

<210> SEQ ID NO 269
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 269

Gly Asp Cys Leu Pro His Leu Lys Arg Cys Lys Glu Asn Asn Asp Cys
1               5                   10                  15

Cys Ser Lys Lys Cys Lys Arg Arg Gly Ala Asn Pro Glu Lys Arg Cys
            20                  25                  30

Arg Lys Lys Tyr Lys Pro Tyr Val Pro Val Thr Thr Asn Pro Asp Glu
        35                  40                  45

Tyr Ile Glu Arg Ala Lys Glu Cys Cys Lys Lys Gln Asp Ile Gln Cys
50                  55                  60

Cys Leu Arg Ile Phe Asp Glu Ser Lys Asp Pro Asn Val Met Leu Ile
65                  70                  75                  80

Cys Leu Phe Cys Trp
                85

<210> SEQ ID NO 270
<211> LENGTH: 83
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 270

Gly Asp Cys Leu Pro His Leu Lys Arg Cys Lys Glu Asn Asn Asp Cys
1               5                   10                  15

Cys Ser Lys Lys Cys Lys Arg Arg Gly Ala Asn Pro Glu Lys Arg Cys
            20                  25                  30

Arg Glu Pro Lys Ser Ser Asp Lys Thr His Thr Pro Glu Tyr Ile
        35                  40                  45

Glu Arg Ala Lys Glu Cys Cys Lys Lys Gln Asp Ile Gln Cys Cys Leu
50                  55                  60

Arg Ile Phe Asp Glu Ser Lys Asp Pro Asn Val Met Leu Ile Cys Leu
65                  70                  75                  80

Phe Cys Trp
```

```
<210> SEQ ID NO 271
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 271

Ser Glu Lys Asp Cys Ile Lys His Leu Gln Arg Cys Arg Glu Asn Lys
1               5                   10                  15

Asp Cys Cys Ser Lys Lys Cys Ser Arg Arg Gly Thr Asn Pro Glu Lys
            20                  25                  30

Arg Cys Arg Gly Gly Ser Gly Gly Ser Gly Gly Ser Pro
        35                  40                  45

Asp Glu Tyr Ile Glu Arg Ala Lys Glu Cys Cys Lys Lys Gln Asp Ile
50                  55                  60

Gln Cys Cys Leu Arg Ile Phe Asp Glu Ser Lys Asp Pro Asn Val Met
65                  70                  75                  80

Leu Ile Cys Leu Phe Cys Trp
                85

<210> SEQ ID NO 272
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272

Ser Glu Lys Asp Cys Ile Lys His Leu Gln Arg Cys Arg Glu Asn Lys
1               5                   10                  15

Asp Cys Cys Ser Lys Lys Cys Ser Arg Arg Gly Thr Asn Pro Glu Lys
            20                  25                  30

Arg Cys Arg Lys Lys Tyr Lys Pro Tyr Val Pro Val Thr Thr Asn Pro
        35                  40                  45

Asp Glu Tyr Ile Glu Arg Ala Lys Glu Cys Cys Lys Lys Gln Asp Ile
50                  55                  60

Gln Cys Cys Leu Arg Ile Phe Asp Glu Ser Lys Asp Pro Asn Val Met
65                  70                  75                  80

Leu Ile Cys Leu Phe Cys Trp
                85

<210> SEQ ID NO 273
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 273

Ser Glu Lys Asp Cys Ile Lys His Leu Gln Arg Cys Arg Glu Asn Lys
1               5                   10                  15

Asp Cys Cys Ser Lys Lys Cys Ser Arg Arg Gly Thr Asn Pro Glu Lys
            20                  25                  30

Arg Cys Arg Glu Pro Lys Ser Ser Asp Lys Thr His Thr Pro Asp Glu
        35                  40                  45

Tyr Ile Glu Arg Ala Lys Glu Cys Cys Lys Lys Gln Asp Ile Gln Cys
50                  55                  60
```

Cys Leu Arg Ile Phe Asp Glu Ser Lys Asp Pro Asn Val Met Leu Ile
65                  70                  75                  80

Cys Leu Phe Cys Trp
                85

<210> SEQ ID NO 274
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 274

Cys Lys Tyr Lys Phe Glu Asn Trp Gly Ala Cys Asp Gly Gly Thr Gly
1               5                   10                  15

Thr Lys Val Arg Gln Gly Thr Leu Lys Lys Ala Arg Tyr Asn Ala Gln
            20                  25                  30

Cys Gln Glu Thr Ile Arg Val Thr Lys Pro Cys Gly Gly Ser Gly
        35                  40                  45

Gly Gly Ser Gly Gly Ser Pro Asp Glu Tyr Ile Glu Arg Ala Lys
    50                  55                  60

Glu Cys Cys Lys Lys Gln Asp Ile Gln Cys Cys Leu Arg Ile Phe Asp
65                  70                  75                  80

Glu Ser Lys Asp Pro Asn Val Met Leu Ile Cys Leu Phe Cys Trp
            85                  90                  95

<210> SEQ ID NO 275
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 275

Cys Lys Tyr Lys Phe Glu Asn Trp Gly Ala Cys Asp Gly Gly Thr Gly
1               5                   10                  15

Thr Lys Val Arg Gln Gly Thr Leu Lys Lys Ala Arg Tyr Asn Ala Gln
            20                  25                  30

Cys Gln Glu Thr Ile Arg Val Thr Lys Pro Cys Lys Lys Tyr Lys Pro
        35                  40                  45

Tyr Val Pro Val Thr Thr Asn Pro Asp Glu Tyr Ile Glu Arg Ala Lys
    50                  55                  60

Glu Cys Cys Lys Lys Gln Asp Ile Gln Cys Cys Leu Arg Ile Phe Asp
65                  70                  75                  80

Glu Ser Lys Asp Pro Asn Val Met Leu Ile Cys Leu Phe Cys Trp
            85                  90                  95

<210> SEQ ID NO 276
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

Cys Lys Tyr Lys Phe Glu Asn Trp Gly Ala Cys Asp Gly Gly Thr Gly
1               5                   10                  15

Thr Lys Val Arg Gln Gly Thr Leu Lys Lys Ala Arg Tyr Asn Ala Gln
            20                  25                  30

Cys Gln Glu Thr Ile Arg Val Thr Lys Pro Cys Glu Pro Lys Ser Ser
        35                  40                  45

Asp Lys Thr His Thr Pro Asp Glu Tyr Ile Glu Arg Ala Lys Glu Cys
    50                  55                  60

Cys Lys Lys Gln Asp Ile Gln Cys Cys Leu Arg Ile Phe Asp Glu Ser
65                  70                  75                  80

Lys Asp Pro Asn Val Met Leu Ile Cys Leu Phe Cys Trp
                85                  90

<210> SEQ ID NO 277
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 277

Ser Gly Ser Asp Gly Gly Val Cys Pro Lys Ile Leu Lys Lys Cys Arg
1               5                   10                  15

Arg Asp Ser Asp Cys Pro Gly Ala Cys Ile Cys Arg Gly Asn Gly Tyr
            20                  25                  30

Cys Gly Gly Gly Ser Gly Gly Ser Gly Gly Ser Pro Asp
        35                  40                  45

Glu Tyr Ile Glu Arg Ala Lys Glu Cys Lys Lys Gln Asp Ile Gln
    50                  55                  60

Cys Cys Leu Arg Ile Phe Asp Glu Ser Lys Asp Pro Asn Val Met Leu
65                  70                  75                  80

Ile Cys Leu Phe Cys Trp
                85

<210> SEQ ID NO 278
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 278

Ser Gly Ser Asp Gly Gly Val Cys Pro Lys Ile Leu Lys Lys Cys Arg
1               5                   10                  15

Arg Asp Ser Asp Cys Pro Gly Ala Cys Ile Cys Arg Gly Asn Gly Tyr
            20                  25                  30

Cys Gly Lys Lys Tyr Lys Pro Tyr Val Pro Val Thr Thr Asn Pro Asp
        35                  40                  45

Glu Tyr Ile Glu Arg Ala Lys Glu Cys Lys Lys Gln Asp Ile Gln
    50                  55                  60

Cys Cys Leu Arg Ile Phe Asp Glu Ser Lys Asp Pro Asn Val Met Leu
65                  70                  75                  80

Ile Cys Leu Phe Cys Trp
                85

<210> SEQ ID NO 279
<211> LENGTH: 84
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 279

Ser Gly Ser Asp Gly Gly Val Cys Pro Lys Ile Leu Lys Lys Cys Arg
1               5                   10                  15

Arg Asp Ser Asp Cys Pro Gly Ala Cys Ile Cys Arg Gly Asn Gly Tyr
            20                  25                  30

Cys Gly Glu Pro Lys Ser Ser Asp Lys Thr His Thr Pro Asp Glu Tyr
        35                  40                  45

Ile Glu Arg Ala Lys Glu Cys Cys Lys Lys Gln Asp Ile Gln Cys Cys
    50                  55                  60

Leu Arg Ile Phe Asp Glu Ser Lys Asp Pro Asn Val Met Leu Ile Cys
65                  70                  75                  80

Leu Phe Cys Trp

<210> SEQ ID NO 280
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(11)
<223> OTHER INFORMATION: D-amino acid

<400> SEQUENCE: 280

Arg Arg Arg Gln Arg Arg Lys Lys Arg Gly Tyr
1               5                   10

<210> SEQ ID NO 281
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: 1-2-napthylalanine

<400> SEQUENCE: 281

Phe Xaa Arg Arg Arg Arg Gln
1               5

<210> SEQ ID NO 282
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 1-10 'Gly Ser'
      repeating units

<400> SEQUENCE: 282

Gly Ser Gly Ser Gly Ser Gly Ser Gly Ser Gly Ser Gly Ser Gly Ser
1               5                   10                  15

Gly Ser Gly Ser
            20

```
<210> SEQ ID NO 283
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(10)
<223> OTHER INFORMATION: This region may encompass 1-10 'Gly' residues
<220> FEATURE:
<221> NAME/KEY: MISC_FEATURE
<222> LOCATION: (11)..(20)
<223> OTHER INFORMATION: This region may encompass 1-10 'Ser' residues

<400> SEQUENCE: 283

Gly Gly Gly Gly Gly Gly Gly Gly Gly Ser Ser Ser Ser Ser Ser
1               5                   10                  15

Ser Ser Ser Ser
            20

<210> SEQ ID NO 284
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 284

His His His His His His
1               5

<210> SEQ ID NO 285
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Thr Asp Leu Glu Ala Leu Phe Asn Ala
1               5

<210> SEQ ID NO 286
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(10)
<223> OTHER INFORMATION: This region may encompass 2-10 'Arg' residues

<400> SEQUENCE: 286

Arg Arg Arg Arg Arg Arg Arg Arg Arg Arg
1               5                   10

<210> SEQ ID NO 287
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
          peptide

<400> SEQUENCE: 287

Arg Arg Arg Arg Arg Arg Trp Trp Trp
1               5

<210> SEQ ID NO 288
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(10)
<223> OTHER INFORMATION: This region may encompass 0-10 'Lys' residues
<220> FEATURE:
<221> NAME/KEY: MISC_FEATURE
<222> LOCATION: (11)..(20)
<223> OTHER INFORMATION: This region may encompass 0-10 'Arg' residues

<400> SEQUENCE: 288

Lys Lys Lys Lys Lys Lys Lys Lys Lys Lys Arg Arg Arg Arg Arg
1               5                   10                  15

Arg Arg Arg Arg
            20

<210> SEQ ID NO 289
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (5)..(11)
<223> OTHER INFORMATION: Any amino acid
<220> FEATURE:
<221> NAME/KEY: MOD_RES
<222> LOCATION: (13)..(13)
<223> OTHER INFORMATION: Any amino acid
<220> FEATURE:
<221> NAME/KEY: MOD_RES
<222> LOCATION: (15)..(19)
<223> OTHER INFORMATION: Any amino acid
<220> FEATURE:
<221> NAME/KEY: MOD_RES
<222> LOCATION: (21)..(25)
<223> OTHER INFORMATION: Any amino acid
<220> FEATURE:
<221> NAME/KEY: MOD_RES
<222> LOCATION: (27)..(36)
<223> OTHER INFORMATION: Any amino acid
<220> FEATURE:
<221> NAME/KEY: MOD_RES
<222> LOCATION: (38)..(40)
<223> OTHER INFORMATION: Any amino acid

<400> SEQUENCE: 289

Xaa Xaa Xaa Cys Xaa Xaa Xaa Xaa Xaa Xaa Xaa Cys Xaa Cys Xaa Xaa
1               5                   10                  15

Xaa Xaa Xaa Cys Xaa Xaa Xaa Xaa Xaa Cys Xaa Xaa Xaa Xaa Xaa Xaa
                20                  25                  30

Xaa Xaa Xaa Xaa Cys Xaa Xaa Xaa
            35                  40
```

```
<210> SEQ ID NO 290
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (5)..(11)
<223> OTHER INFORMATION: Any amino acid
<220> FEATURE:
<221> NAME/KEY: MOD_RES
<222> LOCATION: (13)..(16)
<223> OTHER INFORMATION: Any amino acid
<220> FEATURE:
<221> NAME/KEY: MOD_RES
<222> LOCATION: (18)..(27)
<223> OTHER INFORMATION: Any amino acid
<220> FEATURE:
<221> NAME/KEY: MOD_RES
<222> LOCATION: (29)..(29)
<223> OTHER INFORMATION: Any amino acid
<220> FEATURE:
<221> NAME/KEY: MOD_RES
<222> LOCATION: (31)..(38)
<223> OTHER INFORMATION: Any amino acid
<220> FEATURE:
<221> NAME/KEY: MOD_RES
<222> LOCATION: (40)..(41)
<223> OTHER INFORMATION: Any amino acid

<400> SEQUENCE: 290

Xaa Xaa Xaa Cys Xaa Xaa Xaa Xaa Xaa Xaa Xaa Cys Xaa Xaa Xaa Xaa
1               5                   10                  15

Cys Xaa Xaa Xaa Xaa Xaa Xaa Xaa Xaa Xaa Cys Xaa Cys Xaa Xaa
            20                  25                  30

Xaa Xaa Xaa Xaa Xaa Xaa Cys Xaa Xaa
        35                  40

<210> SEQ ID NO 291
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(6)
<223> OTHER INFORMATION: Any amino acid
<220> FEATURE:
<221> NAME/KEY: MOD_RES
<222> LOCATION: (8)..(13)
<223> OTHER INFORMATION: Any amino acid
<220> FEATURE:
<221> NAME/KEY: MOD_RES
<222> LOCATION: (15)..(18)
<223> OTHER INFORMATION: Any amino acid
<220> FEATURE:
<221> NAME/KEY: MOD_RES
<222> LOCATION: (21)..(24)
<223> OTHER INFORMATION: Any amino acid
<220> FEATURE:
<221> NAME/KEY: MOD_RES
<222> LOCATION: (26)..(31)
<223> OTHER INFORMATION: Any amino acid
<220> FEATURE:
<221> NAME/KEY: MOD_RES
```

<222> LOCATION: (33)..(35)
<223> OTHER INFORMATION: Any amino acid

<400> SEQUENCE: 291

Xaa Xaa Xaa Xaa Xaa Xaa Cys Xaa Xaa Xaa Xaa Xaa Xaa Cys Xaa Xaa
1               5                   10                  15

Xaa Xaa Cys Cys Xaa Xaa Xaa Xaa Cys Xaa Xaa Xaa Xaa Xaa Cys
            20                  25                  30

Xaa Xaa Xaa
        35

<210> SEQ ID NO 292
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(8)
<223> OTHER INFORMATION: Any amino acid
<220> FEATURE:
<221> NAME/KEY: MOD_RES
<222> LOCATION: (10)..(15)
<223> OTHER INFORMATION: Any amino acid
<220> FEATURE:
<221> NAME/KEY: MOD_RES
<222> LOCATION: (18)..(25)
<223> OTHER INFORMATION: Any amino acid
<220> FEATURE:
<221> NAME/KEY: MOD_RES
<222> LOCATION: (27)..(27)
<223> OTHER INFORMATION: Any amino acid
<220> FEATURE:
<221> NAME/KEY: MOD_RES
<222> LOCATION: (29)..(38)
<223> OTHER INFORMATION: Any amino acid
<220> FEATURE:
<221> NAME/KEY: MOD_RES
<222> LOCATION: (40)..(40)
<223> OTHER INFORMATION: Any amino acid
<220> FEATURE:
<221> NAME/KEY: MOD_RES
<222> LOCATION: (42)..(43)
<223> OTHER INFORMATION: Any amino acid

<400> SEQUENCE: 292

Xaa Cys Xaa Xaa Xaa Xaa Xaa Xaa Cys Xaa Xaa Xaa Xaa Xaa Cys
1               5                   10                  15

Cys Xaa Xaa Xaa Xaa Xaa Xaa Xaa Xaa Cys Xaa Cys Xaa Xaa Xaa Xaa
            20                  25                  30

Xaa Xaa Xaa Xaa Xaa Cys Xaa Cys Xaa Xaa
        35                  40

<210> SEQ ID NO 293
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(5)
<223> OTHER INFORMATION: Any amino acid
<220> FEATURE:

```
<221> NAME/KEY: MOD_RES
<222> LOCATION: (7)..(10)
<223> OTHER INFORMATION: Any amino acid
<220> FEATURE:
<221> NAME/KEY: MOD_RES
<222> LOCATION: (12)..(14)
<223> OTHER INFORMATION: Any amino acid
<220> FEATURE:
<221> NAME/KEY: MOD_RES
<222> LOCATION: (16)..(24)
<223> OTHER INFORMATION: Any amino acid
<220> FEATURE:
<221> NAME/KEY: MOD_RES
<222> LOCATION: (26)..(29)
<223> OTHER INFORMATION: Any amino acid
<220> FEATURE:
<221> NAME/KEY: MOD_RES
<222> LOCATION: (31)..(31)
<223> OTHER INFORMATION: Any amino acid
<220> FEATURE:
<221> NAME/KEY: MOD_RES
<222> LOCATION: (33)..(37)
<223> OTHER INFORMATION: Any amino acid

<400> SEQUENCE: 293

Xaa Xaa Xaa Xaa Xaa Cys Xaa Xaa Xaa Xaa Cys Xaa Xaa Xaa Cys Xaa
1               5                   10                  15

Xaa Xaa Xaa Xaa Xaa Xaa Xaa Xaa Cys Xaa Xaa Xaa Xaa Cys Xaa Cys
            20                  25                  30

Xaa Xaa Xaa Xaa Xaa
        35

<210> SEQ ID NO 294
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (5)..(10)
<223> OTHER INFORMATION: Any amino acid
<220> FEATURE:
<221> NAME/KEY: MOD_RES
<222> LOCATION: (12)..(19)
<223> OTHER INFORMATION: Any amino acid
<220> FEATURE:
<221> NAME/KEY: MOD_RES
<222> LOCATION: (21)..(30)
<223> OTHER INFORMATION: Any amino acid
<220> FEATURE:
<221> NAME/KEY: MOD_RES
<222> LOCATION: (32)..(34)
<223> OTHER INFORMATION: Any amino acid
<220> FEATURE:
<221> NAME/KEY: MOD_RES
<222> LOCATION: (36)..(37)
<223> OTHER INFORMATION: Any amino acid
<220> FEATURE:
<221> NAME/KEY: MOD_RES
<222> LOCATION: (39)..(40)
<223> OTHER INFORMATION: Any amino acid

<400> SEQUENCE: 294

Xaa Xaa Xaa Cys Xaa Xaa Xaa Xaa Xaa Xaa Cys Xaa Xaa Xaa Xaa Xaa
1               5                   10                  15

Xaa Xaa Xaa Cys Xaa Xaa Xaa Xaa Xaa Xaa Xaa Xaa Xaa Xaa Cys Xaa
            20                  25                  30
```

```
Xaa Xaa Cys Xaa Xaa Cys Xaa Xaa
        35              40

<210> SEQ ID NO 295
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (5)..(10)
<223> OTHER INFORMATION: Any amino acid
<220> FEATURE:
<221> NAME/KEY: MOD_RES
<222> LOCATION: (12)..(17)
<223> OTHER INFORMATION: Any amino acid
<220> FEATURE:
<221> NAME/KEY: MOD_RES
<222> LOCATION: (20)..(27)
<223> OTHER INFORMATION: Any amino acid
<220> FEATURE:
<221> NAME/KEY: MOD_RES
<222> LOCATION: (29)..(29)
<223> OTHER INFORMATION: Any amino acid
<220> FEATURE:
<221> NAME/KEY: MOD_RES
<222> LOCATION: (31)..(41)
<223> OTHER INFORMATION: Any amino acid
<220> FEATURE:
<221> NAME/KEY: MOD_RES
<222> LOCATION: (43)..(43)
<223> OTHER INFORMATION: Any amino acid
<220> FEATURE:
<221> NAME/KEY: MOD_RES
<222> LOCATION: (45)..(46)
<223> OTHER INFORMATION: Any amino acid

<400> SEQUENCE: 295

Xaa Xaa Xaa Cys Xaa Xaa Xaa Xaa Xaa Xaa Cys Xaa Xaa Xaa Xaa Xaa
1               5                   10                  15

Xaa Cys Cys Xaa Xaa Xaa Xaa Xaa Xaa Xaa Cys Xaa Cys Xaa Xaa
            20                  25                  30

Xaa Xaa Xaa Xaa Xaa Xaa Xaa Xaa Xaa Cys Xaa Cys Xaa Xaa
        35                  40                  45

<210> SEQ ID NO 296
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(6)
<223> OTHER INFORMATION: Any amino acid
<220> FEATURE:
<221> NAME/KEY: MOD_RES
<222> LOCATION: (8)..(13)
<223> OTHER INFORMATION: Any amino acid
<220> FEATURE:
<221> NAME/KEY: MOD_RES
<222> LOCATION: (15)..(21)
<223> OTHER INFORMATION: Any amino acid
<220> FEATURE:
<221> NAME/KEY: MOD_RES
<222> LOCATION: (24)..(27)
```

```
<223> OTHER INFORMATION: Any amino acid
<220> FEATURE:
<221> NAME/KEY: MOD_RES
<222> LOCATION: (29)..(29)
<223> OTHER INFORMATION: Any amino acid
<220> FEATURE:
<221> NAME/KEY: MOD_RES
<222> LOCATION: (31)..(35)
<223> OTHER INFORMATION: Any amino acid
<220> FEATURE:
<221> NAME/KEY: MOD_RES
<222> LOCATION: (37)..(37)
<223> OTHER INFORMATION: Any amino acid
<220> FEATURE:
<221> NAME/KEY: MOD_RES
<222> LOCATION: (39)..(40)
<223> OTHER INFORMATION: Any amino acid

<400> SEQUENCE: 296

Xaa Xaa Xaa Xaa Xaa Xaa Cys Xaa Xaa Xaa Xaa Xaa Xaa Cys Xaa Xaa
 1               5                  10                  15

Xaa Xaa Xaa Xaa Xaa Cys Cys Xaa Xaa Xaa Cys Xaa Cys Xaa Xaa
            20                  25                  30

Xaa Xaa Xaa Cys Xaa Cys Xaa Xaa
        35                  40

<210> SEQ ID NO 297
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (5)..(10)
<223> OTHER INFORMATION: Any amino acid
<220> FEATURE:
<221> NAME/KEY: MOD_RES
<222> LOCATION: (12)..(17)
<223> OTHER INFORMATION: Any amino acid
<220> FEATURE:
<221> NAME/KEY: MOD_RES
<222> LOCATION: (20)..(23)
<223> OTHER INFORMATION: Any amino acid
<220> FEATURE:
<221> NAME/KEY: MOD_RES
<222> LOCATION: (25)..(38)
<223> OTHER INFORMATION: Any amino acid
<220> FEATURE:
<221> NAME/KEY: MOD_RES
<222> LOCATION: (40)..(42)
<223> OTHER INFORMATION: Any amino acid

<400> SEQUENCE: 297

Xaa Xaa Xaa Cys Xaa Xaa Xaa Xaa Xaa Xaa Cys Xaa Xaa Xaa Xaa Xaa
 1               5                  10                  15

Xaa Cys Cys Xaa Xaa Xaa Xaa Cys Xaa Xaa Xaa Xaa Xaa Xaa Xaa Xaa
            20                  25                  30

Xaa Xaa Xaa Xaa Xaa Xaa Cys Xaa Xaa Xaa
        35                  40

<210> SEQ ID NO 298
<211> LENGTH: 39
<212> TYPE: PRT
<213> ORGANISM: Artificial Sequence
<220> FEATURE:
```

```
<223> OTHER INFORMATION: Description of Artificial Sequence: Synthetic
      polypeptide
<220> FEATURE:
<221> NAME/KEY: MOD_RES
<222> LOCATION: (1)..(5)
<223> OTHER INFORMATION: Any amino acid
<220> FEATURE:
<221> NAME/KEY: MOD_RES
<222> LOCATION: (7)..(9)
<223> OTHER INFORMATION: Any amino acid
<220> FEATURE:
<221> NAME/KEY: MOD_RES
<222> LOCATION: (11)..(19)
<223> OTHER INFORMATION: Any amino acid
<220> FEATURE:
<221> NAME/KEY: MOD_RES
<222> LOCATION: (21)..(23)
<223> OTHER INFORMATION: Any amino acid
<220> FEATURE:
<221> NAME/KEY: MOD_RES
<222> LOCATION: (25)..(28)
<223> OTHER INFORMATION: Any amino acid
<220> FEATURE:
<221> NAME/KEY: MOD_RES
<222> LOCATION: (30)..(35)
<223> OTHER INFORMATION: Any amino acid
<220> FEATURE:
<221> NAME/KEY: MOD_RES
<222> LOCATION: (37)..(39)
<223> OTHER INFORMATION: Any amino acid

<400> SEQUENCE: 298

Xaa Xaa Xaa Xaa Xaa Cys Xaa Xaa Xaa Cys Xaa Xaa Xaa Xaa Xaa
1               5                   10                  15

Xaa Xaa Xaa Cys Xaa Xaa Xaa Cys Xaa Xaa Xaa Xaa Cys Xaa Xaa Xaa
            20                  25                  30

Xaa Xaa Xaa Cys Xaa Xaa Xaa
        35

<210> SEQ ID NO 299
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(12)
<223> OTHER INFORMATION: Any amino acid
<220> FEATURE:
<221> NAME/KEY: MOD_RES
<222> LOCATION: (14)..(18)
<223> OTHER INFORMATION: Any amino acid
<220> FEATURE:
<221> NAME/KEY: MOD_RES
<222> LOCATION: (20)..(22)
<223> OTHER INFORMATION: Any amino acid
<220> FEATURE:
<221> NAME/KEY: MOD_RES
<222> LOCATION: (24)..(32)
<223> OTHER INFORMATION: Any amino acid
<220> FEATURE:
<221> NAME/KEY: MOD_RES
<222> LOCATION: (34)..(39)
<223> OTHER INFORMATION: Any amino acid
<220> FEATURE:
<221> NAME/KEY: MOD_RES
<222> LOCATION: (41)..(41)
<223> OTHER INFORMATION: Any amino acid
<220> FEATURE:
```

```
<221> NAME/KEY: MOD_RES
<222> LOCATION: (43)..(45)
<223> OTHER INFORMATION: Any amino acid
<220> FEATURE:
<221> NAME/KEY: MOD_RES
<222> LOCATION: (47)..(47)
<223> OTHER INFORMATION: Any amino acid

<400> SEQUENCE: 299

Xaa Cys Xaa Xaa Xaa Xaa Xaa Xaa Xaa Xaa Xaa Cys Xaa Xaa Xaa
1               5                   10                  15

Xaa Xaa Cys Xaa Xaa Xaa Cys Xaa Xaa Xaa Xaa Xaa Xaa Xaa Xaa
            20                  25                  30

Cys Xaa Xaa Xaa Xaa Xaa Xaa Cys Xaa Cys Xaa Xaa Xaa Cys Xaa
        35                  40                  45

<210> SEQ ID NO 300
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(3)
<223> OTHER INFORMATION: Any amino acid
<220> FEATURE:
<221> NAME/KEY: MOD_RES
<222> LOCATION: (5)..(7)
<223> OTHER INFORMATION: Any amino acid
<220> FEATURE:
<221> NAME/KEY: MOD_RES
<222> LOCATION: (9)..(13)
<223> OTHER INFORMATION: Any amino acid
<220> FEATURE:
<221> NAME/KEY: MOD_RES
<222> LOCATION: (15)..(19)
<223> OTHER INFORMATION: Any amino acid
<220> FEATURE:
<221> NAME/KEY: MOD_RES
<222> LOCATION: (21)..(21)
<223> OTHER INFORMATION: Any amino acid
<220> FEATURE:
<221> NAME/KEY: MOD_RES
<222> LOCATION: (23)..(30)
<223> OTHER INFORMATION: Any amino acid
<220> FEATURE:
<221> NAME/KEY: MOD_RES
<222> LOCATION: (32)..(34)
<223> OTHER INFORMATION: Any amino acid

<400> SEQUENCE: 300

Xaa Xaa Xaa Cys Xaa Xaa Xaa Cys Xaa Xaa Xaa Xaa Cys Xaa Xaa
1               5                   10                  15

Xaa Xaa Xaa Cys Xaa Cys Xaa Xaa Xaa Xaa Xaa Xaa Xaa Cys Xaa
            20                  25                  30

Xaa Xaa

<210> SEQ ID NO 301
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(2)
<223> OTHER INFORMATION: Any amino acid
<220> FEATURE:
```

```
<221> NAME/KEY: MOD_RES
<222> LOCATION: (4)..(9)
<223> OTHER INFORMATION: Any amino acid
<220> FEATURE:
<221> NAME/KEY: MOD_RES
<222> LOCATION: (11)..(15)
<223> OTHER INFORMATION: Any amino acid
<220> FEATURE:
<221> NAME/KEY: MOD_RES
<222> LOCATION: (18)..(20)
<223> OTHER INFORMATION: Any amino acid
<220> FEATURE:
<221> NAME/KEY: MOD_RES
<222> LOCATION: (22)..(27)
<223> OTHER INFORMATION: Any amino acid
<220> FEATURE:
<221> NAME/KEY: MOD_RES
<222> LOCATION: (29)..(33)
<223> OTHER INFORMATION: Any amino acid
<220> FEATURE:
<221> NAME/KEY: MOD_RES
<222> LOCATION: (35)..(37)
<223> OTHER INFORMATION: Any amino acid
<220> FEATURE:
<221> NAME/KEY: MOD_RES
<222> LOCATION: (39)..(40)
<223> OTHER INFORMATION: Any amino acid

<400> SEQUENCE: 301

Xaa Xaa Cys Xaa Xaa Xaa Xaa Xaa Xaa Cys Xaa Xaa Xaa Xaa Xaa Cys
1               5                   10                  15

Cys Xaa Xaa Xaa Cys Xaa Xaa Xaa Xaa Xaa Xaa Cys Xaa Xaa Xaa Xaa
            20                  25                  30

Xaa Cys Xaa Xaa Xaa Cys Xaa Xaa
        35                  40

<210> SEQ ID NO 302
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(5)
<223> OTHER INFORMATION: Any amino acid
<220> FEATURE:
<221> NAME/KEY: MOD_RES
<222> LOCATION: (7)..(12)
<223> OTHER INFORMATION: Any amino acid
<220> FEATURE:
<221> NAME/KEY: MOD_RES
<222> LOCATION: (14)..(18)
<223> OTHER INFORMATION: Any amino acid
<220> FEATURE:
<221> NAME/KEY: MOD_RES
<222> LOCATION: (20)..(22)
<223> OTHER INFORMATION: Any amino acid
<220> FEATURE:
<221> NAME/KEY: MOD_RES
<222> LOCATION: (24)..(24)
<223> OTHER INFORMATION: Any amino acid
<220> FEATURE:
<221> NAME/KEY: MOD_RES
<222> LOCATION: (26)..(30)
<223> OTHER INFORMATION: Any amino acid
<220> FEATURE:
<221> NAME/KEY: MOD_RES
<222> LOCATION: (32)..(33)
<223> OTHER INFORMATION: Any amino acid

<400> SEQUENCE: 302

Xaa Xaa Xaa Xaa Xaa Cys Xaa Xaa Xaa Xaa Xaa Xaa Cys Xaa Xaa Xaa
```

```
                1               5                  10                 15
Xaa Xaa Cys Xaa Xaa Xaa Cys Xaa Cys Xaa Xaa Xaa Xaa Cys Xaa
                20                 25                 30
Xaa
```

<210> SEQ ID NO 303
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(2)
<223> OTHER INFORMATION: Any amino acid
<220> FEATURE:
<221> NAME/KEY: MOD_RES
<222> LOCATION: (4)..(8)
<223> OTHER INFORMATION: Any amino acid
<220> FEATURE:
<221> NAME/KEY: MOD_RES
<222> LOCATION: (10)..(14)
<223> OTHER INFORMATION: Any amino acid
<220> FEATURE:
<221> NAME/KEY: MOD_RES
<222> LOCATION: (16)..(23)
<223> OTHER INFORMATION: Any amino acid
<220> FEATURE:
<221> NAME/KEY: MOD_RES
<222> LOCATION: (25)..(25)
<223> OTHER INFORMATION: Any amino acid
<220> FEATURE:
<221> NAME/KEY: MOD_RES
<222> LOCATION: (27)..(35)
<223> OTHER INFORMATION: Any amino acid
<220> FEATURE:
<221> NAME/KEY: MOD_RES
<222> LOCATION: (37)..(37)
<223> OTHER INFORMATION: Any amino acid

<400> SEQUENCE: 303

```
Xaa Xaa Cys Xaa Xaa Xaa Xaa Xaa Cys Xaa Xaa Xaa Xaa Xaa Cys Xaa
1               5                   10                  15

Xaa Xaa Xaa Xaa Xaa Xaa Xaa Cys Xaa Cys Xaa Xaa Xaa Xaa Xaa Xaa
                20                  25                  30

Xaa Xaa Xaa Cys Xaa
        35
```

<210> SEQ ID NO 304
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(6)
<223> OTHER INFORMATION: Any amino acid
<220> FEATURE:
<221> NAME/KEY: MOD_RES
<222> LOCATION: (8)..(12)
<223> OTHER INFORMATION: Any amino acid
<220> FEATURE:
<221> NAME/KEY: MOD_RES
<222> LOCATION: (14)..(17)
<223> OTHER INFORMATION: Any amino acid
<220> FEATURE:
<221> NAME/KEY: MOD_RES
<222> LOCATION: (19)..(25)
<223> OTHER INFORMATION: Any amino acid

```
<220> FEATURE:
<221> NAME/KEY: MOD_RES
<222> LOCATION: (27)..(30)
<223> OTHER INFORMATION: Any amino acid
<220> FEATURE:
<221> NAME/KEY: MOD_RES
<222> LOCATION: (32)..(32)
<223> OTHER INFORMATION: Any amino acid
<220> FEATURE:
<221> NAME/KEY: MOD_RES
<222> LOCATION: (34)..(36)
<223> OTHER INFORMATION: Any amino acid

<400> SEQUENCE: 304

Xaa Xaa Xaa Xaa Xaa Xaa Cys Xaa Xaa Xaa Xaa Xaa Cys Xaa Xaa Xaa
1               5                   10                  15

Xaa Cys Xaa Xaa Xaa Xaa Xaa Xaa Cys Xaa Xaa Xaa Xaa Cys Xaa
            20                  25                  30

Cys Xaa Xaa Xaa
        35
```

PEPTIDE COMPOSITIONS AND METHODS OF USE THEREOF FOR DISRUPTING TEAD INTERACTIONS

CROSS REFERENCE

This application is a U.S. National Phase Application under 35 U.S.C. § 371 of International Application No. PCT/US2018/014203, filed Jan. 18, 2018, which claims the benefit of U.S. Provisional Patent Application No. 62/447,864, filed Jan. 18, 2017, and U.S. Provisional Patent Application No. 62/510,719, filed May 24, 2017, the disclosures of which are incorporated herein in their entireties.

SEQUENCE LISTING

The instant application contains a Sequence Listing which has been submitted electronically in ASCII format and is hereby incorporated by reference in its entirety. Said ASCII copy, created on Jan. 17, 2018, is named 44189-718_601_SL.txt and is 177,067 bytes in size.

BACKGROUND

Cancer is a leading cause of death worldwide, with more than 90% of all cancer-related deaths caused by metastasis. The HIPPO signaling pathway is important for cell growth, cell contact inhibition, and organogenesis. If the HIPPO pathway is disrupted, oncogenes can be left unchecked, causing overexpression of downstream genes that favor cell proliferation, tumor progression, and metastasis. As such, there is need for inhibitors of the HIPPO pathway with high affinity and specificity so that unchecked oncogenes can be suppressed. Such HIPPO pathway modulators, including inhibitors, can be used to prevent or treat cancers, tumor progression, metastasis, or other disease or condition associated with a dysregulated HIPPO pathway.

SUMMARY

The present disclosure provides compositions and methods for disrupting TEAD interactions.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In various aspects, the present disclosure provides a composition, comprising a non-naturally occurring, synthetic, or engineered peptide capable of binding to TEAD, or a variant, homolog, or analog thereof. In some aspects, the peptide binds to TEAD and disrupts TEAD interactions. In some aspects, the TEAD interactions comprise TEAD interaction with TAZ, YAP, or any combination thereof.

In some aspects, the peptide disrupts or inhibits one or more components of a HIPPO signaling pathway. In other aspects, the peptide modulates one or more components of a HIPPO signaling pathway. In some aspects, the peptide suppresses an oncogene in a HIPPO signaling pathways.

In some aspects, the peptide comprises from 1 to 10 contiguous amino acids from YAP peptide. In further aspects, the from 1 to 10 contiguous amino acids are selected from one or more of amino acid residues: 53-55, 55-57, 64-68, 64-69, 86-89, or 94-96 of the B chain of PDB 3KYS. In some aspects, the from 1 to 10 contiguous amino acids is grafted onto a peptide comprising three disulfide cross-linkers. In various aspects, the peptide comprising three disulfide cross-linkers is a knottin. In some aspects, the from 1 to 10 contiguous amino acids is grafted onto a cell-penetrating peptide. In further aspects, the cell-penetrating peptide is maurocalcin, imperatoxin, hadrucalcin, hemicalcin, opicalcin-1, opicalcin-2, midkine (62-104), MCoTI-II, or chlorotoxin. In various aspects, the cell-penetrating peptide comprises at least 60%, 70%, 80%, 90%, 95%, or 100% sequence identity with any one of SEQ ID NO: 168-SEQ ID NO: 176.

In some aspects, the peptide comprises a sequence of any one of SEQ ID NO: 1-SEQ ID NO: 42, or a variant or fragment thereof. In further aspects, the peptide comprises a sequence that has at least 80% sequence identity with any one of SEQ ID NO: 1-SEQ ID NO: 42, or a variant or a fragment thereof. In still further aspects, the peptide comprises a sequence that has at least 85%, at least 90%, or at least 95% sequence identity with any one of SEQ ID NO: 1-SEQ ID NO: 42 or a variant or a fragment thereof.

In some aspects, the peptide comprises a sequence of any one of SEQ ID NO: 43-SEQ ID NO: 84, or a variant or a fragment thereof. In further aspects, the peptide comprises a sequence that has at least 80% sequence identity with any one of SEQ ID NO: 45-SEQ ID NO: 84, or a variant or a fragment thereof. In still further aspects, the peptide comprises a sequence that has at least 85%, at least 90%, or at least 95% sequence identity with any one of SEQ ID NO: 43-SEQ ID NO: 84 or a variant or a fragment thereof. In some aspects, the peptide is a knotted peptide or is derived from a knotted peptide.

In other aspects, the peptide competes with YAP or TAZ for binding to TEAD. In some aspects the peptide sequesters TEAD or prevents another protein from binding to TEAD. In further aspects, the peptide has equal or greater affinity or specificity for TEAD as compared to that of YAP or TAZ. In some aspects, the peptide has equal or lower dissociation constant for TEAD as compared to that of YAP or TAZ. In further aspects, the peptide has a $K_D$ of less than 40 nM, less than 30 nM, less than 20 nM, less than 10 nM, less than 1 nM, or less than 0.1 nM.

In some aspects, the peptide can penetrate or localize into a target cell. In other aspects, the peptide penetrates or localizes into a target cell by formulation with, fusion to, or conjugation to a cell-penetrating moiety. In some aspects, the cell-penetrating moiety comprises polycations, polyorganic acids, endosomal releasing polymers, poly(2-propylacrylic acid), poly(2-ethylacrylic acid), Tat peptide, Arg patch, a knotted peptide, CysTAT, S19-TAT, R8 (SEQ ID NO: 146), pAntp, Pas-TAT, Pas-R8 (SEQ ID NO: 149), Pas-FHV, Pas-pAntP, F2R4 (SEQ ID NO: 152), B55, aurin, IMT-P8, BR2, OMOTAG1, OMOTAG2, pVEC, SynB3, DPV1047, C105Y, Transpotan, MTS, hLF, PFVYLI (SEQ ID NO: 166), maurocalcine, imperatoxin, hadrucalin, hemicalcin, opicalcin-1, opicalcin-2, midkin(62-104), MCoTI-II, chlorotoxin, DRI-TAT, cFΦR4 (SEQ ID NO: 281), myristate, yBBR, or a fragment or variant thereof, or any combination thereof. In further aspects, the cell-penetrating moiety comprises at least 80%, 90%, 95%, 98%, or 100% sequence identity with any sequence of SEQ ID NO: 143-SEQ ID NO: 176. I other aspects, the peptide fusion to the cell-penetrating moiety comprises at least 80%, 90%, 95%, 98%, or 100% sequence identity with SEQ ID NO: 85-SEQ ID NO: 142 or SEQ ID NO: 222-SEQ ID NO: 279.

In other aspects, the peptide can localize into a target cell's nucleus. In further aspects, the peptide localizes into the target cell's nucleus by formulation with, fusion to, or conjugation to a nuclear localization signal peptide or moiety. In some aspects, the peptide is further conjugated to, linked to, or fused to a moiety or a second peptide that targets, homes, or selectively penetrates a cancer cell. In some aspects, the moiety or a second peptide is a knotted peptide or variant or fragment thereof. In further aspects, the knotted peptide targets or homes the peptide across the blood brain barrier.

In some aspects, the peptide is conjugated to, linked to, or fused to a moiety that targets TEAD inactivation or degradation. In some aspects, the moiety that targets TEAD inactivation or degradation results in post-translational modification of TEAD. In some aspects, the post-translational modification of TEAD comprises ubiquitination.

In other aspects, the target cell is a cell with a dysregulated HIPPO pathway. In some aspects, the target cell is a cell with uncontrolled or dysregulated cell growth. In some aspects, the target cell is a cancerous cell or a tumor cell. In other aspects, the target cell is a pancreatic cell, liver cell, colon cell, ovarian cell, breast cell, lung cell, brain cell, or any combination thereof.

In some aspects, the peptide comprises a disulfide through disulfide knot. In some aspects, the peptide comprises a plurality of disulfide bridges formed between cysteine residues. In some aspects, the peptide comprises three or more disulfide bridges formed between cysteine residues, wherein one of the disulfide bridges passes through a loop formed by two other disulfide bridges. In other aspects, the peptide comprises no disulfide bond or a disulfide knot.

In some aspects, at least one amino acid residue of the peptide is in an L configuration or, wherein at least one amino acid residue is in a D configuration. In some aspects, the peptide comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 positively charged residues.

In other aspects, the peptide comprises at least 2, at least 3, at least 4, at least 5, at least 6, at least 7, at least 8, at least 9, or at least 10 consecutive positively charged residues. In some aspects, the positively charged residues are Arg, Lys, or any combination thereof.

In still other aspects, the peptide comprises an Arg patch. In some aspects, the peptide comprises two or more consecutive Arg residues at the N-terminus. In some aspects, the peptide comprises a Tat peptide, or a fragment thereof. In some aspects, the Tat peptide comprises a sequence YGRKKRRQRRR (SEQ ID NO: 195), GRKKRRQRRR (SEQ ID NO: 143), or a fragment or variant thereof.

In some aspects, the Tat peptide is appended to the N-terminus or C-terminus of the peptide using a linker having a sequence of $(GS)_x$ (SEQ ID NO: 282) or $G_xS_y$ (SEQ ID NO: 283), wherein x and y is independently 1, 2, 3, 4, 5, 6, 7, 8, 9, or 10. In other aspects, the Tat peptide is appended to any residue of the peptide. In still other aspects, the Tat peptide is appended to any residue of the peptide without interfering with TEAD-binding activity.

In some aspects, the peptide comprises at least 4, at least 5, at least 6, at least 7, at least 8, at least 9, at least 10, at least 11, at least 12, at least 13, at least 14, at least 15, or at least 16 cysteine residues. In other aspects, the peptide comprises one, two, three, four, five, or six Cys residues.

In some aspects, the peptide comprises, is mutated to comprise, or is grafted to comprise $LX_1X_2LF$ (SEQ ID NO: 217), wherein $X_1$ and $X_2$ is any amino acid. In further aspects, $X_1$ and $X_2$ in the $LX_1X_2LF$ (SEQ ID NO: 217) comprises EA, IC, EC, MC, VC, or FC. In some aspects, the peptide comprises, is mutated to comprise, or is grafted to comprise a $LX_1X_2LF$ (SEQ ID NO: 217) motif, wherein $X_1$ and $X_2$ is any amino acid. In further aspects, $X_1$ and $X_2$ in the $LX_1X_2LF$ (SEQ ID NO: 217) motif comprises EA, IC, EC, MC, VC, or FC. In some aspects, the peptide comprises a mutation at positions: L23, L26, and F27. In other aspects, the peptide comprises a mutation at positions: G15, Y23, E25, G28, and P40. In still other aspects, the peptide comprises a mutation at positions: G15, Y23, and P40.

In still other aspects, the peptide comprises a mutation at position P40. In some aspects, the peptide comprises one or more mutations selected from the group consisting of: G15Q, Y23I, E25D, G28K, and P40W. In some aspects, the peptide comprises E25D, G28K, and P40W.

In some aspects, the peptide comprises one or more regions of negatively charged residues. In some aspects, the peptide comprises one or more regions of positively charged residues. In some aspects, the peptide sequence comprises at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58 residues, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, or at least 81 residues.

In some aspects, the peptide comprises or is derived from the group consisting of: chlorotoxins, brazzeins, circulins, stecrisps, hanatoxins, midkines, hefutoxins, potato carboxypeptidase inhibitors, bubble proteins, attractins, α-GI, α-GID, μ-pIIIA, ω-MVIIA, ω-CVID, χ-MrIA, ρ-TIA, conantokin G, contulakin G, GsMTx4, margatoxins, shK, toxin K, chymotrypsin inhibitors (CTI), EGF epiregulin core, hainantoxins, theraphotoxins, hexatoxins, opicalcins, imperatoxins, defensins, and insectotoxins.

In some aspects, the peptide comprises or is derived from a human protein or peptide. In some aspects, the peptide is arranged in a multimeric structure with at least one other peptide. In further aspects, the multimeric structure comprises a dimer, trimer, tetramer, pentamer, hexamer, or heptamer.

In some aspects, the peptide comprises an isoelectric point within a range from about 3.0 to about 10.0. In other aspects, the peptide comprises an isoelectric point within a range from about 4.5 to about 8.9. In some aspects, the peptide comprises a non-uniform charge distribution. In some aspects, the peptide is stable at physiological or intracellular pH values. In other aspects, the peptide is stable at pH of about 7 or 7.5. In still other aspects, the peptide is stable at pH of about 6.5 to 7.5. In still other aspects, the peptide is stable at pH values less than or equal to about 5.0, less than or equal to about 3.0, or within a range from about 3.0 to about 5.0. In other aspects, the peptide is stable at pH values within a range from about 5.0 to about 7.0. In some aspects, the peptide comprises a hydrophobic core.

In some aspects, the peptide is resistant to protease degradation. In further aspects, the protease is any one of pepsin, trypsin, chymotrypsin, serum proteases, intracellular proteases, or any combination thereof. In other aspects, the peptide is resistant to reduction or is stable in a reducing environment.

In further aspects, the reduction or reducing environment comprises DDT or GSH. In some aspects, the peptide is stable at an elevated temperature. In some aspects, the peptide is capable of penetrating a cell membrane. In some aspects, the peptide exhibits an anti-cancer effect. In some aspects, the peptide comprises one or more chemical modifications. In further aspects, the chemical modification extends the half-life or modifies a pharmacokinetics of the peptide. In some aspects, the chemical modification is blocking the N-terminus of the peptide. In some aspects, the chemical modification is methylation, acetylation, or acylation.

In some aspects, the chemical modification is: methylation of one or more lysine residues or analogue thereof; methylation of the N-terminus; or methylation of one or more lysine residue or analogue thereof and methylation of the N-terminus. In other aspects, the peptide is linked to an acyl adduct.

In some aspects, the peptide is conjugated to, linked to, or fused with an active agent. In further aspects, the active agent is conjugated to, linked to, or fused with the peptide at an N-terminus or a C-terminus of the peptide. In some aspects, the active agent is an antibody, antibody fragment, Fc, or single chain Fv. In other aspects, the peptide is conjugated to, linked to, fused to, or is embedded in an Fc domain. In some aspects, 1, 2, 3, 4, 5, 6, 7, 8, 9, or 10 active agents are linked to the peptide.

In further aspects, the peptide is linked to the active agent via a cleavable linker or a pH sensitive linker. In some aspects, the peptide is linked to the active agent at an N-terminus, at the epsilon amine of an internal lysine residue, at the carboxylic acid of an aspartic acid or glutamic acid residue, or a C-terminus of the peptide by a linker. In other aspects, the composition further comprises a non-natural amino acid, wherein the non-natural amino acid is an insertion, appendage, or substitution for another amino acid.

In other aspects, the peptide is linked to the active agent at the non-natural amino acid by a linker. In some aspects, the linker comprises an amide bond, an ester bond, a carbamate bond, a carbonate bond, a hydrazone bond, an oxime bond, a disulfide bond, a thioester bond, a thioether bond, or a carbon-nitrogen bond. In some aspects, the cleavable linker comprises a cleavage site for matrix metalloproteinases, thrombin, cathepsins, or beta-glucuronidase. In other aspects, the linker is a hydrolytically labile linker.

In still other aspects, the peptide is linked to the active agent via a noncleavable linker. In some aspects, the active agent is an anti-cancer agent. In further aspects, the active agent is an auristatin, MMAE, a maytansinoid, DM1, DM4, doxorubicin, a calicheamicin, a platinum compound, cisplatin, a taxane, paclitaxel, SN-38, a BACE inhibitor, a Bcl-xL inhibitor, WEHI-539, venetoclax, ABT-199, navitoclax, AT-101, obatoclax, a pyrrolobenzodiazepine or pyrrolobenzodiazepine dimer, or dolastatin.

In other aspects, the composition further comprises a half-life modifying agent coupled to the peptide. In some aspects, the half-life modifying agent comprises a polymer, a polyethylene glycol (PEG), a hydroxyethyl starch, polyvinyl alcohol, a water soluble polymer, a zwitterionic water soluble polymer, a water soluble poly(amino acid), a water soluble polymer of proline, alanine and serine, a water soluble polymer containing glycine, glutamic acid, and serine, an Fc region, a fatty acid, palmitic acid, or a molecule that binds to albumin.

In some aspects, the composition further comprises a detectable agent coupled to the peptide. In some aspects, the detectable agent is conjugated to, linked to, or fused with the peptide at an N-terminus or a C-terminus of the peptide. In some aspects, 1, 2, 3, 4, 5, 6, 7, 8, 9, or 10 detectable agents are linked to the peptide. In some aspects, the peptide is linked to the detectable agent via a cleavable linker. In other aspects, the peptide is linked to the detectable agent at an N-terminus, at the epsilon amine of an internal lysine residue, or a C-terminus of the peptide by a linker. In some aspects, the composition further comprises a non-natural amino acid, wherein the non-natural amino acid is an insertion, appendage, or substitution for another amino acid.

In other aspects, the peptide is linked to the detectable agent at the non-natural amino acid by a linker. In some aspects, the linker comprises an amide bond, an ester bond, a carbamate bond, a hydrazone bond, an oxime bond, or a carbon-nitrogen bond. In some aspects, the cleavable linker comprises a cleavage site for matrix metalloproteinases, thrombin, cathepsins, or beta-glucuronidase.

In still other aspects, the peptide is linked to the detectable agent via a noncleavable linker. In some aspects, the detectable agent is a fluorophore, a near-infrared dye, a contrast agent, a nanoparticle, a metal-containing nanoparticle, a metal chelate, an X-ray contrast agent, a PET agent, a radioisotope, or a radionuclide chelator. In some aspects, the detectable agent is a fluorescent dye.

In various aspects, the present disclosure provides a pharmaceutical composition comprising any of the compositions described above, or a salt thereof, and a pharmaceutically acceptable carrier. In some aspects, the pharmaceutical composition is formulated for administration to a subject. In some aspects, the pharmaceutical composition is formulated for oral administration, intravenous administration, subcutaneous administration, intramuscular administration, or a combination thereof.

In various aspects, the present disclosure provides a method of treating a condition in a subject in need thereof, the method comprising: administering to the subject any of the compositions described above or any of the pharmaceutical compositions described above. In some aspects, the composition is administered by inhalation, intranasally, orally, topically, intravenously, subcutaneously, intramuscularly administration, intraperitoneally, intratumoral, or a combination thereof. In other aspects, the composition is administered intravenously as a bolus, infusion, or prolonged infusion.

In some aspects, the composition or pharmaceutical composition disrupts YAP interactions with TEAD. In some aspects, the composition or pharmaceutical composition prevents YAP from binding to TEAD. In other aspects, the composition or pharmaceutical composition competes with YAP for binding to TEAD. In some aspects, the composition or pharmaceutical composition binds to TEAD. In some aspects, the composition or pharmaceutical composition inhibits an oncogene in a HIPPO signaling pathway.

In some aspects, the composition or pharmaceutical composition is internalized by a cell. In other aspects, the composition or pharmaceutical composition penetrates a cell membrane of a target cell. In some aspects, the condition is diabetes. In other aspects, the condition is a cancer or a tumor. In further aspects, the cancer is pancreatic cancer, liver cancer, colon cancer, ovarian cancer, brain cancer, or lung cancer.

In some aspects, the cancer is associated with a mutation in the HIPPO pathway. In some aspects, the condition comprises unregulated cell growth or dysregulated HIPPO pathway. In some aspects, the composition or the pharmaceutical composition is administered multiple times a day, twice a day, once a day, twice a week, three times a week, once a week, once every two weeks, or once a month or once every three months. In other aspects, the composition is administered subcutaneously once a day, once a week, or once a month.

In some aspects, a method for designing a peptide capable of binding to TEAD comprises: a) using a computer program to identify a peptide from a library of peptides with optimized stability and folding, wherein each peptide of the library of peptides comprises at least three disulfide cross-linkers; b) using a computer program to superimpose amino acid residues of a binding patch from a peptide:TEAD complex to determine a stable peptide that binds to TEAD after grafting the binding patch onto the peptide; and c) grafting the binding patch onto the peptide to produce the stable peptide. In some aspects, the method further comprising performing site saturation mutagenesis to obtain a mutated peptide with a higher binding affinity for TEAD than the stable peptide. In other aspects, the peptide from a library of peptides is between 20 and 55 amino acid residues in length. In additional aspects, the method further comprises designing a peptide capable of cell penetration comprising: e) using a computer program to identify a peptide from a library of peptides with optimized stability and folding, wherein each peptide of the library of peptides comprises is capable of cell penetration; f) using a computer program to superimpose amino acid residues of a binding patch from the mutant peptide:TEAD complex to determine a new peptide that binds to TEAD after grafting the binding patch onto the peptide; and g) grafting the binding patch onto the mutant peptide to produce the new peptide.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 illustrates validation and functional analysis of the produced biotinylated TEAD and Siderocalin-fused YAP.

FIG. 1A illustrates SDS-PAGE with a band near 55 kDa corresponding to a sample of Siderocalin-YAP.

FIG. 1B illustrates surface plasmon resonance (SPR) data showing that Siderocalin-fused YAP binds to biotinylated TEAD immobilized on an SPR chip with a dissociation constant ($K_D$) of 570 nM.

FIG. 1C illustrates that HEK-293 cells expressing surface-tethered YAP (50-171) is stained by Alexa Fluorophore (AF)-647 conjugated to Streptavidin (AF657-Streptavidin) bound to biotinylated TEAD, corresponding to the right peak. Cells expressing the Machupo virus (MACV) glycoprotein, a specific ligand for human transferrin receptor, are not stained by AF-647, indicating that TEAD does not bind MACV, corresponding to the left peak.

FIG. 2 illustrates how the surface display GFP FasL (SDGF) vector provides an effective mammalian display method for identifying and evaluating protein-protein interactions, such as peptide-TEAD binding and knotted peptide binding to another moiety or protein.

FIG. 3 illustrates screening a designed or engineered library of peptides for TEAD-binding.

FIG. 4 illustrates the structures of peptides of SEQ ID NO: 1 and SEQ ID NO: 2 and the modeled TEAD interface with YAP overlaid with the structures of peptides of SEQ ID NO: 1 and SEQ ID NO: 2.

FIG. 4B illustrates flow cytometry plots showing TEAD binding to HEK-293 suspension cells transfected with SDGF-SEQ ID NO: 2 versus TEAD binding to HEK-293 suspension cells transfected with SDGF-L23A variant of SEQ ID NO: 2 (lysine to alanine variant of SEQ ID NO: 2 at position 23).

FIG. 4C illustrates flow cytometry plots showing TEAD binding to HEK-293 suspension cells transfected with SDGF-SEQ ID NO: 2 versus TEAD binding to HEK-293 suspension cells transfected with SDGF-L26A variant of SEQ ID NO: 2 (lysine to alanine variant of SEQ ID NO: 2 at position 26).

FIG. 4D illustrates flow cytometry plots showing TEAD binding to HEK-293 suspension cells transfected with SDGF-SEQ ID NO: 2 versus TEAD binding to HEK-293 suspension cells transfected with SDGF-F27A variant of SEQ ID NO: 2 (phenylalanine to alanine variant of SEQ ID NO: 2 at position 27).

FIG. 4E illustrates flow cytometry plots showing TEAD binding to HEK-293 suspension cells transfected with SDGF-SEQ ID NO: 2 versus TEAD binding to HEK-293 suspension cells transfected with SDGF-6×CS variant of SEQ ID NO: 2 (a variant of SEQ ID NO: 2 in which all 6 cysteines are mutated to serines).

FIG. 4F illustrates flow cytometry plots showing TEAD binding to HEK-293 suspension cells transfected with SDGF-SEQ ID NO: 1 versus TEAD binding to HEK-293 suspension cells transfected with a peptide of SEQ ID NO: 4 (SDGF-E25A variant of SEQ ID NO: 1, which is a glutamic acid to alanine variant of SEQ ID NO: 1 at position 25).

FIG. 4G illustrates flow cytometry plots showing TEAD binding to HEK-293 suspension cells transfected with SDGF-SEQ ID NO: 1 versus TEAD binding to HEK-293 suspension cells transfected with a peptide of SEQ ID NO: 6 (SDGF-M33A variant of SEQ ID NO: 1, which is a methionine to alanine variant of SEQ ID NO: 1 at position 33).

FIG. 5 illustrates binding of soluble TEAD-binding peptides and variants thereof to TEAD. Gels show peptides in reducing conditions in NuPAGE at one-tenth the final volume, in which DTT is at 50 mM. HPLC shows peptides in reducing conditions in Dulbecco's phosphate-buffered saline (DPBS) with a final DTT concentration of 40 mM. Non-reducing conditions are designated as "NR" and reducing conditions are designated as "R."

FIG. 5A illustrates an SDS-PAGE gel of a peptide of SEQ ID NO: 1 treated with non-reducing conditions or reducing conditions.

FIG. 5B illustrates HPLC chromatograms showing peaks representing a peptide of SEQ ID NO: 1 in non-reducing (NR) conditions or in reducing (R) conditions with DTT.

FIG. 5C illustrates SPR binding assay data of a peptide of SEQ ID NO: 1 to biotinylated TEAD immobilized on an SPR chip with a dissociation constant ($K_D$) of 31 nM.

FIG. 5D illustrates an SDS-PAGE gel of a peptide of SEQ ID NO: 5 treated with non-reducing conditions or reducing conditions.

FIG. 5E illustrates HPLC chromatograms showing peaks representing a peptide of SEQ ID NO: 5 in non-reducing conditions or in reducing conditions with DTT.

FIG. 5F illustrates SPR binding assay data of a peptide of SEQ ID NO: 5 to biotinylated TEAD immobilized on an SPR chip with a dissociation constant ($K_D$) of 280 nM.

FIG. 5G illustrates an SDS-PAGE gel of a peptide of SEQ ID NO: 7 treated with non-reducing conditions or reducing conditions.

FIG. 5H illustrates HPLC chromatograms showing peaks representing a peptide of SEQ ID NO: 7 in non-reducing conditions or in reducing conditions with DTT.

FIG. 5I illustrates SPR binding assay data of a peptide of SEQ ID NO: 7 to biotinylated TEAD immobilized on an SPR chip with a dissociation constant ($K_D$) of 23 µM.

FIG. 5J illustrates an SDS-PAGE gel of a peptide of SEQ ID NO: 3 treated with non-reducing conditions or reducing conditions.

FIG. 5K illustrates HPLC chromatograms showing peaks representing a peptide of SEQ ID NO: 3 in non-reducing conditions or in reducing conditions with DTT.

FIG. 5L illustrates SPR binding assay data of a peptide of SEQ ID NO: 3 to biotinylated TEAD immobilized on an SPR chip with a dissociation constant ($K_D$) of 12 µM.

FIG. 6 illustrates results from co-immunoprecipitation assays evaluating disruption of the YAP-TEAD interaction with a soluble peptide of SEQ ID NO: 1.

FIG. 7 illustrates the results of a site-saturation mutagenesis screen of SEQ ID NO: 1 variants with improved binding activity to TEAD. Flow cytometry plots show the fluorescence of the peptide construct expression on the x-axis (GFP) and TEAD (AF647) on the y-axis. Double-positive cells (upper right hand quadrant) indicate peptide-expressing cells that are bound to TEAD. Panels labeled "SSM01" indicate cells transduced with the full library of peptide variants.

FIG. 8 illustrates enrichment scores at each position for the variants of SEQ ID NO: 1 generated in the site-saturation (SSM) mutagenesis screen and a structural model of the binding interface between the peptide or variant peptide and TEAD.

FIG. 9 illustrates that combinations of enriched mutations identified in a peptide of SEQ ID NO: 1 by SSM resulted in improved TEAD binding.

FIG. 10 illustrates binding to TEAD by variants of a peptide of SEQ ID NO: 1 as soluble peptides. Non-reducing conditions are designated as "NR" and reducing conditions are designated as "R."

FIG. 10A illustrates an SDS-PAGE of a soluble peptide of SEQ ID NO: 9 in non-reduced (NR) or reduced (R) conditions.

FIG. 10B illustrates an HPLC chromatogram of a peptide of SEQ ID NO: 9 in non-reduced or reduced conditions.

FIG. 10C illustrates SPR data showing binding of a peptide of SEQ ID NO: 9 to biotinylated TEAD immobilized on an SPR chip. SPR experiments for a peptide of SEQ ID NO: 9 were conducted by single cycle kinetic analysis and the $K_D$ was determined to be 368 µM.

FIG. 10D illustrates an SDS-PAGE of a soluble peptide of SEQ ID NO: 10 in non-reduced (NR) or reduced (R) conditions.

FIG. 10E illustrates an HPLC chromatogram of a peptide of SEQ ID NO: 10 in non-reduced or reduced conditions.

FIG. 10F illustrates SPR data showing binding of a peptide of SEQ ID NO: 10 to biotinylated TEAD immobilized on an SPR chip. SPR experiments for a peptide of SEQ ID NO: 10 were conducted by single cycle kinetic analysis and the $K_D$ was determined to be 372 µM.

FIG. 11 illustrates inhibition of YAP binding to TEAD with a soluble peptide of SEQ ID NO: 9 as compared to inhibition of YAP binding to TEAD with a soluble peptide of SEQ ID NO: 1.

FIG. 12 illustrates stability of TEAD-binding peptides in the presence of reducing agents.

FIG. 13 illustrates binding to TEAD after cells expressing SDGF-SEQ ID NO: 9 are exposed to a reducing agent.

FIG. 14 illustrates protease resistance of a peptide of SEQ ID NO: 9.

FIG. 15 shows the results of Surface Plasmon Resonance (SPR) experiments.

FIG. 15A shows the raw data from SPR experiments illustrating binding of SEQ ID NO: 1 at various concentrations.

FIG. 15B illustrates the data from SPR fit with the 1:1 binding model for single cycle kinetics.

FIG. 15C shows the raw data from SPR experiments illustrating binding of SEQ ID NO: 5 at various concentrations.

FIG. 15D illustrates the data from SPR fit with the 1:1 binding model for single cycle kinetics.

FIG. 15E shows the raw data from SPR experiments illustrating binding of SEQ ID NO: 7 at various concentrations.

FIG. 15F illustrates the data from SPR fit with the 1:1 binding model for single cycle kinetics.

FIG. 15G shows the raw data from SPR experiments illustrating binding of SEQ ID NO: 8 at various concentrations.

FIG. 15H illustrates the data from SPR fit with the 1:1 binding model for single cycle kinetics.

FIG. 15I shows the raw data from SPR experiments illustrating binding of SEQ ID NO: 11 at various concentrations.

FIG. 15J illustrates the data from SPR fit with the 1:1 binding model for single cycle kinetics.

FIG. 16 illustrates data from SPR experiments illustrating binding of peptides of the present disclosure to TEAD.

FIG. 17 illustrates mammalian surface display screening for identifying TEAD-binding peptides.

FIG. 18 illustrates that SEQ ID NO: 9 significantly reduces YAP:TEAD dimers in the nucleus.

FIG. 18A illustrates the relative luminescence units of SEQ ID NO: 1 or SEQ ID NO: 9 expressed directly into the cytosol as part of an mCherry-T2a-peptide fusion construct, co-transfected with YAP and 8×GTIIC (TEAD luciferase reporter). This was done in 24-well plate wells, in which 293 T cells were transfected with 50 ng FLAG-YAP, 300 ng 8×GTIIC, and either 100 or 250 ng mCherry-T2a-peptide plasmids. *: $P<0.05$, **: $P<0.005$ vs. YAP only.

FIG. 18B illustrates the FLAG-tagged SEQ ID NO: 7, FLAG-tagged SEQ ID NO: 1, FLAG-tagged SEQ ID NO: 9, or FLAG-tagged SEQ ID NO: 177 in the mCherry-T2a-peptide construct SDS-PAGE gel mobility shift upon DTT reduction by Western blot (anti-FLAG M2 antibody). Shown are the bands corresponding to the size of the uncleaved fusion protein. SEQ ID NO: 177 is SEQ ID NO: 9-6×CS, in which all six cysteines were mutated to serines, simulating non-oxidizable sulfhydryls.

FIG. 18C illustrates SEQ ID NO: 9-DyLight488 that was introduced to the cytosol/nucleus of HeLa cells using 5 μM dfTAT, which induces endosomal leakage. dfTAT was visible in the TRITC channel, while SEQ ID NO: 9-DyLight488 was seen in the FITC channel (FIG. 18D).

FIG. 18D illustrates SEQ ID NO: 9-DyLight488 that was introduced to the cytosol/nucleus of HeLa cells using 5 μM dfTAT, which induces endosomal leakage. SEQ ID NO: 9-DyLight488 was seen in the FITC channel, while dfTAT was visible in the TRITC channel (FIG. 18C).

FIG. 18E illustrates a proximity ligation assay (PLA) in HeLa cells. Using primary antibodies against YAP and TEAD, speckles (APC channel) overlapping DAPI-stained nuclei (UV channel) were produced. Shown is a representative image of cells treated with 5 μM dfTAT only.

FIG. 18F illustrates a proximity ligation assay (PLA) in HeLa cells. Using primary antibodies against YAP and TEAD, speckles (APC channel) overlapping DAPI-stained nuclei (UV channel) were produced. Shown is a representative image of cells treated with 5 μM dfTAT and 5 μM SEQ ID NO: 9.

FIG. 18G illustrates a representative image of a control proximity ligation assay (PLA) reaction with anti-YAP primary antibodies omitted in which some speckles were non-specific to YAP:TEAD dimers.

FIG. 18H illustrates a representative image of a control proximity ligation assay (PLA) reaction with anti-TEAD primary antibodies omitted in which some speckles were non-specific to YAP:TEAD dimers.

FIG. 18I illustrates a dot graph of automated counting of YAP:TEAD proximity ligation assay (PLA) speckles per nucleus of HeLa cells treated with 5 μM dfTAT and/or 5 μM TEAD-binding peptides. Each dot represents a single nucleus, with the bars representing the median ±95% confidence intervals. A line was drawn at the sum of the two antibody omission samples' average speckle counts, representing the approximate value attributable to non-specific speckles. ****: $P<0.0001$ vs. any other sample. All P-values determined by two-tailed T-test.

FIG. 19 illustrates a site saturation mutagenesis (SSM) library of SEQ ID NO: 1 variants. This library contains improved TEAD binders.

Figure 19A:
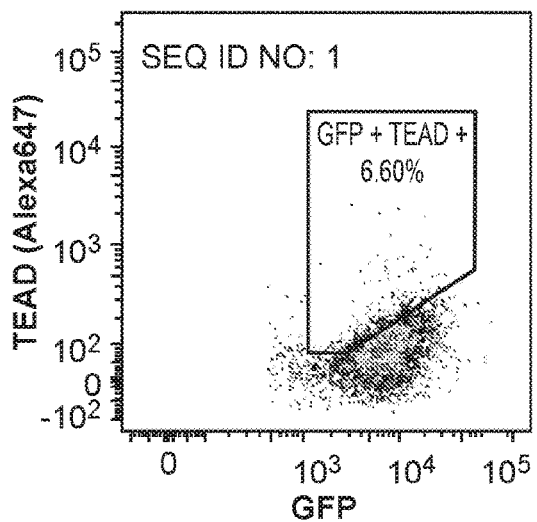

FIG. 19A illustrates the binding profile of SEQ ID NO: 1. SEQ ID NO: 1 binding was apparent but weak under a 20 nM TEAD concentration and 2-step staining binding conditions.

Figure 19B:
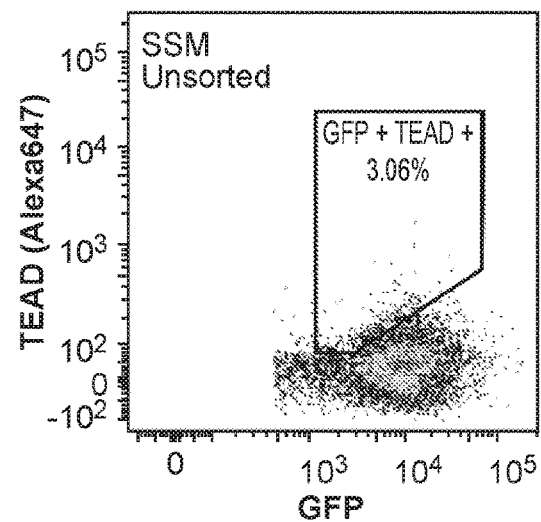

FIG. 19B illustrates the binding profile of unsorted site saturation mutagenesis (SSM) library stained with TEAD followed by streptavidin-Alexa647.

Figure 19C:
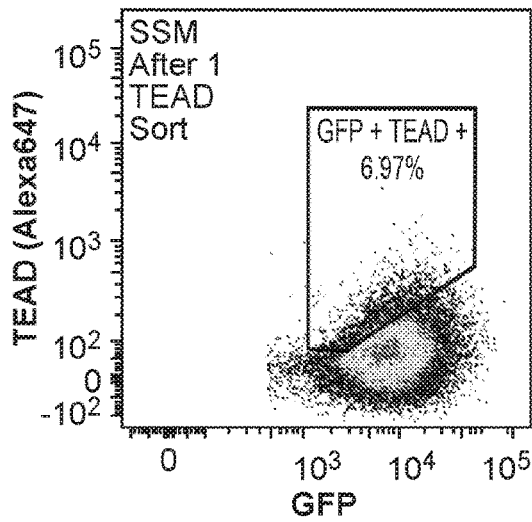

FIG. 19C illustrates the binding profile of sorted once site saturation mutagenesis (SSM) library stained with TEAD followed by streptavidin-Alexa647.

Figure 19D:
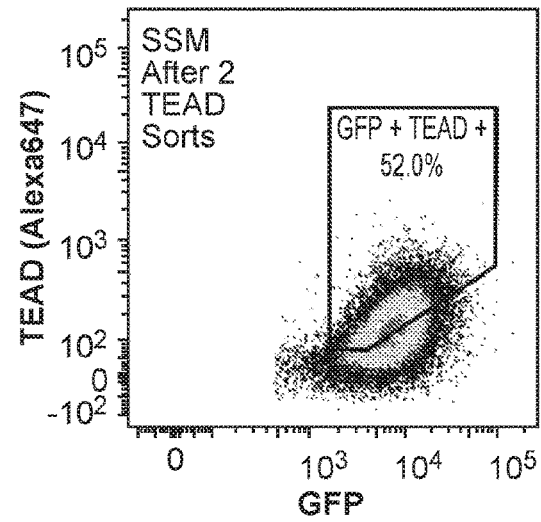

FIG. 19D illustrates the binding profile of sorted twice site saturation mutagenesis (SSM) library stained with TEAD followed by streptavidin-Alexa647.

Figure 19E:
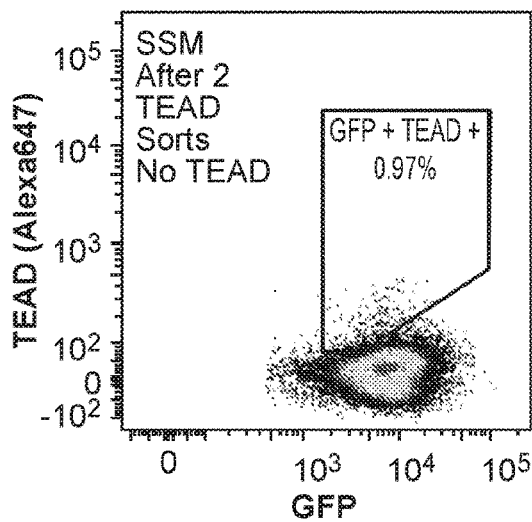

FIG. 19E illustrates the binding profile of the population in FIG. 19D stained with streptavidin-Alexa647 only, without TEAD.

FIG. 20 illustrates SEQ ID NO: 9 and variants of SEQ ID NO: 9 are stable in extreme heat.

Figure 20A:
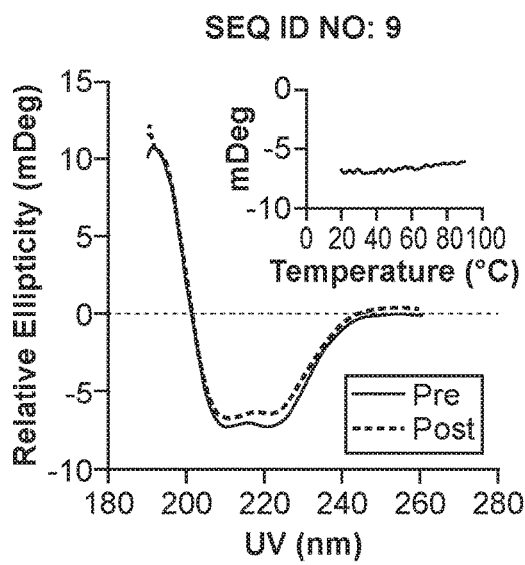

FIG. 20A illustrates circular dichroism spectra of SEQ ID NO: 9, which demonstrates the structure is dominated by α-helical elements, and that this secondary structure signature is identical before (Pre) and after (Post) incubation at 95° C. Inset: relative ellipticity at 220 nm during heating from 20° C. to 95° C.

Figure 20B:
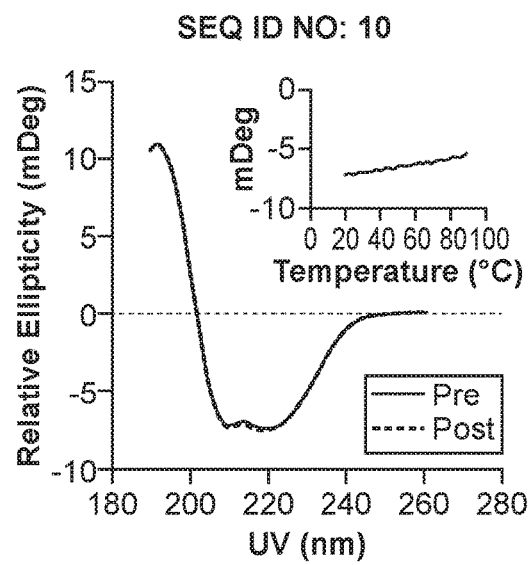

FIG. 20B illustrates circular dichroism spectra of SEQ ID NO: 10, which demonstrates the structure is dominated by α-helical elements, and that this secondary structure signature is identical before (Pre) and after (Post) incubation at 95° C. Inset: relative ellipticity at 220 nm during heating from 20° C. to 95° C.

Figure 20C:
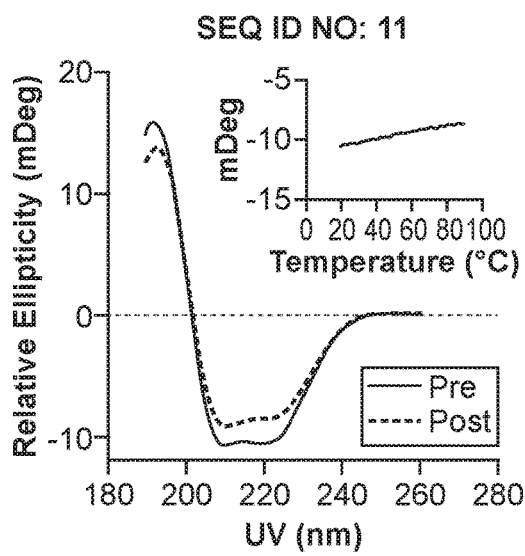

FIG. 20C illustrates circular dichroism spectra of SEQ ID NO: 11, which demonstrates the structure is dominated by α-helical elements, and that this secondary structure signature is identical before (Pre) and after (Post) incubation at 95° C. Inset: relative ellipticity at 220 nm during heating from 20° C. to 95° C.

Figure 20D:
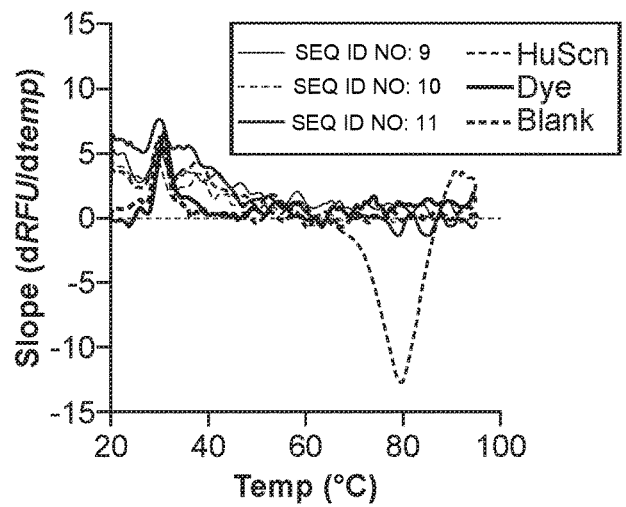

FIG. 20D illustrates a SYPRO Orange melting assay of peptides. Shown is the slope of the change in relative fluorescence units (dRFU/dtemp) during heating from 20° C. to 95° C. Human siderocalin (HuScn) demonstrated an expected melting temperature of 79° C., as interpreted by the peak of its RFU vs temperature slope. Conversely, no melting temperature could be determined for the three peptides tested (SEQ ID NO: 9, SEQ ID NO: 10, and SEQ ID NO: 11).

FIG. 21 illustrates biotinylated TEAD with streptavidin-Alexa647 stained cells expressing surface-displayed YAP.

Figures 21A, 21B:
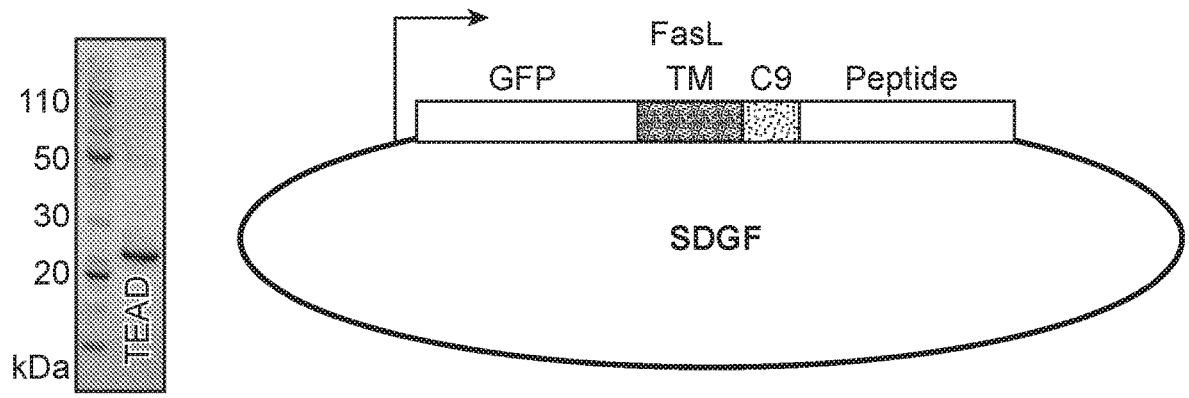

FIG. 21A illustrates TEAD produced in Hi5 insect cells.

FIG. 21B illustrates a cartoon of the surface display GFP FasL (SDGF) vector comprising a bovine rhodopsin C9 tag, and the peptide.

Figure 21C:
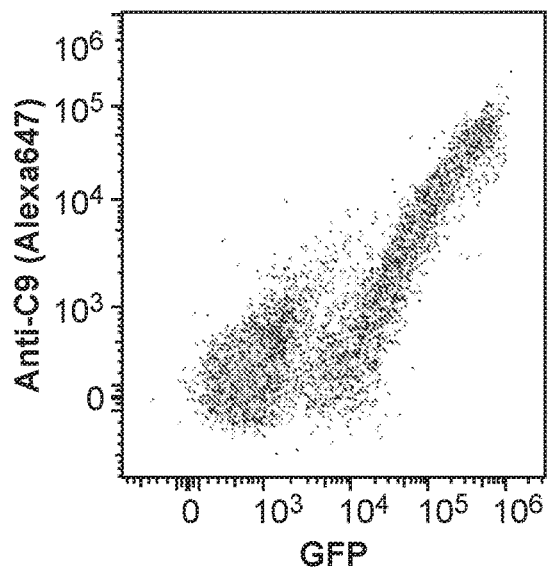

FIG. 21C illustrates a flow cytometry profile of a suspension of HEK-293 Freestyle (293F) cells transfected with surface display GFP FasL (SDGF)-control peptide stained with anti-C9-Alexa647.

Figure 21D:
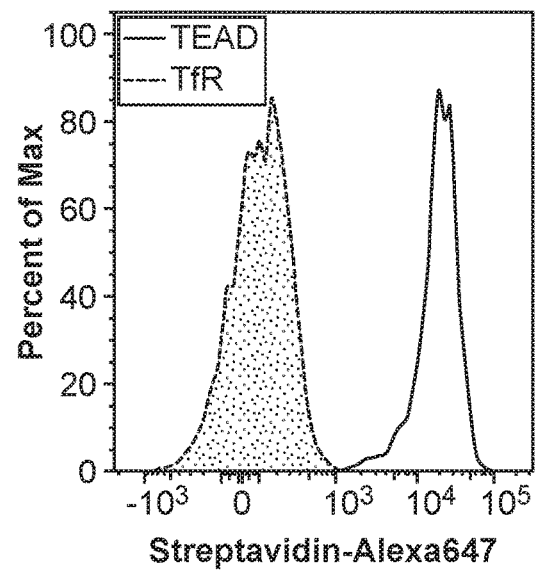

FIG. 21D illustrates 293F cells transfected with SDGF-YAP are stained by streptavidin-Alexa647 after co-incubation with biotinylated TEAD compared to after co-incubated with a control protein (biotinylated TfR ectodomain).

Figure 22:
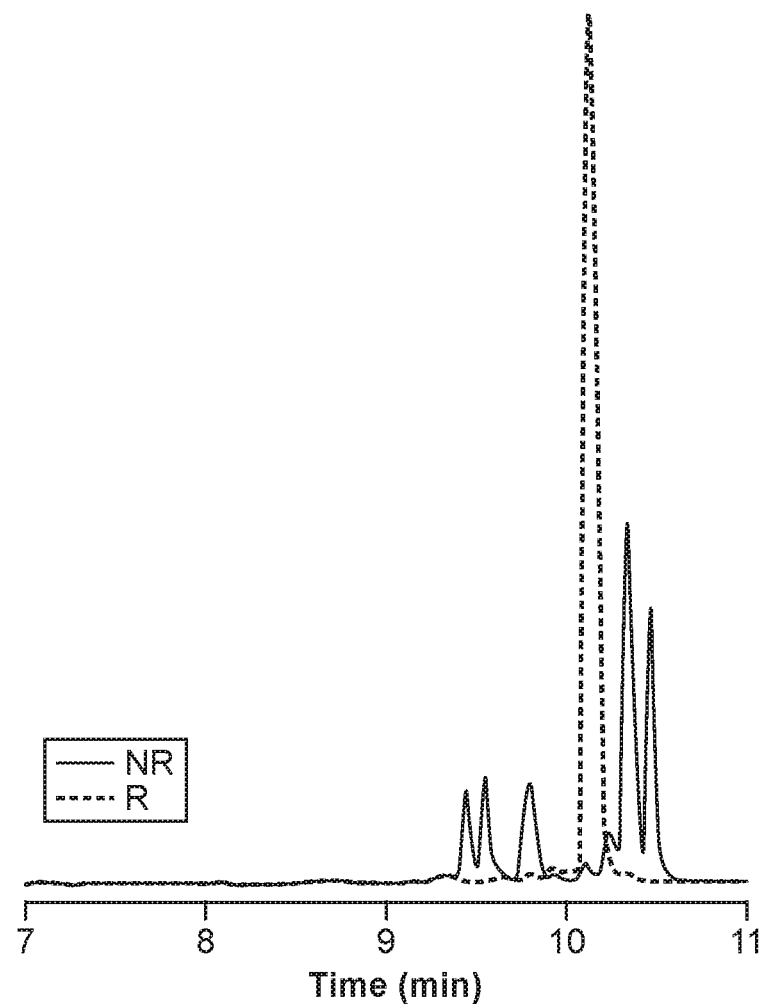

FIG. 22 illustrates SEQ ID NO: 2 (TB2G1) soluble peptide has multiple disulfide connection patterns. The reversed-phase chromatography (RPC) traces of the non-reduced (NR) and 10 mM DTT-reduced (R) TB2G1 peptide indicate multiple species prior to reduction. Because they have the same mobility upon elimination of disulfide bonds, there is most likely only one peptide product and the different species are the peptide existing in different disulfide connection patterns.

Figure 23:
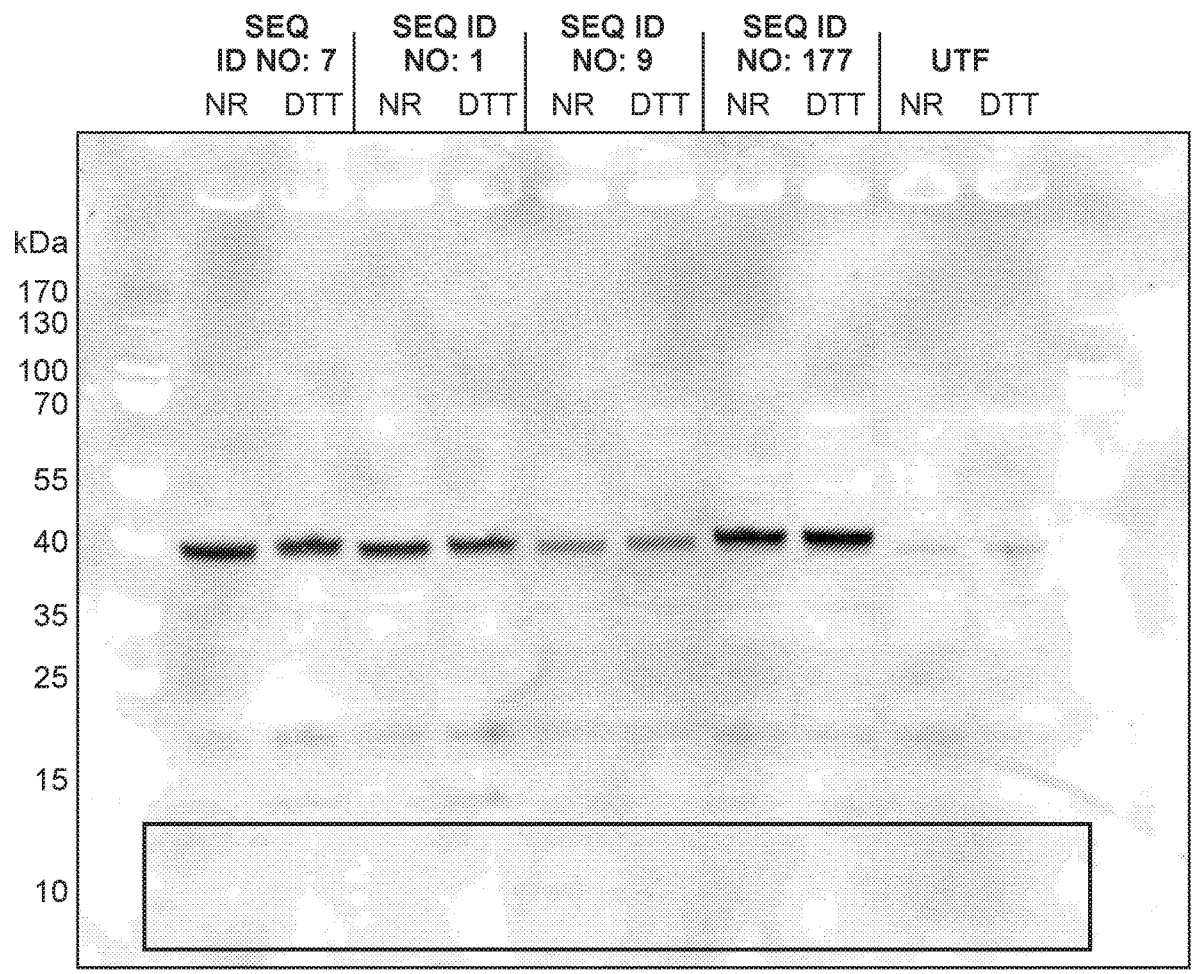

FIG. 23 illustrates the full anti-FLAG M2 Western blot from FIG. 18B of the mCherry-T2a-FLAG-peptide constructs (FLAG-SEQ ID NO: 7, FLAG SEQ ID NO: 1, FLAG SEQ ID NO: 9, or FLAG SEQ ID NO: 184). 293T cells were transfected with 500 ng of construct. As indicated by the Western blot, intact fusion but not cleaved, soluble peptides were found in 293T cell lysate. The prominent bands correspond to the expected size of the intact mCherry-T2a-peptide. The box shows the region where T2a-cleaved, FLAG-tagged peptides would be expected to run, based on SDS-PAGE of soluble, untagged peptides. NR: non-reduced. DTT: 5 mM DTT, added immediately before loading SDS-PAGE gel. UTF: Untransfected 293T lysate.

FIG. 24 illustrates a surface plasmon resonance (SPR) equilibrium analysis fit curves for TEAD-binding $K_D$ determination. This analytical method was used because the separate on- and off-rates of these peptides were faster than the SPR instrument could resolve.

Figure 24A:
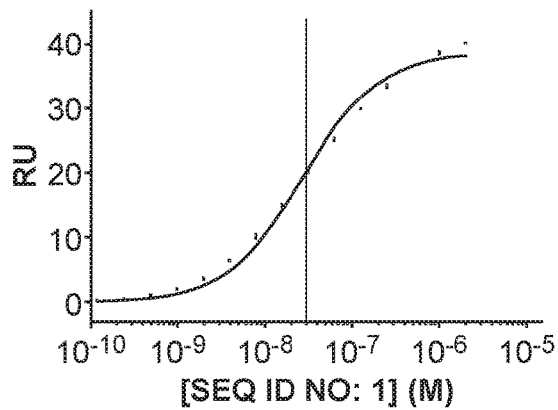

FIG. 24A illustrates the $K_D$ of SEQ ID NO: 1 using surface plasmon resonance (SPR) equilibrium analysis.

Figure 24B:
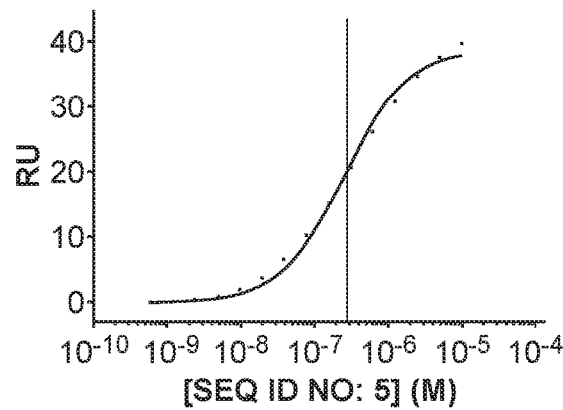

FIG. 24B illustrates the $K_D$ of SEQ ID NO: 5 using surface plasmon resonance (SPR) equilibrium analysis.

Figure 24C:
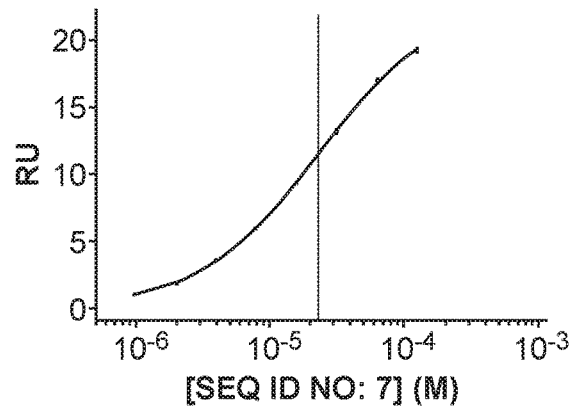

FIG. 24C illustrates the $K_D$ of SEQ ID NO: 7 using surface plasmon resonance (SPR) equilibrium analysis.

Figure 25:
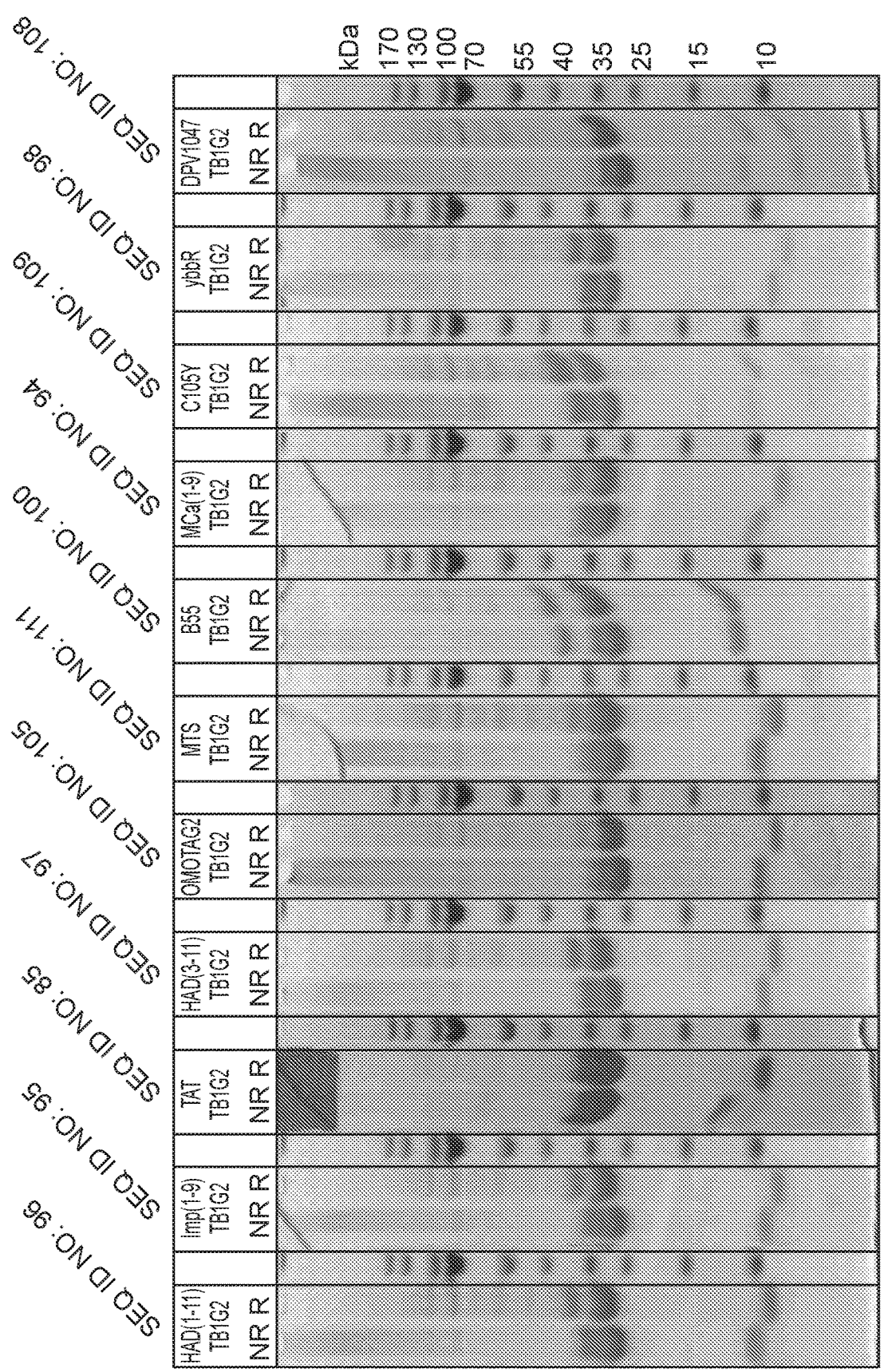

FIG. 25 illustrates SDS-PAGE gels of TEAD Binder-Cell Penetrating Peptide fusions (CPP fusions) and Tandem-Cysteine Dense Peptides (Tandem-CDPs) under non-reduced (NR) and reduced (R) conditions. The tested CPP fusions were SEQ ID NO: 96, SEQ ID NO: 95, SEQ ID NO: 85, SEQ ID NO: 97, SEQ ID NO: 105, SEQ ID NO: 111, SEQ ID NO: 100, SEQ ID NO: 94, SEQ ID NO: 109, SEQ ID NO: 98, and SEQ ID NO: 108. The tested Tandem-CDPs were SEQ ID NO: 134, SEQ ID NO: 124, SEQ ID NO: 117, SEQ ID NO: 125, SEQ ID NO: 132, SEQ ID NO: 119, SEQ ID NO: 141, SEQ ID NO: 130, and SEQ ID NO: 138. The CPP fusions and Tandem-CDPs were produced at small scale in 1 mL cultures and TEV-cleaved to separate the peptide (lower band(s) in FIG. 25) from the siderocalin carrier (middle band(s) in FIG. 25). Uncleaved fusion proteins appear as the top-most band(s). This figure illustrates use of a spacer of sequence GGGS (SEQ ID NO: 203) in SEQ ID NO: 134, SEQ ID NO: 125, and SEQ ID NO: 119.

Figure 26:
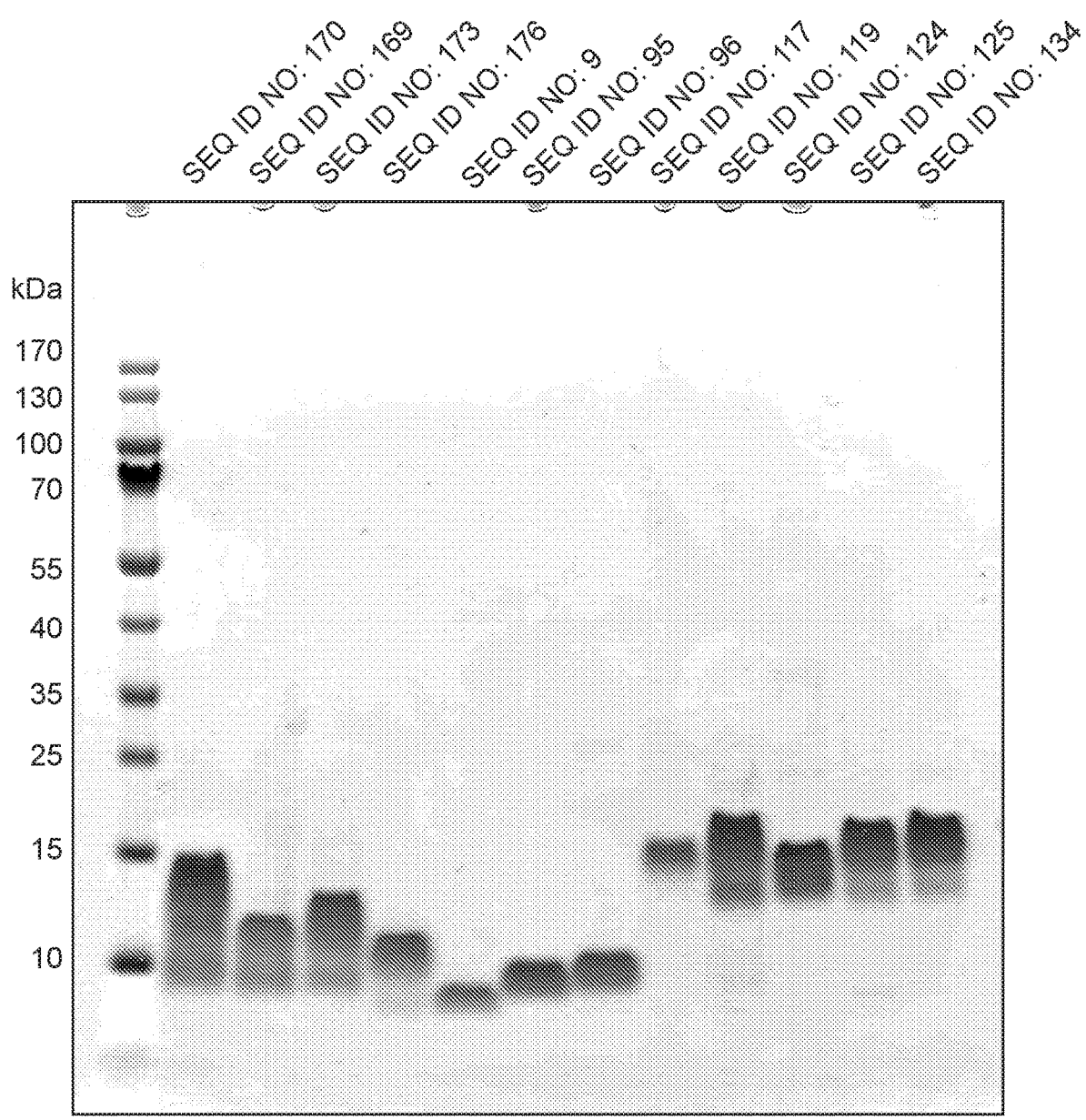

FIG. 26 illustrates SDS-PAGE gel, from left to right, of hadrucalcin (SEQ ID NO: 170), imperatoxin (SEQ ID NO: 169), opicalcin-2 (SEQ ID NO: 173), chlorotoxin (SEQ ID NO: 176), the TEAD Binder (SEQ ID NO: 9), CPP fusions of SEQ ID NO: 95 and SEQ ID NO: 96, and Tandem-CDPs of SEQ ID NO: 117, SEQ ID NO: 119, SEQ ID NO: 124, SEQ ID NO: 125, and SEQ ID NO: 134.

Figure 27:
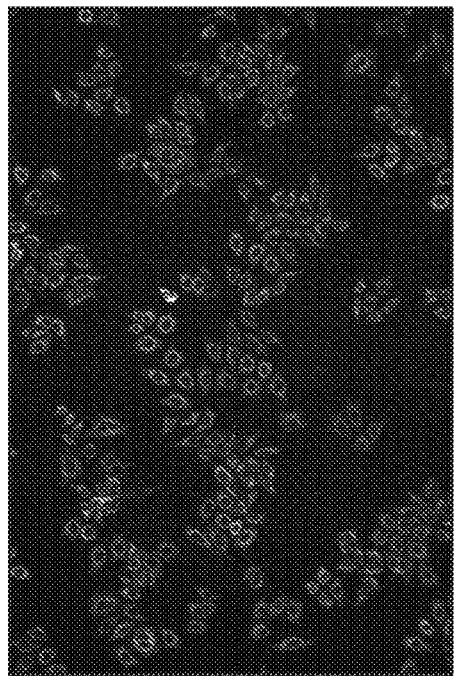
Figure 27:
Figure 27:
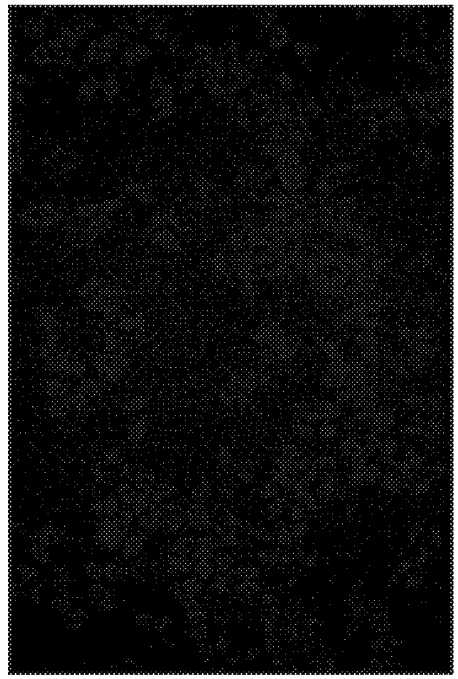
Figure 27:
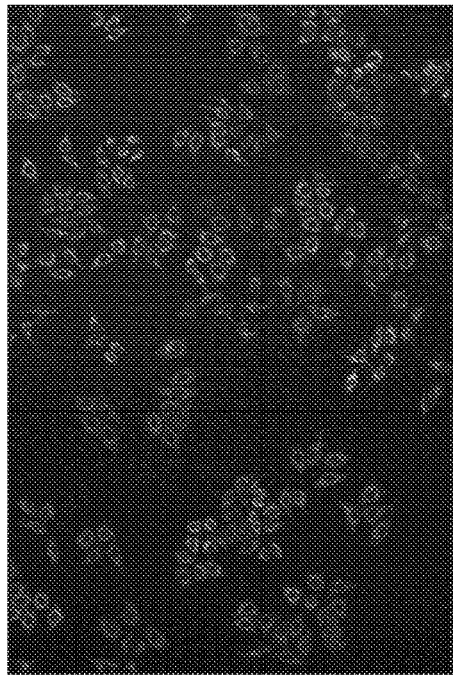

FIG. 27 illustrates microscopy images of HeLa cells evaluated for cell penetration with a Halo assay. The top left image shows the fluorescence of cells treated with a test solution with 1 µM HT (no protein). The top right image shows the fluorescence of cells treated with buffer only. The bottom left image shows the fluorescence of cells treated with 1 µM HT-SEQ ID NO: 9 (bottom left). The bottom right image shows the fluorescence of cells treated with 1 µM HT-SEQ ID NO: 124 (bottom right). The peptide of SEQ ID NO: 124 (bottom right) exhibited high cell penetration.

Figure 28:
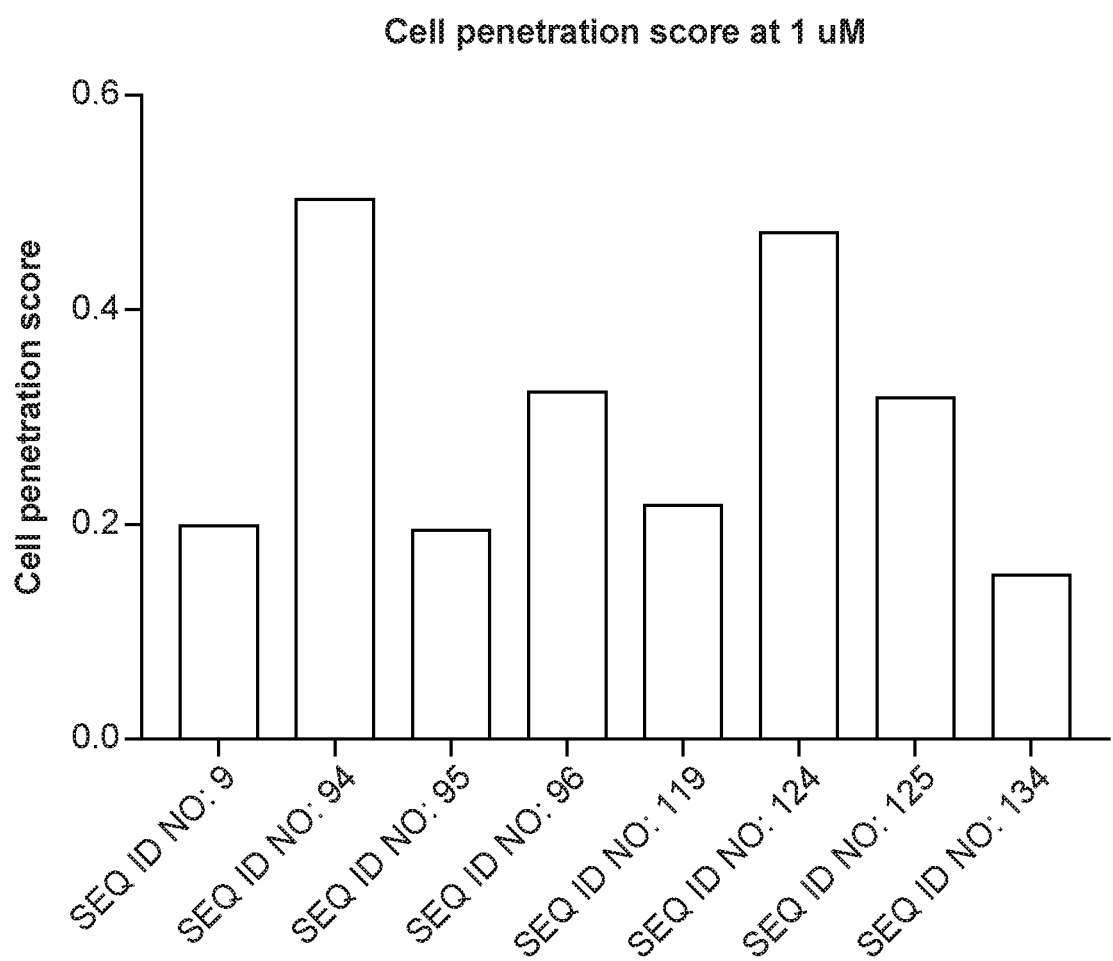

FIG. 28 illustrates cell-by-cell quantitation of average fluorescence in the red channel of HeLa cells. Cells were incubated with no HaloTag (HT) (not shown in figure; used for calibration as 0 cell penetration score (CPS)), 1 µM HT (not shown in graph; used for calibration as 1 CPS), 1 µM HT-SEQ ID NO: 9 (a control TEAD binder), 1 µM SEQ ID NO: 94, 1 µM HT-SEQ ID NO: 95, 1 µM HT-SEQ ID NO: 96, 1 µM HT-SEQ ID NO: 119, 1 µM HT-SEQ ID NO: 124, 1 µM HT-SEQ ID NO: 125, or 1 µM HT-SEQ ID NO: 134.

Figure 8A:
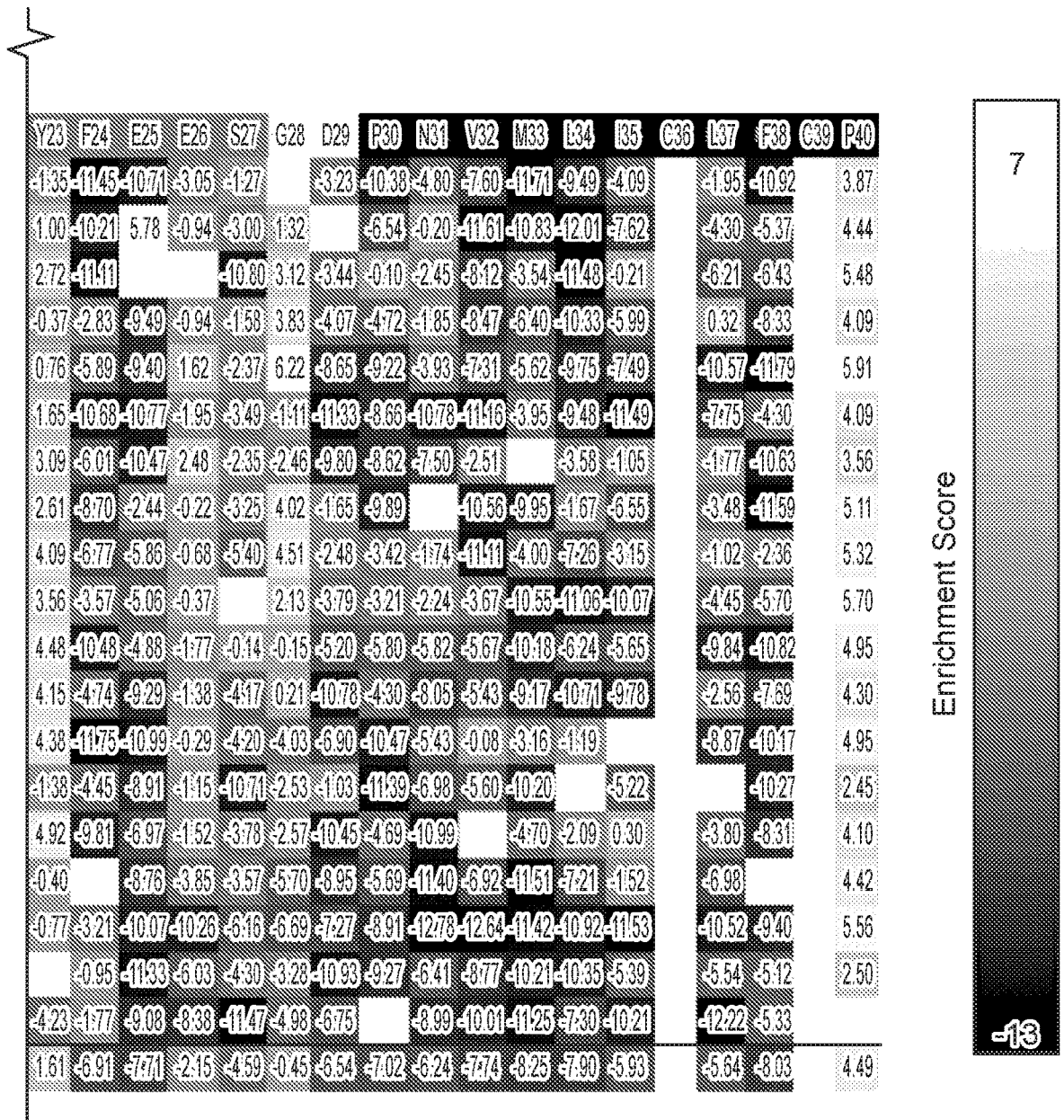
FIG. 8A illustrates a matrix of variants of a peptide of SEQ ID NO: 1 generated in the SSM screen. The x-axis shows the sequence of a peptide of SEQ ID NO: 1 versus all substituted non-cysteine residues on the y-axis, after two rounds of sorting. The enrichment score (log 2 change in relative abundance after two rounds of sorting versus input abundance) is indicated on a greyscale. Positive or high enrichment scores (lighter shades of grey) correspond to residues that are more tolerant to substitutions. Negative or lower enrichment scores (darker shades of grey) correspond to residues that are less tolerant to substitution, such as residues that are important to binding. As disclosed herein, amino acid residue position counting does not include the N-terminal GS.

FIG. 29 and FIG. 30 illustrate another representation of FIG. 8A, showing the SSM screen for improved variants of SEQ ID NO: 1, which provided insight into the structure and tolerance to mutation at each position of the peptide.

DETAILED DESCRIPTION

The HIPPO signaling pathway plays a critical role in contact inhibition, cell density regulation, cell proliferation, organ size and development (organogenesis), and tissue homeostasis, which are important in cancer development, tumor progression, and metastasis (Hong et al. The YAP and TAZ transcription co-activators: key downstream effectors of the mammalian Hippo pathway. Semin Cell Dev Biol. 2012 September; 23(7):785-93, Santucci et al. The Hippo Pathway and YAP/TAZ-TEAD Protein-Protein Interaction as Targets for Regenerative Medicine and Cancer Treatment. J Med Chem. 2015 Jun. 25; 58(12):4857-73.). This pathway is often dysregulated in many human cancers and other diseases associated with uncontrolled cell growth, including liver, pancreas, colon, ovarian, breast, brain, and lung cancers, melanoma, medulloblastoma, and diabetes (Types I and II), as its dysregulation can result in increased cell proliferation, reduced apoptosis and differentiation, tissue overgrowth, and tumorigenesis. For example, the HIPPO pathway can be disregulated in osteosarcoma, hepatocellular carcinoma, malignant mesothelioma, schwannoma, meningioma, renal carcinoma, cholangiocarcinoma, bile duct hamartoma, soft tissue carcinoma, ovarian carcinoma, colonic adenoma, T cell acute lymphoblastic leukaemia, gastrointestinal hyperplasia, skin cancer, fibrosarcoma, pancreatic ductal metaplasia, squamous cell carcinoma, kaposis sarcoma, and HIV-induced non-Hodgkin's lymphoma.

Components of the HIPPO pathway are evolutionarily conserved in vertebrates and mammals. In mammals, the HIPPO pathway involves a core kinase cascade involving Mst1 or Mst2, which forms a complex with adaptor protein WW45 and phosphorylates kinases LATS1 and LATS2 and adaptor protein MOB. The LATS/MOB complex can then phosphorylate and repress transcriptional coactivators Yes-associated protein (YAP) and TAZ. Phosphorylation of YAP can promote YAP ubiquitination and subsequent degradation. Various other proteins and complexes regulate YAP protein levels at multiple points, including FERM domain proteins Merlin/NF2 and FRMD6, junctional proteins ZO-2 and AJUB, polarity complex proteins Crumbs, Angiomotin, Scribble, and KIBRA, and protein phosphatases PP2A and ASPP1. Tight regulation of YAP is physiologically important, as YAP acts like an oncogene, and its overexpression is implicated in several human cancers. Increased YAP expression and nuclear localization are associated with tumor progression (Hong et al. The YAP and TAZ transcription co-activators: key downstream effectors of the mammalian Hippo pathway. Semin Cell Dev Biol. 2012 September; 23(7):785-93, Santucci et al. The Hippo Pathway and YAP/TAZ-TEAD Protein-Protein Interaction as Targets for Regenerative Medicine and Cancer Treatment. J Med Chem. 2015 Jun. 25; 58(12):4857-73).

YAP is a transcription coactivator and is a key regulator of organ growth and cell proliferation in the HIPPO pathway. YAP interacts with several transcription factors that mediate biological functions of YAP in promoting cell growth, including ErbB4, Runx2, TEAD, and p73. TEAD is one of the most potent targets of YAP, as TEAD is required for YAP to stimulate gene expression and cell growth by activating various genes downstream from YAP. YAP binds to TEAD to mediate YAP-dependent gene induction. For example, interaction between YAP and TEAD can activate connective tissue growth factor (CTGF). Inhibitors that can disrupt the interaction between YAP and TEAD provide a powerful approach to preventing and/or treating cancers or other diseases associated with dysregulation of the HIPPO pathway and/or cell growth, such as diabetes (Type I or Type II). (Hong et al. The YAP and TAZ transcription co-activators: key downstream effectors of the mammalian Hippo pathway. Semin Cell Dev Biol. 2012 September; 23(7):785-93, Santucci et al. The Hippo Pathway and YAP/TAZ-TEAD Protein-Protein Interaction as Targets for Regenerative Medicine and Cancer Treatment. J Med Chem. 2015 Jun. 25; 58(12):4857-73). As described herein, TEAD can be TEAD1, TEAD2, TEAD3, TEAD4, or a fragment, recombinant protein, homolog, or a variant thereof.

The HIPPO pathway relies on the intranuclear interaction of the transcriptional coactivator YAP and the transcription factor TEAD (1-4). This pathway also plays a crucial role in recovery from injury; for example, its regulated repression allows hepatocytes to divide and replace tissue lost to a partial hepatectomy, after which its activation suppresses cell growth and prevents tissue overgrowth. Designing drugs that target cell growth signaling via protein-protein interactions has proven difficult because targeting protein-protein interactions requires efficient intracellular, and sometimes intranuclear, delivery. While antibodies can be effective in targeting extracellular or cell surface epitopes, intracellular and intranuclear targets, such as the interaction between YAP and TEAD or TEAD and other proteins, are not amenable to antibody-based therapeutics because antibodies generally cannot penetrate the cell membrane to access cytosolic and nuclear target proteins.

Finding therapeutic agents that can disrupt intracellular protein-protein interactions can be challenging, as such methods require high specificity or targeting, high affinity binders that can disrupt YAP-TEAD interactions, the ability to penetrate cells or the nucleus to act on the target proteins, and having low off-target adverse effects. With few exceptions, high throughput screening campaigns with small molecule libraries failed to provide specific, high affinity binders capable of disrupting larger protein-protein interfaces, such as YAP-TEAD.

Described herein are peptides and methods of screening peptides for binding to a target protein of interest, such as TEAD, and hence peptides that can disrupt YAP-TEAD interaction or TEAD interaction with other proteins in a cell. The same methods can also be applied to identify peptides that bind to any other target protein or receptor, or any protein of interest, such that peptide binding results in an inhibition or disruption in binding between the target protein of interest and its natural binders or substrates. Examples of target protein include, but not limited to, receptors, such as transferrin receptor (TfR), insulin receptor (InsR), leptin receptor (ObR), and apolipoprotein E3 (ApoE).

Described herein are peptides, including, but not limited to, designed or engineered peptides, recombinant peptides, and small disulfide-knotted peptides (knottins or knotted peptides), that are large enough to interfere with protein-protein interactions, but small enough to access cellular compartments, such as the cytosol or the nucleus, or tissues, such as the middle of solid tumors, that are generally or often beyond the reach of antibodies. Examples include the calcines, activators of sarcoplasmic reticulum ryanodine receptors, and BLZ-100, a peptide-fluorophore conjugate or fusion that is capable of accumulating in a wide range of tumor types. Because the YAP-TEAD interface is structurally well-characterized (Li et al., 2010; RCSB Protein Data Bank ID: 3KYS, crystal structure of human YAP and TEAD complex), the disclosure provides, in some embodiments, a protein design approach based on the 3D protein complex structure for identifying peptides capable of binding to TEAD and preventing YAP from binding.

Additional aspects and advantages of the present disclosure will become apparent to those skilled in this art from the following detailed description, wherein illustrative embodiments of the present disclosure are shown and described. As will be realized, the present disclosure is capable of other and different embodiments, and its several details are capable of modifications in various respects, all without departing from the disclosure. Accordingly, the drawings and description are to be regarded as illustrative in nature, and not as restrictive.

As used herein, the abbreviations for the natural L-enantiomeric amino acids are conventional and are as follows: alanine (A, Ala); arginine (R, Arg); asparagine (N, Asn); aspartic acid (D, Asp); cysteine (C, Cys); glutamic acid (E, Glu); glutamine (Q, Gln); glycine (G, Gly); histidine (H, His); isoleucine (I, Ile); leucine (L, Leu); lysine (K, Lys); methionine (M, Met); phenylalanine (F, Phe); proline (P, Pro); serine (S, Ser); threonine (T, Thr); tryptophan (W, Trp); tyrosine (Y, Tyr); valine (V, Val). Typically, Xaa can indicate any amino acid. In some embodiments, X can be asparagine (N), glutamine (Q), histidine (H), lysine (K), or arginine (R).

The present disclosure refers to amino acid residues and positions of amino acid residues within a sequence. As referred to herein, a position can be referred to as "position X," wherein X is the position number within a sequence not counting, if present, the N-terminal GS. For example, position 15 in SEQ ID NO: 1 (GSPDEYIERAKE-CCKKGDIQCCLRYFEESGDPNVMLICLFCP) refers to the "G" residue at position 15 within the sequence, wherein position 1 does not count the N-terminal "GS," and is, thus, the first P residue. As another example, position 10 in SEQ ID NO: 2 (GSLERLKKCCNQGLDCEEARWKCEL-EALFQGKNRETCLEEC) refers to the "Q" residue within the sequence at position 10, wherein position 1 does not count the N-terminal "GS," and is, thus, the first L residue. As yet another example, position 10 in SEQ ID NO: 43 (PDEYIERAKECCKKGDIQCCLRYFEESGDPNVMLI-CLFCP) refers to the "E" residue at position 10 within the sequence, wherein position 1 is the very first P residue and there is no N-terminal GS. As also referred to herein, a position can be referred to as "XY," wherein X is the single-letter abbreviation for an amino acid and wherein Y is the position number within a sequence not counting, if present, the N-terminal GS. For example, G15 refers to the "G" residue at position 15 within a sequence, not counting, if present, an N-terminal GS. As another example, Y23 refers to the "Y" residue at position 23 within a sequence, not counting, if present, an N-terminal GS. As yet another example, E25 refers to the "E" residue at position 25 within a sequence, not counting, if present, an N-terminal GS. As also referred to herein, a position can be referred to as "XYZ," wherein X and Z are the single-letter abbreviation for an amino acid and wherein Y is the position number within a sequence not counting, if present, the N-terminal GS. For example, L23A refers to a "L" residue at position 23 within a sequence (not counting, if present, an N-terminal GS), which has been substituted with a "A" residue. As another example, E25A refers to an "E" residue at position 25 within a sequence (not counting, if present, an N-terminal GS), which has been substituted with an "A" residue. As yet another example, F27A refers to an "F" residue at position 27 within a sequence (not counting, if present, an N-terminal GS), which has been substituted with an "A" residue.

Some embodiments of the disclosure contemplate D-amino acid residues of any standard or non-standard amino acid or analogue thereof. When an amino acid sequence is represented as a series of three-letter or one-letter amino acid abbreviations, the left-hand direction is the amino terminal direction and the right-hand direction is the carboxy terminal direction, in accordance with standard usage and convention.

Peptides

Disclosed herein are peptide sequences, such as those listed in TABLE 1, capable of binding to TEAD or disrupting YAP-TEAD interaction, TEAD interaction with other proteins, or interaction between homologs, derivatives, or variants of YAP and TEAD. In some embodiments, peptides disclosed herein can penetrate or enter target cells, such as cancerous or tumor cells, liver cells, pancreas cells, colon cells, ovarian cells, breast cells, and/or lung cells, or any combination thereof.

In some embodiments, peptides can penetrate a nucleus of a cell to modulate transcription activity of a gene. In other embodiments, peptides described herein compete with YAP for binding to TEAD or displace YAP from binding to TEAD. In some embodiments, peptides described herein bind to TEAD, or a variant, homolog, or derivative thereof. In other embodiments, peptides described herein are capable of binding to TEAD and disrupting or inhibiting interaction between TEAD and other proteins or coactivators, such as TAZ. As described herein, "compete" or peptide competition for binding to TEAD or any target protein interest encompasses, but not limited to, steric hindrance, occupying binding sites of TEAD, non-covalent interactions, such as salt bridges or hydrophobic interactions, crosslinking, covalent interactions, sequestration of TEAD, binding to TEAD that prevents localization to the nucleus, and any combination thereof.

In some embodiments, peptides bind to TEAD with equal, similar, or greater affinity (lower dissociation constant $K_D$) as compared to YAP binding to TEAD. In some embodiments, peptides described herein bind to TEAD with similar, same or equal, or lower dissociation constant as compared to YAP's dissociation constant. In some embodiments, the peptide can have a $K_D$ of less than 40 nM, less than 30 nM, less than 20 nM, less than 10 nM, less than 1 nM, or less than 0.1 nM. In other embodiments, one or more conserved residues at the YAP-TEAD interface are also present in the peptides described here.

In some embodiments, peptides bind to TEAD at residues found in the YAP-TEAD interface. In some embodiments, a peptide that binds to TEAD comprises at least 70% homology, at least 75% homology, at least 80% homology, at least 85% homology, at least 90% homology, at least 95% homology, or at least 99% homology as the binding interface or the sequence of a protein or co-factor known to bind TEAD. In other embodiments, a peptide described herein binds to a protein of interest, which comprises at least 70% homology, at least 75% homology, at least 80% homology, at least 85% homology, at least 90% homology, at least 95% homology, or at least 99% homology as TEAD, a fragment, homolog, or a variant thereof.

In some embodiments, peptides can bind to any of the four TEAD homologs, including TEAD1, TEAD2, TEAD3, TEAD4, or any combination thereof. In other embodiments, peptides are capable of binding to one, one or more, two, two or more, three, three or more, or all four TEAD homologs. In some embodiments, peptides of the present disclosure can prevent or disrupt binding between TEAD and any other protein or co-factor known to interact with TEAD. For example, in some embodiments, a peptide of the present disclosure can prevent or interfere with binding between TEAD and TAZ, thereby preventing or reducing oncogenic effects or transcription of a downstream oncogene. YAP and TAZ are two well-known TEAD-binding transcriptional cofactors. TAZ binding to TEAD is similar to YAP binding to TEAD, having similar protein-protein interface or protein binding interactions with TEAD that can be blocked by SEQ ID NO: 1 and its derivatives or variants (e.g. SEQ ID NO: 9; or any of SEQ ID NO: 1-SEQ ID NO: 84), and containing the leucine-$X_1$-$X_2$-leucine-phenylalanine (L$X_1X_2$LF, SEQ ID NO: 217), wherein $X_1$ and $X_2$ can be any amino acid, or containing the leucine-$X_1$-$X_2$-leucine-phenylalanine (L$X_1X_2$LF, SEQ ID NO: 217) motif, wherein $X_1$ and $X_2$ can be any amino acid. In some embodiments, the $X_1X_2$ in the L$X_1X_2$LF (SEQ ID NO: 217) can be EA, as shown in SEQ ID NO: 2, or IC as shown in SEQ ID NO: 1. In other embodiments, the $X_1X_2$ in the L$X_1X_2$LF (SEQ ID NO: 217) can also be EC, MC, VC, or FC. The L$X_1X_2$LF (SEQ ID NO: 217) is present in both TAZ and YAP, wherein it is found in a helix comprising amino acids TDLEALFNA (SEQ ID NO: 285). In some embodiments, the $X_1X_2$ in the L$X_1X_2$LF (SEQ ID NO: 217) motif can be EA, as shown in SEQ ID NO: 2, or IC as shown in SEQ ID NO: 1. In other embodiments, the $X_1X_2$ in the L$X_1X_2$LF (SEQ ID NO: 217) motif can also be EC, MC, VC, or FC. The L$X_1X_2$LF (SEQ ID NO: 217) motif is present in both TAZ and YAP, wherein the motif is found in a helix comprising amino acids TD LEALFNA (SEQ ID NO: 285). TAZ is also implicated in many of the same cancers as YAP, but is not as well studied. (Hong et al. The YAP and TAZ transcription co-activators: key downstream effectors of the mammalian Hippo pathway. Semin Cell Dev Biol. 2012 September; 23(7):785-93, Santucci et al. The Hippo Pathway and YAP/TAZ-TEAD Protein-Protein Interaction as Targets for Regenerative Medicine and Cancer Treatment. J Med Chem. 2015 Jun. 25; 58(12):4857-73). In some embodiments, peptides of the present disclosure can prevent or interfere with binding between TEAD and any TEAD-binding homolog or TEAD-binding moiety. In some embodiments, a peptide that disrupts TEAD binding or interactions comprises a sequence of $LX_1X_2LF$ (SEQ ID NO: 217), or variant thereof. In other embodiments, a nucleic acid, vector, plasmid, or donor DNA comprises a sequence that encodes a peptide, or variant or fragment thereof, of the present disclosure. In further embodiments, $LX_1X_2LF$ (SEQ ID NO: 217) can be grafted onto peptide of a sequence of any one of SEQ ID NO: 1-SEQ ID NO: 84. The $LX_1X_2LF$ (SEQ ID NO: 217) can be grafted onto the peptide at any position along the peptide. This position can be optimized to allow for the $LX_1X_2LF$ (SEQ ID NO: 217) to be available for binding. For example, it can be grafted into the peptide sequence at a position in the secondary structure that is at the surface of the peptide when folded. Alternatively, the position can be optimized according to higher binding affinity to TEAD and/or to better antagonist TEAD function.

In some embodiments, peptides inhibit binding between TEAD and YAP, or between YAP and any other protein. In some embodiments, peptides prevent TEAD from protein-protein interaction and/or prevent TEAD localization to a cell's nucleus. In some cases, peptides deactivate TEAD. In some embodiments, peptides can cause TEAD to be degraded, or prevent TEAD from localization to a cell's nucleus, or prevent TEAD from interacting with YAP or YAP-like proteins.

In some embodiments, peptides inhibit binding between TEAD and YAP, or between YAP and any other protein by binding to a certain amino acid residue or motif of amino acid residues in TEAD. In some embodiments, peptides prevent TEAD from protein-protein interaction and/or prevent TEAD localization to a cell's nucleus by binding to a certain amino acid residue or motif of amino acid residues in TEAD. In some cases, peptides deactivate TEAD by binding to a certain amino acid residue or motif of amino acid residues in TEAD. In some embodiments, peptides can cause TEAD to be degraded, or prevent TEAD from localization to a cell's nucleus, or prevent TEAD from interacting with YAP or YAP-like proteins by binding to a certain amino acid residue or motif of amino acid residues in TEAD. Furthermore, a peptide can be selected for further testing or use based upon its ability to bind to the certain amino acid residue or motif of amino acid residues. The certain amino acid residue or motif of amino acid residues in TEAD can be identified an amino acid residue or sequence of amino acid residues that are involved in the binding of TEAD to YAP. A certain amino acid residue or motif of amino acid residues can be identified from a crystal structure of the YAP:TEAD complex. For example, TEAD amino acid residues F314, K316, V318, Y346, F350, K353, V366, or any combination thereof can be target residues for TEAD binding to a peptide as disclosed herein based on the YAP:TEAD crystal structure modeled to bind to SEQ ID NO: 1.

In some embodiments, a peptide or a library of peptides is designed in silico without derivation from a naturally occurring knottin scaffold. In other embodiments, a peptide or a library of peptides is designed in silico by derivation, grafting relevant or important protein-binding residues, or conserved residues, in the protein-binding interface, or structural modeling based on a naturally occurring peptide or protein known to bind to a protein or receptor of interest.

In some embodiments, a peptide with SEQ ID NO: 1 is used as a scaffold or base sequence for further modifications, including addition, deletion, or amino acid substitution. In some embodiments, residues GS are added at the N-terminus of a peptide. In some cases, peptides lack GS at the N-terminus. In some instances, peptides undergo one or more post-translational modifications.

TABLE 1 lists exemplary peptide sequences according to the present disclosure.

TABLE 1

Exemplary Peptide Sequences

| SEQ ID NO | Amino Acid Sequence |
| --- | --- |
| SEQ ID NO: 1 | GSPDEYIERAKECCKKGDIQCCLRYFEESGDPNVMLICLFCP |
| SEQ ID NO: 2 | GSLERLKKCCNQGLDCEEARWKCELEALFQGKNRETCLEEC |
| SEQ ID NO: 3 | GSFGLYDNQCATSDACSAICKYWTGSGQGKCQNNQCRCY |
| SEQ ID NO: 4 | GSPDEYIERAKECCKKGDIQCCLRYFAESGDPNVMLICLFCP |
| SEQ ID NO: 5 | GSPDEYIERAKECCKKGDIQCCLRYFEESGDPNVMLICAFCP |
| SEQ ID NO: 6 | GSPDEYIERAKECCKKGDIQCCLRYFEESGDPNVALICLFCP |
| SEQ ID NO: 7 | GSPDEYIERAKECCKKGDIQCCLRYFEESGDPNVMLICLACP |
| SEQ ID NO: 8 | GSPDEYIERARRCCRRGDIQCCLRYFEESGDPNVMLICLFCP |
| SEQ ID NO: 9 | GSPDEYIERAKECCKKQDIQCCLRIFDESGDPNVMLICLFCW |
| SEQ ID NO: 10 | GSPDEYIERAKECCKKQDIQCCLRIFDESGDPNVMLICLFCW |
| SEQ ID NO: 11 | GSPDEYIERAKECCKKQDIQCCLRIFDESKDPNVMLICLFCP |
| SEQ ID NO: 12 | GSPDEYIERAKECCKKGDIQCCLRIFDESKDPNVMLICLFCW |
| SEQ ID NO: 13 | GSPDEYIERAKECCKKQDIQCCLRYFDESKDPNVMLICLFCW |

TABLE 1-continued

Exemplary Peptide Sequences

| SEQ ID NO | Amino Acid Sequence |
|---|---|
| SEQ ID NO: 14 | GSPDEYIERAKECCKKQDIQCCLRIFEESKDPNVMLICLFCW |
| SEQ ID NO: 15 | GSPDEYIERAKECCKKGDIQCCLRYFDESKDPNVMLICLFCW |
| SEQ ID NO: 16 | GSPDEYIERAKECCKKGDIQCCLRIFEESKDPNVMLICLFCW |
| SEQ ID NO: 17 | GSPDEYIERAKECCKKGDIQCCLRIFDESGDPNVMLICLFCW |
| SEQ ID NO: 18 | GSPDEYIERAKECCKKGDIQCCLRIFDESKDPNVMLICLFCP |
| SEQ ID NO: 19 | GSPDEYIERAKECCKKQDIQCCLRYFEESKDPNVMLICLFCW |
| SEQ ID NO: 20 | GSPDEYIERAKECCKKQDIQCCLRYFDESGDPNVMLICLFCW |
| SEQ ID NO: 21 | GSPDEYIERAKECCKKQDIQCCLRYFDESKDPNVMLICLFCP |
| SEQ ID NO: 22 | GSPDEYIERAKECCKKQDIQCCLRIFEESGDPNVMLICLFCW |
| SEQ ID NO: 23 | GSPDEYIERAKECCKKQDIQCCLRIFEESKDPNVMLICLFCP |
| SEQ ID NO: 24 | GSPDEYIERAKECCKKQDIQCCLRIFDESGDPNVMLICLFCP |
| SEQ ID NO: 25 | GSPDRYIERAKRCCKRQDIQCCLRIFDESKDPNVMLICLFCW |
| SEQ ID NO: 26 | GSPDRYIREAKRCCRKQDIQCCLRIFDESKDPNVMLICLFCW |
| SEQ ID NO: 27 | GSPDRYIERAKRCCRRQDIQCCLRIFDESKDPNVMLICLFCW |
| SEQ ID NO: 28 | GSPDRYIREARRCCRKQDIQCCLRIFDESKDPNVMLICLFCW |
| SEQ ID NO: 29 | GSPDRYIRRAKRCCRKQDIQCCLRIFDESKDPNVMLICLFCW |
| SEQ ID NO: 30 | GSPDRYIRRAKRCCKRQDIQCCLRIFDESKDPNVMLICLFCW |
| SEQ ID NO: 31 | GSPDRYIRRAKRCCRRQDIQCCLRIFDESKDPNVMLICLFCW |
| SEQ ID NO: 32 | GSPDRYIERAKRCCKRQDIQCCLRIFDESGDPNVMLICLFCW |
| SEQ ID NO: 33 | GSPDRYIREAKRCCRKQDIQCCLRIFDESGDPNVMLICLFCW |
| SEQ ID NO: 34 | GSPDRYIERAKRCCRRQDIQCCLRIFDESGDPNVMLICLFCW |
| SEQ ID NO: 35 | GSPDRYIREARRCCRKQDIQCCLRIFDESGDPNVMLICLFCW |
| SEQ ID NO: 36 | GSPDRYIRRAKRCCRKQDIQCCLRIFDESGDPNVMLICLFCW |
| SEQ ID NO: 37 | GSPDRYIRRAKRCCKRQDIQCCLRIFDESGDPNVMLICLFCW |
| SEQ ID NO: 38 | GSPDRYIRRAKRCCRRQDIQCCLRIFDESGDPNVMLICLFCW |
| SEQ ID NO: 39 | GSLERLKKCCNQGLDCEEARAKCELEALFQGKNRETCLEEC |
| SEQ ID NO: 40 | GSLERLKKCCNQGLDCEEARWKCEAEALFQGKNRETCLEEC |
| SEQ ID NO: 41 | GSLERLKKCCNQGLDCEEARWKCELEAAFQGKNRETCLEEC |
| SEQ ID NO: 42 | GSLERLKKCCNQGLDCEEARWKCELEALAQGKNRETCLEEC |
| SEQ ID NO: 43 | PDEYIERAKECCKKGDIQCCLRYFEESGDPNVMLICLFCP |
| SEQ ID NO: 44 | LERLKKCCNQGLDCEEARWKCELEALFQGKNRETCLEEC |
| SEQ ID NO: 45 | FGLYDNQCATSDACSAICKYWTGSGQGKCQNNQCRCY |
| SEQ ID NO: 46 | PDEYIERAKECCKKGDIQCCLRYFAESGDPNVMLICLFCP |
| SEQ ID NO: 47 | PDEYIERAKECCKKGDIQCCLRYFEESGDPNVMLICAFCP |
| SEQ ID NO: 48 | PDEYIERAKECCKKGDIQCCLRYFEESGDPNVALICLFCP |
| SEQ ID NO: 49 | PDEYIERAKECCKKGDIQCCLRYFEESGDPNVMLICLACP |
| SEQ ID NO: 50 | PDEYIERARRCCRRGDIQCCLRYFEESGDPNVMLICLFCP |
| SEQ ID NO: 51 | PDEYIERAKECCKKQDIQCCLRIFDESKDPNVMLICLFCW |

TABLE 1-continued

Exemplary Peptide Sequences

| SEQ ID NO | Amino Acid Sequence |
|---|---|
| SEQ ID NO: 52 | PDEYIERAKECCKKQDIQCCLRIFDESGDPNVMLICLFCW |
| SEQ ID NO: 53 | PDEYIERAKECCKKQDIQCCLRIFDESKDPNVMLICLFCP |
| SEQ ID NO: 54 | PDEYIERAKECCKKGDIQCCLRIFDESKDPNVMLICLFCW |
| SEQ ID NO: 55 | PDEYIERAKECCKKQDIQCCLRYFDESKDPNVMLICLFCW |
| SEQ ID NO: 56 | PDEYIERAKECCKKQDIQCCLRIFEESKDPNVMLICLFCW |
| SEQ ID NO: 57 | PDEYIERAKECCKKGDIQCCLRYFDESKDPNVMLICLFCW |
| SEQ ID NO: 58 | PDEYIERAKECCKKGDIQCCLRIFEESKDPNVMLICLFCW |
| SEQ ID NO: 59 | PDEYIERAKECCKKGDIQCCLRIFDESGDPNVMLICLFCW |
| SEQ ID NO: 60 | PDEYIERAKECCKKGDIQCCLRIFDESKDPNVMLICLFCP |
| SEQ ID NO: 61 | PDEYIERAKECCKKQDIQCCLRYFEESKDPNVMLICLFCW |
| SEQ ID NO: 62 | PDEYIERAKECCKKQDIQCCLRYFDESGDPNVMLICLFCW |
| SEQ ID NO: 63 | PDEYIERAKECCKKQDIQCCLRYFDESKDPNVMLICLFCP |
| SEQ ID NO: 64 | PDEYIERAKECCKKQDIQCCLRIFEESGDPNVMLICLFCW |
| SEQ ID NO: 65 | PDEYIERAKECCKKQDIQCCLRIFEESKDPNVMLICLFCP |
| SEQ ID NO: 66 | PDEYIERAKECCKKQDIQCCLRIFDESGDPNVMLICLFCP |
| SEQ ID NO: 67 | PDRYIERAKRCCKRQDIQCCLRIFDESKDPNVMLICLFCW |
| SEQ ID NO: 68 | PDRYIREAKRCCRKQDIQCCLRIFDESKDPNVMLICLFCW |
| SEQ ID NO: 69 | PDRYIERAKRCCRRQDIQCCLRIFDESKDPNVMLICLFCW |
| SEQ ID NO: 70 | PDRYIEARRCCRKQDIQCCLRIFDESKDPNVMLICLFCW |
| SEQ ID NO: 71 | PDRYIRRAKRCCRKQDIQCCLRIFDESKDPNVMLICLFCW |
| SEQ ID NO: 72 | PDRYIRRAKRCCKRQDIQCCLRIFDESKDPNVMLICLFCW |
| SEQ ID NO: 73 | PDRYIRRAKRCCRRQDIQCCLRIFDESKDPNVMLICLFCW |
| SEQ ID NO: 74 | PDRYIERAKRCCKRQDIQCCLRIFDESGDPNVMLICLFCW |
| SEQ ID NO: 75 | PDRYIREAKRCCRKQDIQCCLRIFDESGDPNVMLICLFCW |
| SEQ ID NO: 76 | PDRYIERAKRCCRRQDIQCCLRIFDESGDPNVMLICLFCW |
| SEQ ID NO: 77 | PDRYIREARRCCRKQDIQCCLRIFDESGDPNVMLICLFCW |
| SEQ ID NO: 78 | PDRYIRRAKRCCRKQDIQCCLRIFDESGDPNVMLICLFCW |
| SEQ ID NO: 79 | PDRYIRRAKRCCKRQDIQCCLRIFDESGDPNVMLICLFCW |
| SEQ ID NO: 80 | PDRYIRRAKRCCRRQDIQCCLRIFDESGDPNVMLICLFCW |
| SEQ ID NO: 81 | LERLKKCCNQGLDCEEARAKCELEALFQGKNRETCLEEC |
| SEQ ID NO: 82 | LERLKKCCNQGLDCEEARWKCEAEALFQGKNRETCLEEC |
| SEQ ID NO: 83 | LERLKKCCNQGLDCEEARWKCELEAAFQGKNRETCLEEC |
| SEQ ID NO: 84 | LERLKKCCNQGLDCEEARWKCELEALAQGKNRETCLEEC |

In some embodiments, a peptide that binds to TEAD comprises Ala at position 8, Asp at position 16, Ser at position 17, Met at position 23, Phe at position 38, or any combination thereof.

See FIG. 8 for exemplary important residues. In some embodiments, a peptide comprises $LX_1X_2FEXS$ (SEQ ID NO: 218), $LX_1X_2FEXSXDPNVML$ (SEQ ID NO: 219), or $LX_1X_2FEXSXDPNVMX_3X_4LF$ (SEQ ID NO: 220), wherein $X_1$, $X_2$, $X_3$, and $X_4$ can be any amino acid.

In some embodiments, peptides of the present disclosure can comprise the amino acid sequence of leucine-$X_1$-$X_2$-leucine-phenylalanine ("$LX_1X_2LF$," SEQ ID NO: 217), in which $X_1$ and $X_2$ are any amino acid residue, as shown in SEQ ID NO: 1 and SEQ ID NO: 2. In some embodiments, peptides with the LX$_1$X$_2$LF (SEQ ID NO: 217) sequence display full TEAD binding. In some embodiments, the X$_1$X$_2$ in the LX$_1$X$_2$LF (SEQ ID NO: 217) sequence can be EA, as shown in SEQ ID NO: 2, or IC as shown in SEQ ID NO: 1. In other embodiments, the X$_1$X$_2$ in the LX$_1$X$_2$LF (SEQ ID NO: 217) sequence can also be EC, MC, VC, or FC. In some embodiments, peptides of the present disclosure can comprise the amino acid sequence motif of leucine-X$_1$-X$_2$-leucine-phenylalanine ("LX$_1$X$_2$LF," SEQ ID NO: 217), in which X$_1$ and X$_2$ are any amino acid residue, as shown in SEQ ID NO: 1 and SEQ ID NO: 2. In some embodiments, peptides with the LX$_1$X$_2$LF (SEQ ID NO: 217) motif display full TEAD binding. In some embodiments, the X$_1$X$_2$ in the LX$_1$X$_2$LF (SEQ ID NO: 217) motif can be EA, as shown in SEQ ID NO: 2, or IC as shown in SEQ ID NO: 1. In other embodiments, the X$_1$X$_2$ in the LX$_1$X$_2$LF (SEQ ID NO: 217) motif can also be EC, MC, VC, or FC.

In some embodiments, a peptide of the present disclosure can comprise a sequence having cysteine residues at one or more of positions 11, 12, 13, 14, 19, 20, 21, 22, 36, 38, 39, 41. In some embodiments, a peptide comprises Cys at positions 11, 12, 19, 20, 36, 39, or any combination thereof. For example, in certain embodiments, a peptide can comprise a sequence having a cysteine residue at position 11. In certain embodiments, a peptide can comprise a sequence having a cysteine residue at position 12. In certain embodiments, a peptide can comprise a sequence having a cysteine residue at position 13. In certain embodiments, a peptide can comprise a sequence having a cysteine residue at position 14. In certain embodiments, a peptide can comprise a sequence having a cysteine residue at position 19. In certain embodiments, a peptide can comprise a sequence having a cysteine residue at position 20. In certain embodiments, a peptide can comprise a sequence having a cysteine residue at position 21. In certain embodiments, a peptide can comprise a sequence having a cysteine residue at position 22. In certain embodiments, a peptide can comprise a sequence having a cysteine residue at position 36. In certain embodiments, a peptide can comprise a sequence having a cysteine residue at position 38. In certain embodiments, a peptide can comprise a sequence having a cysteine residue at position 39. In certain embodiments, a peptide can comprise a sequence having a cysteine residue at position 41. In some embodiments, the first cysteine residue in the sequence can be disulfide bonded with the 4th cysteine residue in the sequence, the 2nd cysteine residue in the sequence can be disulfide bonded to the 5th cysteine residue in the sequence, and the 3rd cysteine residue in the sequence can be disulfide bonded to the 6th cysteine residue in the sequence. Optionally, a peptide can comprise one disulfide bridge that passes through a ring formed by two other disulfide bridges, also known as a "two-and-through" structure system. In some embodiments, the peptides disclosed herein can have one or more cysteines mutated to serine. For example, SEQ ID NO: 9 can have one or more cysteines mutated to a serine, such as GSPDEYIERAKESSKKQDIQSSLRIFDESKDPNVMLISLFSW (SEQ ID NO: 177); GSPDEYIERAKESCKKQDIQSCLRIFDESKDPNVMLICLFCW (SEQ ID NO: 178); GSPDEYIERAKECSKKQDIQCCLRIFDESKDPNVMLICLFSW (SEQ ID NO: 179); GSPDEYIERAKECCKKQDIQCSLRIFDESKDPNVMLISLFCW (SEQ ID NO: 180); GSPDEYIERAKESSKKQDIQSCLRIFDESKDPNVMLICLFSW (SEQ ID NO: 181); GSPDEYIERAKECSKKQDIQCSLRIFDESKDPNVMLISLFSW(SEQ ID NO: 182); or GSPDEYIERAKESCKKQDIQSSLRIFDESKDPNVMLISLFCW(SEQ ID NO: 183). SEQ ID NO: 51 can have one or more cysteines mutated to serines, such as PDEYIERAKESSKKQDIQSSLRIFDESKDPNVMLISLFSW (SEQ ID NO: 186); PDEYIERAKESCKKQDIQSCLRIFDESKDPNVMLICLFCW (SEQ ID NO: 187); PDEYIERAKECSKKQDIQCCLRIFDESKDPNVMLICLFSW (SEQ ID NO: 188); PDEYIERAKECCKKQDIQCSLRIFDESKDPNVMLISLFCW (SEQ ID NO: 189); PDEYIERAKESSKKQDIQSCLRIFDESKDPNVMLICLFSW (SEQ ID NO: 190); PDEYIERAKECSKKQDIQCSLRIFDESKDPNVMLISLFSW(SEQ ID NO: 191); or PDEYIERAKESCKKQDIQSSLRIFDESKDPNVMLISLFCW(SEQ ID NO: 192). SEQ ID NO: 1 can have one or more cysteines mutated to serines, such as GSPDEYIERAKESSKKGDIQSSLRYFEESGDPNVMLISLFSP (SEQ ID NO: 184). SEQ ID NO: 1 can have one or more cysteines mutated to serines, such as PDEYIERAKESSKKGDIQSSLRYFEESGDPNVMLISLFSP (SEQ ID NO: 193). SEQ ID NO: 2 can have one or more cysteines mutated to serines, such as GSLERLKKSSNQGLDSEEARWKSELEALFQGKNRETSLEES (SEQ ID NO: 185). SEQ ID NO: 2 can have one or more cysteines mutated to serines, such as LERLKKSSNQGLDSEEARWKSELEALFQGKNRETSLEES (SEQ ID NO: 194).

In some embodiments, peptides can comprise at least one or more tag peptide sequences for improved cell penetration. For example, peptides can comprise at least one or multiple Arg residues or residues from Tat protein for improved cell penetration property. Additional tag peptide sequences can include CysTat (CYRKKRRQRRR; SEQ ID NO: 144), S19-TAT (PFVIGAGVLGALGTGIGGIGRKKRRQRRR; SEQ ID NO: 145), R8 (RRRRRRRR; SEQ ID NO: 146), pAntp (RQIKIWFQNRRMKWKK; SEQ ID NO: 147), Pas-TAT (FFLIPKGGRKKRRQRRR; SEQ ID NO: 148), Pas-R8 (FFLIPKGRRRRRRRR; SEQ ID NO: 149), PasFHV (FFLIPKGRRRRNRTRRNRRRVR; SEQ ID NO: 150), Pas-pAntP (FFLIPKGRQIKIWFQNRRMKWKK; SEQ ID NO: 151), F2R4 (FFRRRR; SEQ ID NO: 152), B55 (KAVLGATKIDLPVDINDPYDLGLLLRHLRHHSNLLANIGDPAVREQVLSAMQEEE; SEQ ID NO: 153), auzurin (LSTAADMQGVVTDGMASGLDKDYLKPDD; SEQ ID NO: 154), IMT-P8 (RRWRRWNRFNRRRCR; SEQ ID NO: 155), BR2 (RAGLQFPVGRLLRRLLR; SEQ ID NO: 156), OMOTAG1 (KRAHHNALERKRR; SEQ ID NO: 157), OMOTAG2 (RRMKANARERNRM; SEQ ID NO: 158), pVEC (LLIILRRRIRKQAHAHSK; SEQ ID NO: 159), SynB3 (RRLSYSRRRF; SEQ ID NO: 160), DPV1047 (VKRGLKLRHVRPRVTRMDV; SEQ ID NO: 161), CY105Y (CSIPPEVKFNKPFVYLI; SEQ ID NO: 162), Transpotan (GWTLNSAGYLLGKINLKALAALAKKIL; SEQ ID NO: 163), MTS (KGEGAAVLLPVLLAAPG; SEQ ID NO: 164), hLF (KCFQWQRNMRKVRGPPVSCIKR; SEQ ID NO: 165), PFVYLI (PFVYLI; SEQ ID NO: 166), and yBBR (VLDSLEFIASKL, SEQ ID NO: 167). For example, in some embodiments, the peptide can comprise an Arginine patch (Arg patch), for example, an RRRRRRRR (SEQ ID NO: 146), or a variant or fragment thereof, sequence can be appended to either the N-terminus or the C-terminus of a peptide. In some embodiments, the Arg patch comprises two or more Arg residues, or Arg$_n$, wherein n is a whole number and can be 2, 3, 4, 5, 6, 7, 8, 9, or 10 (SEQ ID NO: 286). In other embodiments, the peptide can comprise a Tat peptide (Tat proteins are reviewed in Gump et al. TAT transduction: the molecular mechanism and therapeutic prospects. Trends Mol Med. 2007 October; 13(10):443-8 and Harada et al. Antitumor protein therapy; application of the protein transduction domain to the development of a protein drug for cancer treatment. Breast Cancer. 2006; 13(1):16-26). The Tat peptide can have a sequence of, for example, YGRKKRRQRRR (SEQ ID NO: 195), GRKKRRQRRR (SEQ ID NO: 143), or any modification, variant, or fragment thereof, can be appended to the N-terminus or C-terminus of any TEAD-binding peptide of the present disclosure. In some embodiments, the Tat peptide sequence can be GRKKRRQRRRPQ (SEQ ID NO: 196), GRKKRRQRRR (SEQ ID NO: 143), or a fragment or variant thereof. In some embodiments, the Tat peptide can be appended to the N-terminus of any TEAD-binding peptide of the present disclosure following an N-terminal GS dipeptide and preceding, for example, a GGGS (SEQ ID NO: 203) spacer. In some embodiments, a cell-penetrating tag peptides, such as any one of SEQ ID NO: 143-SEQ ID NO: 167, can be appended to either the N-terminus or C-terminus of any peptide disclosed herein using a peptide linker such as $G_xS_y$ (SEQ ID NO: 283) peptide linker, wherein x and y can be any whole number, such as 1, 2, 3, 4, 5, 6, 7, 8, 9, and 10. In other embodiments, a cell-penetrating peptide, such as a Tat peptide or an Arg patch, or any other moiety, can be appended to either the N-terminus or C-terminus of any peptide disclosed herein using a peptide linker such as $G_xS_y$ peptide linker, wherein x and y can be any whole number, such as 1, 2, 3, 4, 5, 6, 7, 8, 9, and 10. In some embodiments, the peptide linker comprises (GS)x (SEQ ID NO: 282), wherein x can be any whole number, such as 1, 2, 3, 4, 5, 6, 7, 8, 9, and 10. In some embodiments, the peptide linker comprises GGSSG (SEQ ID NO: 204), GGGGG (SEQ ID NO: 205), GSGSGSGS (SEQ ID NO: 206), GSGG (SEQ ID NO: 207), GGGGS (SEQ ID NO: 208), GGGS (SEQ ID NO: 203), GGS (SEQ ID NO: 209), GGGSGGGSGGGS (SEQ ID NO: 210), or a variant or fragment thereof. Additionally, KKYKPYVPVTTN (SEQ ID NO: 211) from DkTx, and EPKSSDKTHT (SEQ ID NO: 212) from human IgG3 can be used as a peptide linker. In other embodiments, the tag peptide can be appended to the peptide at any amino acid residue. In further embodiments, the tag peptide can be appended to the peptide at any amino acid residue without interfering with TEAD-binding activity. In some embodiments, the tag peptide is appended via conjugation, linking, or fusion techniques. In other embodiments, the Tat peptide can be appended to the peptide at any amino acid residue. In further embodiments, the Tat peptide can be appended to the peptide at any amino acid residue without interfering with TEAD-binding activity. In some embodiments, the Tat peptide is appended via conjugation, linking, or fusion techniques. Additional exemplary TEAD Binder-Cell Penetrating Peptide fusion (CPP fusion) sequences that can improve cell penetration are in TABLE 2.

TABLE 2

Exemplary TEAD Binder-Cell Penetrating Peptide Fusion Sequences

| Fusion | SEQ ID NO: | Sequence |
|---|---|---|
| GS-Tat-SEQ ID NO: 9 | SEQ ID NO: 85 | GSGRKKRRQRRRGGSPDEYIERAKECCKKQDIQCCLRIFDESKDPNVMLICLFCW |
| GS-CysTat-SEQ ID NO: 9 | SEQ ID NO: 86 | GSCYRKKRRQRRRGGSPDEYIERAKECCKKQDIQCCLRIFDESKDPNVMLICLFCW |
| GS-S19-Tat-SEQ ID NO: 9 | SEQ ID NO: 87 | GSPFVIGAGVLGALGTGIGGIGRKKRRQRRRGGSPDEYIERAKECCKKQDIQCCLRIFDESKDPNVMLICLFCW |
| GS-Pas-Tat-SEQ ID NO: 9 | SEQ ID NO: 88 | GSFFLIPKGGRKKRRQRRRGGSPDEYIERAKECCKKQDIQCCLRIFDESKDPNVMLICLFCW |
| GS-R8-SEQ ID NO: 9 | SEQ ID NO: 89 | GSRRRRRRRRGGSPDEYIERAKECCKKQDIQCCLRIFDESKDPNVMLICLFCW |
| GS-Pas-R8-SEQ ID NO: 9 | SEQ ID NO: 90 | GSFFLIPKGRRRRRRRRGGSPDEYIERAKECCKKQDIQCCLRIFDESKDPNVMLICLFCW |
| GS-pAntp-SEQ ID NO: 9 | SEQ ID NO: 91 | GSRQIKIWFQNRRMKWKKGGSPDEYIERAKECCKKQDIQCCLRIFDESKDPNVMLICLFCW |
| GS-Pas-pAntp-SEQ ID NO: 9 | SEQ ID NO: 92 | GSFFLIPKGRQIKIWFQNRRMKWKKGGSPDEYIERAKECCKKQDIQCCLRIFDESKDPNVMLICLFCW |
| GS-Pas-FHV-SEQ ID NO: 9 | SEQ ID NO: 93 | GSFFLIPKGRRRRNRTRRNRRRVRGGSPDEYIERAKECCKKQDIQCCLRIFDESKDPNVMLICLFCW |
| GS-MCa(1-9)-SEQ ID NO: 9 | SEQ ID NO: 94 | GSGDALPHLKLGGSPDEYIERAKECCKKQDIQCCLRIFDESKDPNVMLICLFCW |
| GS-Imp(1-9)-SEQ ID NO: 9 | SEQ ID NO: 95 | GSGDALPHLKRGGSPDEYIERAKECCKKQDIQCCLRIFDESKDPNVMLICLFCW |
| GS-Had(1-11)-SEQ ID NO: 9 | SEQ ID NO: 96 | GSSEKDAIKHLQRGGSPDEYIERAKECCKKQDIQCCLRIFDESKDPNVMLICLFCW |
| GS-Had(3-11)-SEQ ID NO: 9 | SEQ ID NO: 97 | GSKDAIKHLQRGGSPDEYIERAKECCKKQDIQCCLRIFDESKDPNVMLICLFCW |
| GS-yBBR-SEQ ID NO: 9 | SEQ ID NO: 98 | GSVLDSLEFIASKLGGSPDEYIERAKECCKKQDIQCCLRIFDESKDPNVMLICLFCW |
| GS-Q15(F2R4)-SEQ ID NO: 9 | SEQ ID NO: 99 | GSPDEYIERAKECCKKFFRRRRDIQCCLRIFDESKDPNVMLICLFCW |

TABLE 2-continued

Exemplary TEAD Binder-Cell Penetrating Peptide Fusion Sequences

| Fusion | SEQ ID NO: | Sequence |
| --- | --- | --- |
| GS-B55-SEQ ID NO: 9 | SEQ ID NO: 100 | GSKAVLGATKIDLPVDINDPYDLGLLLRHLRHHSNLLANIGDPAVREQVLSAMQEEEGGSPDEYIERAKECCKKQDIQCCLRIFDESKDPNVMLICLFCW |
| GS-azu-SEQ ID NO: 9 | SEQ ID NO: 101 | GSLSTAADMQGVVTDGMASGLDKDYLKPDDGGSPDEYIERAKECCKKQDIQCCLRIFDESKDPNVMLICLFCW |
| GS-IMT-P8-SEQ ID NO: 9 | SEQ ID NO: 102 | GSRRWRRWNRFNRRRCRGGSPDEYIERAKECCKKQDIQCCLRIFDESKDPNVMLICLFCW |
| GS-BR2-SEQ ID NO: 9 | SEQ ID NO: 103 | GSRAGLQFPVGRLLRRLLRGGSPDEYIERAKECCKKQDIQCCLRIFDESKDPNVMLICLFCW |
| GS-OMOTAG1-SEQ ID NO: 9 | SEQ ID NO: 104 | GSKRAHHNALERKRRGGSPDEYIERAKECCKKQDIQCCLRIFDESKDPNVMLICLFCW |
| GS-OMOTAG2-SEQ ID NO: 9 | SEQ ID NO: 105 | GSRRMKANARERNRMGGSPDEYIERAKECCKKQDIQCCLRIFDESKDPNVMLICLFCW |
| GS-pVEC-SEQ ID NO: 9 | SEQ ID NO: 106 | GSLLIILRRRIRKQAHAHSKGGSPDEYIERAKECCKKQDIQCCLRIFDESKDPNVMLICLFCW |
| GS-SynB3-SEQ ID NO: 9 | SEQ ID NO: 107 | GSRRLSYSRRRFGGSPDEYIERAKECCKKQDIQCCLRIFDESKDPNVMLICLFCW |
| GS-DPV1047-SEQ ID NO: 9 | SEQ ID NO: 108 | GSVKRGLKLRHVRPRVTRMDVGGSPDEYIERAKECCKKQDIQCCLRIFDESKDPNVMLICLFCW |
| GS-C105Y-SEQ ID NO: 9 | SEQ ID NO: 109 | GSCSIPPEVKFNKPFVYLIGGSPDEYIERAKECCKKQDIQCCLRIFDESKDPNVMLICLFCW |
| GS-Transportan-SEQ ID NO: 9 | SEQ ID NO: 110 | GSGWTLNSAGYLLGKINLKALAALAKKILGGSPDEYIERAKECCKKQDIQCCLRIFDESKDPNVMLICLFCW |
| GS-MTS-SEQ ID NO: 9 | SEQ ID NO: 111 | GSKGEGAAVLLPVLLAAPGGGSPDEYIERAKECCKKQDIQCCLRIFDESKDPNVMLICLFCW |
| GS-hLF-SEQ ID NO: 9 | SEQ ID NO: 112 | GSKCFQWQRNMRKVRGPPVSCIKRGGSPDEYIERAKECCKKQDIQCCLRIFDESKDPNVMLICLFCW |
| GS-PFVYL-SEQ ID NO: 9 | SEQ ID NO: 113 | GSPFVYLIGGSPDEYIERAKECCKKQDIQCCLRIFDESKDPNVMLICLFCW |
| GS-R8-SEQ ID NO: 1 | SEQ ID NO: 114 | GSRRRRRRRRGGGSPDEYIERAKECCKKGDIQCCLRYFEESGDPNVMLICLFCP |
| GS-Tat-SEQ ID NO: 1 | SEQ ID NO: 115 | GSYGRKKRRQRRRGGGSPDEYIERAKECCKKGDIQCCLRYFEESGDPNVMLICLFCP |
| Tat-SEQ ID NO: 9 | SEQ ID NO: 222 | GRKKRRQRRRGGSPDEYIERAKECCKKQDIQCCLRIFDESKDPNVMLICLFCW |
| CysTat-SEQ ID NO: 9 | SEQ ID NO: 223 | CYRKKRRQRRRGGSPDEYIERAKECCKKQDIQCCLRIFDESKDPNVMLICLFCW |
| S19-Tat-SEQ ID NO: 9 | SEQ ID NO: 224 | PFVIGAGVLGALGTGIGGIGRKKRRQRRRGGSPDEYIERAKECCKKQDIQCCLRIFDESKDPNVMLICLFCW |
| Pas-Tat-SEQ ID NO: 9 | SEQ ID NO: 225 | FFLIPKGGRKKRRQRRRGGSPDEYIERAKECCKKQDIQCCLRIFDESKDPNVMLICLFCW |
| R8-SEQ ID NO: 9 | SEQ ID NO: 226 | RRRRRRRRGGSPDEYIERAKECCKKQDIQCCLRIFDESKDPNVMLICLFCW |
| Pas-R8-SEQ ID NO: 9 | SEQ ID NO: 227 | FFLIPKGRRRRRRRRGGSPDEYIERAKECCKKQDIQCCLRIFDESKDPNVMLICLFCW |
| pAntp-SEQ ID NO: 9 | SEQ ID NO: 228 | RQIKIWFQNRRMKWKKGGSPDEYIERAKECCKKQDIQCCLRIFDESKDPNVMLICLFCW |
| Pas-pAntp-SEQ ID NO: 9 | SEQ ID NO: 229 | GSFFLIPKGRQIKIWFQNRRMKWKKGGSPDEYIERAKECCKKQDIQCCLRIFDESKDPNVMLICLFCW |

TABLE 2-continued

Exemplary TEAD Binder-Cell Penetrating Peptide Fusion Sequences

| Fusion | SEQ ID NO: | Sequence |
|---|---|---|
| Pas-FHV-SEQ ID NO: 9 | SEQ ID NO: 230 | FFLIPKGRRRRNRTRRNRRRVRGGSPDEYIERAKECCKKQDIQCCLRIFDESKDPNVMLICLFCW |
| MCa(1-9)-SEQ ID NO: 9 | SEQ ID NO: 231 | GDALPHLKLGGSPDEYIERAKECCKKQDIQCCLRIFDESKDPNVMLICLFCW |
| Imp(1-9)-SEQ ID NO: 9 | SEQ ID NO: 232 | GDALPHLKRGGSPDEYIERAKECCKKQDIQCCLRIFDESKDPNVMLICLFCW |
| Had(1-11)-SEQ ID NO: 9 | SEQ ID NO: 233 | SEKDAIKHLQRGGSPDEYIERAKECCKKQDIQCCLRIFDESKDPNVMLICLFCW |
| Had(3-11)-SEQ ID NO: 9 | SEQ ID NO: 234 | KDAIKHLQRGGSPDEYIERAKECCKKQDIQCCLRIFDESKDPNVMLICLFCW |
| yBBR-SEQ ID NO: 9 | SEQ ID NO: 235 | VLDSLEFIASKLGGSPDEYIERAKECCKKQDIQCCLRIFDESKDPNVMLICLFCW |
| Q15 (F2R4)-SEQ ID NO: 9 | SEQ ID NO: 236 | PDEYIERAKECCKKFFRRRRDIQCCLRIFDESKDPNVMLICLFCW |
| B55-SEQ ID NO: 9 | SEQ ID NO: 237 | KAVLGATKIDLPVDINDPYDLGLLLRHLRHHSNLLANIGDPAVREQVLSAMQEEEGGSPDEYIERAKECCKKQDIQCCLRIFDESKDPNVMLICLFCW |
| azu-SEQ ID NO: 9 | SEQ ID NO: 238 | LSTAADMQGVVTDGMASGLDKDYLKPDDGGSPDEYIERAKECCKKQDIQCCLRIFDESKDPNVMLICLFCW |
| IMT-P8-SEQ ID NO: 9 | SEQ ID NO: 239 | RRWRRWNRFNRRRCRGGSPDEYIERAKECCKKQDIQCCLRIFDESKDPNVMLICLFCW |
| BR2-SEQ ID NO: 9 | SEQ ID NO: 240 | RAGLQFPVGRLLRRLLRGGSPDEYIERAKECCKKQDIQCCLRIFDESKDPNVMLICLFCW |
| OMOTAG1-SEQ ID NO: 9 | SEQ ID NO: 241 | KRAHHNALERKRRGGSPDEYIERAKECCKKQDIQCCLRIFDESKDPNVMLICLFCW |
| OMOTAG2-SEQ ID NO: 9 | SEQ ID NO: 242 | RRMKANARERNRMGGSPDEYIERAKECCKKQDIQCCLRIFDESKDPNVMLICLFCW |
| pVEC-SEQ ID NO: 9 | SEQ ID NO: 243 | LLIILRRRIRKQAHAHSKGGSPDEYIERAKECCKKQDIQCCLRIFDESKDPNVMLICLFCW |
| SynB3-SEQ ID NO: 9 | SEQ ID NO: 244 | RRLSYSRRRFGGSPDEYIERAKECCKKQDIQCCLRIFDESKDPNVMLICLFCW |
| DPV1047-SEQ ID NO: 9 | SEQ ID NO: 245 | VKRGLKLRHVRPRVTRMDVGGSPDEYIERAKECCKKQDIQCCLRIFDESKDPNVMLICLFCW |
| C105Y-SEQ ID NO: 9 | SEQ ID NO: 246 | CSIPPEVKFNKPFVYLIGGSPDEYIERAKECCKKQDIQCCLRIFDESKDPNVMLICLFCW |
| Transportan-SEQ ID NO: 9 | SEQ ID NO: 247 | GWTLNSAGYLLGKINLKALAALAKKILGGSPDEYIERAKECCKKQDIQCCLRIFDESKDPNVMLICLFCW |
| MTS-SEQ ID NO: 9 | SEQ ID NO: 248 | KGEGAAVLLPVLLAAPGGGSPDEYIERAKECCKKQDIQCCLRIFDESKDPNVMLICLFCW |
| hLF-SEQ ID NO: 9 | SEQ ID NO: 249 | KCFQWQRNMRKVRGPPVSCIKRGGSPDEYIERAKECCKKQDIQCCLRIFDESKDPNVMLICLFCW |
| PFVYL-SEQ ID NO: 9 | SEQ ID NO: 250 | PFVYLIGGSPDEYIERAKECCKKQDIQCCLRIFDESKDPNVMLICLFCW |
| R8-SEQ ID NO: 1 | SEQ ID NO: 251 | RRRRRRRRGGGSPDEYIERAKECCKKGDIQCCLRYFEESGDPNVMLICLFCP |
| Tat-SEQ ID NO: 1 | SEQ ID NO: 252 | YGRKKRRQRRRGGGSPDEYIERAKECCKKGDIQCCLRYFEESGDPNVMLICLFCP |

In some embodiments, a peptide is conjugated to, linked to, or fused to one or more cell-penetrating peptides, such as arginine-rich, amphipathic and lysine-rich, and hydrophobic residues or peptides capable of penetrating plasma membrane or nucleus for in vivo delivery of a protein or macromolecular cargo. Conjugation or fusion can be direct or with a spacer in between (chemical or peptide-based). A spacer can be any peptide linker. For example, a spacer can be GGGSGGGSGGGS (SEQ ID NO: 210), KKYKPYVPVTTN (SEQ ID NO: 211) from DkTx, EPKSSDKTHT (SEQ ID NO: 212) from human IgG3 or any variant or fragment thereof. Cell-penetrating peptides include, but are not limited to, short amphipathic or cationic short peptides with a positive net charge and are capable of penetrating cellular membrane and transferring a molecular or cargo either covalently or non-covalently attached to the peptides into a cell. Such cell-penetrating peptides can be synthesized or derived from known proteins, such as penetratin, Tat peptide, pVEC, or chimeric peptides, such as transportan, MPG, Pep-1, or synthetic peptides, such as polyarginines, MAP, and $R_6W_3$ (SEQ ID NO: 287).

In some embodiments, peptides can comprise at least one or more cell penetrating peptide sequences for improved cell penetration. For example, a cell penetrating peptide can include maurocaline (GDCLPHLKLCKENKDCCSKKCK-RRGTNIEKRCR; SEQ ID NO: 168), imperatoxin (GDCL-PHLKRCKADNDCCGKKCKRRGTNAEKRCR; SEQ ID NO: 169), hadrucalcin (SEKDCIKHLQRCREN-KDCCSKKCSRRGTNPEKRCR; SEQ ID NO: 170), hemicalcin (GDCLPHLKLCKADKDCCSKKCKRRGTN-PEKRCR; SEQ ID NO: 171), opicalcin-1 (GDCLPHLKRCKENNDCCSKKCKRRGTNPEKRCR; SEQ ID NO: 172), opicalcin-2 (GDCLPHLKRCKEN-NDCCSKKCKRRGANPEKRCR; SEQ ID NO: 173), midkine (62-104) (CKYKFENWGACDGGTGTKVRQGTLK-KARYNAQCQETIRVTKPC; SEQ ID NO: 174), MCoTI-II (SGSDGGVCPKILKKCRRDSDCPGACICRGNGYCG; SEQ ID NO: 175), or chlorotoxin (MCMPCFTTDHQ-MARKCDDCCGGKGRGKCYGPQCLCR; SEQ ID NO: 176). In some embodiments, the cell penetrating peptide can have at least 80%, 90%, 95%, or 99% sequence identity with any sequence of SEQ ID NO: 168-SEQ ID NO: 176. In some some embodiments, the cell penetrating peptide sequence can be appended to either the N-terminus or the C-terminus of a peptide. In some embodiments, the cell penetrating peptide can be appended to the N-terminus of any TEAD-binding peptide of the present disclosure following an N-terminal GS dipeptide and preceding, for example, a GGGS (SEQ ID NO: 203) spacer. In some embodiments, a cell-penetrating tag peptides, such as any one of SEQ ID NO: 168-SEQ ID NO: 176, can be appended to either the N-terminus or C-terminus of any peptide disclosed herein using a peptide linker such as $G_xS_y$ (SEQ ID NO: 283) peptide linker, wherein x and y can be any whole number, such as 1, 2, 3, 4, 5, 6, 7, 8, 9, and 10. In some embodiments, the peptide linker comprises GGS (SEQ ID NO: 209), GGSSG (SEQ ID NO: 204), GGGGG (SEQ ID NO: 205), GSGSGSGS (SEQ ID NO: 206), GSGG (SEQ ID NO: 207), GGGGS (SEQ ID NO: 208), GGGS (SEQ ID NO: 203), GGGSGGGSGGGS (SEQ ID NO: 210), or a variant or fragment thereof. Additionally, KKYKPYVPVTTN (SEQ ID NO: 211) from DkTx, and EPKSSDKTHT (SEQ ID NO: 212) from human IgG3 can be used as a peptide linker. In other embodiments, the cell penetrating peptide can be appended to the peptide at any amino acid residue. In further embodiments, the cell penetrating peptide can be appended to the peptide at any amino acid residue without interfering with TEAD-binding activity. In some embodiments, the cell penetrating peptide is appended via conjugation, linking, or fusion techniques. In other embodiments, the cell penetrating peptide can be appended to the peptide at any amino acid residue. Additional exemplary cell penetrating Tandem-Cysteine Dense Peptide (Tandem-CDP) sequences that can improve cell penetration are in TABLE 3.

TABLE 3

Exemplary Cell Penetrating Tandem-Cysteine Dense Peptide Sequences

| Fusion* | SEQ ID NO: | Sequence |
|---|---|---|
| GS-Chlorotoxin-GlySer linker-SEQ ID NO: 9 | SEQ ID NO: 116 | GSMCMPCFTTDHQMARKCDDCCGGKGRGKC YGPQCLCRGGGSGGGSGGGSPDEYIERAKECC KKQDIQCCLRIFDESKDPNVMLICLFCW |
| GS-Chlorotoxin-DkTx-SEQ ID NO: 9 | SEQ ID NO: 117 | GSMCMPCFTTDHQMARKCDDCCGGKGRGKC YGPQCLCRKKYKPYVPVTTNPDEYIERAKECC KKQDIQCCLRIFDESKDPNVMLICLFCW |
| GS-Chlorotoxin-hIgG3-SEQ ID NO: 9 | SEQ ID NO: 118 | GSMCMPCFTTDHQMARKCDDCCGGKGRGKC YGPQCLCREPKSSDKTHTPDEYIERAKECCKKQ DIQCCLRIFDESKDPNVMLICLFCW |
| GS-Maurocalcine-GlySer linker-SEQ ID NO: 9 | SEQ ID NO: 119 | GSGDCLPHLKLCKENKDCCSKKCKRRGTNIEK RCRGGGSGGGSGGGSPDEYIERAKECCKKQDI QCCLRIFDESKDPNVMLICLFCW |
| GS-Maurocalcin-DkTx-SEQ ID NO: 9 | SEQ ID NO: 120 | GSGDCLPHLKLCKENKDCCSKKCKRRGTNIEK RCRKKYKPYVPVTTNPDEYIERAKECCKKQDI QCCLRIFDESKDPNVMLICLFCW |
| GS-Maurocalcin-hIgG3-SEQ ID NO: 9 | SEQ ID NO: 121 | GSGDCLPHLKLCKENKDCCSKKCKRRGTNIEK RCREPKSSDKTHTPDEYIERAKECCKKQDIQCC LRIFDESKDPNVMLICLFCW |
| GS-Imperatoxin-GlySer linker-SEQ ID NO: 9 | SEQ ID NO: 122 | GSGDCLPHLKRCKADNDCCGKKCKRRGTNAE KRCRGGGSGGGSGGGSPDEYIERAKECCKKQD IQCCLRIFDESKDPNVMLICLFCW |

TABLE 3-continued

Exemplary Cell Penetrating Tandem-Cysteine Dense Peptide Sequences

| Fusion* | SEQ ID NO: | Sequence |
|---|---|---|
| GS-Imperatoxin-DkTx-SEQ ID NO: 9 | SEQ ID NO: 123 | GSGDCLPHLKRCKADNDCCGKKCKRRGTNAEKRCRKKYKPYVPVTTNPDEYIERAKECCKKQDIQCCLRIFDESKDPNVMLICLFCW |
| GS-Imperatoxin-hIgG3-SEQ ID NO: 9 | SEQ ID NO: 124 | GSGDCLPHLKRCKADNDCCGKKCKRRGTNAEKRCREPKSSDKTHTPDEYIERAKECCKKQDIQCCLRIFDESKDPNVMLICLFCW |
| GS-Hemicalcin-GlySer linker-SEQ ID NO: 9 | SEQ ID NO: 125 | GSGDCLPHLKLCKADKDCCSKKCKRRGTNPEKRCRGGGSGGGSGGGSPDEYIERAKECCKKQDIQCCLRIFDESKDPNVMLICLFCW |
| GS-Hemicalcin-DkTx-SEQ ID NO: 9 | SEQ ID NO: 126 | GSGDCLPHLKLCKADKDCCSKKCKRRGTNPEKRCRKKYKPYVPVTTNPDEYIERAKECCKKQDIQCCLRIFDESKDPNVMLICLFCW |
| GS-Hemicalcin-hIgG3-SEQ ID NO: 9 | SEQ ID NO: 127 | GSGDCLPHLKLCKADKDCCSKKCKRRGTNPEKRCREPKSSDKTHTPDEYIERAKECCKKQDIQCCLRIFDESKDPNVMLICLFCW |
| GS-Opicalcin 1-GlySer linker-SEQ ID NO: 9 | SEQ ID NO: 128 | GSGDCLPHLKRCKENNDCCSKKCKRRGTNPEKRCRGGGSGGGSGGGSPDEYIERAKECCKKQDIQCCLRIFDESKDPNVMLICLFCW |
| GS-Opicalcin 1-DkTx-SEQ ID NO: 9 | SEQ ID NO: 129 | GSGDCLPHLKRCKENNDCCSKKCKRRGTNPEKRCRKKYKPYVPVTTNPDEYIERAKECCKKQDIQCCLRIFDESKDPNVMLICLFCW |
| GS-Opicalcin 1-hIgG3-SEQ ID NO: 9 | SEQ ID NO: 130 | GSGDCLPHLKRCKENNDCCSKKCKRRGTNPEKRCREPKSSDKTHTPDEYIERAKECCKKQDIQCCLRIFDESKDPNVMLICLFCW |
| GS-Opicalcin 2-GlySer linker-SEQ ID NO: 9 | SEQ ID NO: 131 | GSGDCLPHLKRCKENNDCCSKKCKRRGANPEKRCRGGGSGGGSGGGSPDEYIERAKECCKKQDIQCCLRIFDESKDPNVMLICLFCW |
| GS-Opicalcin 2-DkTx-SEQ ID NO: 9 | SEQ ID NO: 132 | GSGDCLPHLKRCKENNDCCSKKCKRRGANPEKRCRKKYKPYVPVTTNPDEYIERAKECCKKQDIQCCLRIFDESKDPNVMLICLFCW |
| GS-Opicalcin 2-hIgG3-SEQ ID NO: 9 | SEQ ID NO: 133 | GSGDCLPHLKRCKENNDCCSKKCKRRGANPEKRCREPKSSDKTHTPDEYIERAKECCKKQDIQCCLRIFDESKDPNVMLICLFCW |
| GS-Hadrucalcin-GlySer linker-SEQ ID NO: 9 | SEQ ID NO: 134 | GSSEKDCIKHLQRCRENKDCCSKKCSRRGTNPEKRCRGGGSGGGSGGGSPDEYIERAKECCKKQDIQCCLRIFDESKDPNVMLICLFCW |
| GS-Hadrucalcin-DkTx-SEQ ID NO: 9 | SEQ ID NO: 135 | GSSEKDCIKHLQRCRENKDCCSKKCSRRGTNPEKRCRKKYKPYVPVTTNPDEYIERAKECCKKQDIQCCLRIFDESKDPNVMLICLFCW |
| GS-Hadrucalcin-hIgG3-SEQ ID NO: 9 | SEQ ID NO: 136 | GSSEKDCIKHLQRCRENKDCCSKKCSRRGTNPEKRCREPKSSDKTHTPDEYIERAKECCKKQDIQCCLRIFDESKDPNVMLICLFCW |
| GS-Midkine(62-104)-GlySer linker-SEQ ID NO: 9 | SEQ ID NO: 137 | GSCKYKFENWGACDGGTGTKVRQGTLKKARYNAQCQETIRVTKPCGGGSGGGSGGGSPDEYIERAKECCKKQDIQCCLRIFDESKDPNVMLICLFCW |
| GS-Midkine(62-104)-DkTx-SEQ ID NO: 9 | SEQ ID NO: 138 | GSCKYKFENWGACDGGTGTKVRQGTLKKARYNAQCQETIRVTKPCKKYKPYVPVTTNPDEYIERAKECCKKQDIQCCLRIFDESKDPNVMLICLFCW |
| GS-Midkine(62-104)-hIgG3- SEQ ID NO: 9 | SEQ ID NO: 139 | GSCKYKFENWGACDGGTGTKVRQGTLKKARYNAQCQETIRVTKPCEPKSSDKTHTPDEYIERAKECCKKQDIQCCLRIFDESKDPNVMLICLFCW |
| GS-MCoTI-II-GlySer linker-SEQ ID NO: 9 | SEQ ID NO: 140 | GSSGSDGGVCPKILKKCRRDSDCPGACICRGNGYCGGGGSGGGSGGGSPDEYIERAKECCKKQDIQCCLRIFDESKDPNVMLICLFCW |
| GS-MCoTI-II-DkTx-SEQ ID NO: 9 | SEQ ID NO: 141 | GSSGSDGGVCPKILKKCRRDSDCPGACICRGNGYCGKKYKPYVPVTTNPDEYIERAKECCKKQDIQCCLRIFDESKDPNVMLICLFCW |

TABLE 3-continued

Exemplary Cell Penetrating Tandem-Cysteine Dense Peptide Sequences

| Fusion* | SEQ ID NO: | Sequence |
|---|---|---|
| GS-MCoTI-II-hIgG3-SEQ ID NO: 9 | SEQ ID NO: 142 | GSSGSDGGVCPKILKKCRRDSDCPGACICRGNGYCGEPKSSDKTHTPDEYIERAKECCKKQDIQCCLRIFDESKDPNVMLICLFCW |
| Chlorotoxin-GlySer linker-SEQ ID NO: 9 | SEQ ID NO: 253 | MCMPCFTTDHQMARKCDDCCGGKGRGKCYGPQCLCRGGGSGGGSGGGSPDEYIERAKECCKKQDIQCCLRIFDESKDPNVMLICLFCW |
| Chlorotoxin-DkTx-SEQ ID NO: 9 | SEQ ID NO: 254 | MCMPCFTTDHQMARKCDDCCGGKGRGKCYGPQCLCRKKYKPYVPVTTNPDEYIERAKECCKKQDIQCCLRIFDESKDPNVMLICLFCW |
| Chlorotoxin-hIgG3-SEQ ID NO: 9 | SEQ ID NO: 255 | MCMPCFTTDHQMARKCDDCCGGKGRGKCYGPQCLCREPKSSDKTHTPDEYIERAKECCKKQDIQCCLRIFDESKDPNVMLICLFCW |
| Maurocalcine-GlySer linker-SEQ ID NO: 9 | SEQ ID NO: 256 | GDCLPHLKLCKENKDCCSKKCKRRGTNIEKRCRGGGSGGGSGGGSPDEYIERAKECCKKQDIQCCLRIFDESKDPNVMLICLFCW |
| Maurocalcin-DkTx-SEQ ID NO: 9 | SEQ ID NO: 257 | GDCLPHLKLCKENKDCCSKKCKRRGTNIEKRCRKKYKPYVPVTTNPDEYIERAKECCKKQDIQCCLRIFDESKDPNVMLICLFCW |
| Maurocalcin-hIgG3-SEQ ID NO: 9 | SEQ ID NO: 258 | GDCLPHLKLCKENKDCCSKKCKRRGTNIEKRCREPKSSDKTHTPDEYIERAKECCKKQDIQCCLRIFDESKDPNVMLICLFCW |
| Imperatoxin-GlySer linker-SEQ ID NO: 9 | SEQ ID NO: 259 | GDCLPHLKRCKADNDCCGKKCKRRGTNAEKRCRGGGSGGGSGGGSPDEYIERAKECCKKQDIQCCLRIFDESKDPNVMLICLFCW |
| Imperatoxin-DkTx-SEQ ID NO: 9 | SEQ ID NO: 260 | GDCLPHLKRCKADNDCCGKKCKRRGTNAEKRCRKKYKPYVPVTTNPDEYIERAKECCKKQDIQCCLRIFDESKDPNVMLICLFCW |
| Imperatoxin-hIgG3-SEQ ID NO: 9 | SEQ ID NO: 261 | GDCLPHLKRCKADNDCCGKKCKRRGTNAEKRCREPKSSDKTHTPDEYIERAKECCKKQDIQCCLRIFDESKDPNVMLICLFCW |
| Hemicalcin-GlySer linker-SEQ ID NO: 9 | SEQ ID NO: 262 | GDCLPHLKLCKADKDCCSKKCKRRGTNPEKRCRGGGSGGGSGGGSPDEYIERAKECCKKQDIQCCLRIFDESKDPNVMLICLFCW |
| Hemicalcin-DkTx-SEQ ID NO: 9 | SEQ ID NO: 263 | GDCLPHLKLCKADKDCCSKKCKRRGTNPEKRCRKKYKPYVPVTTNPDEYIERAKECCKKQDIQCCLRIFDESKDPNVMLICLFCW |
| Hemicalcin-hIgG3-SEQ ID NO: 9 | SEQ ID NO: 264 | GDCLPHLKLCKADKDCCSKKCKRRGTNPEKRCREPKSSDKTHTPDEYIERAKECCKKQDIQCCLRIFDESKDPNVMLICLFCW |
| Opicalcin 1-GlySer linker-SEQ ID NO: 9 | SEQ ID NO: 265 | GDCLPHLKRCKENNDCCSKKCKRRGTNPEKRCRGGGSGGGSGGGSPDEYIERAKECCKKQDIQCCLRIFDESKDPNVMLICLFCW |
| Opicalcin 1-DkTx-SEQ ID NO: 9 | SEQ ID NO: 266 | GDCLPHLKRCKENNDCCSKKCKRRGTNPEKRCRKKYKPYVPVTTNPDEYIERAKECCKKQDIQCCLRIFDESKDPNVMLICLFCW |
| Opicalcin 1-hIgG3-SEQ ID NO: 9 | SEQ ID NO: 267 | GDCLPHLKRCKENNDCCSKKCKRRGTNPEKRCREPKSSDKTHTPDEYIERAKECCKKQDIQCCLRIFDESKDPNVMLICLFCW |
| Opicalcin 2-GlySer linker-SEQ ID NO: 9 | SEQ ID NO: 268 | GDCLPHLKRCKENNDCCSKKCKRRGANPEKRCRGGGSGGGSGGGSPDEYIERAKECCKKQDIQCCLRIFDESKDPNVMLICLFCW |
| Opicalcin 2-DkTx-SEQ ID NO: 9 | SEQ ID NO: 269 | GDCLPHLKRCKENNDCCSKKCKRRGANPEKRCRKKYKPYVPVTTNPDEYIERAKECCKKQDIQCCLRIFDESKDPNVMLICLFCW |
| Opicalcin 2-hIgG3-SEQ ID NO: 9 | SEQ ID NO: 270 | GDCLPHLKRCKENNDCCSKKCKRRGANPEKRCREPKSSDKTHTPDEYIERAKECCKKQDIQCCLRIFDESKDPNVMLICLFCW |

TABLE 3-continued

Exemplary Cell Penetrating Tandem-Cysteine Dense Peptide Sequences

| Fusion* | SEQ ID NO: | Sequence |
|---|---|---|
| Hadrucalcin-GlySer linker-SEQ ID NO: 9 | SEQ ID NO: 271 | SEKDCIKHLQRCRENKDCCSKKCSRRGTNPEK RCRGGGSGGGSGGGSPDEYIERAKECCKKQDI QCCLRIFDESKDPNVMLICLFCW |
| Hadrucalcin-DkTx-SEQ ID NO: 9 | SEQ ID NO: 272 | SEKDCIKHLQRCRENKDCCSKKCSRRGTNPEK RCRKKYKPYVPVTTNPDEYIERAKECCKKQDI QCCLRIFDESKDPNVMLICLFCW |
| Hadrucalcin-hIgG3-SEQ ID NO: 9 | SEQ ID NO: 273 | SEKDCIKHLQRCRENKDCCSKKCSRRGTNPEK RCREPKSSDKTHTPDEYIERAKECCKKQDIQCC LRIFDESKDPNVMLICLFCW |
| Midkine(62-104)-GlySer linker-SEQ ID NO: 9 | SEQ ID NO: 274 | CKYKFENWGACDGGTGTKVRQGTLKKARYN AQCQETIRVTKPCGGGSGGGSGGGSPDEYIERA KECCKKQDIQCCLRIFDESKDPNVMLICLFCW |
| Midkine(62-104)-DkTx-SEQ ID NO: 9 | SEQ ID NO: 275 | CKYKFENWGACDGGTGTKVRQGTLKKARYN AQCQETIRVTKPCKKYKPYVPVTTNPDEYIERA KECCKKQDIQCCLRIFDESKDPNVMLICLFCW |
| Midkine(62-104)-hIgG3 SEQ ID NO: 9 | SEQ ID NO: 276 | CKYKFENWGACDGGTGTKVRQGTLKKARYN AQCQETIRVTKPCEPKSSDKTHTPDEYIERAKE CCKKQDIQCCLRIFDESKDPNVMLICLFCW |
| MCoTI-II-GlySer linker-SEQ ID NO: 9 | SEQ ID NO: 277 | SGSDGGVCPKILKKCRRDSDCPGACICRGNGY CGGGGSGGGSGGGSPDEYIERAKECCKKQDIQ CCLRIFDESKDPNVMLICLFCW |
| MCoTI-II-DkTx-SEQ ID NO: 9 | SEQ ID NO: 278 | SGSDGGVCPKILKKCRRDSDCPGACICRGNGY CGKKYKPYVPVTTNPDEYIERAKECCKKQDIQ CCLRIFDESKDPNVMLICLFCW |
| MCoTI-II-hIgG3-SEQ ID NO: 9 | SEQ ID NO: 279 | SGSDGGVCPKILKKCRRDSDCPGACICRGNGY CGEPKSSDKTHTPDEYIERAKECCKKQDIQCCL RIFDESKDPNVMLICLFCW |

*IgG3 = SEQ ID NO: 212 (peptide linker)
DkTx = SEQ ID NO: 211 (peptide linker)
GlySer linker = SEQ ID NO: 210 (peptide linker)

In some embodiments, nuclear localization signals can be couple to, conjugated to, linked to, or fused to a peptide described herein to promote nuclear localization. In some embodiments, TEAD-binding peptides are conjugated to, linked to, or fused to a nuclear localization signal, such as a four-residue sequence of K-K/R-X-K/R (SEQ ID NO: 202), wherein X can be any amino acid, or a variant thereof. In some embodiments, TEAD-binding peptides are conjugated to, linked to, or fused to a nuclear localization signal as described in Lange et al, J Biol Chem. 2007 Feb. 23; 282(8):5101-5, such as PKKKRRV (SEQ ID NO: 197) or KRPAATKKAGQAKKKK (SEQ ID NO: 198). In some embodiments, a peptide described herein is conjugated to, linked to, or fused to a nuclear localization signal comprising KxRy (SEQ ID NO: 288), wherein x and y independently can be 0, 1, 2, 3, 4, 5, 6, 7, 8, 9, or 10, such as KKRR (SEQ ID NO: 199), KKKRR (SEQ ID NO: 200), or KKKK (SEQ ID NO: 201). Other cell penetrating moieties can also be linked to, conjugated to, linked to, or fused to the peptides described herein, including, but not limited to, polycations, polyorganic acids, endosomal releasing polymers, poly(2-propylacrylic acid), poly(2-ethylacrylic acid), or any combination thereof.

In other embodiments, TAT or dfTAT can be conjugated to, linked to, or fused to a peptide described herein, allowing the linked, conjugate, or fusion peptide or protein to use the endocytic pathway as a route of in vivo delivery or a way to penetrate a cell or nucleus. In some embodiments, it is contemplated that dfTAT can facilitate cytosolic delivery of TEAD-binding peptides. Co-delivery of dfTAT with TEAD-binding peptide can facilitate cytosolic uptake of TEAD-binding peptide into a cell. Efficient cell penetration of the peptides as described herein can interact with TEAD to downregulate or suppress genes, such as oncogenes, driven by YAP/TAZ-TEAD transcriptional activation.

In other embodiments, cell penetration can be increased by using high dosage of a peptide described here, such as up to 10 µM, or 10 µM or more of the peptide. In some cases, an Arg patch can be fused, conjugated to, linked to, or co-delivered with a peptide. Up 10 µM, or 10 µM or more Arg patch may be co-delivered with a peptide to facilitate cell penetration. Protein transfection agents can also be used to increase cell penetration of a peptide. In some embodiments, direct cytosolic expression of a peptide can be used. In other embodiments, physical disruption methods such as electroporation can be used to improve delivery of a peptide into a cell.

In some embodiments, cell penetrance of a peptide described herein can be improved. For example, the binding interface of a peptide described herein can be grafted on a scaffold that is naturally cell-penetrant, such as a calcine. Some non-limiting examples of calcines can be imperatoxin-A, maurocalcine, hemicalcin, opiclacin 1, opicalcin 2, and hadrucalcin. The scaffold can comprise at least 60%, 70%, 80%, 90%, 95%, or 98% with any one of SEQ ID NO: 168-SEQ ID NO: 176. In some embodiments, the cell penetrance peptide can be calcines, modified calcines, derivatizes of calcines, or fragments thereof, which can be used to increase cell penetration. Modified calcines, derivatives of calcines, or fragments can be screened for cell penetration activity such as activation of sarcoplasmic reticulum ryanodine receptors, activity on ryanodine-sensitive $Ca^{2+}$ channels RyR1, Ryr2, or both, or as a selective agonist of the foregoing. Moreover, modified calcines can include substitution, addition or reduction of Lysine residues, or other charged residues, within a native calcine in order to modify activity and optimize such calcine cell-penetration activity or activity on the RyR1 or RyR2 receptors. As an example, the six amino acid portion of helix 3 (MLICLF; SEQ ID NO: 221), which can be a major component of SEQ ID NO: 9 binding to TEAD, can be transplanted onto a calcine or modified calcine scaffold to produce a bi-functional peptide that retains the cell penetration of the calcine with the novel SEQ ID NO: 9 TEAD binding function. As another example, a peptide as described herein can have improved cell penetrating capabilities using cis-acting elements, including inclusion of K/R-rich sequences like TAT or octa-arginine (SEQ ID NO: 146), intra-helical arginine patches, or fusion to larger fragments of proteins identified in cell penetration screening like penetratin or melittin.

In some cases, peptides can penetrate into a target cell or a nucleus of a target cell. Examples of target cells include cancerous cells, tumors, and other cell types wherein the HIPPO pathway is dysregulated. The target cell can be a human cell, a mammalian cell, a human or mammalian cell line, a cancer cell line, a cell extracted from a subject, in vivo, or in vitro.

In some instances, the peptide can contain only one lysine residue, or no lysine residues. In some instances, some or all of the lysine residues in the peptide are replaced with arginine residues. In some instances, some or all of the methionine residues in the peptide are replaced by leucine or isoleucine. Some or all of the tryptophan residues in the peptide can be replaced by phenylalanine or tyrosine. In some instances, some or all of the asparagine residues in the peptide are replaced by glutamine. In some embodiments, some or all of the aspartic acid residues can be replaced by glutamic acid residues. In some cases, the N-terminus of the peptide is blocked, such as by an acetyl group. Alternatively or in combination, in some instances, the C-terminus of the peptide is blocked, such as by an amide group. In some embodiments, the peptide is modified by methylation on free amines. For example, full methylation can be accomplished through the use of reductive methylation with formaldehyde and sodium cyanoborohydride.

In some cases, GS can be added as the first two N-terminal amino acids, as shown in SEQ ID NO: 1-SEQ ID NO: 42, or such N-terminal amino acids (GS) can be absent as shown in SEQ ID NO: 43-SEQ ID NO: 84, or can be substituted by any other one or two amino acids. In some embodiments, GS is used as a linker or used to couple to a linker to make a protein conjugate or fusion. In some embodiments, the linker comprises a $G_xS_y$ (SEQ ID NO: 283) peptide, wherein x and y independently can be any whole number, such as 1, 2, 3, 4, 5, 6, 7, 8, 9, and 10. In some embodiments, the peptide linker comprises (GS)x (SEQ ID NO: 282), wherein x can be any whole number, such as 1, 2, 3, 4, 5, 6, 7, 8, 9, and 10. In some embodiments, the peptide linker comprises GGSSG (SEQ ID NO: 204), GGGGG (SEQ ID NO: 205), GSGSGSGS (SEQ ID NO: 206), GGGGS (SEQ ID NO: 208), GGGS (SEQ ID NO: 203), or a variant or fragment thereof.

In some cases, the C-terminal Arg residues of a peptide is modified to another residue such as Ala, Asn, Asp, Gln, Glu, Gly, His, Leu, Lys, Met, Phe, Pro, Ser, Thr, Trp, Tyr, or Val. For example, the C-terminal Arg residue of a peptide can be modified to Ile. Alternatively, the C-terminal Arg residue of a peptide can be modified to any non-natural amino acid. This modification can prevent clipping of the C-terminal residue during expression, synthesis, processing, storage, in vitro, or in vivo including during treatment, while still allowing maintenance of a key hydrogen bond. A key hydrogen bond can be the hydrogen bond formed during the initial folding nucleation and is critical for forming the initial hairpin.

In some cases the peptide comprises the sequence of any one of SEQ ID NO: 1-SEQ ID NO: 84. A peptide can be a fragment comprising a contiguous fragment of any one of SEQ ID NO: 1-SEQ ID NO: 84 that is at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46 at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76 residues long, at least 77, at least 78, at least 79, at least 80, or at least 81 residues long, wherein the peptide fragment is selected from any portion of the peptide. In some embodiments, the peptide sequence is flanked by additional amino acids. One or more additional amino acids can, for example, confer a desired in vivo charge, isoelectric point, chemical conjugation site, stability, or physiologic property to a peptide.

In some instances, peptides capable of disrupting YAP-TEAD interact comprise no more than 60 amino acids in length, or no more than 50, no more than 45, no more than 40, no more than 35, no more than 30, no more than 25, no more than 20, no more than 15, or no more than 10 amino acids in length.

In some embodiments, peptide sequences comprise primarily beta-sheets and/or alpha-helix structures. In some embodiments, designed or engineered TEAD-binding peptides of the present disclosure are small, compact mini-proteins stabilized by intra-chain disulfide bonds (mediated by cysteines) and a well-packed hydrophobic core. In some embodiments, engineered TEAD-binding peptides have structures comprising helical bundles with at least one disulfide bridge between each of the alpha helices, thereby stabilizing the peptides. In other embodiments, the engineered TEAD-binding peptides comprise structures with three alpha helices and three intra-chain disulfide bonds, one between each of the three alpha helices in the bundle. In certain embodiments, one alpha helix in the bundle, comprising at least two helical turns, can present the leucine-$X_1$-$X_2$-leucine-phenylalanine ($LX_1X_2LF$, SEQ ID NO: 217) motif on the surface of the folded structure of the engineered TEAD-binding peptide, wherein $X_1$ and $X_2$ can be any amino acid. The $LX_1X_2LF$ (SEQ ID NO: 217) motif is a key binding motif found in the YAP sequence and is at the core of the binding interface between YAP and TEAD.

In other embodiments, peptides can be conjugated to, linked to, or fused to a carrier or a molecule with targeting or homing function for a cell of interest or a target cell. In other embodiments, peptides can be conjugated to, linked to, or fused to a molecule that extends half-life or modifies the pharmacodynamic and/or pharmacokinetic properties of the peptides, or any combination thereof.

In some instances, a peptide comprises at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 positively charged residues, such as Arg or Lys, or any combination thereof. In some instances, one or more lysine residues in the peptide are replaced with arginine residues. In some cases, peptides comprise one or more Arg patches. In some embodiments, an Arg patch is positioned in the N-terminus of a peptide. In other aspects, an Arg patch is positioned in the C-terminus of a peptide. In some embodiments, an Arg patch comprises 8 consecutive Arg residues (SEQ ID NO: 146). In some cases, 1 or more, 2 or more, 3 or more, 4 or more, 5 or more, 6 or more, 7 or more, 8 or more, 9 or more, or 10 or more Arg or Lys residues are solvent exposed on a peptide. In some embodiments, an Arg patch can be two or more consecutive Arg residues. In some embodiments, an Arg patch comprises one or more Arg substituted with Lys.

The peptides of the present disclosure can further comprise neutral amino acid residues. In some cases, the peptide has 35 or fewer neutral amino acid residues. In other cases, the peptide has 81 or fewer neutral amino acid residues, 70 or fewer neutral amino acid residues, 60 or fewer neutral amino acid residues, 50 or fewer neutral amino acid residues, 40 or fewer neutral amino acid residues, 36 or fewer neutral amino acid residues, 33 or fewer neutral amino acid residues, 30 or fewer neutral amino acid residues, 25 or fewer neutral amino acid residues, or 10 or fewer neutral amino acid residues.

The peptides of the present disclosure can further comprise negative amino acid residues. In some cases the peptide has 6 or fewer negative amino acid residues, 5 or fewer negative amino acid residues, 4 or fewer negative amino acid residues, 3 or fewer negative amino acid residues, 2 or fewer negative amino acid residues, or 1 or fewer negative amino acid residues. While negative amino acid residues can be selected from any negatively charged amino acid residues, in some embodiments, the negative amino acid residues are either E, or D, or a combination of both E and D.

In some cases, a peptide comprises no Cys or disulfides. In some cases, a peptide comprises 1 or more, 2 or more, 3 or more, 4 or more, 5 or more, 6 or more, 7 or more, 8 or more, 9 or more, 10 or more, 11 or more, 12 or more, 13 or more, 14 or more, or 15 or more Cys or disulfides. In other embodiments, 1 or more, 2 or more, 3 or more, 4 or more, 5 or more, 6 or more, 7 or more, 8 or more, 9 or more, 10 or more Cys residues have been replaced with Ser residues. In some embodiments, 1 or more, 2 or more, 3 or more, 4 or more, 5 or more, 6 or more, 7 or more, 8 or more, 9 or more, 10 or more Cys residues have been replaced with Thr residues.

In some instances, some or all of the methionine residues in the peptide are replaced by leucine or isoleucine. In some instances, some or all of the tryptophan residues in the peptide are replaced by phenylalanine or tyrosine. In some instances, some or all of the asparagine residues in the peptide are replaced by glutamine. In some cases, the N-terminus of the peptide is blocked, such as by an acetyl group. Alternatively or in combination, in some instances, the C-terminus of the peptide is blocked, such as by an amide group. In some embodiments, the peptide is modified by methylation on free amines. For example, full methylation may be accomplished through the use of reductive methylation with formaldehyde and sodium cyanoborohydride. In some cases, the C-terminal Arg residues of a peptide is modified to another residue such as Ala, Asn, Asp, Gln, Glu, Gly, His, Leu, Lys, Met, Phe, Pro, Ser, Thr, Trp, Tyr, or Val. For example, the C-terminal Arg residue of a peptide can be modified to Ile. Alternatively, the C-terminal Arg residue of a peptide can be modified to any non-natural amino acid. This modification can prevent clipping of the C-terminal residue during expression, synthesis, processing, storage, in vitro, or in vivo including during treatment, while still allowing maintenance of a key hydrogen bond. A key hydrogen bond can be the hydrogen bond formed during the initial folding nucleation and is critical for forming the initial hairpin.

Generally, the NMR solution structures of related structural homologs can be used to inform mutational strategies that may improve the folding, stability, manufacturability, while maintaining a particular biological function. They can be used to predict the 3D pharmacophore of a group of structurally homologous scaffolds, as wells as to predict possible graft regions of related proteins to create chimeras with improved properties. For example, this strategy was used to identify critical amino acid positions and loops that may be used to design peptides with improved cell penetrating properties, high affinity for either TEAD or YAP, high expression, high stability in vivo, or any combination thereof.

In some embodiments, a peptide capable of disrupting YAP-TEAD interaction comprises a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with any one of the exemplary peptide sequences listed in TABLE 1, or a fragment thereof. Two or more peptides can share a degree of sequence identity or homology and share similar properties in vivo. For instance, a peptide can share a degree of sequence identity or homology with any one of the peptides of SEQ ID NO: 1-SEQ ID NO: 84. In some cases, one or more peptides of the disclosure can have up to about 20% pairwise sequence identity or homology, up to about 25% pairwise sequence identity or homology, up to about 30% pairwise sequence identity or homology, up to about 35% pairwise sequence identity or homology, up to about 40% pairwise sequence identity or homology, up to about 45% pairwise sequence identity or homology, up to about 50% pairwise sequence identity or homology, up to about 55% pairwise sequence identity or homology, up to about 60% pairwise sequence identity or homology, up to about 65% pairwise sequence identity or homology, up to about 70% pairwise sequence identity or homology, up to about 75% pairwise sequence identity or homology, up to about 80% pairwise sequence identity or homology, up to about 85% pairwise sequence identity or homology, up to about 90% pairwise sequence identity or homology, up to about 95% pairwise sequence identity or homology, up to about 96% pairwise sequence identity or homology, up to about 97% pairwise sequence identity or homology, up to about 98% pairwise sequence identity or homology, up to about 99% pairwise sequence identity or homology, up to about 99.5% pairwise sequence identity or homology, or up to about 99.9% pairwise sequence identity or homology. In some cases, one or more peptides of the disclosure can have at least about 20% pairwise sequence identity or homology, at least about 25% pairwise sequence identity or homology, at least about 30% pairwise sequence identity or homology, at least about 35% pairwise sequence identity or homology, at least about 40% pairwise sequence identity or homology, at least about 45% pairwise sequence identity or homology, at least about 50% pairwise sequence identity or homology, at least about 55% pairwise sequence identity or homology, at least about 60% pairwise sequence identity or homology, at least about 65% pairwise sequence identity or homology, at least about 70% pairwise sequence identity or homology, at least about 75% pairwise sequence identity or homology, at least about 80% pairwise sequence identity or homology, at least about 85% pairwise sequence identity or homology, at least about 90% pairwise sequence identity or homology, at least about 95% pairwise sequence identity or homology, at least about 96% pairwise sequence identity or homology, at least about 97% pairwise sequence identity or homology, at least about 98% pairwise sequence identity or homology, at least about 99% pairwise sequence identity or homology, at least about 99.5% pairwise sequence identity or homology, at least about 99.9% pairwise sequence identity or homology with a second peptide.

Various methods and software programs can be used to determine the homology between two or more peptides, such as NCBI BLAST, Clustal W, MAFFT, Clustal Omega, AlignMe, Praline, or another suitable method or algorithm. Pairwise sequence alignment is used to identify regions of similarity that may indicate functional, structural and/or evolutionary relationships between two biological sequences (protein or nucleic acid). By contrast, multiple sequence alignment (MSA) is the alignment of three or more biological sequences. From the output of MSA applications, homology can be inferred and the evolutionary relationship between the sequences assessed. One of skill in the art would recognize as used herein, "sequence homology" and "sequence identity" and "percent (%) sequence identity" and "percent (%) sequence homology" have been used interchangeably to mean the sequence relatedness or variation, as appropriate, to a reference polynucleotide or amino acid sequence.

In some instances, the peptide is any one of SEQ ID NO: 1-SEQ ID NO: 84 or a functional fragment thereof. In other embodiments, the peptide of the disclosure further comprises a peptide with 99%, 95%, 90%, 85%, or 80% sequence identity or homology to any one of SEQ ID NO: 1-SEQ ID NO: 84 or fragment thereof.

In other instances, the peptide can be a peptide that is homologous to any one of SEQ ID NO: 1-SEQ ID NO: 84 or a functional fragment thereof. The term "homologous" is used herein to denote peptides having at least 70%, at least 80%, at least 90%, at least 95%, or greater than 95% sequence identity or homology to a sequence of any one of SEQ ID NO: 1-SEQ ID NO: 84 or a functional fragment thereof.

In still other instances, the variant nucleic acid molecules that encode a peptide of any one of SEQ ID NO: 1-SEQ ID NO: 84 can be identified by either a determination of the sequence identity or homology of the encoded peptide amino acid sequence with the amino acid sequence of any one of SEQ ID NO: 1-SEQ ID NO: 84, or by a nucleic acid hybridization assay. Such peptide variants of any one of SEQ ID NO: 1-SEQ ID NO: 84 can be characterized as nucleic acid molecules (1) that remain hybridized with a nucleic acid molecule having the nucleotide sequence of any one of SEQ ID NO: 1-SEQ ID NO: 84 (or its complement) under highly stringent washing conditions, in which the wash stringency is equivalent to 0.1×-0.2×SSC with 0.1% SDS at 50-65° C., and (2) that encode a peptide having at least 70%, at least 80%, at least 90%, at least 95% or greater than 95% sequence identity or homology to the amino acid sequence of any one of SEQ ID NO: 1-SEQ ID NO: 84.

Knottin Peptides

In some embodiments, TEAD binding peptides as described herein contain no disulfides or Cys. In other embodiments, TEAD binding peptides comprise one or more Cys, or one or more disulfide bond. In some embodiments, the TEAD binding peptides are derived from knotted or knottin peptides. In some embodiments, such knotted peptides can bind TEAD, thereby preventing TEAD interactions, such as YAP-TEAD interactions. In some embodiments, a peptide that disrupts TEAD binding interactions comprises one or more properties of some knottin peptides, such as stability, resistance to proteolysis, resistance to reducing conditions, and/or ability to cross the blood brain barrier.

In other embodiments, knotted peptides can be conjugated to, linked to, or fused to TEAD binding peptides, such as those described in TABLE 1, to provide homing or targeting function to a target cell, such as a cancer cell, pancreatic cell, liver cell, colon cell, ovarian cell, breast cell, lung cell, or any combination thereof. In some embodiments, such knotted peptides selectively target or home to a cancer cell, such as a breast cancer, liver cancer, colon cancer, brain cancer, or tumor cell. In some embodiments, such knotted peptides can home to or target an unhealthy or diseased cell or a cancer cell across the blood brain barrier. In some cases, knotted peptides are conjugated to, linked to, or fused to TEAD binding peptides and are capable of localizing TEAD binding peptides across the blood brain barrier to deliver TEAD binding peptides to target cells in the central nervous system. In some embodiments, such targeting or homing peptides or knotted peptides can be used to deliver a cytotoxic agent to the target cell or target TEAD in a target cell for degradation or inactivation, such as targeting TEAD for ubiquitination or other post-translation modification that targets TEAD for degradation or inactivation.

Knottins are a class of peptides, usually ranging from about 11 to about 81 amino acids in length that are often folded into a compact structure. Knottins are typically assembled into a complex tertiary structure that is characterized by a number of intramolecular disulfide crosslinks and may contain beta strands, alpha helices, and other secondary structures. The presence of the disulfide bonds gives knottins remarkable environmental stability, allowing them to withstand extremes of temperature and pH and to resist the proteolytic enzymes of the blood stream. The presence of a disulfide knot may provide resistance to reduction by reducing agents. The rigidity of knottins also allows them to bind to targets without paying the "entropic penalty" that a floppy peptide accrues upon binding a target. For example, binding is adversely affected by the loss of entropy that occurs when a peptide binds a target to form a complex. Therefore, "entropic penalty" is the adverse effect on binding, and the greater the entropic loss that occurs upon this binding, the greater the "entropic penalty." Furthermore, unbound molecules that are flexible lose more entropy when forming a complex than molecules that are rigidly structured, because of the loss of flexibility when bound up in a complex. However, rigidity in the unbound molecule also generally increases specificity by limiting the number of complexes that molecule can form. The knotted peptides can bind targets with antibody-like affinity, or with nanomolar or picomolar affinity. A wider examination of the sequence structure and sequence identity or homology of knottins reveals that they have arisen by convergent evolution in all kinds of animals and plants. In animals, they are often found in venoms, for example, the venoms of spiders and scorpions and have been implicated in the modulation of ion channels. The knottin proteins of plants can inhibit the proteolytic enzymes of animals or have antimicrobial activity, suggesting that knottins can function in the native defense of plants.

The present disclosure provides peptides that comprise or are derived from these knotted peptides (or knottins). As used herein, the term "knotted peptide" is considered to be interchangeable with the terms "knottin" and "peptide."

The peptides of the present disclosure comprise cysteine amino acid residues. In some cases, the peptide has at least 1, at least 2, at least 3, at least 4, at least 5, at least 6, at least 7, at least 8, at least 9, or at least 10 cysteine amino acid residues. In some cases, the peptide has at least 8 cysteine amino acid residues. In other cases, the peptide has at least 10 cysteine amino acid residues, at least 12 cysteine amino acid residues, at least 14 cysteine amino acid residues or at least 16 cysteine amino acid residues.

A knotted peptide can comprise disulfide bridges. A knotted peptide can be a peptide wherein 5% or more of the residues are cysteines forming intramolecular disulfide bonds. A disulfide-linked peptide can be a drug scaffold. In some embodiments, the disulfide bridges form a knot. A disulfide bridge can be formed between cysteine residues, for example, between cysteines 1 and 4, 2 and 5, or, 3 and 6. In some cases, one disulfide bridge passes through a loop formed by the other two disulfide bridges, for example, to form the knot. In other cases, the disulfide bridges can be formed between any two cysteine residues.

The present disclosure further includes peptide scaffolds that, e.g., can be used as a starting point for generating additional peptides. In some embodiments, these scaffolds can be derived from a variety of knotted peptides (or knottins). In certain embodiments, knotted peptides are assembled into a complex tertiary structure that is characterized by a number of intramolecular disulfide crosslinks, and optionally contain beta strands and other secondary structures such as an alpha helix. For example, knotted peptides include, in some embodiments, small disulfide-rich proteins characterized by a disulfide through disulfide knot. This knot can be, e.g., obtained when one disulfide bridge crosses the macrocycle formed by two other disulfides and the interconnecting backbone. In some embodiments, the knotted peptides can include growth factor cysteine knots or inhibitor cysteine knots. Other possible peptide structures include peptide having two parallel helices linked by two disulfide bridges without β-sheets (e.g., hefutoxin).

A knotted peptide can comprise at least one amino acid residue in an L configuration. A knotted peptide can comprise at least one amino acid residue in a D configuration. In some embodiments, a knotted peptide is 15-40 amino acid residues long. In other embodiments, a knotted peptide is 11-57 amino acid residues long. In still other embodiments, a knotted peptide is 11-81 amino acid residues long. In further embodiments, a knotted peptide is at least 20 amino acid residues long.

Knotted peptides or peptides can be derived from a class of proteins known to be present or associated with toxins or venoms. In some cases, the peptide can be derived from toxins or venoms associated with scorpions or spiders. The peptide can be derived from venoms and toxins of spiders and scorpions of various genus and species. For example, the peptide can be derived from a venom or toxin of the *Leiurus quinquestriatus hebraeus, Buthus occitanus tunetanus, Hottentotta judaicus, Mesobuthus eupeus, Buthus occitanus israelis, Hadrurus gertschi, Androctonus australis, Centruroides noxius, Heterometrus laoticus, Opistophthalmus carinatus, Haplopelma schmidti, Isometrus maculatus, Haplopelma huwenum, Haplopelma hainanum, Haplopelma schmidti, Agelenopsis aperta, Haydronyche versuta, Selenocosmia huwena, Heteropoda venatoria, Grammostola rosea, Ornithoctonus huwena, Hadronyche versuta, Atrax robustus, Angelenopsis aperta, Psalmopoeus cambridgei, Hadronyche infensa, Paracoelotes luctosus,* and *Chilobrachys jingzhaoor* another suitable genus or species of scorpion or spider. In some cases, a peptide can be derived from a *Buthus martensii* Karsh (scorpion) toxin.

Sequence Identity and Homology

Percent sequence identity or homology is determined by conventional methods. See, for example, Altschul et al., Bull. Math. Bio. 48:603 (1986), and Henikoff and Henikoff, Proc. Natl. Acad. Sci. USA 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (Id.). The sequence identity or homology is then calculated as: ([Total number of identical matches]/[length of the longer sequence plus the number of gaps introduced into the longer sequence in order to align the two sequences])(100).

Additionally, there are many established algorithms available to align two amino acid sequences. For example, the "FASTA" similarity search algorithm of Pearson and Lipman is a suitable protein alignment method for examining the level of sequence identity or homology shared by an amino acid sequence of a peptide disclosed herein and the amino acid sequence of a peptide variant. The FASTA algorithm is described by Pearson and Lipman, Proc. Nat'l Acad. Sci. USA 85:2444 (1988), and by Pearson, Meth. Enzymol. 183:63 (1990). Briefly, FASTA first characterizes sequence similarity by identifying regions shared by the query sequence (e.g., SEQ ID NO: 1) and a test sequence that has either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, J. Mol. Biol. 48:444 (1970); Sellers, Siam J. Appl. Math. 26:787 (1974)), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, Meth. Enzymol. 183:63 (1990).

FASTA can also be used to determine the sequence identity or homology of nucleic acid molecules using a ratio as disclosed above. For nucleotide sequence comparisons, the ktup value can range between one to six, preferably from three to six, most preferably three, with other parameters set as described above.

Some examples of common amino acids that are a "conservative amino acid substitution" are illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. The BLOSUM62 table is an amino acid substitution matrix derived from about 2,000 local multiple alignments of protein sequence segments, representing highly conserved regions of more than 500 groups of related proteins (Henikoff and Henikoff, Proc. Nat'l Acad. Sci. USA 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

Determination of amino acid residues that are within regions or domains that are critical to maintaining structural integrity can be determined. Within these regions one can determine specific residues that can be more or less tolerant of change and maintain the overall tertiary structure of the molecule. Methods for analyzing sequence structure include, but are not limited to, alignment of multiple sequences with high amino acid or nucleotide identity or homology and computer analysis using available software (e.g., the Insight II® viewer and homology modeling tools; MSI, San Diego, Calif.), secondary structure propensities, binary patterns, complementary packing and buried polar interactions (Barton, G. J., Current Opin. Struct. Biol. 5:372-6 (1995) and Cordes, M. H. et al., Current Opin. Struct. Biol. 6:3-10 (1996)). In general, when designing modifications to molecules or identifying specific fragments determination of structure can typically be accompanied by evaluating activity of modified molecules.

At physiological pH, peptides can have a net charge, for example, of −5, −4, −3, −2, −1, 0, +1, +2, +3, +4, or +5. When the net charge is zero, the peptide can be uncharged or zwitterionic. In some embodiments, the peptide contains one or more disulfide bonds and has a positive net charge at physiological pH where the net charge can be +0.5 or less than +0.5, +1 or less than +1, +1.5 or less than +1.5, +2 or less than +2, +2.5 or less than +2.5, +3 or less than +3, +3.5 or less than +3.5, +4 or less than +4, +4.5 or less than +4.5, +5 or less than +5, +5.5 or less than +5.5, +6 or less than +6, +6.5 or less than +6.5, +7 or less than +7, +7.5 or less than +7.5, +8 or less than +8, +8.5 or less than +8.5, +9 or less than +9.5, +10 or less than +10. In some embodiments, the peptide has a negative net charge at physiological pH where the net charge can be −0.5 or less than −0.5, −1 or less than −1, −1.5 or less than −1.5, −2 or less than −2, −2.5 or less than −2.5, −3 or less than −3, −3.5 or less than −3.5, −4 or less than −4, −4.5 or less than −4.5, −5 or less than −5, −5.5 or less than −5.5, −6 or less than −6, −6.5 or less than −6.5, −7 or less than −7, −7.5 or less than −7.5, −8 or less than −8, −8.5 or less than −8.5, −9 or less than −9.5, −10 or less than −10.

In some embodiments, peptides of the present disclosure can have an isoelectric point (pI) value from 3 and 10. In other embodiments, peptides of the present disclosure can have a pI value from 4.3 and 8.9. In some embodiments, peptides of the present disclosure can have a pI value from 3-4. In some embodiments, peptides of the present disclosure can have a pI value from 3-5. In some embodiments, peptides of the present disclosure can have a pI value from 3-6. In some embodiments, peptides of the present disclosure can have a pI value from 3-7. In some embodiments, peptides of the present disclosure can have a pI value from 3-8. In some embodiments, peptides of the present disclosure can have a pI value from 3-9. In some embodiments, peptides of the present disclosure can have a pI value from 4-5. In some embodiments, peptides of the present disclosure can have a pI value from 4-6. In some embodiments, peptides of the present disclosure can have a pI value from 4-7. In some embodiments, peptides of the present disclosure can have a pI value from 4-8. In some embodiments, peptides of the present disclosure can have a pI value from 4-9. In some embodiments, peptides of the present disclosure can have a pI value from 4-10. In some embodiments, peptides of the present disclosure can have a pI value from 5-6. In some embodiments, peptides of the present disclosure can have a pI value from 5-7. In some embodiments, peptides of the present disclosure can have a pI value from 5-8. In some embodiments, peptides of the present disclosure can have a pI value from 5-9. In some embodiments, peptides of the present disclosure can have a pI value from 5-10. In some embodiments, peptides of the present disclosure can have a pI value from 6-7. In some embodiments, peptides of the present disclosure can have a pI value from 6-8. In some embodiments, peptides of the present disclosure can have a pI value from 6-9. In some embodiments, peptides of the present disclosure can have a pI value from 6-10. In some embodiments, peptides of the present disclosure can have a pI value from 7-8. In some embodiments, peptides of the present disclosure can have a pI value from 7-9. In some embodiments, peptides of the present disclosure can have a pI value from 7-10. In some embodiments, peptides of the present disclosure can have a pI value from 8-9. In some embodiments, peptides of the present disclosure can have a pI value from 8-10. In some embodiments, peptides of the present disclosure can have a pI value from 9-10.

In some cases, the engineering of one or more mutations within a peptide yields a peptide with an altered isoelectric point, charge, surface charge, or rheology at physiological pH. Such engineering of a mutation to a peptide derived from a scorpion or spider can change the net charge of the complex, for example, by decreasing the net charge by 1, 2, 3, 4, or 5, or by increasing the net charge by 1, 2, 3, 4, or 5. In such cases, the engineered mutation can facilitate the ability of the peptide to penetrate a cell, an endosome, or the nucleus. Suitable amino acid modifications for improving the rheology and potency of a peptide can include conservative or non-conservative mutations.

A peptide can comprise at most 1 amino acid mutation, at most 2 amino acid mutations, at most 3 amino acid mutations, at most 4 amino acid mutations, at most 5 amino acid mutations, at most 6 amino acid mutations, at most 7 amino acid mutations, at most 8 amino acid mutations, at most 9 amino acid mutations, at most 10 amino acid mutations, or another suitable number as compared to the sequence of the venom or toxin component that the peptide is derived from. In other cases, a peptide, or a functional fragment thereof, comprises at least 1 amino acid mutation, at least 2 amino acid mutations, at least 3 amino acid mutations, at least 4 amino acid mutations, at least 5 amino acid mutations, at least 6 amino acid mutations, at least 7 amino acid mutations, at least 8 amino acid mutations, at least 9 amino acid mutations, at least 10 amino acid mutations, or another suitable number as compared to the sequence of the venom or toxin component that the peptide is derived from. In some embodiments, mutations can be engineered within a peptide to provide a peptide that has a desired charge or stability at physiological pH.

Generally, the NMR solution structures, the x-ray crystal structures, as well as the primary structure sequence alignment of related structural homologs or in silico design can be used to inform mutational strategies that can improve the folding, stability, and/or manufacturability, while maintaining a particular biological function. The general strategy for producing homologs or in silico designed peptides or proteins can include identification of a charged surface patch or conserved residues of a protein, mutation of critical amino acid positions and loops, and testing of sequences. This strategy can be used to design peptides with improved properties or to correct deleterious mutations that complicate folding and manufacturability. These key amino acid positions and loops can be retained while other residues in the peptide sequences can be mutated to improve, change, remove, or otherwise modify function, such as binding or ability to penetrate a cell, endosome, or nucleus in a cell, homing, or another activity of the peptide.

The present disclosure also encompasses multimers of the various peptides described herein. Examples of multimers include dimers, trimers, tetramers, pentamers, hexamers, heptamers, and so on. A multimer may be a homomer formed from a plurality of identical subunits or a heteromer formed from a plurality of different subunits. In some embodiments, a peptide of the present disclosure is arranged in a multimeric structure with at least one other peptide, or two, three, four, five, six, seven, eight, nine, ten, or more other peptides. In certain embodiments, the peptides of a multimeric structure each have the same sequence. In alternative embodiments, some or all of the peptides of a multimeric structure have different sequences.

The present disclosure further includes peptide scaffolds that, e.g., can be used as a starting point for generating additional peptides. In some embodiments, these scaffolds can be derived from a variety of knotted peptides or knottins. Some suitable peptides for scaffolds can include, but are not limited to, chlorotoxin, brazzein, circulin, stecrisp, hanatoxin, midkine, hefutoxin, potato carboxypeptidase inhibitor, bubble protein, attractin, α-GI, α-GID, μ-PIIIA, ω-MVIIA, ω-CVID, χ-MrIA, ρ-TIA, conantokin G, contulakin G, GsMTx4, margatoxin, shK, toxin K, chymotrypsin inhibitor (CTI), and EGF epiregulin core. In some embodiments, the peptide sequence is flanked by additional amino acids. One or more additional amino acids can, for example, confer a desired in vivo charge, isoelectric point, chemical conjugation site, stability, or physiologic property to a peptide.

Chemical Modifications

A peptide can be chemically modified one or more of a variety of ways. In some embodiments, the peptide can be mutated to add function, delete function, or modify the in vivo behavior. For example, in some embodiments, peptides of the presenting disclosure may be chemically modified with a molecule that would lead to proteasomal degradation of TEAD (e.g., ubiquitin ligase engaging conjugate or fusion or cereblon-binding molecule). One or more loops between the disulfide linkages can be modified or replaced to include active elements from other peptides (such as described in Moore and Cochran, Methods in Enzymology, 503, p. 223-251, 2012). Amino acids can also be mutated, such as to increase half-life, modify, add or delete binding behavior in vivo, add new targeting function, modify surface charge and hydrophobicity, or allow conjugation sites. N-methylation is one example of methylation that can occur in a peptide of the disclosure. In some embodiments, the peptide is modified by methylation on free amines. For example, full methylation may be accomplished through the use of reductive methylation with formaldehyde and sodium cyanoborohydride.

A chemical modification can, for instance, extend the half-life of a peptide or change the biodistribution or pharmacokinetic profile. A chemical modification can comprise a polymer, a polyether, polyethylene glycol, a biopolymer, a polyamino acid, a fatty acid, a dendrimer, an Fc region, a simple saturated carbon chain such as palmitate or myristolate, or albumin. A polyamino acid can include, for example, a poly amino acid sequence with repeated single amino acids (e.g., poly glycine), and a poly amino acid sequence with mixed poly amino acid sequences (e.g., gly-ala-gly-ala) that may or may not follow a pattern, or any combination of the foregoing. The peptides of the present disclosure can be modified such that the modification increases the stability and/or the half-life of the peptides. The attachment of a hydrophobic moiety, such as to the N-terminus, the C-terminus, or an internal amino acid, can be used to extend half-life of a peptide of the present disclosure. The peptides can also be modified to increase or decrease the gut permeability or cellular permeability of the peptide. The peptide of the present disclosure can include post-translational modifications (e.g., methylation and/or amidation and/or glycosylation), which can affect, e.g., serum half-life. In some embodiments, simple carbon chains (e.g., by myristoylation and/or palmitoylation) can be conjugated to, linked to, the fusion proteins or peptides. The simple carbon chains can render the fusion proteins or peptides easily separable from the unconjugated material. For example, methods that can be used to separate the fusion proteins or peptides from the unconjugated material include, but are not limited to, solvent extraction and reverse phase chromatography. Lipophilic moieties can extend half-life through reversible binding to serum albumin. Conjugated moieties can, e.g., be lipophilic moieties that extend half-life of the peptides through reversible binding to serum albumin. In some embodiments, the lipophilic moiety can be cholesterol or a cholesterol derivative including cholestenes, cholestanes, cholestadienes and oxysterols. In some embodiments, the peptides can be conjugated to, linked to, myristic acid (tetradecanoic acid) or a derivative thereof. In other embodiments, the peptides of the present disclosure can be coupled (e.g., conjugated, linked, or fused) to a half-life modifying agent. Examples of half-life modifying agents can include, but is not limited to: a polymer, a polyethylene glycol (PEG), a hydroxyethyl starch, polyvinyl alcohol, a water soluble polymer, a zwitterionic water soluble polymer, a water soluble poly(amino acid), a water soluble polymer of proline, alanine and serine, a water soluble polymer containing glycine, glutamic acid, and serine, an Fc region, a fatty acid, palmitic acid, or a molecule that binds to albumin. Additionally, conjugation of the peptide to a near infrared dye, such as Cy5.5, or to an albumin binder such as Albu-tag can extend serum half-life of any peptide as described herein. In some embodiments, immunogenicity is reduced by using minimal non-human protein sequences to extend serum half-life of the peptide.

In some embodiments, the first two N-terminal amino acids (GS) of SEQ ID NO: 1-SEQ ID NO: 84 serve as a spacer or linker in order to facilitate conjugation or fusion to another molecule, as well as to facilitate cleavage of the peptide from such conjugated to, linked to, or fused molecules. In some embodiments, the fusion proteins or peptides of the present disclosure can be conjugated to, linked to, or fused to other moieties that, e.g., can modify or effect changes to the properties of the peptides.

Active Agent Peptide Conjugates

In some embodiments, the peptides of the present disclosure can themselves be used to inhibit YAP binding to TEAD. In other embodiments, peptides of the present disclosure can also be used to deliver another active agent. Peptides according to the present disclosure can be conjugated to, linked to, or fused to an agent for use in the treatment of tumors and cancers. For example, in certain embodiments, the peptides described herein are fused to another molecule, such as an active agent that provides an additional functional capability. A peptide can be fused with an active agent through expression of a vector containing the sequence of the peptide with the sequence of the active agent. In various embodiments, the sequence of the peptide and the sequence of the active agent can be expressed from the same Open Reading Frame (ORF). In various embodiments, the sequence of the peptide and the sequence of the active agent can comprise a contiguous sequence. The peptide and the active agent can each retain similar functional capabilities in the fusion peptide compared with their functional capabilities when expressed separately. In certain embodiments, examples of active agents can include other peptides.

As another example, in certain embodiments, the peptides described herein are attached to another molecule, such as an active agent that provides a functional capability. In some embodiments, TEAD-binding peptides can direct the active agent into the cell. In further embodiments, TEAD-binding peptides can direct the active agent into the nucleus. In some embodiments, the active agent has intrinsic tumor-homing properties or the active agent can be engineering to have tumor-homing properties. In some embodiments, 1, 2, 3, 4, 5, 6, 7, 8, 9, or 10 active agents can be linked to a peptide. Multiple active agents can be attached by methods such as conjugating to multiple lysine residues and/or the N-terminus, or by linking the multiple active agents to a scaffold, such as a polymer or dendrimer and then attaching that agent-scaffold to the peptide (such as described in Yurkovetskiy, A. V., Cancer Res 75(16): 3365-72 (2015)). Examples of active agents include but are not limited to: a peptide, an oligopeptide, a polypeptide, a peptidomimetic, a polynucleotide, a polyribonucleotide, a DNA, a cDNA, a ssDNA, a RNA, a dsRNA, a micro RNA, an oligonucleotide, an antibody, a single chain variable fragment (scFv), an antibody fragment, an aptamer, a cytokine, an interferon, a hormone, an enzyme, a growth factor, a checkpoint inhibitor, a PD-1 inhibitor, a PD-L1 inhibitor, a CTLA4 inhibitor, a CD antigen, a chemokine, a neurotransmitter, an ion channel inhibitor, an ion channel activator, a G-protein coupled receptor inhibitor, a G-protein coupled receptor activator, a chemical agent, a radiosensitizer, a radioprotectant, a radionuclide, a therapeutic small molecule, a steroid, a corticosteroid, an anti-inflammatory agent, an immune modulator, a complement fixing peptide or protein, a tumor necrosis factor inhibitor, a tumor necrosis factor activator, a tumor necrosis factor receptor family agonist, a tumor necrosis receptor antagonist, a Tim-3 inhibitor, a protease inhibitor, an amino sugar, a chemotherapeutic, a cytotoxic molecule, a toxin, a tyrosine kinase inhibitor, an anti-infective agent, an antibiotic, an anti-viral agent, an anti-fungal agent, an aminoglycoside, a nonsteroidal anti-inflammatory drug (NSAID), a statin, a nanoparticle, a liposome, a polymer, a biopolymer, a polysaccharide, a proteoglycan, a glycosaminoglycan, polyethylene glycol, a lipid, a dendrimer, a fatty acid, or an Fc region, or an active fragment or a modification thereof. In some embodiments, the peptide is covalently or non-covalently linked to an active agent, e.g., directly or via a linker. For example, cytotoxic molecules that can be used include auristatins, MMAE, MMAF, dolostatin, auristatin F, monomethylauristatin D, DM1, DM4, maytansinoids, maytansine, calicheamicins, N-acetyl-γ-calicheamicin, pyrrolobenzodiazepines, PBD dimers, doxorubicin, vinca alkaloids (4-deacetylvinblastine), duocarmycins, cyclic octapeptide analogs of mushroom amatoxins, epothilones, and anthracylines, CC-1065, taxanes, paclitaxel, cabazitaxel, docetaxel, SN-38, irinotecan, vincristine, vinblastine, platinum compounds, cisplatin, methotrexate, and BACE inhibitors. Additional examples of active agents are described in McCombs, J. R., AAPS J, 17(2): 339-51 (2015), Ducry, L., Antibody Drug Conjugates (2013), and Singh, S. K., Pharm Res. 32(11): 3541-3571 (2015). Exemplary linkers suitable for use with the embodiments herein are discussed in further detail below.

As compared to antibody-drug conjugates (e.g., Adcetris, Kadcyla, Mylotarg), in some aspects the peptide conjugated to, linked to, or fused to an active agent as described herein can exhibit better penetration of solid tumors due to its smaller size. In certain aspects, the peptide conjugated to, linked to, or fused to an active agent as described herein can carry different or higher doses of active agents as compared to antibody-drug conjugates. In still other aspects, the peptide conjugated to, linked to, or fused to an active agent as described herein can have better site specific delivery of defined drug ratio as compared to antibody-drug conjugates. In other aspects, the peptide can be amenable to solvation in organic solvents (in addition to water), which can allow more synthetic routes for solvation and conjugation of a drug (which often has low aqueous solubility) and higher conjugation yields, higher ratios of drug conjugated to, linked to, or fused to peptide (versus an antibody), and/or reduce aggregate/high molecular weight species formation during conjugation. Additionally, a unique amino acid residue(s) can be introduced into the peptide via a residue that is not otherwise present in the short sequence or via inclusion of a non-natural amino acid, allowing site specific conjugation to the peptide.

The peptides or fusion peptides of the present disclosure can also be conjugated to, linked to, or fused to other moieties that can serve other roles, such as providing an affinity handle (e.g., biotin) for retrieval of the peptides from tissues or fluids. For example, peptides or fusion peptides of the present disclosure can also be conjugated to, linked to, or fused to biotin. In addition to extension of half-life, biotin can also act as an affinity handle for retrieval of peptides or fusion peptides from tissues or other locations. In some embodiments, fluorescent biotin conjugates that can act both as a detectable label and an affinity handle can be used. Non limiting examples of commercially available fluorescent biotin conjugates can include Atto 425-Biotin, Atto 488-Biotin, Atto 520-Biotin, Atto-550 Biotin, Atto 565-Biotin, Atto 590-Biotin, Atto 610-Biotin, Atto 620-Biotin, Atto 655-Biotin, Atto 680-Biotin, Atto 700-Biotin, Atto 725-Biotin, Atto 740-Biotin, fluorescein biotin, biotin-4-fluorescein, biotin-(5-fluorescein) conjugate, and biotin-B-phycoerythrin, Alexa fluor 488 biocytin, Alexa flour 546, Alexa Fluor 549, lucifer yellow cadaverine biotin-X, Lucifer yellow biocytin, Oregon green 488 biocytin, biotin-rhodamine and tetramethylrhodamine biocytin. In some other examples, the conjugates can include chemiluminescent compounds, colloidal metals, luminescent compounds, enzymes, radioisotopes, and paramagnetic labels. In some embodiments, the peptide described herein can also be attached to another molecule. For example, the peptide sequence also can be attached to another active agent (e.g., small molecule, peptide, polypeptide, polynucleotide, antibody, aptamer, cytokine, growth factor, neurotransmitter, an active fragment or modification of any of the preceding agents, fluorophore, radioisotope, radionuclide chelator, acyl adduct, chemical linker, or sugar). In some embodiments, the peptide can be conjugated to, linked to, or fused with, or covalently or non-covalently linked to an active agent.

Additionally, more than one peptide sequence derived from a toxin or venom knottin protein can be present on, conjugated to, linked to, or fused with a particular peptide. A peptide can be incorporated into a biomolecule by various techniques. A peptide can be incorporated by a chemical transformation, such as the formation of a covalent bond, such as an amide bond. A peptide can be incorporated, for example, by solid phase or solution phase peptide synthesis. A peptide can be incorporated by preparing a nucleic acid sequence encoding the biomolecule, wherein the nucleic acid sequence includes a subsequence that encodes the peptide. The subsequence can be in addition to the sequence that encodes the biomolecule, or can substitute for a subsequence of the sequence that encodes the biomolecule.

Detectable Agent Peptide Conjugates

A peptide can be conjugated to, linked to, or fused to an agent used in imaging, research, therapeutics, theranostics, pharmaceuticals, chemotherapy, chelation therapy, targeted drug delivery, and radiotherapy. In some embodiments, a peptide is conjugated to, linked to, or fused with detectable agents, such as a fluorophore, a near-infrared dye, a contrast agent, a nanoparticle, a metal-containing nanoparticle, a metal chelate, an X-ray contrast agent, a PET agent, a metal, a radioisotope, a dye, radionuclide chelator, or another suitable material that can be used in imaging. In some embodiments, 1, 2, 3, 4, 5, 6, 7, 8, 9, or 10 detectable agents can be linked to a peptide. Non-limiting examples of radioisotopes include alpha emitters, beta emitters, positron emitters, and gamma emitters. In some embodiments, the metal or radioisotope is selected from the group consisting of actinium, americium, bismuth, cadmium, cesium, cobalt, europium, gadolinium, iridium, lead, lutetium, manganese, palladium, polonium, radium, ruthenium, samarium, strontium, technetium, thallium, and yttrium. In some embodiments, the metal is actinium, bismuth, lead, radium, strontium, samarium, or yttrium. In some embodiments, the radioisotope is actinium-225 or lead-212. In some embodiments, the near-infrared dyes are not easily quenched by biological tissues and fluids. In some embodiments, the fluorophore is a fluorescent agent emitting electromagnetic radiation at a wavelength between 650 nm and 4000 nm, such emissions being used to detect such agent. Non-limiting examples of fluorescent dyes that could be used as a conjugating molecule in the present disclosure include DyLight-680, DyLight-750, VivoTag-750, DyLight-800, IRDye-800, VivoTag-680, Cy5.5, or indocyanine green (ICG). In some embodiments, near infrared dyes often include cyanine dyes (e.g., Cy7, Cy5.5, and Cy5). Additional non-limiting examples of fluorescent dyes for use as a conjugating molecule in the present disclosure include acradine orange or yellow, Alexa Fluors (e.g., Alexa Fluor 790, 750, 700, 680, 660, and 647) and any derivative thereof, 7-actinomycin D, 8-anilinonaphthalene-1-sulfonic acid, ATTO dye and any derivative thereof, auramine-rhodamine stain and any derivative thereof, bensantrhone, bimane, 9-10-bis(phenylethynyl)anthracene, 5,12-bis(phenylethynyl)naththacene, bisbenzimide, brainbow, calcein, carbodyfluorescein and any derivative thereof, 1-chloro-9,10-bis(phenylethynyl)anthracene and any derivative thereof, DAPI, DiOC6, DyLight Fluors and any derivative thereof, epicocconone, ethidium bromide, FlAsH-EDT2, Fluo dye and any derivative thereof, FluoProbe and any derivative thereof, Fluorescein and any derivative thereof, Fura and any derivative thereof, GelGreen and any derivative thereof, GelRed and any derivative thereof, fluorescent proteins and any derivative thereof, m isoform proteins and any derivative thereof such as for example mCherry, hetamethine dye and any derivative thereof, hoeschst stain, iminocoumarin, indian yellow, indo-1 and any derivative thereof, laurdan, lucifer yellow and any derivative thereof, luciferin and any derivative thereof, luciferase and any derivative thereof, mercocyanine and any derivative thereof, nile dyes and any derivative thereof, perylene, phloxine, phyco dye and any derivative thereof, propium iodide, pyranine, rhodamine and any derivative thereof, ribogreen, RoGFP, rubrene, stilbene and any derivative thereof, sulforhodamine and any derivative thereof, SYBR and any derivative thereof, synaptopHluorin, tetraphenyl butadiene, tetrasodium tris, Texas Red, Titan Yellow, TSQ, umbelliferone, violanthrone, yellow fluroescent protein and YOYO-1. Other Suitable fluorescent dyes include, but are not limited to, fluorescein and fluorescein dyes (e.g., fluorescein isothiocyanine or FITC, naphthofluorescein, 4',5'-dichloro-2',7'-dimethoxyfluorescein, 6-carboxyfluorescein or FAM, etc.), carbocyanine, merocyanine, styryl dyes, oxonol dyes, phycoerythrin, erythrosin, eosin, rhodamine dyes (e.g., carboxytetramethylrhodamine or TAMRA, carboxyrhodamine 6G, carboxy-X-rhodamine (ROX), lissamine rhodamine B, rhodamine 6G, rhodamine Green, rhodamine Red, tetramethylrhodamine (TMR), etc.), coumarin and coumarin dyes (e.g., methoxycoumarin, dialkylaminocoumarin, hydroxycoumarin, aminomethylcoumarin (AMCA), etc.), Oregon Green Dyes (e.g., Oregon Green 488, Oregon Green 500, Oregon Green 514, etc.), Texas Red, Texas Red-X, SPECTRUM RED, SPECTRUM GREEN, cyanine dyes (e.g., CY-3, Cy-5, CY-3.5, CY-5.5, etc.), ALEXA FLUOR dyes (e.g., ALEXA FLUOR 350, ALEXA FLUOR 488, ALEXA FLUOR 532, ALEXA FLUOR 546, ALEXA FLUOR 568, ALEXA FLUOR 594, ALEXA FLUOR 633, ALEXA FLUOR 660, ALEXA FLUOR 680, etc.), BODIPY dyes (e.g., BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665, etc.), IRDyes (e.g., IRD40, IRD 700, IRD 800, etc.), and the like. Additional suitable detectable agents are described in PCT/US14/56177. Non-limiting examples of radioisotopes include alpha emitters, beta emitters, positron emitters, and gamma emitters. In some embodiments, the metal or radioisotope is selected from the group consisting of actinium, americium, bismuth, cadmium, cesium, cobalt, europium, gadolinium, iridium, lead, lutetium, manganese, palladium, polonium, radium, ruthenium, samarium, strontium, technetium, thallium, and yttrium. In some embodiments, the metal is actinium, bismuth, lead, radium, strontium, samarium, or yttrium. In some embodiments, the radioisotope is actinium-225 or lead-212.

Peptides can be conjugated to, linked to, or fused to a radiosensitizer or photosensitizer. Examples of radiosensitizers include but are not limited to: ABT-263, ABT-199, WEHI-539, paclitaxel, carboplatin, cisplatin, oxaliplatin, gemcitabine, etanidazole, misonidazole, tirapazamine, and nucleic acid base derivatives (e.g., halogenated purines or pyrimidines, such as 5-fluorodeoxyuridine). Examples of photosensitizers can include but are not limited to: fluorescent molecules or beads that generate heat when illuminated, nanoparticles, porphyrins and porphyrin derivatives (e.g., chlorins, bacteriochlorins, isobacteriochlorins, phthalocyanines, and naphthalocyanines), metalloporphyrins, metallophthalocyanines, angelicins, chalcogenapyrrillium dyes, chlorophylls, coumarins, flavins and related compounds such as alloxazine and riboflavin, fullerenes, pheophorbides, pyropheophorbides, cyanines (e.g., merocyanine 540), pheophytins, sapphyrins, texaphyrins, purpurins, porphycenes, phenothiaziniums, methylene blue derivatives, naphthalimides, nile blue derivatives, quinones, perylenequinones (e.g., hypericins, hypocrellins, and cercosporins), psoralens, quinones, retinoids, rhodamines, thiophenes, verdins, xanthene dyes (e.g., eosins, erythrosins, rose bengals), dimeric and oligomeric forms of porphyrins, and prodrugs such as 5-aminolevulinic acid. Advantageously, this approach can allow for highly specific targeting of diseased cells (e.g., cancer cells) using both a therapeutic agent (e.g., drug) and electromagnetic energy (e.g., radiation or light) concurrently. In some embodiments, the peptide is conjugated to, linked to, fused with, or covalently or non-covalently linked to the agent, e.g., directly or via a linker. Exemplary linkers suitable for use with the embodiments herein are discussed in further detail below.

Linkers

Peptides according to the present disclosure can be attached to another moiety (e.g., an active agent or an detectable agent), such as a small molecule, a second peptide, a protein, an antibody, an antibody fragment, an aptamer, polypeptide, polynucleotide, a fluorophore, a radioisotope, a radionuclide chelator, a polymer, a biopolymer, a fatty acid, an acyl adduct, a chemical linker, or sugar or other active agent or detectable agent described herein through a linker, or directly in the absence of a linker. In the absence of a linker, for example, an active agent or an detectable agent can be conjugated to, linked to, or fused to the N-terminus or the C-terminus of a peptide to create an active agent or detectable agent fusion peptide. In other embodiments, the link can be made by a peptide fusion via reductive alkylation. In some embodiments, a cleavable linker is used for in vivo delivery of the peptide, such as a linker that can be cleaved or degraded upon entry in a cell, endosome, or a nucleus. In some embodiments, in vivo delivery of a peptide requires a small linker that does not interfere with penetration of a cell or localization to a nucleus of a cell. A linker can also be used to covalently attach a peptide as described herein to another moiety or molecule having a separate function, such a targeting, cytotoxic, therapeutic, homing, imaging, or diagnostic functions.

Direct attachment can be through covalent attachment of a peptide to a region of the other molecule. For example, an active agent or a detectable agent can be conjugated to, linked to, or fused to the N-terminus or the C-terminus of a peptide to create an active agent or detectable agent fusion peptide. As another example, the peptide can be attached at the N-terminus, an internal lysine, glutamic acid, or aspartic acid residue, or the C-terminus to a terminus of the amino acid sequence of the other molecule by a linker. If the attachment is at an internal lysine residue, the other molecule can be linked to the peptide at the epsilon amine of the internal lysine residue. In some further examples, the peptide can be attached to the other molecule by a side chain, such as the side chain of a lysine, serine, threonine, cysteine, tyrosine, aspartic acid, a non-natural amino acid residue, or glutamic acid residue. A linker can be an amide bond, an ester bond, an ether bond, a carbamate bond, a carbonate bond, a carbon-nitrogen bond, a triazole, a macrocycle, an oxime bond, a thioester bond, a thioether bond a hydrazone bond, a carbon-carbon single, double, or triple bond, a disulfide bond, a two carbon bridge between two cysteines, a three carbon bridge between two cysteines, or a thioether bond. In still other embodiments, the peptide can comprise a non-natural amino acid, wherein the non-natural amino acid can be an insertion, appendage, or substitution for another amino acid, and the peptide can be linked to the active agent at the non-natural amino acid by a linker. In some embodiments, similar regions of the disclosed peptide(s) itself (such as a terminus of the amino acid sequence, an amino acid side chain, such as the side chain of a lysine, serine, threonine, cysteine, tyrosine, aspartic acid, a non-natural amino acid residue, or glutamic acid residue, via an amide bond, an ester bond, an ether bond, a carbamate bond, a carbon-nitrogen bond, a triazole, a macrocycle, an oxime bond, a hydrazone bond, a carbon-carbon single, double, or triple bond, a disulfide bond, a thioether bond, or other linker as described herein) can be used to link other molecules.

Attachment via a linker involves incorporation of a linker moiety between the other molecule and the peptide. The peptide and the other molecule can both be covalently attached to the linker. The linker can be cleavable, non-cleavable, self-immolating, hydrophilic, or hydrophobic. The linker has at least two functional groups, one bonded to the other molecule, and one bonded to the peptide, and a linking portion between the two functional groups. Some example linkers are described in Jain, N., Pharm Res. 32(11): 3526-40 (2015), Doronina, S. O., Bioconj Chem. 19(10): 1960-3 (2008), Pillow, T. H., J Med Chem. 57(19): 7890-9 (2014), Dorywalksa, M., Bioconj Chem. 26(4): 650-9 (2015), Kellogg, B. A., Bioconj Chem. 22(4): 717-27 (2011), and Zhao, R. Y., J Med Chem. 54(10): 3606-23 (2011).

Non-limiting examples of the functional groups for attachment can include functional groups capable of forming, for example, an amide bond, an ester bond, an ether bond, a carbonate bond, a carbamate bond, a carbon-nitrogen bond, a triazole, a macrocycle, an oxime bond, a hydrazone bond, a carbon-carbon single, double, or triple bond, a disulfide bond or a thioether bond. Non-limiting examples of functional groups capable of forming such bonds include amino groups; carboxyl groups; aldehyde groups; azide groups; alkyne and alkene groups; ketones; hydrazides; hydrazines; acid halides such as acid fluorides, chlorides, bromides, and iodides; acid anhydrides, including symmetrical, mixed, and cyclic anhydrides; carbonates; carbonyl functionalities bonded to leaving groups such as cyano, succinimidyl, and N-hydroxysuccinimidyl; maleimides; linkers containing maleimide groups that are designed to hydrolyze; maleimidocaproyl; MCC ([N-maleimidomethyl]cyclohexane-1-carboxylate); N-ethylmaleimide; maleimide alkane; mc-vc-PABC; DUBA (Duocarmycinhydroxy-Benzamide-Azaindole linker); SMCC Succinimidyl-4-(N-maleimidomethyl) cyclohexane-1-carboxylate; SPDP (N-succinimidyl-3-(2-pyridyldithio) propionate); SPDB N-succinimidyl-4-(2-pyridyldithio) butanoate; sulfo-SPDB N-succinimidyl-4-(2-pyridyldithio)-2-sulfo butanoate; SPP N-succinimidyl 4-(2-pyridyldithio)pentanoate; a dithiopyridylmaleimide (DTM); a hydroxylamine, a vinyl-halo group; haloacetamido groups; bromoacetamido; hydroxyl groups; sulfhydryl groups; and molecules possessing, for example, alkyl, alkenyl, alkynyl, allylic, or benzylic leaving groups, such as halides, mesylates, tosylates, triflates, epoxides, phosphate esters, sulfate esters, and besylates.

Non-limiting examples of the linking portion can include alkylene, alkenylene, alkynylene, polyether, such as polyethylene glycol (PEG), polyester, polyamide, polyamino acids, polypeptides, cleavable peptides, Val-Cit, Phe-Lys, Val-Lys, Val-Ala, other peptide linkers as given in Doronina et al., 2008, linkers cleavable by beta glucuronidase, linkers cleavable by a cathepsin or by cathepsin B, D, E, H, L, S, C, K, O, F, V, X, or W, Val-Cit-p-aminobenzyloxycarbonyl, glucuronide-MABC, aminobenzylcarbamates, D-amino acids, and polyamine, any of which being unsubstituted or substituted with any number of substituents, such as halogens, hydroxyl groups, sulfhydryl groups, amino groups, nitro groups, nitroso groups, cyano groups, azido groups, sulfoxide groups, sulfone groups, sulfonamide groups, carboxyl groups, carboxaldehyde groups, imine groups, alkyl groups, halo-alkyl groups, alkenyl groups, halo-alkenyl groups, alkynyl groups, halo-alkynyl groups, alkoxy groups, aryl groups, aryloxy groups, aralkyl groups, arylalkoxy groups, heterocyclyl groups, acyl groups, acyloxy groups, carbamate groups, amide groups, urethane groups, epoxides, charged groups, zwitterionic groups, and ester groups. Other non-limiting examples of reactions to link, fuse, or conjugate molecules together include click chemistry, copper-free click chemistry, HIPS ligation, Staudinger ligation, and hydrazine-iso-Pictet-Spengler.

Non-limiting examples of linkers include:

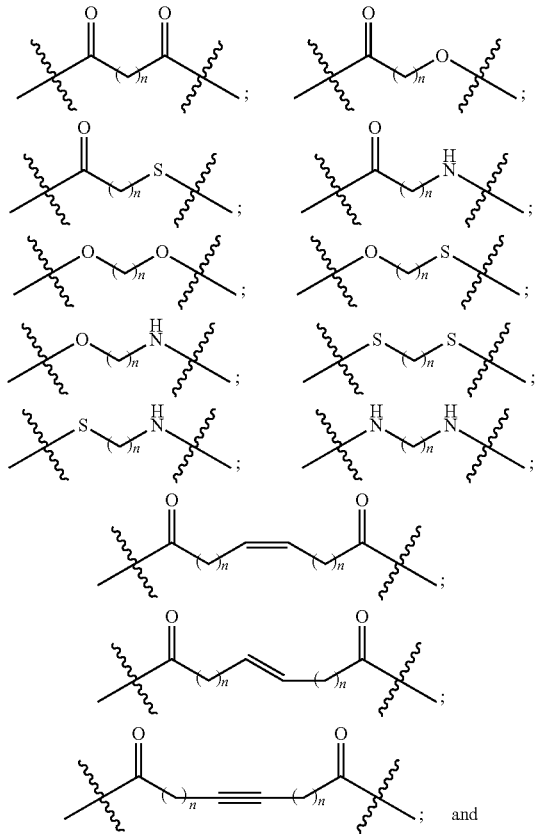

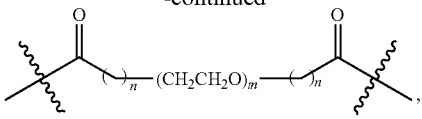

wherein each n is independently 0 to about 1,000; 1 to about 1,000; 0 to about 500; 1 to about 500; 0 to about 250; 1 to about 250; 0 to about 200; 1 to about 200; 0 to about 150; 1 to about 150; 0 to about 100; 1 to about 100; 0 to about 50; 1 to about 50; 0 to about 40; 1 to about 40; 0 to about 30; 1 to about 30; 0 to about 25; 1 to about 25; 0 to about 20; 1 to about 20; 0 to about 15; 1 to about 15; 0 to about 10; 1 to about 10; 0 to about 5; or 1 to about 5. In some embodiments, each n is independently 0, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, or about 50. In some embodiments, m is 1 to about 1,000; 1 to about 500; 1 to about 250; 1 to about 200; 1 to about 150; 1 to about 100; 1 to about 50; 1 to about 40; 1 to about 30; 1 to about 25; 1 to about 20; 1 to about 15; 1 to about 10; or 1 to about 5. In some embodiments, m is 0, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, or about 50, or any linker as disclosed in Jain, N., Pharm Res. 32(11): 3526-40 (2015) or Ducry, L., Antibody Drug Conjugates (2013).

In some cases a linker can be a succinic linker, and a drug can be attached to a peptide via an ester bond or an amide bond with two methylene carbons in between. In other cases, a linker can be any linker with both a hydroxyl group and a carboxylic acid, such as hydroxy hexanoic acid or lactic acid.

In some embodiments, the linker can release the active agent in an unmodified form. In other embodiments, the active agent can be released with chemical modification. In still other embodiments, catabolism can release the active agent still linked to parts of the linker and/or peptide.

The linker can be a noncleavable linker or a cleavable linker. In some embodiments, the noncleavable linker can slowly release the conjugated moiety by an exchange of the conjugated moiety onto the free thiols on serum albumin. In some embodiments, the use of a cleavable linker can permit release of the conjugated moiety (e.g., a therapeutic agent) from the peptide, e.g., after administration to a subject in need thereof. In other embodiments, the use of a cleavable linker can permit the release of the conjugated therapeutic from the peptide. In some cases the linker is enzyme cleavable, e.g., a valine-citrulline linker. In some embodiments, the linker contains a self-immolating portion. In other embodiments, the linker includes one or more cleavage sites for a specific protease, such as a cleavage site for matrix metalloproteases (MMPs), thrombin, cathepsins, peptidases, or beta-glucuronidase. Alternatively or in combination, the linker is cleavable by other mechanisms, such as via pH, reduction, or hydrolysis.

The rate of hydrolysis or reduction of the linker can be fine-tuned or modified depending on an application. For example, the rate of hydrolysis of linkers with unhindered esters can be faster compared to the hydrolysis of linkers with bulky groups next to an ester carbonyl. A bulky group can be a methyl group, an ethyl group, a phenyl group, a ring, or an isopropyl group, or any group that provides steric bulk. In some cases, the steric bulk can be provided by the drug itself, such as by ketorolac when conjugated, linked, or fused via its carboxylic acid. The rate of hydrolysis of the linker can be tuned according to the residency time of the conjugate or fusion in the target location. For example, when a peptide is cleared from a tumor, or the brain, relatively quickly, the linker can be tuned to rapidly hydrolyze. When a peptide has a longer residence time in the target location, a slower hydrolysis rate would allow for extended delivery of an active agent. "Programmed hydrolysis in designing paclitaxel prodrug for nanocarrier assembly" Sci Rep 2015, 5, 12023 Fu et al., provides an example of modified hydrolysis rates.

Peptide Stability

A peptide of the present disclosure can be stable in various biological or physiological conditions, such as the pH or reducing environments inside a cell, in the cytosol, in a cell nucleus, or endosome. For example, any peptide of SEQ ID NO: 1-SEQ ID NO: 84 can exhibit resistance to reducing agents, proteases, oxidative conditions, or acidic conditions.

In some cases, biologic molecules (such as peptides and proteins) can provide therapeutic functions, but such therapeutic functions are decreased or impeded by instability caused by the in vivo environment. (Moroz et al. Adv Drug Deliv Rev 101:108-21 (2016), Mitragotri et al. Nat Rev Drug Discov 13(9):655-72 (2014), Bruno et al. Ther Deliv (11):1443-67 (2013), Sinha et al. Crit Rev Ther Drug Carrier Syst. 24(1):63-92 (2007), Hamman et al. BioDrugs 19(3): 165-77 (2005)). For instance, the GI tract can contain a region of low pH (e.g. pH ~1), a reducing environment, or a protease-rich environment that can degrade peptides and proteins. Proteolytic activity in other areas of the body, such as the mouth, eye, lung, intranasal cavity, joint, skin, vaginal tract, mucous membranes, and serum, can also be an obstacle to the delivery of functionally active peptides and polypeptides. Additionally, the half-life of peptides in serum can be very short, in part due to proteases, such that the peptide can be degraded too quickly to have a lasting therapeutic effect when administering reasonable dosing regimens. Likewise, proteolytic activity in cellular compartments such as lysosomes and reduction activity in lysosomes and the cytosol can degrade peptides and proteins such that they may be unable to provide a therapeutic function on intracellular targets. Therefore, peptides that are resistant to reducing agents, proteases, and low pH may be able to provide enhanced therapeutic effects or enhance the therapeutic efficacy of co-formulated or conjugated, linked, or fused active agents in vivo.

Additionally, oral delivery of drugs can be desirable in order to target certain areas of the body (e.g., disease in the GI tract such as colon cancer, irritable bowel disorder, infections, metabolic disorders, and constipation) despite the obstacles to the delivery of functionally active peptides and polypeptides presented by this method of administration. For example, oral delivery of drugs can increase compliance by providing a dosage form that is more convenient for patients to take as compared to parenteral delivery. Oral delivery can be useful in treatment regimens that have a large therapeutic window. Therefore, peptides that are resistant to reducing agents, proteases, and low pH can allow for oral delivery of peptides without nullifying their therapeutic function.

Peptide Resistance to Reducing Agents. Peptides of this disclosure can contain one or more cysteines, which can participate in disulfide bridges that can be integral to preserving the folded state of the peptide. Exposure of peptides to biological environments with reducing agents can result in unfolding of the peptide and loss of functionality and bioactivity. For example, glutathione (GSH) is a reducing agent that can be present in many areas of the body and in cells, and can reduce disulfide bonds. As another example, a peptide can become reduced during trafficking of a peptide across the gastrointestinal epithelium after oral administration. A peptide can become reduced upon exposure to various parts of the GI tract. The GI tract can be a reducing environment, which can inhibit the ability of therapeutic molecules with disulfide bonds to have optimal therapeutic efficacy, due to reduction of the disulfide bonds. A peptide can also be reduced upon entry into a cell, such as after internalization by endosomes or lysosomes or into the cytosol, or other cellular compartments. Reduction of the disulfide bonds and unfolding of the peptide can lead to loss of functionality or affect key pharmacokinetic parameters such as bioavailability, peak plasma concentration, bioactivity, and half-life. Reduction of the disulfide bonds can also lead to loss of functionality due to increased susceptibility of the peptide to subsequent degradation by proteases, resulting in rapid loss of intact peptide after administration. In some embodiments, a peptide that is resistant to reduction can remain intact and can impart a functional activity for a longer period of time in various compartments of the body and in cells, as compared to a peptide that is more readily reduced.

In certain embodiments, the peptides of this disclosure can be analyzed for the characteristic of resistance to reducing agents to identify stable peptides. In some embodiments, the peptides of this disclosure can remain intact after being exposed to different molarities of reducing agents such as 0.00001 M-0.0001 M, 0.0001 M-0.001 M, 0.001 M-0.01 M, 0.01 M-0.05 M, 0.05 M-0.1 M, for 15 minutes or more. In some embodiments, the reducing agent used to determine peptide stability can be dithiothreitol (DTT), Tris(2-carboxyethyl)phosphine HCl (TCEP), 2-Mercaptoethanol, (reduced) glutathione (GSH), or any combination thereof. In some embodiments, at least 5%-10%, at least 10%-20%, at least 20%-30%, at least 30%-40%, at least 40%-50%, at least 50%-60%, at least 60%-70%, at least 70%-80%, at least 80%-90%, or at least 90%-100% of the peptide remains intact after exposure to a reducing agent. In some embodiments, peptides are completely resistant to GSH reducing conditions and are partially resistant to degradation in DTT reducing conditions. In some embodiments, peptides described herein can withstand or are resistant to degradation in physiological reducing conditions.

Peptide Resistance to Proteases. The stability of peptides of this disclosure can be determined by resistance to degradation by proteases. Proteases, also referred to as peptidases or proteinases, are enzymes that can degrade peptides and proteins by breaking bonds between adjacent amino acids. Families of proteases with specificity for targeting specific amino acids can include serine proteases, cysteine proteases, threonine proteases, aspartic proteases, glutamic proteases, and asparagine proteases. Additionally, metalloproteases, matrix metalloproteases, elastase, carboxypeptidases, Cytochrome P450 enzymes, and cathepsins can also digest peptides and proteins. Proteases can be present at high concentration in blood, in mucous membranes, lungs, skin, the GI tract, the mouth, nose, eye, and in compartments of the cell. Misregulation of proteases can also be present in various diseases such as rheumatoid arthritis and other immune disorders. Degradation by proteases can reduce bioavailability, biodistribution, half-life, and bioactivity of therapeutic molecules such that they are unable to perform their therapeutic function. In some embodiments, peptides that are resistant to proteases can better provide therapeutic activity at reasonably tolerated concentrations in vivo.

In some embodiments, peptides of this disclosure can resist degradation by any class of protease. In certain embodiments, peptides of this disclosure resist degradation by pepsin (which can be found in the stomach), trypsin (which can be found in the duodenum), serum proteases, or any combination thereof. In some embodiments, the proteases used to determine peptide stability can be pepsin, trypsin, chymotrypsin, or any combination thereof. In certain embodiments, peptides of this disclosure can resist degradation by lung proteases (e.g., serine, cysteinyl, and aspartyl proteases, metalloproteases, neutrophil elastase, alpha-1 antitrypsin, secretory leucoprotease inhibitor, and elafin), or any combination thereof. In some embodiments, at least 5%-10%, at least 10%-20%, at least 20%-30%, at least 30%-40%, at least 40%-50%, at least 50%-60%, at least 60%-70%, at least 70%-80%, at least 80%-90%, or at least 90%-100% of the peptide remains intact after exposure to a protease.

Peptide Stability in Acidic Conditions. Peptides of this disclosure can be administered in biological environments that are acidic. For example, after oral administration, peptides can experience acidic environmental conditions in the gastric fluids of the stomach and gastrointestinal (GI) tract. The pH of the stomach can range from about 1-4 and the pH of the GI tract ranges from acidic to normal physiological pH descending from the upper GI tract to the colon. In addition, the vagina, late endosomes, and lysosomes can also have acidic pH values, such as less than pH 7. These acidic conditions can lead to denaturation of peptides and proteins into unfolded states. Unfolding of peptides and proteins can lead to increased susceptibility to subsequent digestion by other enzymes as well as loss of biological activity of the peptide. In certain embodiments, the peptides of this disclosure can resist denaturation and degradation in acidic conditions and in buffers, which simulate acidic conditions. In certain embodiments, peptides of this disclosure can resist denaturation or degradation in buffer with a pH less than 1, a pH less than 2, a pH less than 3, a pH less than 4, a pH less than 5, a pH less than 6, a pH less than 7, or a pH less than 8. In some embodiments, peptides of this disclosure remain intact at a pH of 1-3. In certain embodiments, at least 5%-10%, at least 10%-20%, at least 20%-30%, at least 30%-40%, at least 40%-50%, at least 50%-60%, at least 60%-70%, at least 70%-80%, at least 80%-90%, or at least 90%-100% of the peptide remains intact after exposure to a buffer with a pH less than 1, a pH less than 2, a pH less than 3, a pH less than 4, a pH less than 5, a pH less than 6, a pH less than 7, or a pH less than 8. In other embodiments, at least 5%-10%, at least 10%-20%, at least 20%-30%, at least 30%-40%, at least 40%-50%, at least 50%-60%, at least 60%-70%, at least 70%-80%, at least 80%-90%, or at least 90%-100% of the peptide remains intact after exposure to a buffer with a pH of 1-3. In other embodiments, the peptides of this disclosure can be resistant to denaturation or degradation in simulated gastric fluid (pH 1-2). In some embodiments, at least 5%-10%, at least 10%-20%, at least 20%-30%, at least 30%-40%, at least 40%-50%, at least 50%-60%, at least 60%-70%, at least 70%-80%, at least 80%-90%, or at least 90%-100% of the peptide remains intact after exposure to simulated gastric fluid. In some embodiments, low pH solutions such as simulated gastric fluid can be used to determine peptide stability.

In some embodiments, the peptides described herein are resistant to degradation in vivo, in the serum of a subject, or inside a cell. In some embodiments, the peptides are stable at physiological pH ranges, such as about pH 7, about pH 7.5, between about pH 5 to 7.5, between about 6.5 to 7.5, between about pH 5 to 8, or between about pH 5 to 7. In some embodiments, the peptides described herein are stable in acidic conditions, such as less than or equal to about pH 5, less than or equal to about pH 3, or within a range from about 3 to about 5. In some embodiments, the peptides are stable in conditions of an endosome or lysosome, or inside a nucleus.

Peptide Stability at High Temperatures. Peptides of this disclosure can be administered in biological environments with high temperatures. For example, after oral administration, peptides can experience high temperatures in the body. Body temperature can range from 36° C. to 40° C. High temperatures can lead to denaturation of peptides and proteins into unfolded states. Unfolding of peptides and proteins can lead to increased susceptibility to subsequent digestion by other enzymes as well as loss of biological activity of the peptide. In some embodiments, a peptide of this disclosure can remain intact at temperatures from 25° C. to 100° C. High temperatures can lead to faster degradation of peptides. Stability at a higher temperature can allow for storage of the peptide in tropical environments or areas where access to refrigeration is limited. In certain embodiments, 5%-100% of the peptide can remain intact after exposure to 25° C. for 6 months to 5 years. 5%-100% of a peptide can remain intact after exposure to 70° C. for 15 minutes to 1 hour. 5%-100% of a peptide can remain intact after exposure to 100° C. for 15 minutes to 1 hour. In other embodiments, at least 5%-10%, at least 10%-20%, at least 20%-30%, at least 30%-40%, at least 40%-50%, at least 50%-60%, at least 60%-70%, at least 70%-80%, at least 80%-90%, or at least 90%-100% of the peptide remains intact after exposure to 25° C. for at least 6 months to 5 years. In other embodiments, at least 5%-10%, at least 10%-20%, at least 20%-30%, at least 30%-40%, at least 40%-50%, at least 50%-60%, at least 60%-70%, at least 70%-80%, at least 80%-90%, or at least 90%-100% of the peptide remains intact after exposure to 70° C. for 15 minutes to 1 hour. In other embodiments, at least 5%-10%, at least 10%-20%, at least 20%-30%, at least 30%-40%, at least 40%-50%, at least 50%-60%, at least 60%-70%, at least 70%-80%, at least 80%-90%, or at least 90%-100% of the peptide remains intact after exposure to 100° C. for 15 minutes to 1 hour.

Methods

Peptide Production and Purification. In some embodiments, sequences from the peptide library generated from computational design can be synthesized using expression vectors or solid phase or solution phase peptide synthesis methods. For example, TEAD-binding peptides, or peptides, and Siderocalin-YAP can be cloned into a secreted, soluble protein production/expression vector and purified, as per Bandaranayake et al., 2011. Purification methods include, but are not limited to, affinity purification columns, ion exchange (cation and/or anion columns), reversed-phase, hydrophobic interaction, and size exchange columns. SDS-PAGE followed by Coomassie staining and reverse phase HPLC can be used to analyze a sample of the purified protein. Protein concentrations were determined by UV spectral absorption and/or amino acid analysis.

Surface Display Vector Construction. In various embodiments, surface display vectors, SDGF and SDPR (a variant of the SDGF vector, but with all basic and aromatic residues within the stalk removed to prevent trypsin/chymotrypsin cleavage, and with a 6×His tag (SEQ ID NO: 284) added to the C-terminus of the peptide) based on the original Daedalus vector (Bandaranayake et al., 2011), can be used to clone and express recombinant peptides as described herein. Peptides can be cloned or expressed with a modified coding sequence and without an IRES-GFP. In some cases, the coding sequence of the vector comprises: GFP; the transmembrane domain of the single pass Type II transmembrane protein FASLG (human Fas ligand); a poly-GGGS spacer (SEQ ID NO: 203); a 9-residue bovine rhodopsin antigen; a poly-GGGS spacer (SEQ ID NO: 203); a TEV-cleavage site, including a GS-linker; the displayed peptide; and for SDPR only, a 6×His tag (SEQ ID NO: 284). As with the original Daedalus vector, the entire construct, in some embodiments, can be cloned with lentiviral LTRs, and introduced to cells by transient transfection or transduction. Peptide sequences can be inserted between unique BamHI and NotI cut sites for SDGF vector, or between unique BamHI and AgeI cut sites for SDPR. In either SDGF or SDPR construct, a number of standard cloning strategies can be used to insert a desired coding sequence, including restriction digestion (BamHI and NotI, NEB; T4 DNA Ligase, Invitrogen), In-Fusion (Clontech), or Gibson Assembly (NEB), with all transformations using Stellar chemically competent cells (Clontech), or electrocompetent cells (NEB 10-beta cells), transformed by electroporation. DNA can be PCR-amplified using exemplary primers such as: SDGF Forward primer: TGTACTTCCAGGGAGGATCC (SEQ ID NO: 213); SDGF Reverse primer: AATGGTGATGAGCGGCC (SEQ ID NO: 214); SDPR Forward primer: CCAGCAGGAGGTGGAAGCG (SEQ ID NO: 215); SDPR Reverse primer: ATGATGGTGATGATGGTGAGATCCTC (SEQ ID NO: 216).

Mammalian Surface Display. Validation of peptides or single candidates for binding to TEAD can be validated using a suspension of HEK-293 cells. In some embodiments, cells are transfected with 2.5 µg SDGF vector comprising a putative or candidate peptide and 3.5 g polyethyleneimine to 2E6 cells in 1 mL media, in a 24-well suspension tissue culture dish. After incubation of cells, all pooled screening can be performed in 293T cells transduced with lentivirus (VSV-G coated, produced by standard methods in 293T cells), delivering the SDGF construct, at an MOI of approximately 1, or up to 5. Transduced or transfected suspension HEK-293 cells can be pelleted (500×g, 5 min) and resuspended at up to 8E6 cells/mL in Flow Buffer (PBS with 0.5% BSA and 2 mM EDTA) containing DAPI and target protein, with or without Alexa Fluor 647-conjugated streptavidin (ThermoFisher) in equimolar quantity to the target protein. All staining incubations took place at 4 C for 30 mins with mild agitation. For the low stringency protocol (initial assay validation and pooled screening), 200 nM target protein can be used, and streptavidin can be pre-mixed with target protein. Cells can be incubated, diluted 10-fold with Flow Buffer, pelleted (500×g, 5 min), and resuspended in fresh Flow Buffer (up to 6.5E6 cells/mL) before flow cytometry. For the medium stringency protocol (SSM maturation), only 20 nM target protein can be used, and cells can be incubated with target protein alone, diluted 10-fold with Flow Buffer, pelleted, and then resuspended with 20 nM streptavidin. Cells were incubated again, diluted 10-fold with Flow Buffer, pelleted (500×g, 5 min), and resuspended in fresh Flow Buffer (up to 6.5E6 cells/mL) before flow cytometry. The high stringency protocol is identical to the medium stringency protocol, except that an additional Flow Buffer-only wash step is included immediately after target protein staining. In some cases, flow sorting is performed on a Beckton-Dickinson Aria II, while analysis is performed on a combination of Beckton-Dickson LSR II and Acea Novo-Cyte flow cytometers. Data analysis can be performed on FlowJo (FlowJo, LLC) and Excel (Microsoft).

SDPR Protease Resistance Testing. In some embodiments, SDPR protease resistance testing can be used with sequencing-grade enzymes, including Trypsin and Chymotrypsin. Trypsin and trypsin inhibitor can be used for HPLC analysis.

Next Generation Sequencing. In some embodiments, screens for enrichment or depletion of variants affecting TEAD binding can be assessed by Illumina sequencing. Such sequencing method involves collecting cell pellets (1.5E6, 3 technical replicates) resuspended in 50 µL Terra Direct PCR Mix (from Clontech) and amplified for 16 cycles using the original cloning primers. Up to four aliquots can be diluted 16-fold into 60 µL Phusion DNA Polymerase reactions and amplified using distinct Illumina primers, containing adaptor sequences for flow cell adherence. Forward primers can include a 6 bp barcode for multiplexing. Illumina HiSeq 2500 in rapid mode can be used to run samples, which Bowtie2 software can be used for mapping, and Excel (Microsoft) and MATLAB (MathWorks) used for data analysis.

His-Avi-TEAD Production, Purification, and Biotinylation. In some embodiments, in vitro assays are used to analyze candidate peptides for ability to inhibit or interfere with YAP-TEAD interaction, or ability to bind to TEAD and thereby sequester TEAD from interaction with YAP. In some cases, biotinylated, His-Avi-TEAD(194-411) can be expressed in Hi5 insect cells using the BacMagic system (EMD Millipore), as per manufacturer protocols. The transgene can be cloned into the pIEX-BAC3 vector and then cotransfected with BacMagic-3 DNA (100 µg vector, 1 µL BacMagic-3) using calfectin II into Sf9 cells in a 12-well dish. Baculovirus encoding His-Avi-TEAD can be amplified in Sf9 cells, and viral supernatant (5 mL) can be used to transduce 2.5E8 Hi5 cells in 250 mL Express Five media supplemented with L-glutamine. Transduced cells can be grown for 72 hrs (expanding to 500 mL) at 27° C. and 140 RPM before collecting the cell pellets for analysis. To harvest, cells can be pelleted (2000×g, 10 min) and resuspended in I-PER buffer (Invitrogen) containing protease inhibitor cocktail (ThermoFisher), benzonase at 1:10,000 (Millipore), 0.5 mM TCEP, and 20 mM imidazole. Lysate can be clarified (10,000×g, 30 min), using nickel NTA resin to purify GST-TEAD. Protein can be buffer exchanged (Zeba spin columns, 5 mL capacity) into thrombin cleavage buffer (25 mM Tris pH 8.4, 150 mM NaCl, 0.1% Triton X100, 10% glycerol, 2.5 mM $CaCl_2$)). Half of the 4 mL eluate can be treated with 5 µL restriction grade thrombin (EMD) overnight at room temperature. TEAD can be re-purified on nickel resin and then by FPLC on a Superdex 200 10/300 GL size exclusion chromatography (SEC) column (GE Healthsciences). SEC running buffer can contain 10 mM phosphate buffer pH 7.2, 50 mM NaCl, 0.5 mM TCEP. Purified TEAD can be biotinylated using the BirA-500 kit (Avidity) as per manufacturer's protocol, followed by a final buffer exchange into PBS containing 5% glycerol, and storage in small aliquots at −80° C.

Fluorophore Conjugation. In some embodiments, screening peptides or a library of peptides involves labeling of a protein of interest or a protein partner with a fluorophore or any other detectable moiety, such that detection of a signal from the fluorophore or detectable moiety is indicative of binding to the peptide. An example of a fluorophore that can be used is Alexa Fluor 647 NHS Ester (Life Technologies), which can be used to label a protein of interest or a protein partner, such as TEAD or YAP, as per manufacturer's protocol. Saturation is approximately 1 fluorophore per molecule, as determined by spectrometry.

Surface Plasmon Resonance (SPR) Interaction Analyses. In some embodiments, TEAD binding can be assessed using surface plasmon resonance. YAP is unstable and precipitates if cleaved from siderocalin, such that it is used as a fusion protein for SPR validation of TEAD-binding. All other peptides are TEV-cleavable and can be analyzed as independent, soluble proteins.

SPR Experiments can be Performed Using Biacore T100 instrument. In some cases, biotinylated TEAD is injected over a flow cell at a specified rate to capture ~300 resonance units (RUs). A reference surface is generated by capturing a molar equivalent of biotinylated human transferrin receptor ectodomain. For analytes that can reach steady-state, serial two-fold dilutions can be prepared in running buffer at concentration ranges that cover the span of each peptide's dissociation constant ($K_D$). Duplicate samples, interspersed with multiple buffer blanks, can be randomly injected for further testing. Regeneration can be accomplished with buffer flow alone. Double-referenced data can fit with either a 1:1 affinity or kinetics binding model using BIAevaluation 2.0.4 software (GE Healthcare). Two samples, SEQ ID NO: 9 and SEQ ID NO: 10 (with GS at the N-terminus), or SEQ ID NO: 51 and SEQ ID NO: 52 (without GS at the N-terminus), can be performed using a single cycle kinetics protocol in the T100 Control 2.0.4 software. Serial 3-fold dilutions (3.6 nM to 0.044 nM) of these peptides can be prepared in running buffer and injected at increasing concentration order with 7 minutes of injection time and 15 minutes dissociation. Two buffer blank cycles for referencing can be run prior to analyte injection and one buffer blank cycle followed which allowed time for complete analyte dissociation prior to the next analyte injection. Double-referenced data were fit with the 1:1 binding model for single cycle kinetics using BIAevaluation 2.0.4 software (GE Healthcare). Figures were made in Prism 7 (GraphPad) for Mac OS X version 7.0a.

YAP-TEAD Disruption and Co-immunoprecipitation. To assay peptides as described herein for ability to disrupt YAP-TEAD interaction, disruption of co-immunoprecipitation of TEAD and YAP can be used. 293T cells can be transfected with either Myc-tagged TEAD expression plasmid pRK5-Myc-TEAD1 or the FLAG-tagged YAP expression plasmid pFLAG-YAP1. After 2 days of growth, cells are lysed with RIPA buffer (ThermoFisher), and lysates are used as follows: 125 μL aliquots of anti-Myc agarose resin (Sigma) can be prepared and used to pull down Myc-TEAD from Myc-TEAD-transfected cell lysate. TEAD-bound beads are then incubated for 30 min at 4 C with 50 μL FLAG-YAP-transfected cell lysate, which is pre-mixed with competitive TEAD-binding peptides, in a final volume of 100 μL. Resin is then washed twice with 500 μL PBS, and then resuspended in 20 μL 2×LDS sample buffer. Beads are then boiled before analyzing the sample using SDS-PAGE and either silver stain or Western Blot using anti-FLAG M2, Sigma, at 1:2000 and/or anti-Myc tag antibody, Abcam, at 1:2000; LiCor secondary antibodies at 1:10,000.

Described herein are various embodiments of peptides, or peptides, with varying affinity for TEAD. Peptides that bind TEAD make TEAD unavailable for binding to YAP, thus inhibiting the YAP-TEAD interaction.

Peptide Library Computational Design: Scaffold Construction. The input topology parameters used for scaffold construction can be as follows: minimum and maximum sequence length: 30 and 41 residues, respectively; secondary structure types: helix, helix, helix; secondary structure length ranges: 6-18 residues; turn lengths: 2-4 residues; number of disulfides: 3; disulfide topology: H1-H2, H1-H3, and H2-H3. Several hundred thousand independent design simulations can be performed to build a large library of candidate scaffolds, which can then be filtered by sequence-structure compatibility, packing, satisfaction of polar groups, and disulfide score. At the start of each design simulation, helix and turn lengths can be sampled randomly from the corresponding length ranges, fixing the secondary structure of the design, which can then be used to select backbone fragments for a low-resolution fragment assembly simulation. At the end of the low-resolution simulation, the protein backbone can be scanned for residue pairs that could be linked by disulfide connections using a library of N—$C_\alpha$—C backbone transforms derived from disulfide bonds in the protein structure database. Backbones with matching residue pairs that satisfied the disulfide topology constraints can be used to initiate an all-atom sequence design simulation consisting of two cycles of alternating fixed-backbone sequence design and fixed-sequence structure relaxation. Final designs can be filtered for packing (sasapack score <0.5), satisfaction of buried polar groups (using a 1.0 A probe radius), and sorted by energy per residue. The top 10% of the filtered designs can be assessed for sequence-structure compatibility by an in silico refolding test in which the design sequence can be used to initiate 3000 independent structure prediction simulations. Success can be measured by assessing the fraction of low-energy structure prediction models within 2A Ca-RMSD of the design model.

Peptide Library Computational Design: Interface Design. The crystal structure of the YAP-TEAD complex (PDB ID 3KYS) can be examined to identify binding patches on TEAD and corresponding backbone elements on YAP to serve as templates for interface design. The following backbone residue segments can be selected as superposition targets for orienting design scaffolds: 3KYS/B/53-55, 3KYS/B/55-57, 3KYS/B/64-68, 3KYS/B/64-69, 3KYS/B/86-89, 3KYS/B/94-96 (given as: PDB ID/chain/residue numbers). For each peptide scaffold, design simulations can be conducted targeting each YAP backbone segment selected for superposition. Each design simulation can consist of the following steps: (1) superimposing the scaffold backbone onto the YAP backbone segment using a scaffold backbone element with matching secondary structure, (2) random small perturbations to generate diversity and relieve backbone clashes, (3) all-atom sequence design alternating between fixed-backbone sequence selection and fixed-sequence structure relaxation. Final interface designs were filtered for satisfaction of polar groups (using a 1.0 A probe radius), interface surface complementarity (sc score>0.5), and interface quality (predicted binding energy per 100 A of buried SASA <−1.1), and sorted by predicted binding energy. Top-scoring designs can be assessed by an in silico redocking test in which the redesigned scaffold peptide can be removed from TEAD, randomly reoriented, and redocked onto the TEAD protein structure. Success can be measured as the fraction of low-energy redocking simulations that reached a final state close to the designed interface conformation.

Circular Dichroism. Protein secondary structures can be assessed using Circular Dichroism (CD). CD spectra can be measured with a Jasco J-720W spectropolarimeter using a 1.0 mm path length cell. Protein samples in 10 mM phosphate buffer (pH=7.4) can be at 25-30 uM protein concentration. Samples can be analyzed at wavelength ranges of 260-190 nM. Data can be expressed in terms of relative ellipticity [θ]; (mdeg). To determine thermal stability of proteins, samples can be subjected to incremental increase in temperature at a ramp of 2° C./min from 20° C. to 95° C. Stability and protein unfolding were monitored at 220 and 215 for α-helix and β-sheet secondary structures, respectively. Data can be expressed in terms of relative ellipticity [θ], reported in mdeg.

Thermal Shift Assay. Protein melting temperature (Tm) determination can be performed by monitoring protein unfolding using SYPRO Orange dye (Molecular Probes). In brief, 0.1 mg/mL protein sample in 20 μL total volume PBS buffer can be mixed with 2 μL of 10×SYPRO Orange dye. Dye intercalation into the hydrophobic protein core following protein unfolding was assayed using the C1000 Touch Thermal Cycler with CFX96 Deep Well Real-Time System (BioRad). Samples were heated from 20° C. to 95° C. with stepwise increments of 0.5° C. per minute and a 5 see hold step for every point, followed by fluorescence reading. Tm were calculated by analyzing the derivatives of Relative florescence Units (RFU).

Cytosolic Peptide Expression. Peptides, FLAG-tagged or not, can be cloned into a mammalian expression vector consisting of a CMV promoter, then a monocistronic mCherry-T2a-peptide sequence. These can be transfected, along with (where indicated) pFLAG-YAP1 and 8×GTIIC-luciferase (Addgene plasmid #34615) into 293T cells. 24 hrs post-transfection, cells can be either harvested for luminescence (ONE-Glo, Promega) or Western blot (anti-FLAG M2, Sigma). Protein Transfection with dfTAT Reagent. Solution was diluted to 50 μM in PBS for a 10× working stock, for a final concentration of 5 μM in culture wells. Peptides as disclosed herein can be fluoresceinated with DyLight 488 NHS-ester (ThermoFisher), with final dye: peptide labeling ratios between 0.8 and 1.4 as assessed by A280 and A488 on a Nanodrop spectrometer (Thermo Scientific). For confirmation of peptide cell penetration, 293T and HeLa cells can be plated in a 96-well plate in DMEM with 10% FBS, 1× penicillin/streptomycin (Pen/Strep) and grown overnight to ~50% confluence. Cells can be gently washed 3 times with PBS containing 1 mM $CaCl_2$) and 0.5 mM MgCl2, then 2 times in serum-free DMEM. Wells (50 μL total) received either 5 μM (final) peptide in PBS, or PBS alone, and can also receive either 5 μM (final) dfTAT reagent in PBS, or PBS alone, before a 60 minute incubation at 37° C. and 5% $CO_2$ in a humidified tissue culture incubator. After incubation, cells can be gently washed 3 times in PBS, which can be followed by fixation at 4° C. for 10 minutes with 4% formaldehyde in PBS. Fixed samples can be washed 3 times with cold PBS, then can be permeabilized at room temperature for 10 minutes with 0.25% Triton X-100 in PBS; permeabilization was done for consistency with later proximity ligation assays. Samples can be rinsed three more times in PBS prior to imaging on an Evos FL microscope (Life Technologies) with a 20× objective. Images were processed in ImageJ for brightness/contrast adjustment.

Proximity Ligation Assay. TEAD-binding peptides can use any peptide as disclosed herein, and can be a 1:1 mix of unaltered peptide and peptide reacted with DyLight 488 NHS-ester, as above. HeLa cells can be seeded in an 8-well chamber slide (Nunc Lab-Tek II) in DMEM+10% FBS and 1× Pen/Strep, and can be grown overnight, reaching ~50% confluence. Cells can be gently washed 3 times with PBS containing 1 mM $CaCl_2$ and 0.5 mM $MgCl_2$, then 2 times in serum-free DMEM. Wells (120 μL total) can receive either 5 μM (final) peptide in PBS, or PBS alone, and can also receive either 5 μM (final) dfTAT reagent in PBS, or PBS alone, before a 90 minute incubation at 37° C. and 5% $CO_2$ in a humidified tissue culture incubator. After incubation, cells can be gently washed 3 times in PBS, followed by fixation at 4° C. for 10 minutes with 4% formaldehyde in PBS. Fixed samples can be washed 3 times with cold PBS, then can be permeabilized at room temperature for 10 minutes with 0.25% Triton X-100 in PBS. Samples can be rinsed three more times in PBS prior to proximity ligation assay (PLA).

PLA can be performed using the Duolink In Situ Fluorescence (Far Red) kit according to manufacturer's instructions, using supplied buffers without substitution and at recommended volumes for 1 $cm^2$ samples. All incubations can take place at 37° C. in a humidified chamber. Samples can be blocked for 30 minutes, which can be followed by incubation for 1 hour with primary antibodies against human YAP (1:100 rabbit anti-YAP1, AbCam catalog number ab52771) and/or human TEAD (1:200 mouse anti-TEF-1, BD Biosciences catalog number 610923). Samples can be washed twice (well dividers can be removed after these washes, and further washes can take place in a Coplin jar), and then ligation can be performed for 30 minutes. After ligation, samples can be washed twice prior to the 100 minute amplification reaction. The slide can then be washed, briefly dried, and mounted with supplied mounting media and a coverslip. Imaging can take place on a DeltaVision Elite (GE) with a 40× objective, and complete Z-stacks can be acquired and deconvolved. For quantitation of nuclear speckles in ImageJ, UV and Cy5.5 filtered images can be Z-projected (maximum intensity), and can be processed using a custom macro to identify nuclear boundaries (UV channel) and speckles (Cy5.5 channel). Overlap and speckle counting can be automated used the Biovoxxel toolbox (Brocher, 2015) with the Speckle Inspector tool. Plots, confidence intervals, and significance calculations can be produced in Prism 7 (GraphPad).

Methods of Manufacture

Various expression vector/host systems can be utilized for the recombinant expression of peptides described herein. Non-limiting examples of such systems include microorganisms such as bacteria transformed with recombinant bacteriophage DNA, plasmid DNA or cosmid DNA expression vectors containing a nucleic acid sequence encoding peptides or peptide fusion proteins/chimeric proteins described herein, yeast transformed with recombinant yeast expression vectors containing the aforementioned nucleic acid sequence, insect cell systems infected with recombinant virus expression vectors (e.g., baculovirus) containing the aforementioned nucleic acid sequence, plant cell systems infected with recombinant virus expression vectors (e.g., cauliflower mosaic virus (CaMV), tobacco mosaic virus (TMV)), or transformed with recombinant plasmid expression vectors (e.g., Ti plasmid) containing the aforementioned nucleic acid sequence, or animal cell systems infected with recombinant virus expression vectors (e.g., adenovirus, vaccinia virus, lentivirus) including cell lines engineered to contain multiple copies of the aforementioned nucleic acid sequence, either stably amplified (e.g., CHO/dhfr, CHO/glutamine synthetase) or unstably amplified in double-minute chromosomes (e.g., murine cell lines). Disulfide bond formation and folding of the peptide could occur during expression or after expression or both.

A host cell can be adapted to express one or more peptides described herein. The host cells can be prokaryotic, eukaryotic, or insect cells. In some cases, host cells are capable of modulating the expression of the inserted sequences, or modifying and processing the gene or protein product in the specific fashion desired. For example, expression from certain promoters can be elevated in the presence of certain inducers (e.g., zinc and cadmium ions for metallothionine promoters). In some cases, modifications (e.g., phosphorylation) and processing (e.g., cleavage) of peptide products can be important for the function of the peptide. Host cells can have characteristic and specific mechanisms for the post-translational processing and modification of a peptide. In some cases, the host cells used to express the peptides secrete minimal amounts of proteolytic enzymes.

In the case of cell- or viral-based samples, organisms can be treated prior to purification to preserve and/or release a target polypeptide. In some embodiments, the cells are fixed using a fixing agent. In some embodiments, the cells are lysed. The cellular material can be treated in a manner that does not disrupt a significant proportion of cells, but which removes proteins from the surface of the cellular material, and/or from the interstices between cells. For example, cellular material can be soaked in a liquid buffer, or, in the case of plant material, can be subjected to a vacuum, in order to remove proteins located in the intercellular spaces and/or in the plant cell wall. If the cellular material is a microorganism, proteins can be extracted from the microorganism culture medium. Alternatively, the peptides can be packed in inclusion bodies. The inclusion bodies can further be separated from the cellular components in the medium. In some embodiments, the cells are not disrupted. A cellular or viral peptide that is presented by a cell or virus can be used for the attachment and/or purification of intact cells or viral particles. In addition to recombinant systems, peptides can also be synthesized in a cell-free system prior to extraction using a variety of known techniques employed in protein and peptide synthesis.

In some cases, a host cell produces a peptide that has an attachment point for a drug. An attachment point could comprise a lysine residue, an N-terminus, a cysteine residue, a cysteine disulfide bond, a glutamic acid or aspartic acid residue, a C-terminus, or a non-natural amino acid. The peptide could also be produced synthetically, such as by solid-phase peptide synthesis, or solution-phase peptide synthesis. Peptide synthesis can be performed by fluorenylmethyloxycarbonyl (Fmoc) chemistry or by butyloxycarbonyl (Boc) chemistry. The peptide could be folded (formation of disulfide bonds) during synthesis or after synthesis or both. Peptide fragments could be produced synthetically or recombinantly. Peptide fragments can be then be joined together enzymatically or synthetically.

In other aspects, the peptides of the present disclosure can be prepared by conventional solid phase chemical synthesis techniques, for example according to the Fmoc solid phase peptide synthesis method ("Fmoc solid phase peptide synthesis, a practical approach," edited by W. C. Chan and P. D. White, Oxford University Press, 2000).

In some embodiments, the peptides of this disclosure can be more stable during manufacturing. For example, peptides of this disclosure can be more stable during recombinant expression and purification, resulting in lower rates of degradation by proteases that are present in the manufacturing process, a higher purity of peptide, a higher yield of peptide, or any combination thereof. In some embodiments, the peptides can also be more stable to degradation at high temperatures and low temperatures during manufacturing, storage, and distribution. For example, in some embodiments peptides of this disclosure can be stable at 25° C. In other embodiments, peptides of this disclosure can be stable at 70° C. or higher than 70° C. In some embodiments, peptides of this disclosure can be stable at 100° C. or higher than 100° C.

Pharmaceutical Compositions

A pharmaceutical composition of the disclosure can be a combination of any peptide as described herein with other chemical components, such as carriers, stabilizers, diluents, dispersing agents, suspending agents, thickening agents, antioxidants, solubilizers, buffers, osmolytes, salts, surfactants, amino acids, encapsulating agents, bulking agents, cryoprotectants, and/or excipients. The pharmaceutical composition facilitates administration of a peptide described herein to an organism. In some cases, the pharmaceutical composition comprises factors that extend half-life of the peptide and/or help the peptide to penetrate the target cells.

Pharmaceutical compositions can be administered in therapeutically-effective amounts as pharmaceutical compositions by various forms and routes including, for example, intravenous, subcutaneous, intramuscular, rectal, aerosol, parenteral, ophthalmic, pulmonary, transdermal, vaginal, optic, nasal, oral, sublingual, inhalation, dermal, intrathecal, intratumoral, intranasal, and topical administration. A pharmaceutical composition can be administered in a local or systemic manner, for example, via injection of the peptide described herein directly into an organ, optionally in a depot.

Parenteral injections can be formulated for bolus injection or continuous infusion. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of a peptide described herein in water-soluble form. Suspensions of peptide-antibody complexes described herein can be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. The suspension can also contain suitable stabilizers or agents which increase the solubility and/or reduce the aggregation of such peptide-antibody complexes described herein to allow for the preparation of highly concentrated solutions.

Formulations or approaches to increase cell penetration or a peptide as describe herein can include, but not limited to, using high dosage of a peptide as described herein, such as up to 10 µM; conjugating or fusing a Tat peptide or a cell-penetrating peptide, or a variant or derivative thereof to a peptide; co-delivering a Tat peptide or a cell-penetrating peptide, or a variant or derivative thereof with a peptide; conjugating or fusing an Arg patch to a peptide; or co-delivering a peptide with an Arg patch peptide, such as up to 10 µM. In some embodiments, protein transfection agents, direct cytosolic expression of the peptide, or electroporation of the peptide can be used to increase cell penetration. In some embodiments, other excipients can be formulated with a peptide in order to increase the cell penetration of the peptide, such as those approaches described in "Protein and Peptide Drug Delivery: Oral Approaches" Indian J. Pharm. Sci., Shaji and Patole, v70(3) 269-277, 2008. Any combination of these formulations or approaches can be used to increase cell penetration of a peptide as described herein.

Alternatively, the peptide described herein can be lyophilized or in powder form for re-constitution with a suitable vehicle, e.g., sterile pyrogen-free water, before use. In some embodiments, a purified peptide is administered intravenously. A peptide described herein can be administered to a subject, home, target, migrate to, or be directed to cancerous cell, a tumor, or a cell with dysregulated HIPPO pathway. In some embodiments, a peptide can be conjugated to, linked to, or fused to another peptide that provides a targeting function to a specific target cell type in the central nervous system or across the blood brain barrier.

A peptide of the disclosure can be applied directly to an organ, or an organ tissue or cells, such as brain or brain tissue or cells, during a surgical procedure. The recombinant peptide described herein can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

In practicing the methods of treatment or use provided herein, therapeutically-effective amounts of a peptide described herein can be administered in pharmaceutical compositions to a subject suffering from a condition that affects the immune system. In some embodiments, the subject is a mammal such as a human or a primate. A therapeutically-effective amount can vary widely depending on the severity of the disease, the age and relative health of the subject, the potency of the compounds used, and other factors.

In some embodiments, a peptide is cloned into a viral or non-viral expression vector. Such expression vector can be packaged in a viral particle, a virion, or a non-viral carrier or delivery mechanism, which is administered to patients in the form of gene therapy. In other embodiments, patient cells are extracted and modified to express a peptide capable of inhibiting YAP-TEAD interaction ex vivo before the modified cells are returned back to the patient in the form of a cell-based therapy, such that the modified cells will express the peptide once transplanted back in the patient.

Pharmaceutical compositions can be formulated using one or more physiologically-acceptable carriers comprising excipients and auxiliaries, which facilitate processing of the active compounds into preparations that can be used pharmaceutically. Formulation can be modified depending upon the route of administration chosen. Pharmaceutical compositions comprising a peptide described herein can be manufactured, for example, by expressing the peptide in a recombinant system, purifying the peptide, lyophilizing the peptide, mixing, dissolving, granulating, dragee-making, levigating, emulsifying, encapsulating, entrapping, or compression processes. The pharmaceutical compositions can include at least one pharmaceutically acceptable carrier, diluent, or excipient and compounds described herein as free-base or pharmaceutically-acceptable salt form.

Methods for the preparation of peptide described herein comprising the compounds described herein include formulating peptide described herein with one or more inert, pharmaceutically-acceptable excipients or carriers to form a solid, semi-solid, or liquid composition. Solid compositions include, for example, powders, tablets, dispersible granules, capsules, cachets, and suppositories. These compositions can also contain minor amounts of nontoxic, auxiliary substances, such as wetting or emulsifying agents, pH buffering agents, and other pharmaceutically-acceptable additives.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each of which is incorporated by reference in its entirety.

Pharmaceutical compositions can also include permeation or absorption enhancers (Aungst et al. AAPS J. 14(1):10-8. (2012) and Moroz et al. Adv Drug Deliv Rev 101:108-21. (2016)). Permeation enhancers can facilitate uptake of molecules from the GI tract into systemic circulation. Permeation enhancers can include salts of medium chain fatty acids, sodium caprate, sodium caprylate, N-(8-[2-hydroxybenzoyl]amino)caprylic acid (SNAC), N-(5-chlorosalicyloyl)-8-aminocaprylic acid (5-CNAC), hydrophilic aromatic alcohols such as phenoxyethanol, benzyl alcohol, and phenyl alcohol, chitosan, alkyl glycosides, dodecyl-2-N,N-dimethylamino propionate (DDAIPP), chelators of divalent cations including EDTA, EGTA, and citric acid, sodium alkyl sulfate, sodium salicylate, lecithin-based, or bile salt-derived agents such as deoxycholates, Compositions can also include protease inhibitors including soy bean trypsin inhibitor, aprotinin, sodium glycocholate, camostat mesilate, vacitracin, or cyclopentadecalactone, Use of Peptides in Treatments In some embodiments, the method includes administering an effective amount of a peptide as described herein to a subject in need thereof.

In one embodiment, the method includes administering an effective amount of a peptide as described herein to a subject in need thereof.

The term "effective amount," as used herein, refers to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. Compositions containing such agents or compounds can be administered for prophylactic, enhancing, and/or therapeutic treatments. An appropriate "effective" amount in any individual case may be determined using techniques, such as a dose escalation study.

The methods, compositions, and kits of this disclosure may comprise a method to prevent, treat, arrest, reverse, or ameliorate the symptoms of a condition. The treatment may comprise treating a subject (e.g., an individual, a domestic animal, a wild animal, or a lab animal afflicted with a disease or condition) with a peptide of the disclosure. The disease may be a cancer or tumor. In treating the disease, the peptide may contact the tumor or cancerous cells. The subject may be a human. Subjects can be humans; non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. A subject can be of any age. Subjects can be, for example, elderly adults, adults, adolescents, pre-adolescents, children, toddlers, infants, and fetuses in utero.

Treatment may be provided to the subject before clinical onset of disease. Treatment may be provided to the subject after clinical onset of disease. Treatment may be provided to the subject after 1 day, 1 week, 6 months, 12 months, or 2 years or more after clinical onset of the disease. Treatment may be provided to the subject for more than 1 day, 1 week, 1 month, 6 months, 12 months, 2 years or more after clinical onset of disease. Treatment may be provided to the subject for less than 1 day, 1 week, 1 month, 6 months, 12 months, or 2 years after clinical onset of the disease. Treatment may also include treating a human in a clinical trial. A treatment can comprise administering to a subject a pharmaceutical composition, such as one or more of the pharmaceutical compositions described throughout the disclosure. A treatment can comprise a once daily dosing. A treatment can comprise delivering a peptide of the disclosure to a subject, either intravenously, subcutaneously, intramuscularly, by inhalation, dermally, topically, by intra-articular injection, orally, sublingually, intrathecally, transdermally, intranasally, via a peritoneal route, directly into a tumor, e.g., injection directly into a tumor, directly into the brain, e.g., via and intracerebral ventricle route, or directly onto a joint, e.g., via topical, intra-articular injection route. A treatment can comprise administering a peptide-active agent complex to a subject, either intravenously, subcutaneously, intramuscularly, by inhalation, by intra-articular injection, dermally, topically, orally, intrathecally, transdermally, intransally, parenterally, orally, via a peritoneal route, nasally, sublingually, or directly onto cancerous tissues.

Disruption of the YAP-TEAD interaction can have implications in a number of diseases, condition, or disorders associated to dysregulated cell growth, cell proliferation, angiogenesis, organogenesis, tumor progression, and/or metastasis. Compositions comprising any one of the peptides that bind TEAD, or a pharmaceutical composition thereof, can be used in a method of treating a cancer, tumor progression, and/or dysregulated cell growth. Exemplary diseases, disorder, or condition include: multiple myeloma, plastic anemia, myelodysplasia, and related bone marrow failure syndromes, myeloproliferative diseases, acute and chronic myeloid leukemia, malignancies of lymphoid cells, hematologic malignancies, plasma cell disorders, skeletal muscle disorder, myopathy, muscular dystrophy (e.g., Becker muscular dystrophy, Duchenne muscular dystrophy, Emery-Dreifuss muscular dystrophy, Facioscapulohumoeral muscular dystrophy, Myotonia congentia, and myotonic dystrophy), and chronic obstructive pulmonary disorder. In some embodiments, compositions/peptides disclosed herein are used to treat dysregulated cell growth, cancer, tumor, and/or metastasis associated with any of the following cell, tissue, or organ types: brain, lung, liver, spleen, kidney, lymph node, small intestine, blood cell, pancreatic, colon, stomach, cervix, breast, endometrial, prostate, testicle, ovarian, skin, head and neck, esophageal, oral tissue, and bone marrow. In further embodiments, compositions/peptides disclosed herein are used to treat nay of the following: osteosarcoma, hepatocellular carcinoma, malignant mesothelioma, schwannoma, meningioma, renal carcinoma, cholangiocarcinoma, bile duct hamartoma, soft tissue carcinoma, ovarian carcinoma, colonic adenoma, T cell acute lymphoblastic leukaemia, gastrointestinal hyperplasia, fibrosarcoma, pancreatic ductal metaplasia, squamous cell carcinoma, kaposis sarcoma, and HIV-induced non-Hodgkin's lymphoma.

In some embodiments, the peptides of this disclosure (SEQ ID NO: 1-SEQ ID NO: 84) can be used to access and treat these disorders due to their enhanced stability in various biological environments, including low pH, protease-rich environments, acidic environments, reducing environments, or environments with varying temperatures.

In some embodiments, compositions comprise any one of the peptides disclosed herein that modulates one or more factors of the HIPPO pathway, and is used to treat a condition or disease associated with a dysregulated HIPPO pathway.

Peptide Kit

In one aspect, peptides described herein can be provided as a kit. In another embodiment, peptide conjugates described herein can be provided as a kit. In another embodiment, a kit comprises amino acids encoding a peptide described herein, a vector, a host organism, and an instruction manual. In some embodiments, a kit includes written instructions on the use or administration of the peptides.

EXAMPLES

The following examples are included to further describe some aspects of the present disclosure, and should not be used to limit the scope of the invention.

Example 1

Manufacture of Peptides

This example describes the manufacture of the peptides described herein. Peptides derived from proteins were generated in mammalian cell culture using a published methodology. (A. D. Bandaranayke, C. Correnti, B. Y. Ryu, M. Brault, R. K. Strong, D. Rawlings. 2011. Daedalus: a robust, turnkey platform for rapid production of decigram quantities of active recombinant proteins in human cell lines using novel lentiviral vectors. Nucleic Acids Research. (39)21, e143).

The peptide sequence was reverse-translated into DNA, synthesized, and cloned in-frame with siderocalin using standard molecular biology techniques (M. R. Green, Joseph Sambrook. Molecular Cloning. 2012 Cold Spring Harbor Press). The resulting construct was packaged into a lentivirus, transduced into HEK-293 cells, expanded, isolated by immobilized metal affinity chromatography (IMAC), cleaved with tobacco etch virus protease, and purified to homogeneity by reverse-phase chromatography. Following purification, each peptide was lyophilized and stored frozen.

Example 2

Peptide Expression Using a Mammalian Expression System

This example describes expression of the peptides using a mammalian expression system. Peptides were expressed according to the methods described in in Bandaranayake et al., Nucleic Acids Res. 2011 November; 39(21): e143. Peptides were cleaved from siderocalin using tobacco etch virus protease and purified by FPLC on a size exclusion chromatography (SEC) column using an isocratic elution over four column volumes in 1×DPBS. Peptides were then stored at 4° C.

Example 3

Production and Validation of TEAD

This example describes production of TEAD-binding peptides. To identify TEAD binders from a designed library, soluble TEAD (194-411) was produced with two C-terminal tags: 6×His (SEQ ID NO: 284), and AviTag. To confirm the stability and YAP-binding capability of His-Avi-TEAD, YAP (50-171) was produced as a soluble siderocalin fusion. FIG. 1 illustrates validation and functional analysis of the produced biotinylated TEAD and Siderocalin-fused YAP. FIG. 1A illustrates and SDS-PAGE with a band near 55 kDa indicating presence of the Siderocalin-YAP. FIG. 1B illustrates surface plasmon resonance (SPR) data showing that Siderocalin-fused YAP binds biotinylated TEAD immobilized on an SPR chip with a dissociation constant ($K_D$) of 570 nM. FIG. 1C illustrates that HEK-293 cells expressing surface-tethered YAP (50-171) is stained by Alexa Fluorophore (AF)-647 conjugated to Streptavidin (AF657-Streptavidin) bound to biotinylated TEAD. Cells expressing the Machupo virus (MACV) glycoprotein, a specific ligand for human transferrin receptor, are not stained by AF-647, indicating that TEAD does not bind MACV.

Example 4

Mammalian Surface Display of TEAD-Binding Peptides

Figure 2A:
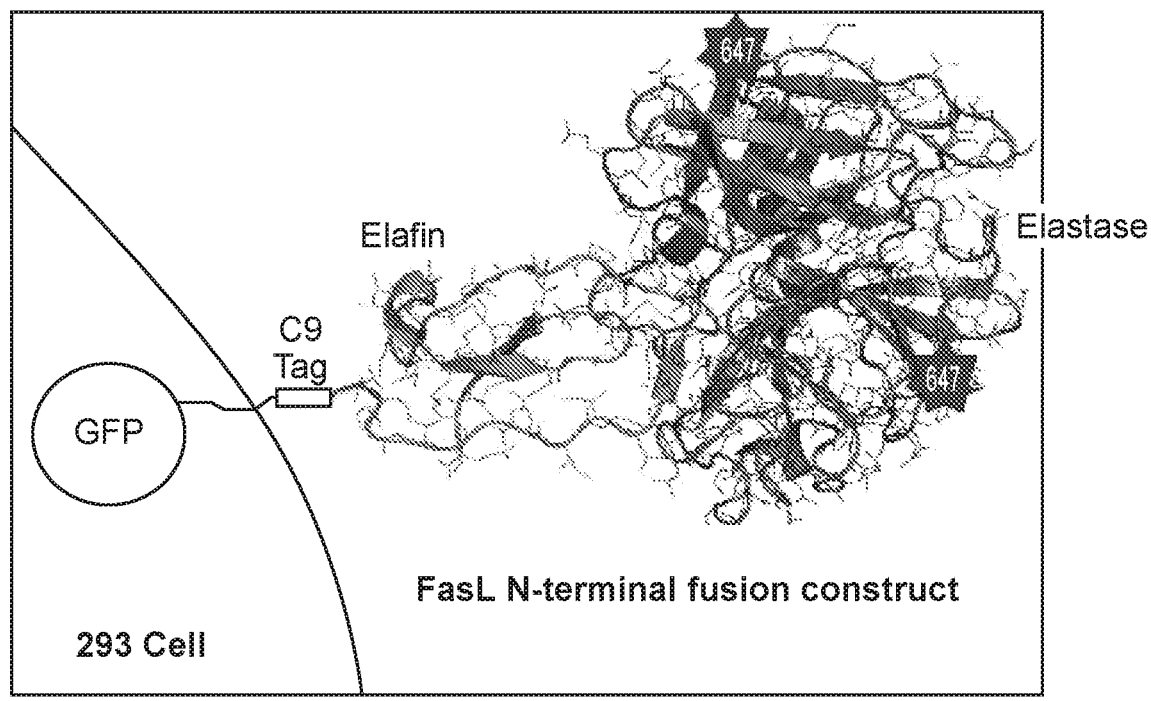
FIG. 2A illustrates a schematic of the SDGF vector. Cytosolic, N-terminal GFP is connected to the extracellular domain of a peptide via a transmembrane domain of human FasL. A bovine rhodopsin C9 tag and/or a short linker can be used to connect the FasL transmembrane domain and the N-terminus of a peptide. Any peptide or a library of peptides, including, but not limited to, knottin peptides, or any recombinant, engineered, or designed peptides, can be screened for binding to a protein of interest using this method. Elastase binding to a GFP-elafin fusion peptide is shown here as an example. The protein of interest, such as elastase in the example, can be tagged or stained with a detectable moiety, such as a fluorescent label, that confers fluorescence or a detectable signal to the cell to indicate protein binding or protein-peptide interaction.
Figure 2B:
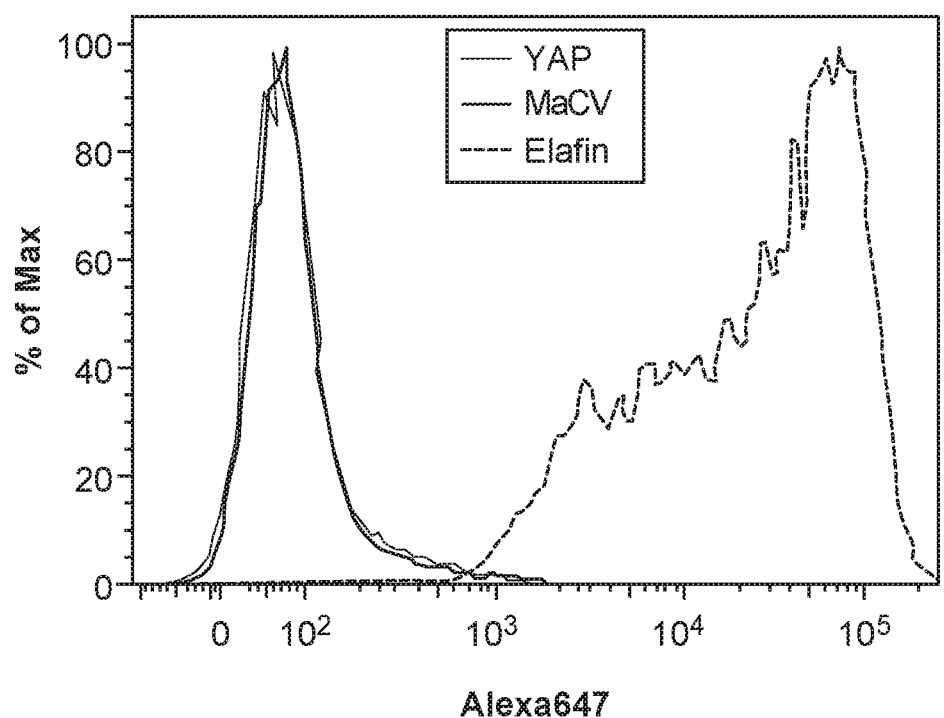
FIG. 2B illustrates flow cytometry histograms showing that HEK-293 suspensions cells expressing SDGF-elafin are stained by AF647-conjugated elastase (as shown by the right-most peak). Negative control experiments with cells expressing either SDGF-YAP (50-171) or SDGF-MACV glycoprotein are not stained by AF647 elastase (as shown by the overlapping left-most peaks).

This example describes mammalian surface display of TEAD-binding peptides of the present disclosure. Screening for TEAD binders was performed by transfecting or transducing mammalian cells to display candidate peptides followed by screening with biotinylated TEAD conjugated to Alexa Fluorophore 647 (AF647). Mammalian cells had improved fidelity in folding disulfide crosslinked proteins, making them a suitable cell type for display of the peptides of the present disclosure. FIG. 2 illustrates that the surface display GFP FasL (SDGF) vector is an effective mammalian display vector for peptide expression and evaluation of knottin peptide binding to another moiety. FIG. 2A illustrates a schematic of the SDGF vector. Cytosolic, N-terminal GFP is connected to the extracellular domain via the transmembrane domain of human FasL. A bovine rhodopsin C9 tag follows, separated by a short linker from the C-terminal knottin (elafin is shown here as a representative example, however any peptide can be used). Specific binding partners (elastase to elafin is shown here as a representative example, however any peptide or library of peptides can be used) will bind to the knottin, and if the binding partner is fluorescently tagged, will confer that fluorescence to the cell. FIG. 2B illustrates flow cytometry histograms showing that HEK-293 suspensions cells expressing SDGF-elafin are stained by AF647-conjugated elastase. Negative control experiments with cells expressing either SDGF-YAP (50-171) or SDGF-MACV glycoprotein are not stained by AF647 elastase.

FIG. 17 further illustrates the method of using mammalian surface display screening for identifying TEAD-binding peptides. FIG. 17A shows a detailed scheme for the screening strategy using a surface display GFP FasL (SDGF) vector. In the vector, FasL-TM is the transmembrane domain of the FasL protein. More specifically, the designed peptides are cloned as a pool into SDGF, which are then made into lentivirus. 293F cells are transduced with this library at a multiplicity of infection of ~1, and after three days of growth, the pool of transduced cells are incubated with Alexa647-labeled TEAD. A percentage of the highest-staining APC-positive cells, from GFP and APC double-positive cells, are sorted and expanded. At every expansion, a portion of the cells are collected, and at the end, the enriched peptides are identified by sequencing.

Example 5

Screening for TEAD-Binding Peptides

Figure 3A:
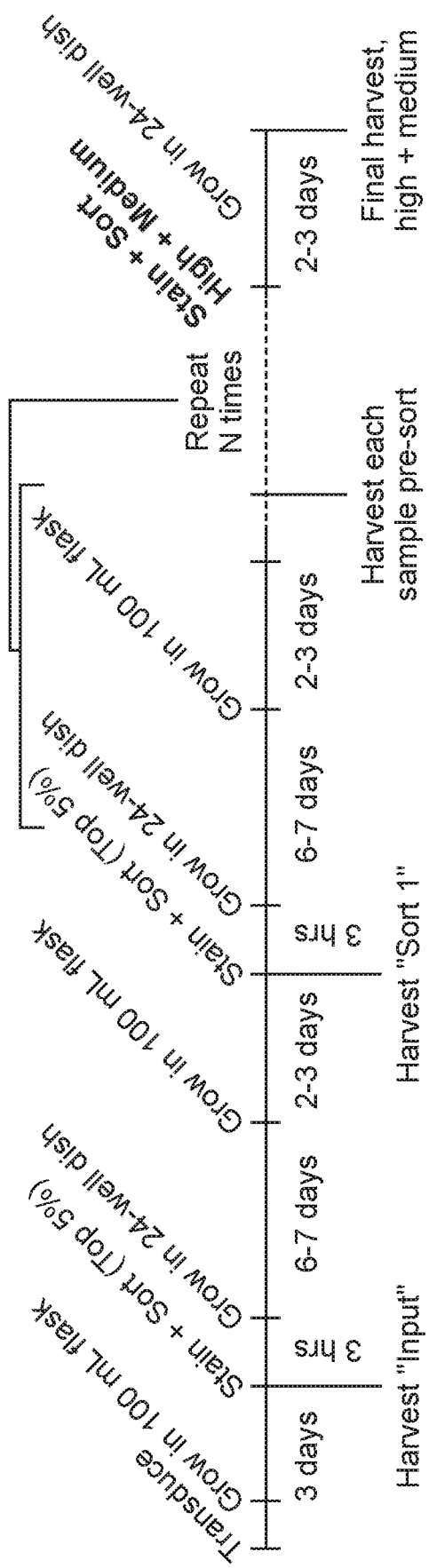
FIG. 3A illustrates a schematic of the screening steps for evaluating SDGF peptide libraries for protein binding.
Figures 3B, 3C:
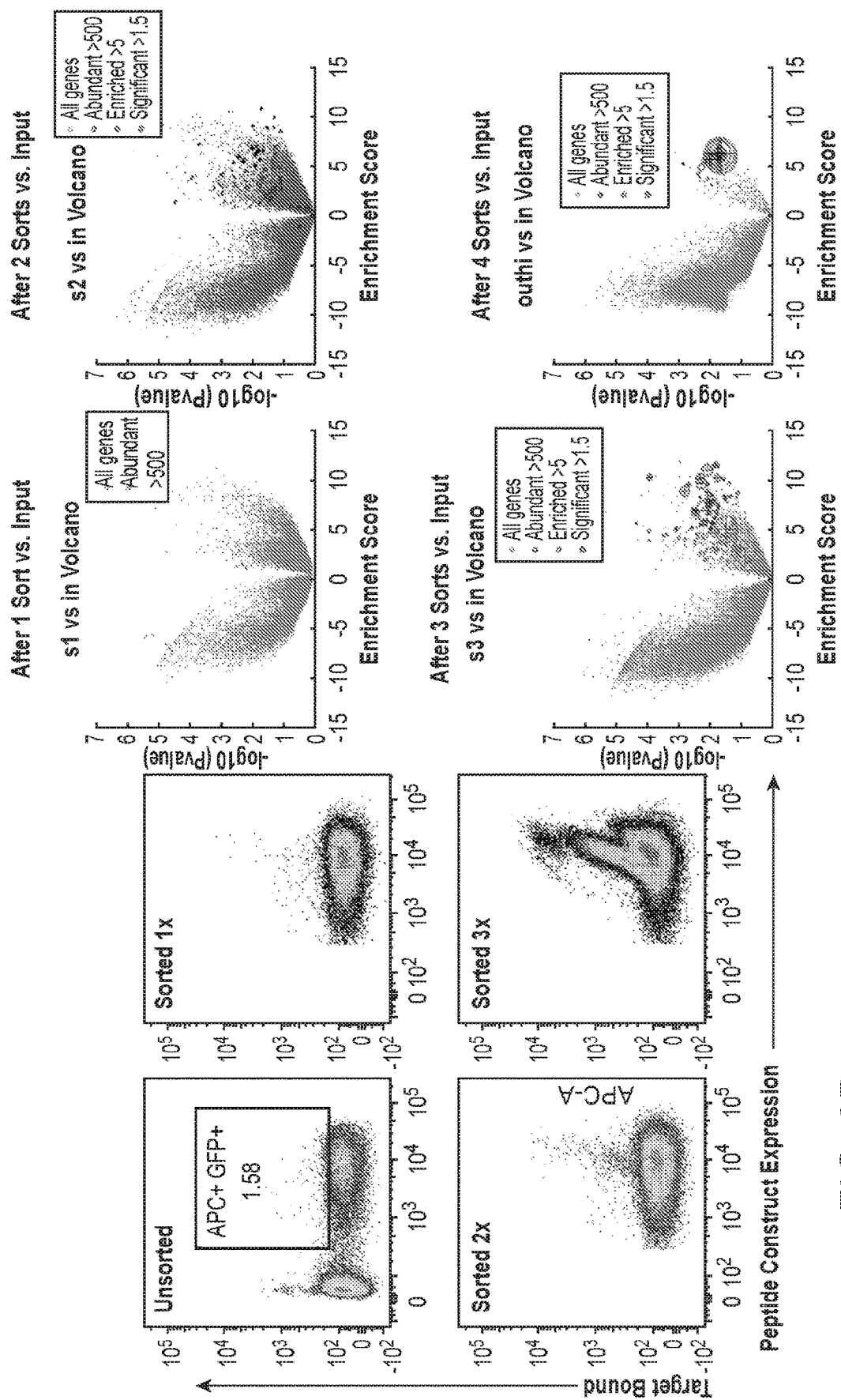
FIG. 3B illustrates flow cytometry plots showing the fluorescence of peptide construct expression (e.g., GFP-fused peptides or peptide library) on the x-axis and target or partner protein of interest bound (e.g., TEAD stained with AF647) to the peptides on the y-axis. Double-positive cells (upper right hand quadrant) indicate peptide-expressing cells that are bound to the target protein or protein of interest, such as TEAD. HEK-293 cells were transduced with the SDGF TEAD-binder peptide library and stained with 200 nM AF647-Streptavidin-TEAD. Flow cytometry plots show unsorted cells, cells sorted after 1, 2, or 3 rounds of sorting.
FIG. 3C illustrates Illumina sequencing data plotting the abundance of each library member versus its abundance prior to the screening and sorting ("input") after round 1, 2, 3, and 4. The x-axis indicates an enrichment score (log 2 ratio of relative abundance versus input abundance) and the y-axis shows log 2 P-value (determined using a Student's t-test). Data are shown from triplicate samples. Library members whose reads were abundant are represented as data points in larger circles. The area of the circle representing a given data point is proportional to the read abundance in the samples.

This example describes screening for TEAD-binding peptides using the mammalian surface display system of EXAMPLE 4. Potential TEAD-binding peptides were cloned into SDGF and effective binders were screened using 200 nM TEAD-streptavidin. FIG. 3 illustrates screening a designed library for TEAD-binding peptides. FIG. 3A illustrates a schematic of the screening steps for SDGF peptide libraries. FIG. 3B illustrates flow cytometry plots showing the fluorescence of peptide construct expression (GFP) on the x-axis and TEAD (AF647) on the y-axis. Double-positive cells (upper right hand quadrant) indicate peptide-expressing cells that are bound to TEAD. HEK-293 cells were transduced with the SDGF TEAD-binder library and stained with 200 nM AF547-Streptavidin-TEAD. Flow cytometry plots show unsorted cells, cells sorted after 1, 2, or 3 rounds of screening.

Figure 3D:
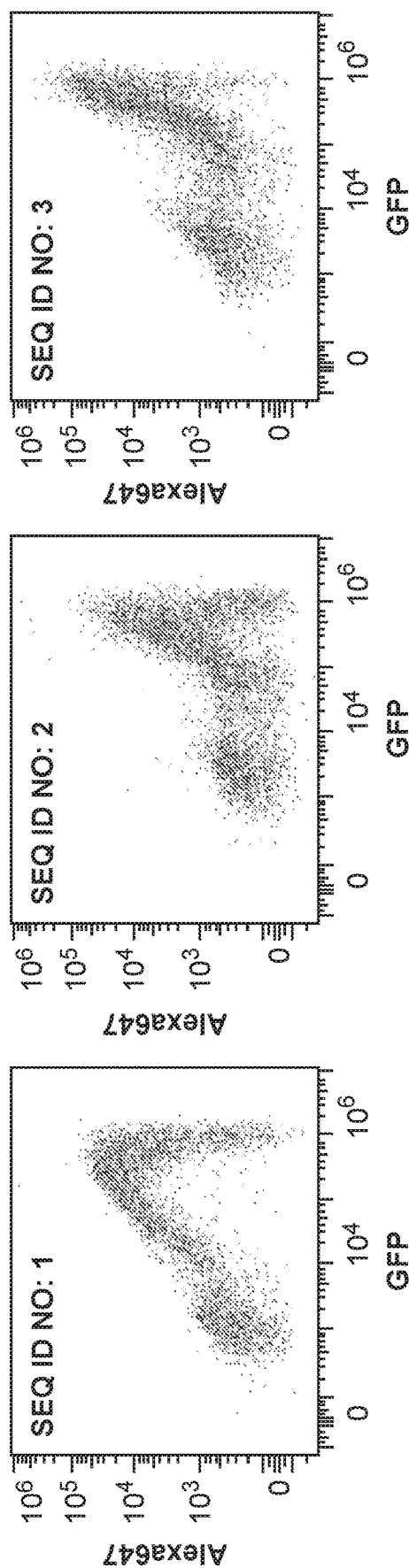
FIG. 3D illustrates flow cytometry plots showing construct expression (GFP) on the x-axis and TEAD (AF647) on the y-axis. Double-positive cells (upper right hand quadrant) indicate peptide-expressing cells that are bound to TEAD. HEK-293 suspension cells were transfected with hits from the screen cloned into the SDGF vector and stained with 200 nm AF647-Streptavidin-TEAD. Peptides tested included peptides of SEQ ID NO: 1, SEQ ID NO: 2, and SEQ ID NO: 3.

Peptide gene sequences were PCR-amplified out of the transduced cells, and candidate TEAD binders were identified by conventional Sanger sequencing and Illumina deep sequencing. FIG. 3C illustrates Illumina sequencing data plotting the abundance of each library member versus its abundance prior to the screening and sorting ("input") after round 1, 2, 3, and 4. The x-axis indicates an enrichment score (log 2 ratio of relative abundance versus input abundance) and the y-axis shows log 2 P-value (determined using a Student's t-test). Data are shown from triplicate samples. TEAD-binding peptides were identified by selecting an enrichment score >5 and applying abundance and statistical significance filters. Enriched hits began appearing after two rounds of sorting. After three rounds of sorting, the majority of remaining cells-expressing peptides were considered to be hits. All peptides identified as hits after the third round of sorting were re-cloned and re-tested. Peptides of SEQ ID NO: 1, SEQ ID NO: 2, and SEQ ID NO: 3 were identified as TEAD binders. Library members whose reads were abundant are represented as data points in larger circles. The area of the circle representing a given data point is proportional to the read abundance in the samples. FIG. 3D illustrates flow cytometry plots showing peptide construct expression (GFP) on the x-axis and TEAD (AF647) on the y-axis. Double-positive cells (upper right hand quadrant) indicate peptide-expressing cells that are bound to TEAD. HEK-293 suspension cells were transfected with hits from the screen cloned into the SDGF vector and stained with 200 nm AF647-Streptavidin-TEAD. Peptides of SEQ ID NO: 1, SEQ ID NO: 2, and SEQ ID NO: 3 expressed by HEK-293 cells displayed binding to TEAD, as demonstrated by cells that fall into the GFP+AF647+ region of the flow cytometry plots.

Figure 17A:
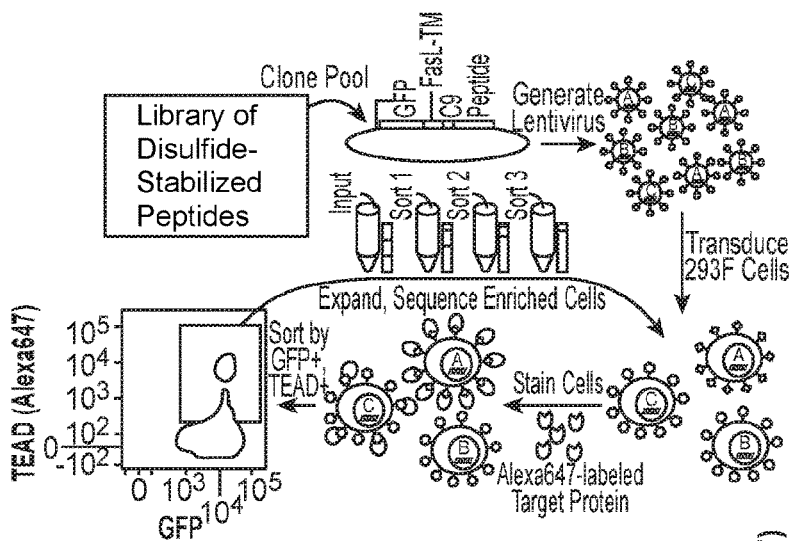
FIG. 17A illustrates a scheme for the screening strategy using a surface display GFP FasL (SDGF) vector. In the vector, FasL-TM is the transmembrane domain of the FasL protein. This figure illustrates that the screening strategy can start with a library of disulfide-stabilized peptides, for example, any one of SEQ ID NO: 289-SEQ ID NO: 304.
Figure 17B:
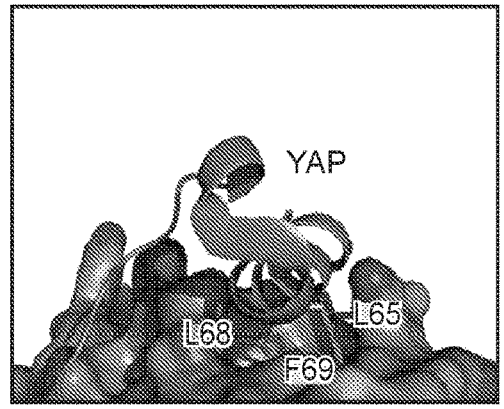
FIG. 17B illustrates the modeled TEAD interface for the YAP-TEAD structure from Protein Data Bank (PDB ID) 3KYS.
Figure 17C:
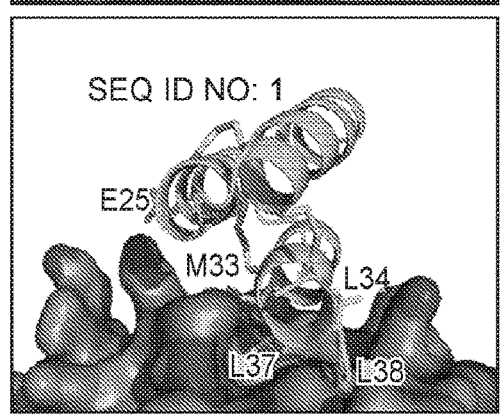
FIG. 17C illustrates the modeled TEAD interface for SEQ ID NO: 1 modeled with the TEAD structure from FIG. 17A.
Figure 17D:
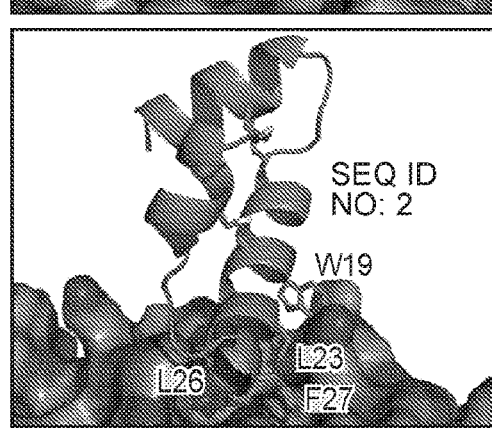
FIG. 17D illustrates the modeled TEAD interface for SEQ ID NO: 2 modeled with the TEAD structure from FIG. 17A.
Figure 17E:
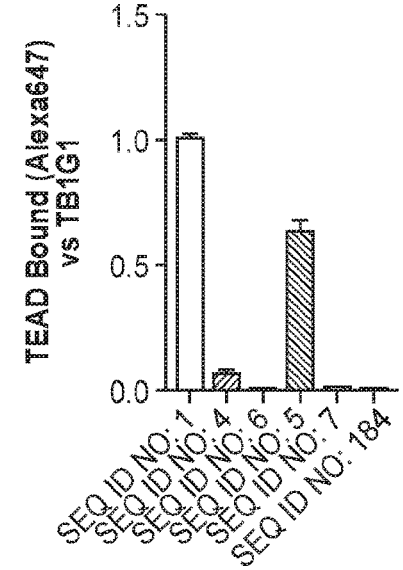
FIG. 17E illustrates the TEAD-binding abilities of 293F cells transfected with surface display GFP FasL (SDGF)-SEQ ID NO: 1 compared to cells displaying alanine substitution mutants at sites found at the modeled TEAD interface (SDGF-SEQ ID NO: 4, SDGF-SEQ ID NO: 6, SDGF-SEQ ID NO: 5, and SDGF-SEQ ID NO: 7). The variant with all Cys converted to Ser (6CS) to eliminate disulfide bonds was also tested (SEQ ID NO: 184). Binding was assessed by quantifying Alexa647 levels in transfected cells using flow cytometry. Shown are the median±95% confidence intervals, normalized to that of cells displaying the parent peptide.
Figure 17F:
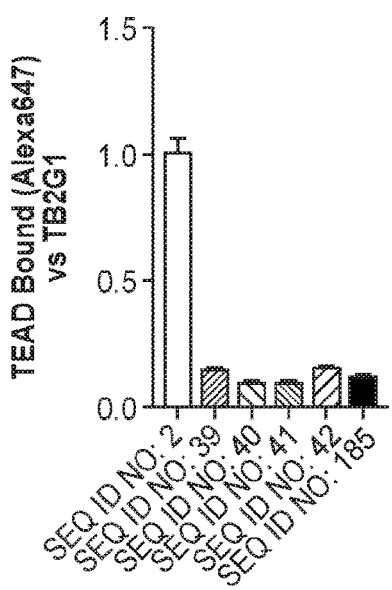
FIG. 17F illustrates the TEAD-binding abilities of 293F cells transfected with surface display GFP FasL (SDGF)-SEQ ID NO: 2 compared to cells displaying alanine substitution mutants at sites found at the modeled TEAD interface (SDGF-SEQ ID NO: 39, SDGF-SEQ ID NO: 40, SDGF-SEQ ID NO: 41, and SDGF-SEQ ID NO: 42). The variant with all Cys converted to Ser (6CS) to eliminate disulfide bonds were also tested (SEQ ID NO: 185). Binding was assessed by quantifying Alexa647 levels in transfected cells using flow cytometry. Shown are the median±95% confidence intervals, normalized to that of cells displaying the parent peptide.

FIG. 17E illustrates the TEAD-binding abilities of 293F cells transfected with surface display GFP FasL (SDGF)-SEQ ID NO: 1 compared to cells displaying alanine substitution mutants at sites found at the modeled TEAD interface (SDGF-SEQ ID NO: 4, SDGF-SEQ ID NO: 6, SDGF-SEQ ID NO: 5, and SDGF-SEQ ID NO: 7). The variant with all Cys converted to Ser (6CS) to eliminate disulfide bonds was also tested (SEQ ID NO: 184). Binding was assessed by quantifying Alexa647 levels in transfected cells using flow cytometry. Shown are the median f 95% confidence intervals, normalized to that of cells displaying the parent peptide. FIG. 17F illustrates the TEAD-binding abilities of 293F cells transfected with surface display GFP FasL (SDGF)-SEQ ID NO: 2 compared to cells displaying alanine substitution mutants at sites found at the modeled TEAD interface (SDGF-SEQ ID NO: 39, SDGF-SEQ ID NO: 40, SDGF-SEQ ID NO: 41, and SDGF-SEQ ID NO: 42). The variant with all Cys converted to Ser (6CS) to eliminate disulfide bonds were also tested (SEQ ID NO: 185). Binding was assessed by quantifying Alexa647 levels in transfected cells using flow cytometry. Shown are the median ±95% confidence intervals, normalized to that of cells displaying the parent peptide.

Example 6

Figure 4A:
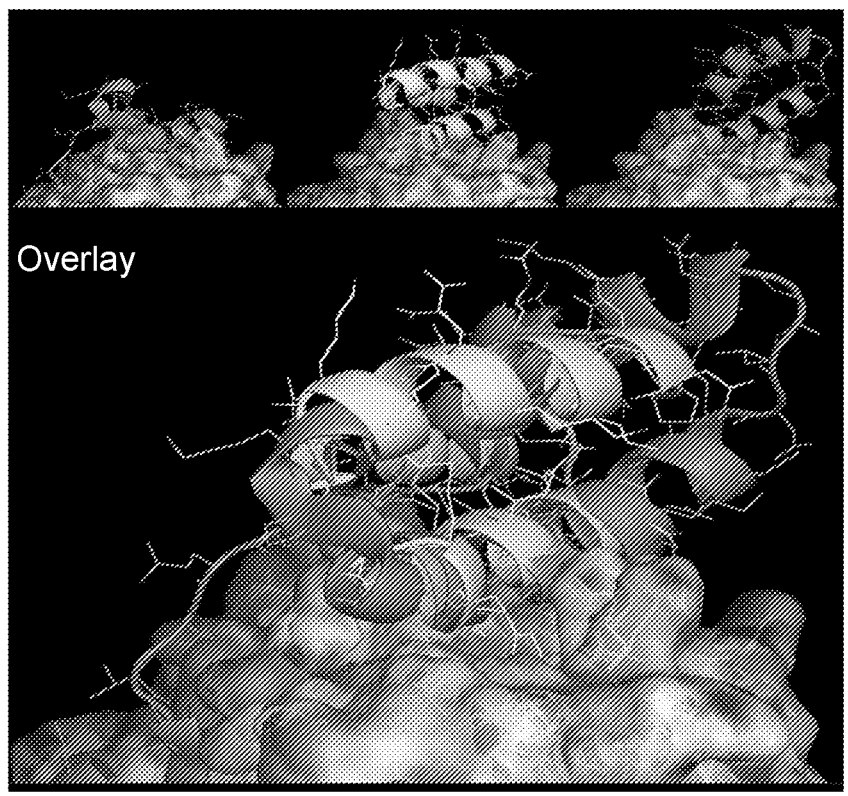
FIG. 4A illustrates that YAP and peptides of SEQ ID NO: 1 and SEQ ID NO: 2 are predicted to bind TEAD at the same site (Site 2). The YAP-TEAD structure (Protein Data Bank (PDB) ID: 3KYS) is available from the Research Collaboratory for Structural Bioinformatics (RCSB). Structures of peptides of SEQ ID NO: 1 and SEQ ID NO: 2 were modeled onto the TEAD structure.
Figure 4J:
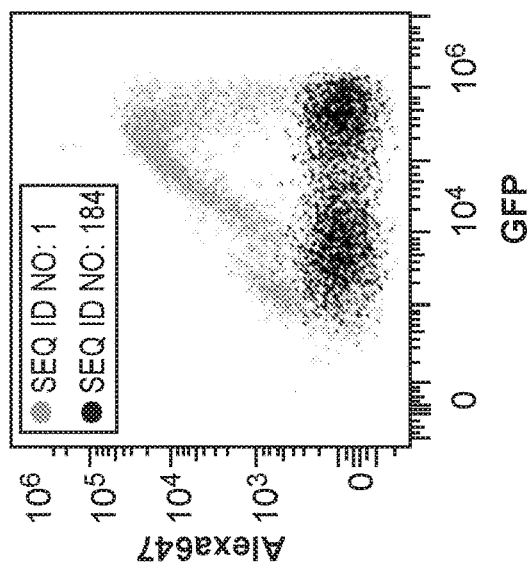
FIG. 4J illustrates flow cytometry plots showing TEAD binding to HEK-293 suspension cells transfected with SDGF-SEQ ID NO: 1 versus TEAD binding to HEK-293 suspension cells transfected with a peptide of SEQ ID NO: 184 (SDGF-6×CS variant of SEQ ID NO: 1, which is a variant of SEQ ID NO: 1 in which all 6 cysteines are mutated to serines).
Figure 4I:
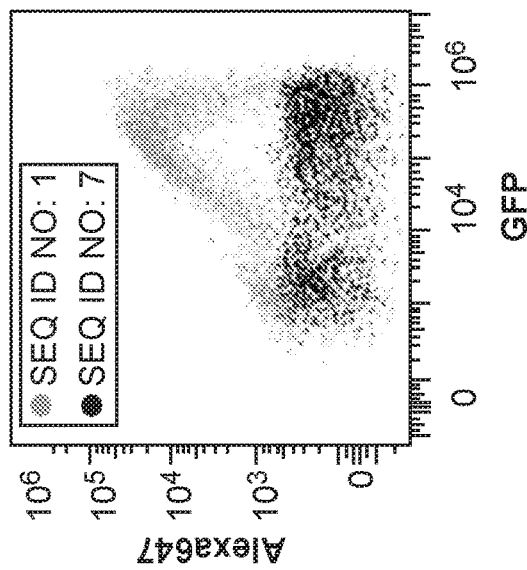
FIG. 4I illustrates flow cytometry plots showing TEAD binding to HEK-293 suspension cells transfected with SDGF-SEQ ID NO: 1 versus TEAD binding to HEK-293 suspension cells transfected with a peptide of SEQ ID NO: 7 (SDGF-F38A variant of SEQ ID NO: 1, which is a phenylalanine to alanine variant of SEQ ID NO: 1 at position 38).
Figure 4H:
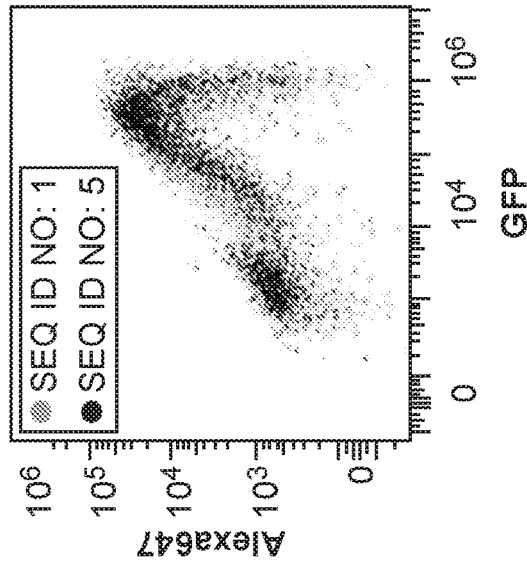
FIG. 4H illustrates flow cytometry plots showing TEAD binding to HEK-293 suspension cells transfected with SDGF-SEQ ID NO: 1 versus TEAD binding to HEK-293 suspension cells transfected with a peptide of SEQ ID NO: 5 (SDGF-L37A variant of SEQ ID NO: 1, which is a leucine to alanine variant of SEQ ID NO: 1 at position 37).

Binding of Cell Surface Displayed TEAD-Binding Peptides and Soluble TEAD-Binding Peptides This example describes binding of TEAD to peptides of this disclosure and variants of peptides of the present disclosure. Peptides of SEQ ID NO: 1 and SEQ ID NO: 2 were designed to bind to TEAD at the same site at which YAP binds (Site 2). Both peptides of SEQ ID NO: 1 and SEQ ID NO: 2 contain the $LX_1X_2LF$ (SEQ ID NO: 217) motif that is also present in YAP helix 2, wherein $X_1$ and $X_2$ can be any amino acid. FIG. 4 illustrates peptides of SEQ ID NO: 1 and SEQ ID NO: 2 and the modeled TEAD interface with YAP and binding of TEAD to variants of SEQ ID NO: 1 and SEQ ID NO: 2. FIG. 4A illustrates that YAP and peptides of SEQ ID NO: 1 and SEQ ID NO: 2 are predicted to bind TEAD at the same site (Site 2). The YAP-TEAD structure (protein data bank (PDB) ID: 3KYS) is from the Research Collaboratory for Structural Bioinformatics (RCSB) PDB. SEQ ID NO: 1 and SEQ ID NO: 2 were modeled bound to the TEAD structure from RCSB 3KYS. FIG. 4B illustrates flow cytometry plots showing TEAD binding to HEK-293 suspension cells transfected with SDGF-SEQ ID NO: 2 versus TEAD binding to HEK-293 suspension cells transfected with SDGF-L23A variant of SEQ ID NO: 2 (lysine to alanine variant of SEQ ID NO: 2 at position 23). Position L23 of SEQ ID NO: 2, analogous to the L65 residue of YAP, when mutated to alanine resulted in loss of binding to TEAD. FIG. 4C illustrates flow cytometry plots showing TEAD binding to HEK-293 suspension cells transfected with SDGF-SEQ ID NO: 2 versus TEAD binding to HEK-293 suspension cells transfected with SDGF-L26A variant of SEQ ID NO: 2 (lysine to alanine variant of SEQ ID NO: 2 at position 26). Position L26 of SEQ ID NO: 2, analogous to the L68 residue of YAP, when mutated to alanine resulted in loss of binding to TEAD. FIG. 4D illustrates flow cytometry plots showing TEAD binding to HEK-293 suspension cells transfected with SDGF-SEQ ID NO: 2 versus TEAD binding to HEK-293 suspension cells transfected with SDGF-F27A variant of SEQ ID NO: 2 (phenylalanine to alanine variant of SEQ ID NO: 2 at position 27). Position F27 of SEQ ID NO: 2, analogous to the F69 residue of YAP, when mutated to alanine resulted in loss of binding to TEAD. FIG. 4E illustrates flow cytometry plots showing TEAD binding to HEK-293 suspension cells transfected with SDGF-SEQ ID NO: 2 versus TEAD binding to HEK-293 suspension cells transfected with SDGF-6×CS variant of SEQ ID NO: 2 (a variant of SEQ ID NO: 2 in which all 6 cysteines are mutated to serines). Mutation of cysteines to serines resulted in loss of binding to TEAD. FIG. 4F illustrates flow cytometry plots showing TEAD binding to HEK-293 suspension cells transfected with SDGF-SEQ ID NO: 1 versus TEAD binding to HEK-293 suspension cells transfected with a peptide of SEQ ID NO: 4 (SDGF-E25A variant of SEQ ID NO: 1, which is a glutamic acid to alanine variant of SEQ ID NO: 1 at position 25). Position E25 of SEQ ID NO: 1, when mutated to alanine, resulted in loss of binding to TEAD. FIG. 4G illustrates flow cytometry plots showing TEAD binding to HEK-293 suspension cells transfected with SDGF-SEQ ID NO: 1 versus TEAD binding to HEK-293 suspension cells transfected with a peptide of SEQ ID NO: 6 (SDGF-M33A variant of SEQ ID NO: 1, which is a methionine to alanine variant of SEQ ID NO: 1 at position 33). Position M33 of SEQ ID NO: 2, when mutated to alanine, resulted in loss of binding to TEAD. FIG. 4H illustrates flow cytometry plots showing TEAD binding to HEK-293 suspension cells transfected with SDGF-SEQ ID NO: 1 versus TEAD binding to HEK-293 suspension cells transfected with a peptide of SEQ ID NO: 5 (SDGF-L37A variant of SEQ ID NO: 1, which is a leucine to alanine variant of SEQ ID NO: 1 at position 37). Position L37 of SEQ ID NO: 1, analogous to the L68 residue of YAP, when mutated to alanine, resulted in a marginal loss of binding to TEAD. FIG. 4I illustrates flow cytometry plots showing TEAD binding to HEK-293 suspension cells transfected with SDGF-SEQ ID NO: 1 versus TEAD binding to HEK-293 suspension cells transfected with a peptide of SEQ ID NO: 7 (SDGF-F38A variant of SEQ ID NO: 1, which is a phenylalanine to alanine variant of SEQ ID NO: 1 at position 38). Position F38 of SEQ ID NO: 1, analogous to the F69 residue of YAP, when mutated to alanine, resulted in loss of binding to TEAD. FIG. 4J illustrates flow cytometry plots showing TEAD binding to HEK-293 suspension cells transfected with SDGF-SEQ ID NO: 1 versus TEAD binding to HEK-293 suspension cells transfected with a peptide of SEQ ID NO: 184 (SDGF-6×CS variant of SEQ ID NO: 1, which is a variant of SEQ ID NO: 1 in which all 6 cysteines are mutated to serines). Mutation of cysteines to serines resulted in loss of binding to TEAD.

Soluble TEAD-binding peptides made using methods of EXAMPLE 1 and then were evaluated for binding by incubation of a dilution series varying from 150 μM to 44 μM (concentration range was varied depending on the TEAD-binding peptide being tested) of TEAD-binding peptides with 2 μg/mL TEAD, capturing ~300 resonance units (RUs) of protein for surface plasmon resonance (SPR, Biacore) experiments. FIG. 5 illustrates binding of soluble TEAD-binding peptides and variants to TEAD. Gels show peptides in reducing conditions in NuPAGE at one-tenth the final volume, in which DTT is at 50 mM. HPLC shows peptides in reducing conditions in Dulbecco's phosphate-buffered saline (DPBS) with a final DTT concentration of 40 mM. Non-reducing conditions are designated as "NR" and reducing conditions are designated as "R." FIG. 5A illustrates an SDS-PAGE gel of a peptide of SEQ ID NO: 1 in non-reducing conditions and reducing conditions. FIG. 5B illustrates HPLC chromatograms showing peaks representing a peptide of SEQ ID NO: 1 in non-reducing conditions and in reducing conditions with DTT. FIG. 5C illustrates SPR binding assay data of a peptide of SEQ ID NO: 1 to biotinylated TEAD immobilized on an SPR chip with a dissociation constant ($K_D$) of 31 nM. FIG. 5D illustrates an SDS-PAGE gel of a peptide of SEQ ID NO: 5 in non-reducing conditions and reducing conditions. FIG. 5E illustrates HPLC chromatograms showing peaks representing a peptide of SEQ ID NO: 5 in non-reducing conditions and in reducing conditions with DTT. FIG. 5F illustrates SPR binding assay data of a peptide of SEQ ID NO: 5 to biotinylated TEAD immobilized on an SPR chip with a dissociation constant ($K_D$) of 280 nM. FIG. 5G illustrates an SDS-PAGE gel of a peptide of SEQ ID NO: 7 in non-reducing conditions and reducing conditions. FIG. 5H illustrates HPLC chromatograms showing peaks representing a peptide of SEQ ID NO: 7 in non-reducing conditions and in reducing conditions with DTT. FIG. 5I illustrates SPR binding assay data of a peptide of SEQ ID NO: 7 to biotinylated TEAD immobilized on an SPR chip with a dissociation constant ($K_D$) of 23 µM. FIG. 5J illustrates an SDS-PAGE gel of a peptide of SEQ ID NO: 3 in non-reducing conditions and reducing conditions. FIG. 5K illustrates HPLC chromatograms showing peaks representing a peptide of SEQ ID NO: 3 in non-reducing conditions and in reducing conditions with DTT. FIG. 5L illustrates SPR binding assay data of a peptide of SEQ ID NO: 3 to biotinylated TEAD immobilized on an SPR chip with a dissociation constant ($K_D$) of 12 µM. A peptide of SEQ ID NO: 5 had reduced affinity for TEAD as compared to a peptide of SEQ ID NO: 1. A peptide of SEQ ID NO: 7 also had reduced affinity for TEAD as compared to a peptide of SEQ ID NO: 1. A peptide of SEQ ID NO: 5 had reduced binding to TEAD as compared to a peptide of SEQ ID NO: 1. A peptide of SEQ ID NO: 3 also showed lower binding affinity for TEAD as compared to a peptide of SEQ ID NO: 1. Since the peptide of SEQ ID NO: 3 was not designed for binding to TEAD, it is possible that the lower affinity for binding to TEAD was a result of poor folding of the peptide.

Example 7

Peptide Disruption of YAP-TEAD Binding

Figure 6A:
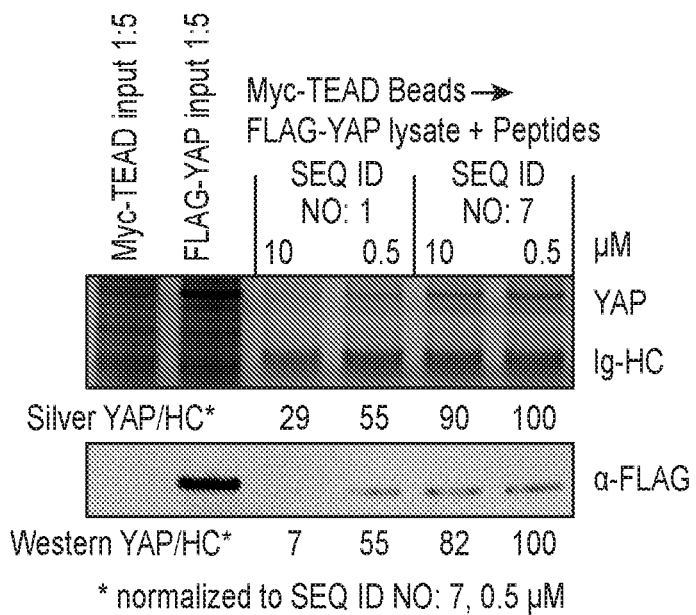
FIG. 6A illustrates a Silver stain (top panel) and a Western blot (lower panel) showing that FLAG-YAP was not pulled down with Myc-TEAD resin or beads in the presence of a peptide of SEQ ID NO: 1 or SEQ ID NO: 7.
Figure 6B:
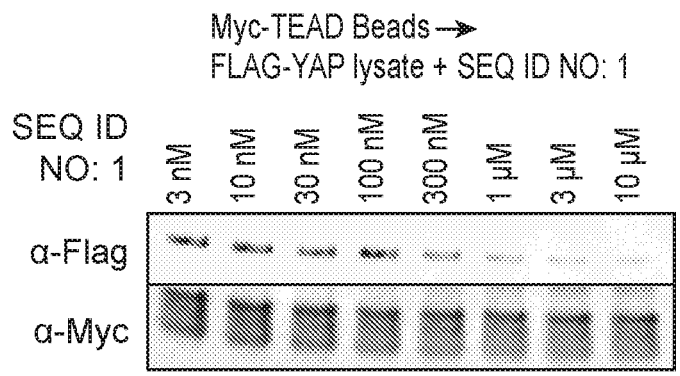
FIG. 6B illustrates a Western blot showing a dilution series of a peptide of SEQ ID NO: 1 demonstrating dose-dependent inhibition of FLAG-YAP binding to Myc-TEAD resin or beads.
Figure 6C:
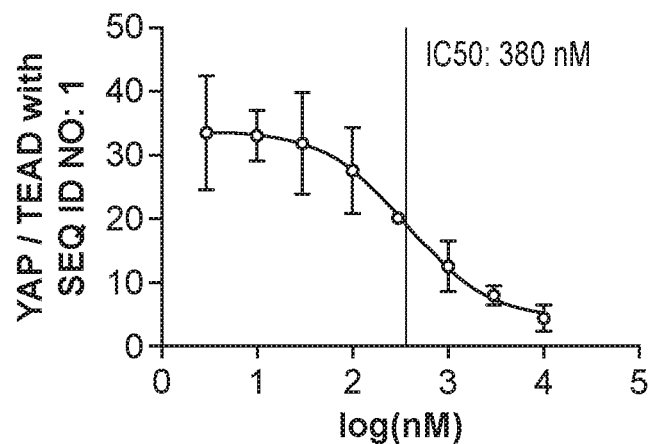
FIG. 6C illustrates quantified densitometry data plotted from FIG. 6B. Error bars show standard deviation from quantification of signal in four lanes per sample in one experiment. Amount of FLAG-YAP pulled down by Myc-TEAD beads was normalized to the Myc-TEAD signal for each sample in the Western blot.

This example describes disruption of YAP-TEAD binding by a peptide of this disclosure. A peptide of SEQ ID NO: 1 was evaluated for disruption of YAP binding to TEAD by co-immunoprecipitation. Two separate populations of HEK-293T suspension cells were transfected with either Myc-TEAD or FLAG-YAP and cells were lysed. Myc-TEAD lysate was incubated with anti-Myc resin to generated TEAD bound resin, which was subsequently incubated for 30 minutes with the YAP lysate and peptides of SEQ ID NO: 1 or SEQ ID NO: 7. Beads were washed and analyzed by a silver stain or a Western blot. A peptide of SEQ ID NO: 1, which comprises the $LX_1X_2LF$ (SEQ ID NO: 217) sequence, demonstrated the ability to bind TEAD, thereby preventing YAP from binding TEAD and being pulled down with the TEAD-bound resin. FIG. 6A illustrates a Silver stain and Western blot showing that FLAG-YAP was not pulled down with Myc-TEAD resins in the presence of a peptide of SEQ ID NO: 1, but was pulled down with the Myc-TEAD resins in the presence of a peptide of SEQ ID NO: 7. FIG. 6B illustrates a Western blot showing a dilution series of a peptide of SEQ ID NO: 1 demonstrating dose-dependent inhibition of FLAG-YAP binding to Myc-TEAD resins. FIG. 6C illustrates quantified densitometry data plotted from FIG. 6B. Error bars show standard deviation from quantification of signal in four lanes per sample in one experiment. FLAG-YAP signal was normalized to Myc-TEAD signal by taking the ratio of each of the four blot lanes of YAP signal (not shown) to the TEAD signal.

Example 8

Site Saturation Mutagenesis of Peptides

Figure 7A:
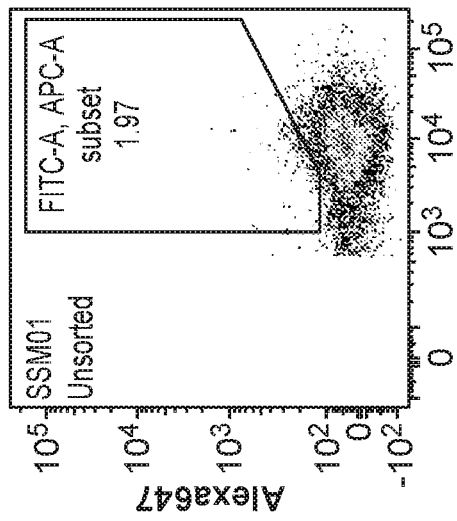
FIG. 7A illustrates a flow cytometry plot showing HEK-293 cells expressing a peptide of SEQ ID NO: 1 alone.
Figure 7B:
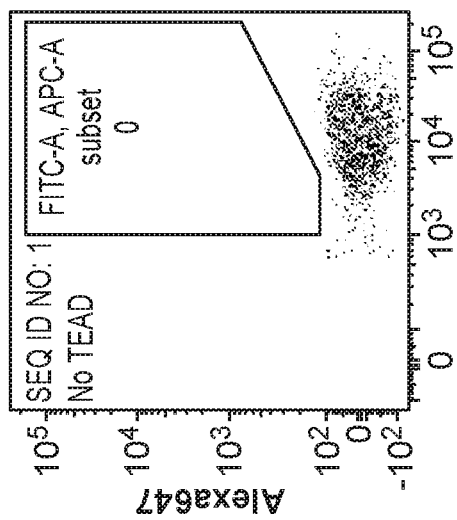
FIG. 7B illustrates a flow cytometry plot showing HEK-293 cells expressing a peptide of SEQ ID NO: 1 incubated with AF647-streptavidin alone, in the absence of biotinylated-TEAD.
Figure 7C:
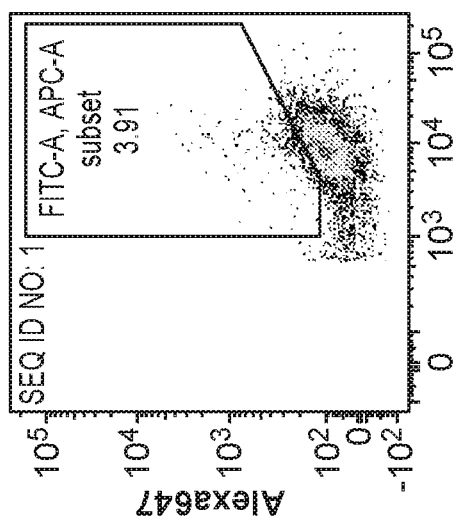
FIG. 7C illustrates a flow cytometry plot showing HEK-293 cells transduced with a library of variants of SEQ ID NO: 1 (site-saturation mutagenesis "SSM01" library containing the original peptide of SEQ ID NO: 1 and 612 variants) incubated with TEAD before sorting.
Figure 7D:
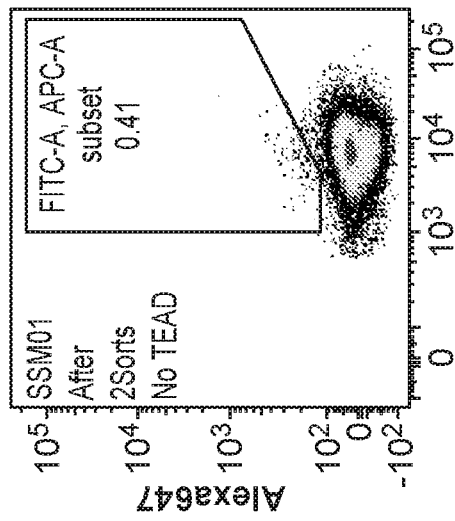
FIG. 7D illustrates a flow cytometry plot showing HEK-293 cells transduced with a library of variants of SEQ ID NO: 1 (site-saturation mutagenesis "SSM01" library containing the original peptide of SEQ ID NO: 1 and 612 variants) incubated with TEAD after one round of sorting.
Figure 7E:
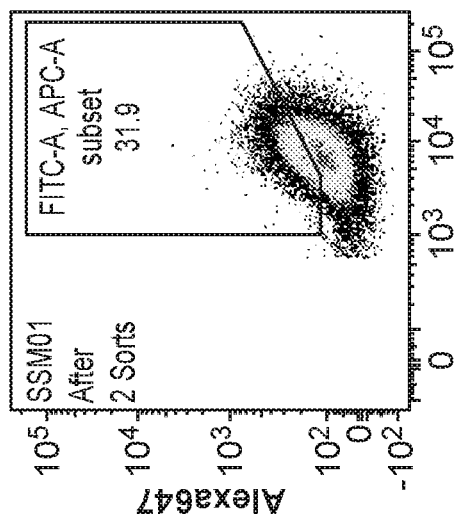
FIG. 7E illustrates a flow cytometry plot showing HEK-293 cells transduced with a library of variants of SEQ ID NO: 1 (site-saturation mutagenesis "SSM01" library containing the original peptide of SEQ ID NO: 1 and 612 variants) incubated with TEAD after two rounds of sorting.
Figure 7F:
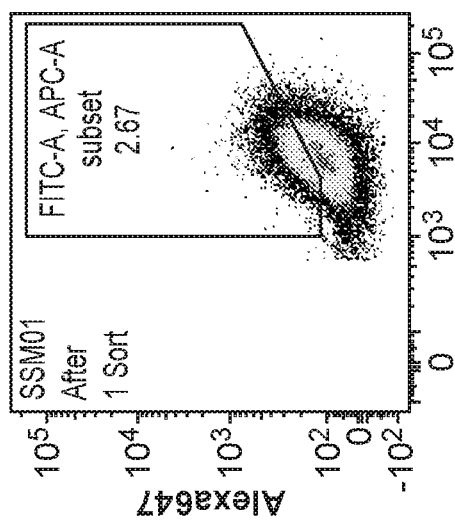
FIG. 7F illustrates a flow cytometry plot showing HEK-293 cells transduced with a library of variants of SEQ ID NO: 1 (site-saturation mutagenesis "SSM01" library containing the original peptide of SEQ ID NO: 1 and 612 variants) incubated with AF647-streptavidin alone, in the absence of biotinylated-TEAD after two rounds of sorting.

This example illustrates site saturation mutagenesis (SSM) of peptides of this disclosure to identify beneficial or deleterious mutations. Site saturation mutagenesis was performed on a peptide of SEQ ID NO: 1. All possible single amino acid substitutions of SEQ ID NO: 1 were cloned except for cysteine residues, which were conserved and not substituted. A peptide of SEQ ID NO: 1 has 34 non-cysteine residues (not counting the N-terminal "GS"). With 18 non-cysteine substitute residues possible at a given position, the SSM library contained 612 total variants of SEQ ID NO: 1, with the library also containing an un-mutated peptide of SEQ ID NO: 1. TEAD binding of mammalian cells expressing peptides of the SSM library was performed as described in EXAMPLE 4 and EXAMPLE 5, but with a higher stringency protocol. The higher stringency protocol included a lower concentration of TEAD (20 nM) and staining in two separate steps—first with biotinylated TEAD followed by AF647-streptavidin. After four rounds of sorting, nearly the entire cell population expressing variants displayed improved binding to TEAD. FIG. 7 illustrates the results of a site-saturation mutagenesis screen in SEQ ID NO: 1 variants with improved binding activity to TEAD. Flow cytometry plot show the fluorescence of peptide construct expression on the x-axis (GFP) and TEAD (AF647) on the y-axis. Double-positive cells (upper right hand quadrant) indicate peptide-expressing cells that are bound to TEAD. Panels labeled "SSM01" indicate cells transduced with the full library of peptide variants. FIG. 7A illustrates a flow cytometry plot showing HEK-293 cells expressing a peptide of SEQ ID NO: 1 alone. FIG. 7B illustrates a flow cytometry plot showing HEK-293 cells expressing a peptide of SEQ ID NO: 1 incubated with AF647-streptavidin alone, in the absence of biotinylated-TEAD. FIG. 7C illustrates a flow cytometry plot showing HEK-293 cells transduced with a library of variants of SEQ ID NO: 1 (site-saturation mutagenesis "SSM01" library containing the original peptide of SEQ ID NO: 1 and 612 variants) incubated with TEAD before sorting. FIG. 7D illustrates a flow cytometry plot showing HEK-293 cells transduced with a library of variants of SEQ ID NO: 1 (site-saturation mutagenesis "SSM01" library containing the original peptide of SEQ ID NO: 1 and 612 variants) incubated with TEAD after 1 round of sorting. FIG. 7E illustrates a flow cytometry plot showing HEK-293 cells transduced with a library of variants of SEQ ID NO: 1 (site-saturation mutagenesis "SSM01" library containing the original peptide of SEQ ID NO: 1 and 612 variants) incubated with TEAD after 2 rounds of sorting. FIG. 7F illustrates a flow cytometry plot showing HEK-293 cells transduced with a library of variants of SEQ ID NO: 1 (site-saturation mutagenesis "SSM01" library containing the original peptide of SEQ ID NO: 1 and 612 variants) incubated with AF647-streptavidin alone, in the absence of biotinylated-TEAD after two rounds of sorting. Results showed that after two rounds of sorting, double positive cells (upper right hand quadrant) were enriched, indicating enhanced inhibition of YAP-TEAD binding. FIG. 19 also illustrates the results of a site-saturation mutagenesis screen in SEQ ID NO: 1 variants with improved binding activity to TEAD. Flow cytometry plot show the fluorescence of peptide construct expression on the x-axis (GFP) and TEAD (AF647) on the y-axis. Double-positive cells (upper right hand quadrant) indicate peptide-expressing cells that are bound to TEAD. Panels labeled "SSM" indicate cells transduced with the full library of peptide variants. FIG. 19A illustrates a flow cytometry plot showing HEK-293 cells expressing a peptide of SEQ ID NO: 1 alone. SEQ ID NO: 1 binding was apparent but weak under a 20 nM TEAD concentration and 2-step staining binding conditions. FIG. 19B illustrates a flow cytometry plot showing HEK-293 cells transduced with a library of variants of SEQ ID NO: 1 (site-saturation mutagenesis "SSM" library containing the original peptide of SEQ ID NO: 1) incubated with TEAD before sorting. FIG. 19C illustrates a flow cytometry plot showing HEK-293 cells transduced with a library of variants of SEQ ID NO: 1 incubated with TEAD after 1 round of sorting. FIG. 19D illustrates a flow cytometry plot showing HEK-293 cells transduced with a library of variants of SEQ ID NO: 1 incubated with TEAD after 2 rounds of sorting. FIG. 19E illustrates a flow cytometry plot showing HEK-293 cells transduced with a library of variants of SEQ ID NO: 1 incubated with AF647-streptavidin alone, in the absence of biotinylated-TEAD, after two rounds of sorting. The distribution of TEAD-binding peptides was evaluated after two rounds of screening were completed. FIG. 8 illustrates enrichment scores at each position for the variants of SEQ ID NO: 1 generated in the site-saturation (SSM) mutagenesis screen and a structural model of the binding interface between the peptide or variant peptide and TEAD. FIG. 8A illustrates a matrix of variants of a peptide of SEQ ID NO: 1 generated in the SSM screen. The x-axis shows the sequence of a peptide of SEQ ID NO: 1, and the y-axis shows each amino acid substitution tested at each position (all non-cysteine residues). The level of enrichment for each single point mutation is indicated in the matrix table after two rounds of sorting. The enrichment score (log 2 change in relative abundance after two rounds of sorting versus input abundance) is indicated on a greyscale and as numerical values. Positive or high enrichment scores (lighter shades of grey) correspond to residues that are more tolerant to substitutions. Examples of residues that are more tolerant of substitutions include residues corresponding to positions 15, 23, and 40 in SEQ ID NO: 1. Negative or lower enrichment scores (darker shades of grey) correspond to residues that are less tolerant to substitution, such as residues that are important to binding.

FIG. 29 and FIG. 30 illustrate another representation of FIG. 8A, showing the SSM screen for improved variants of SEQ ID NO: 1, which provided insight into the structure and tolerance to mutation at each position of the peptide. In the matrix of FIG. 29 and FIG. 30 each amino acid residue of SEQ ID NO: 1 sequence is shown in the columns, with all the substituted non-Cys residues shown in the rows, after two rounds of sorting. Grey shading (or cells without numbers) indicates either the native amino acid at the position or an unchanged Cys. The level of enrichment for each single point mutation is indicated as a numerical score in the FIG. 29 and FIG. 30. FIG. 29 shows amino acid residues at positions 1-20 of SEQ ID NO: 1. FIG. 30 shows amino acid residues at positions 21-40 of SEQ ID NO: 1.

Figure 8B:
FIG. 8B illustrates a model of the SEQ ID NO: 1-TEAD interface, in which shading intensity on a greyscale correlates to the average enrichment score at each residue or position. Positive or higher enrichment scores (lighter shades of grey) correspond to residues that are more tolerant to substitutions. Negative or lower enrichment scores (darker shades of grey) correspond to residues that are less tolerant to substitution, such as residues that are important to binding. These residues are most important to retain in a peptide that is desired to block YAP-TEAD interactions; the residues more tolerant of substitution can be varied. Black indicates cysteine residues. As disclosed herein, amino acid residue position counting does not include the N-terminal GS.

Overall, G15 and G28 (present in the interhelix loop) mutations to hydrophilic amino acid residues displayed a higher enrichment score indicating better binding. This is likely due to improved folding kinetics or improved solubility. A mutation at E25 to aspartate lead better binding, and this was the most enriched variant after four rounds of screening. Mutations at Y23 were overall beneficial for improving binding, with the exception of mutations to aromatic residues. This may likely be due to the fact that the Y23 residue is in part shielded from solvent and in part exposed to solvent. Thus, substitutions to smaller aliphatic residues may improve interhelix interactions and substitutions to hydrophilic residues may improve solubility. Mutations at the P40 residue improved binding, and may be due to improved stability by eliminating the proline-induced kink in the alpha helix. FIG. 8B illustrates a model of the SEQ ID NO: 1-TEAD interface, in which shading intensity on a greyscale indicates the average enrichment score at each residue. Positive or high enrichment scores (lighter shades of grey) correspond to residues that are more tolerant to substitutions. Negative or lower enrichment scores (darker shades of grey) correspond to residues that are less tolerant to substitution, such as residues that are important to binding. Black indicates cysteine residues. This model indicated that residues exposed to solvent were more tolerant of mutations at a given position, whereas residues on the interior of the TEAD binding region or residues at the peptide-TEAD interface where less tolerant to mutations at a given position. Mutations of SEQ ID NO: 1 at G15, Y23, and P40 all resulted in average enrichment scores greater than zero.

Example 9

TEAD Binding of SSM-Generated Variant TEAD-Binding Peptides

This example describes TEAD binding of SSM-generated variant TEAD-binding peptides made in EXAMPLE 8. SSM screening generated many beneficial mutations, from which we selected five especially beneficial mutations to a peptide of SEQ ID NO: 1 including G15Q, Y23I, E25D, G28K, and P40W. Variants of SEQ ID NO: 1 with these mutations were made in which ten triple mutants were made including all combinations in which three of the five mutations described above, five quadruple mutants were made including all combinations in which four of the five mutations described above, and the quintuple mutant. The TEAD binding assays described in EXAMPLE 4 and EXAMPLE 5 tested at the same stringency as was used in EXAMPLE 8. TEAD binding assays were also described in which an extra wash step was introduced between incubation with biotinylated TEAD and incubation with the AF647-streptavidin. Altered binding due to an additional wash step informed us about the kinetics of a candidate peptide's binding, specifically the $k_{off}$ value, to TEAD.

Figure 9A:
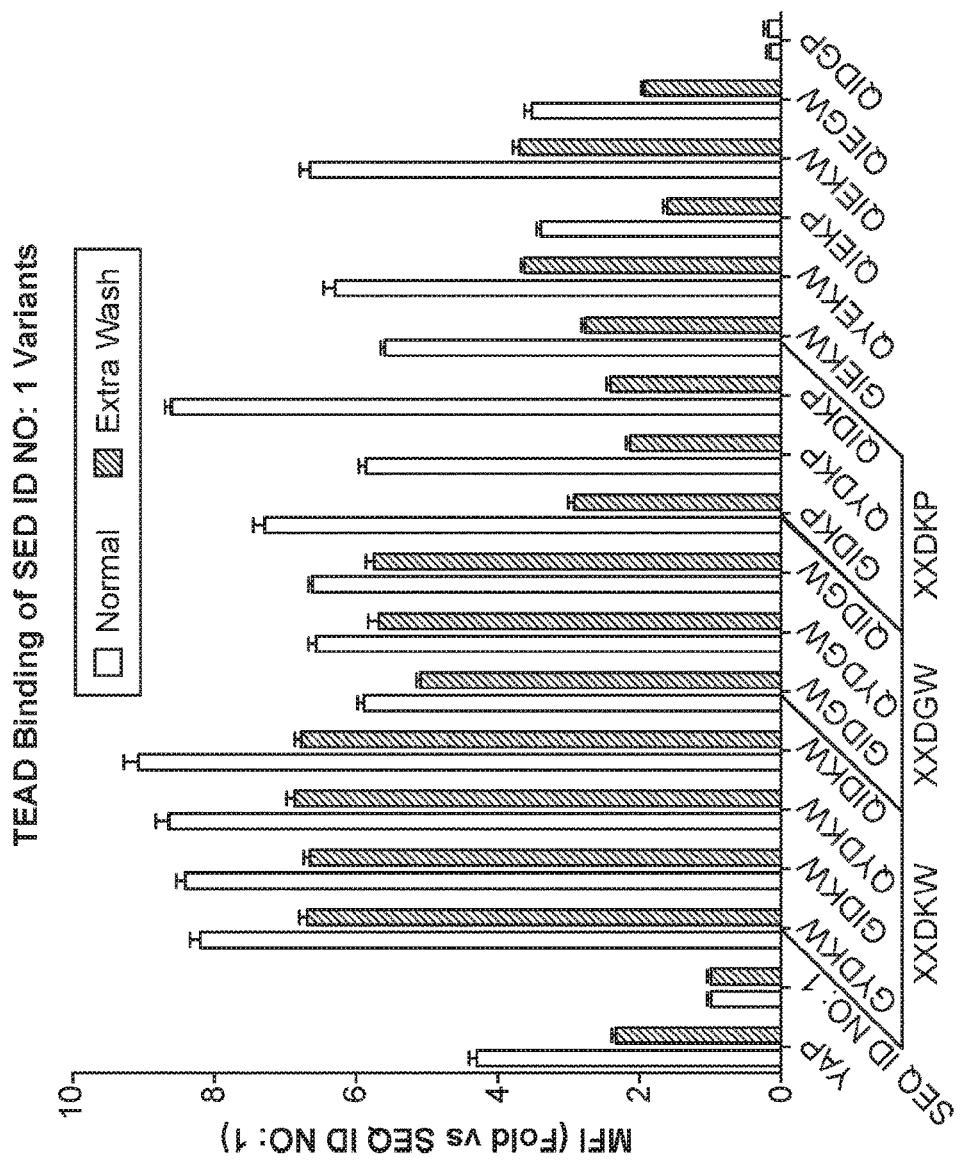
FIG. 9A illustrates a schematic of the staining protocols used to evaluate TEAD binding. Both the "Normal" and "Extra Wash" protocols used 20 nM of TEAD.
Figure 9B:
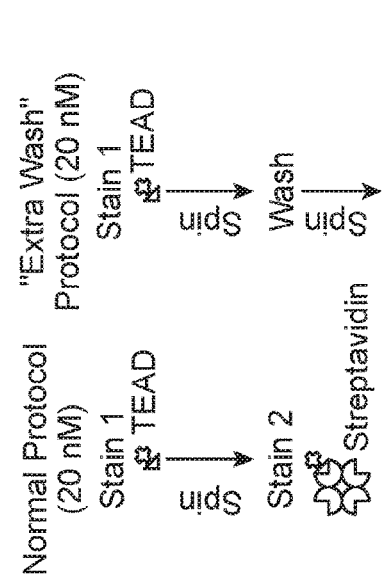
FIG. 9B illustrates flow cytometry plots showing HEK-293 suspension cells expressing SDGF-SEQ ID NO: 1, SDGF-SEQ ID NO: 9 (QIDKW variant of SEQ ID NO: 1), and YAP. Five-letter codes (e.g. QIDKW) represent variants of a peptide of SEQ ID NO: 1 at residues 15 (G or Q), 23 (Y or 1), 25 (E or D), 28 (G or K), and 40 (P or W).
Figure 9C:
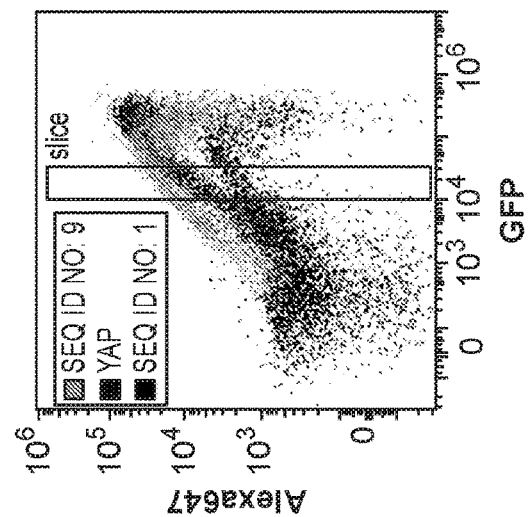
FIG. 9C illustrates quantification of the mean fluorescence intensity (MFI) of cells that fall in the "slice" gate indicated in FIG. 9B. The x-axis indicates the variant that was tested and all MFI values were normalized to the MFI value for a peptide of SEQ ID NO: 1. Shading of groups of labels on the x-axis represents clustering of mutations found in the variants, e.g., XXDKW (left most group); XXDGW (middle group); XXDKP (right most group).
Figure 10I:
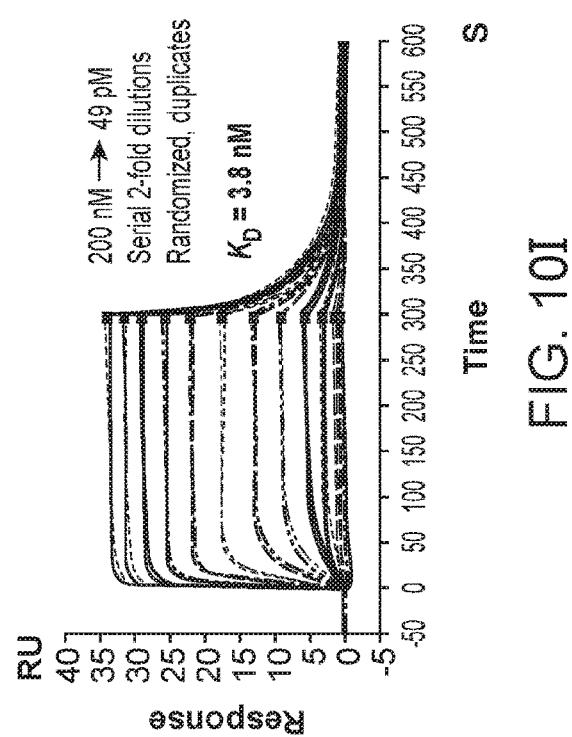
FIG. 10I illustrates SPR data showing binding of a peptide of SEQ ID NO: 11 to biotinylated TEAD immobilized on an SPR chip. SPR experiments for a peptide of SEQ ID NO: 11 were conducted by steady state analysis and the $K_D$ was determined to be 3.8 nM.
Figure 10H:
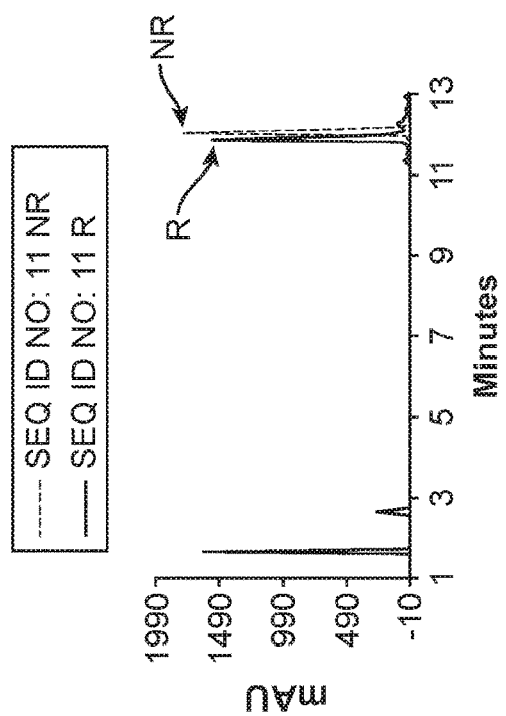
FIG. 10H illustrates an HPLC chromatogram of a peptide of SEQ ID NO: 1 in non-reduced or reduced conditions.
Figure 10G:
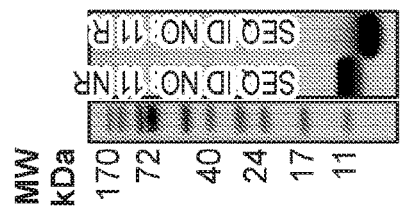
FIG. 10G illustrates an SDS-PAGE of a soluble peptide of SEQ ID NO: 11 in non-reduced (NR) or reduced (R) conditions.
Figure 11A:
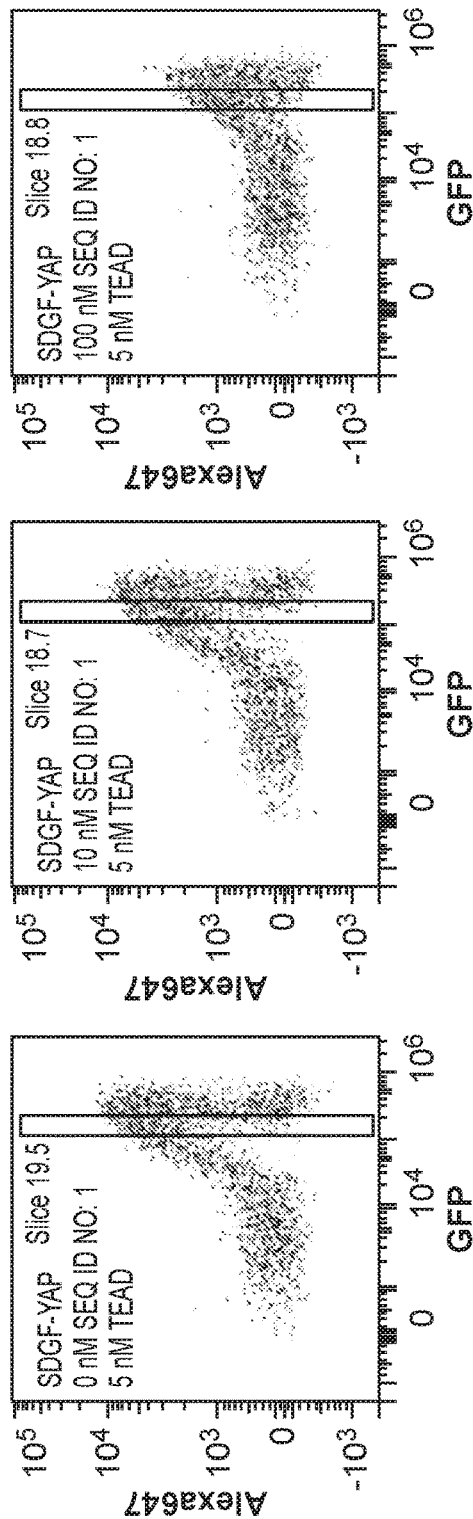
FIG. 11A illustrates flow cytometry plots showing HEK-293 suspension cells transfected with SDGF-YAP and incubated with 0 nM, 10 nM, or 100 nM of a peptide of SEQ ID NO: 1, followed by incubation with 5 nM biotinylated TEAD, and 5 nM AF647-streptavidin.
Figure 11B:
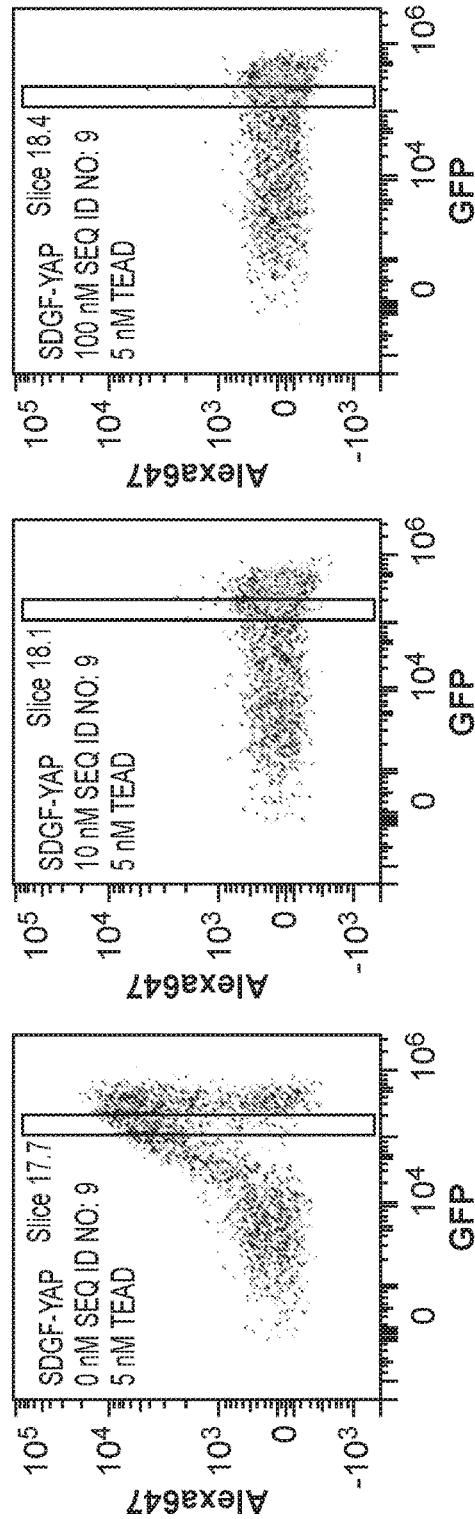
FIG. 11B illustrates flow cytometry plots showing HEK-293 suspension cells transfected with SDGF-YAP and incubated with 0 nM, 10 nM, or 100 nM of a peptide of SEQ ID NO: 9, followed by incubation with 5 nM biotinylated TEAD, and 5 nM AF647-streptavidin.
Figure 11C:
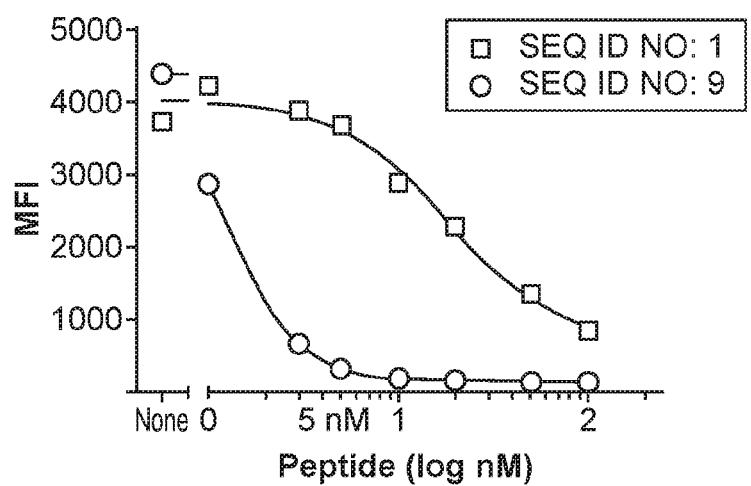
FIG. 11C illustrates a dose response curve quantifying the MFI of cells falling within the "slice" gate (representative of YAP-TEAD binding) shown in FIG. 11A and FIG. 11B. Doses below 5 nM TEAD staining does not provide data relevant to IC50 or Ki determination, as cells were stained with 5 nM TEAD.
Figure 11D:
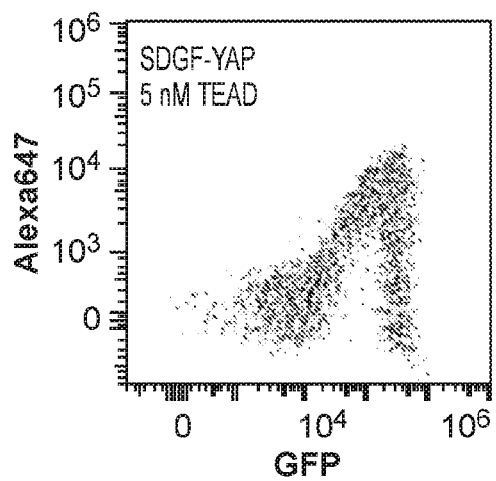
FIG. 11D illustrates a flow cytometry plot of cells expressing SDGF-YAP that were incubated with 5 nM TEAD and then washed. Cells were immediately stained with AF647-streptavidin and analyzed for YAP-expressing cells that have bound TEAD.
Figure 11E:
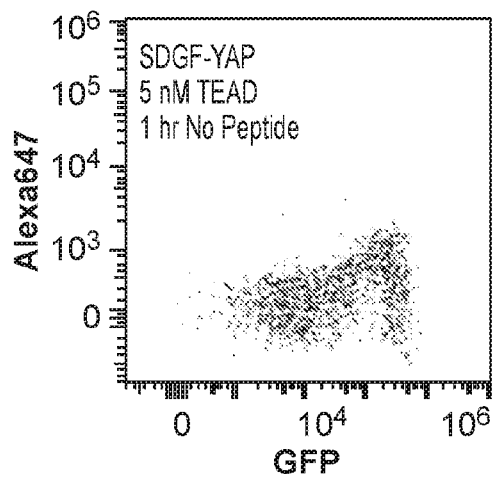
FIG. 11E illustrates a flow cytometry plot of cells expressing SDGF-YAP that were incubated with 5 nM TEAD and then washed. Cells were incubated on ice for 1 hour, stained with AF647-streptavidin and analyzed for YAP-expressing cells that have bound TEAD.
Figure 11F:
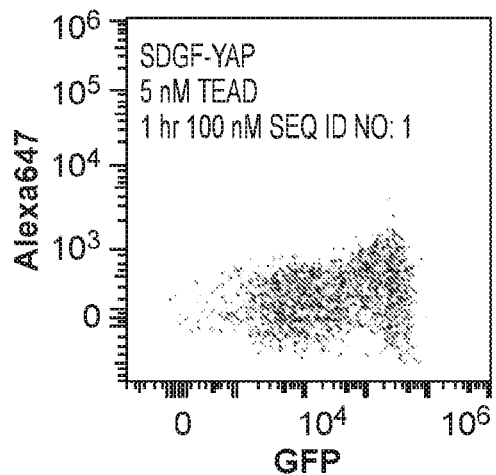
FIG. 11F illustrates a flow cytometry plot of cells expressing SDGF-YAP that were incubated with 5 nM TEAD and then washed. Cells were incubated on ice for 1 hour with 100 nM of a peptide of SEQ ID NO: 1, stained with AF647-streptavidin and analyzed for YAP-expressing cells that have bound TEAD.
Figure 11G:
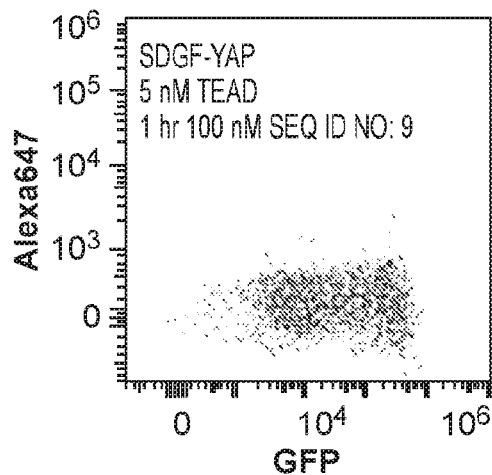
FIG. 11G illustrates a flow cytometry plot of cells expressing SDGF-YAP that were incubated with 5 nM TEAD and then washed. Cells were incubated on ice for 1 hour with 100 nM of a peptide of SEQ ID NO: 9, stained with AF647-streptavidin and analyzed for YAP-expressing cells that have bound TEAD.

FIG. 9 illustrates that combinations of enriched mutations identified in a peptide of SEQ ID NO: 1 by SSM result in improved TEAD binding. FIG. 9A illustrates a schematic of the staining protocols used to evaluate TEAD binding. Both the "Normal" and "Extra Wash" protocols use 20 nM of TEAD. FIG. 9B illustrates flow cytometry plots showing HEK-293 suspension cells expressing SDGF-SEQ ID NO: 1, SDGF-SEQ ID NO: 9 (QIDKW variant of SEQ ID NO: 1), and YAP. Five-letter codes (e.g. QIDKW) represent variants of a peptide of SEQ ID NO: 1 at residues 15 (G or Q), 23 (Y or I), 25 (E or D), 28 (G or K), and 40 (P or W). FIG. 9C illustrates quantification of the mean fluorescence intensity (MFI) of cells that fall in the "slice" gate indicated in FIG. 9B. The x-axis indicates the variant that was tested and all MFI values are normalized to the MFI value for a peptide of SEQ ID NO: 1. Shaded groups are clusters with particular combinations of mutations: XXDKW; XXDGW; XXDKP. The quintuple variant "QIDKW" performed the best, but only marginally better than those variants in which three or four mutations were made and contained at least E25D, G28K, and P40W. E25D is a conservative mutation, or, in other words, a biochemically similar mutation (i.e., glutamic acid and aspartic acid are residues with negatively charged side chains), at a salt bridge modeled to be formed with K152 on TEAD. Residue G28 of a peptide of SEQ ID NO: 1, whether or not mutated to K, does not appear to directly bind TEAD as predicted by the computational model. However, improved binding may be a result of the mutation G28K stabilizing the peptide, thereby mitigating any entropic penalty from binding and dimerization. All variants in which the E25D and P40W mutation was made but G28 was retained (XXDGW box) had only marginally lower binding than those variants containing all three mutations. All variants have the mutations E25D and G28K but retaining P40 resulted in lower binding in the screen with the extra wash step. This indicated that the P40W mutation may result in a slower off rate. Three variants were tested as soluble peptides including peptides of SEQ ID NO: 9 (quintuple mutant, G15Q, Y23I, E25D, G28K, P40W), SEQ ID NO: 10 (quadruple mutant without the G28K mutation), and SEQ ID NO: 11 (quadruple mutant without P40W). These peptides may be amphipathic, resulting in longer retention times observed by HPLC. FIG. 10 illustrates binding to TEAD by variants of a peptide of SEQ ID NO: 1 as soluble peptides. Non-reducing conditions are designated as "NR" and reducing conditions are designated as "R." FIG. 10A illustrates an SDS-PAGE of a soluble peptide of SEQ ID NO: 9 in non-reduced (NR) and reduced (R) conditions. FIG. 10B illustrates an HPLC chromatogram of a peptide of SEQ ID NO: 9 in non-reduced or reduced conditions. In FIG. 10B, FIG. 10E, and FIG. 10H, early peaks (<3 mins) seen on the reduced (R) peptide HPLC chromatograms are reduced and oxidized DTT species. FIG. 10C illustrates SPR data showing binding of a peptide of SEQ ID NO: 9 to biotinylated TEAD immobilized on an SPR chip. SPR experiments for a peptide of SEQ ID NO: 9 were conducted by single cycle kinetic analysis and the $K_D$ was determined to be 368 µM. FIG. 10D illustrates an SDS-PAGE of a soluble peptide of SEQ ID NO: 10 in non-reduced (NR) or reduced (R) conditions. FIG. 10E illustrates an HPLC chromatogram of a peptide of SEQ ID NO: 10 in non-reduced or reduced conditions. FIG. 10F illustrates SPR data showing binding of a peptide of SEQ ID NO: 10 to biotinylated TEAD immobilized on an SPR chip. SPR experiments for a peptide of SEQ ID NO: 10 were conducted by single cycle kinetic analysis and the $K_D$ was determined to be 372 µM. FIG. 10G illustrates an SDS-PAGE of a soluble peptide of SEQ ID NO: 11 in non-reduced (NR) and reduced (R) conditions. FIG. 10H illustrates an HPLC chromatogram of a peptide of SEQ ID NO: 11 in non-reduced or reduced conditions. FIG. 10I illustrates SPR data showing binding of a peptide of SEQ ID NO: 11 to biotinylated TEAD immobilized on an SPR chip. SPR experiments for a peptide of SEQ ID NO: 11 were conducted by steady state analysis and the $K_D$ was determined to be 3.8 nM. Overall, the data also shows that the three variants had better binding to TEAD than the parent peptide of SEQ ID NO: 1. Furthermore, the diminished binding observed when the extra wash step was incorporated for a peptide of SEQ ID NO: 11 as opposed to what was observed for SEQ ID NO: 9 and SEQ ID NO: 10, was driven by the faster off rate of a peptide of SEQ ID NO: 11.

Example 10

Competitive Binding of Peptides to TEAD Versus Cell Surface-Displayed YAP

This example describes competitive binding of peptides of this disclosure to TEAD, or disruption of TEAD binding to surface-displayed YAP. HEK-293 suspension cells expressing SDGF-YAP were first incubated with either a peptide of SEQ ID NO: 1 or SEQ ID NO: 9. The cell culture was next stained with 5 nM of biotinylated TEAD as shown in FIG. 11.

FIG. 11 illustrates inhibition of YAP binding to TEAD with a soluble peptide of SEQ ID NO: 9 as compared to inhibition of YAP binding to TEAD with a soluble peptide of SEQ ID NO: 1. FIG. 11A illustrates flow cytometry plots showing HEK-293 suspension cells transfected with SDGF-YAP and incubated with 0 nM, 10 nM, or 100 nM of a peptide of SEQ ID NO: 1, followed by incubation with 5 nM biotinylated TEAD, and 5 nM AF647-streptavidin. FIG. 11B illustrates flow cytometry plots showing HEK-293 suspension cells transfected with SDGF-YAP and incubated with 0 nM, 10 nM, or 100 nM of a peptide of SEQ ID NO: 9, followed by incubation with 5 nM biotinylated TEAD, and 5 nM AF647-streptavidin. FIG. 11C illustrates a dose response curve quantifying the MFI of cells falling within the "slice" gate shown in FIG. 11A and FIG. 11B. Doses below 5 nM TEAD staining does not provide data relevant to IC50 or Ki determination, as cells were stained with 5 nM TEAD. FIG. 11D illustrates a flow cytometry plot of cells expressing SDGF-YAP that were incubated with 5 nM TEAD and then washed. Cells were immediately stained with AF647-streptavidin and analyzed for YAP-expressing cells that have bound TEAD. FIG. 11E illustrates a flow cytometry plot of cells expressing SDGF-YAP that were incubated with 5 nM TEAD and then washed. Cells were incubated on ice for 1 hour, stained with AF647-streptavidin and analyzed for YAP-expressing cells that have bound TEAD. FIG. 11F illustrates a flow cytometry plot of cells expressing SDGF-YAP that were incubated with 5 nM TEAD and then washed. Cells were incubated on ice for 1 hour with 100 nM of a peptide of SEQ ID NO: 1, stained with AF647-streptavidin and analyzed for YAP-expressing cells that have bound TEAD. FIG. 11G illustrates a flow cytometry plot of cells expressing SDGF-YAP that were incubated with 5 nM TEAD and then washed. Cells were incubated on ice for 1 hour with 100 nM of a peptide of SEQ ID NO: 9, stained with AF647-streptavidin and analyzed for YAP-expressing cells that have bound TEAD.

The results of flow cytometry analysis of the competitive binding assay demonstrated that ~30 nM of a peptide of SEQ ID NO: 1 resulted in half-maximal inhibition of TEAD binding to YAP. This confirmed previously obtained results as shown in EXAMPLE 6, in which it was determined that a peptide of SEQ ID NO: 1 had a $K_D$ of 31 nM. The results of flow cytometry analysis of the competitive binding assay also demonstrated that a peptide of SEQ ID NO: 9 resulted in near complete elimination of TEAD binding to YAP, as indicated by the lack of staining of YAP-displaying cells by TEAD-AF647. The same results of near complete elimination of TEAD binding to YAP was also observed when YAP-displaying cells are first incubated with TEAD prior to the addition of a peptide of SEQ ID NO: 9.

Example 11

Peptide Stability in Reducing Conditions

Figure 12A:
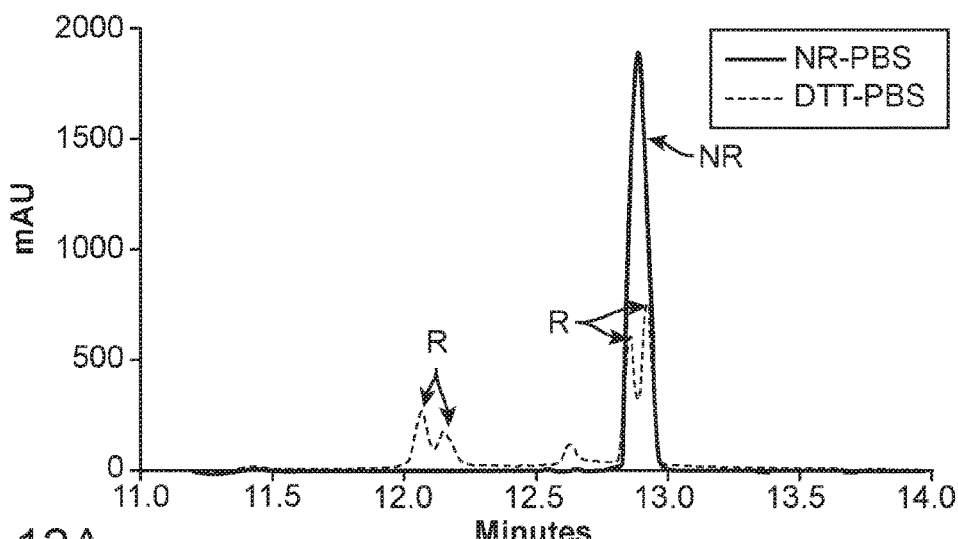
FIG. 12A illustrates HPLC chromatograms of a peptide of SEQ ID NO: 9 in non-reducing conditions or in 10 mM DTT reducing conditions. Under the HPLC chromatogram is a total ion chromatogram showing the various peaks of SEQ ID NO: 9 after exposure to DTT. A representative mass spectrometry peak profile is shown under the total ion chromatogram.
Figure 12B:
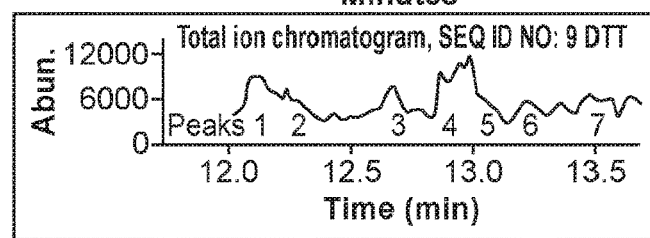
FIG. 12B illustrates HPLC chromatograms of peptides of SEQ ID NO: 1 and SEQ ID NO: 9 with or without incubation in 10 mM glutathione (GSH).
Figure 12B:
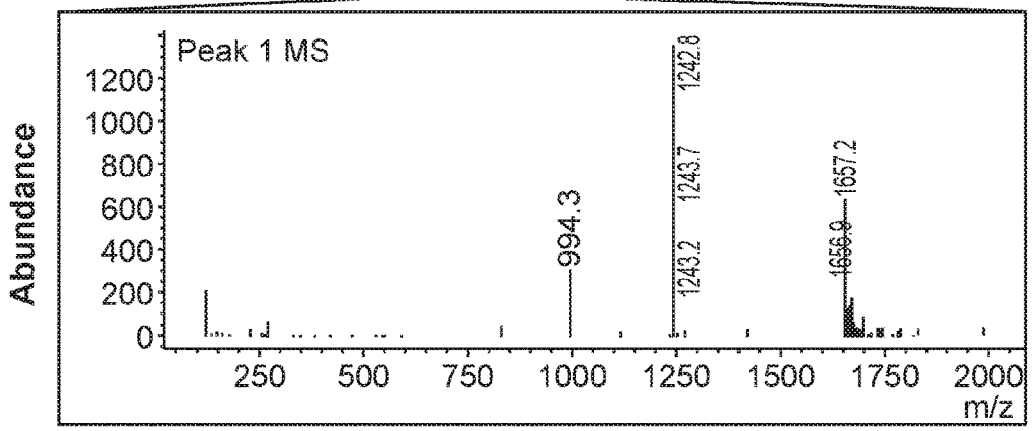
Figure 12B:
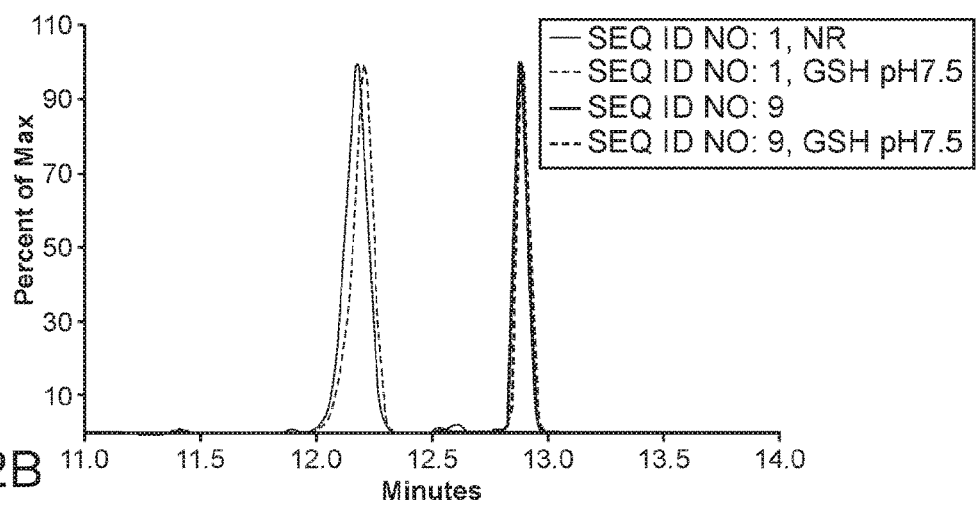

This example describes stability of peptides under reducing conditions. Peptides that target TEAD in the nucleus are exposed to reducing conditions in the cytosolic compartment of cells. Thus, it is advantageous for peptides of this disclosure to display stability in reducing conditions. Stability of peptides of this disclosure was tested in 10 mM DTT and 10 mM GSH. GSH is a more physiologically relevant reducing agent for testing peptide stability in intracellular conditions. As shown in FIG. 12B, when peptides of SEQ ID NO: 1 and SEQ ID NO: 9 were exposed to reducing conditions under GSH, a reducing agent that is more representative of the reducing environment in the cellular cytosolic compartment, both SEQ ID NO: 1 and SEQ ID NO: 9 were resistant to GSH reducing conditions, as neither peptide displayed peaks that were significantly shifted as observed by HPLC in comparison to non-reduced peptides. In a stronger reducing condition, such as in 10 mM DTT, as shown in FIG. 10B, a peptide of SEQ ID NO: 9 was partially resistant to DTT reduction. In line mass spectrometry of a peptide of SEQ ID NO: 9 in DTT reducing conditions revealed fragments within ~6 Da of the non-reduced peptide, thus demonstrating that a peptide of SEQ ID NO: 9 is partially resistant to reduction in DTT.

FIG. 12 illustrates stability of TEAD-binding peptides to reducing agents. FIG. 12A illustrates HPLC chromatograms of a peptide of SEQ ID NO: 9 in non-reducing conditions and in 10 mM DTT reducing conditions. A representative mass spectrometry peak profile is shown in the inset. FIG. 12B illustrates HPLC chromatograms of peptides of SEQ ID NO: 1 and SEQ ID NO: 9 in with or without incubation in 10 mM glutathione (GSH).

Figure 13A:
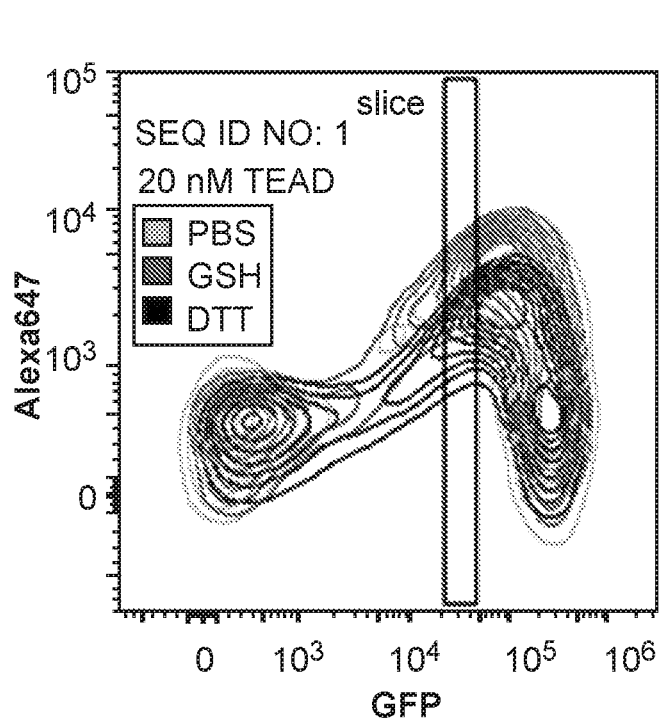
FIG. 13A illustrates a flow cytometry plot showing binding of HEK-293 suspension cells transfected with SDGF-SEQ ID NO: 1 (GFP) incubated for 5 minutes in PBS, 10 mM DTT, or 10 mM glutathione (GSH) before staining with 20 nM biotinylated TEAD, followed by a wash and then incubation with 20 nM AF647-streptavidin.
Figure 13B:
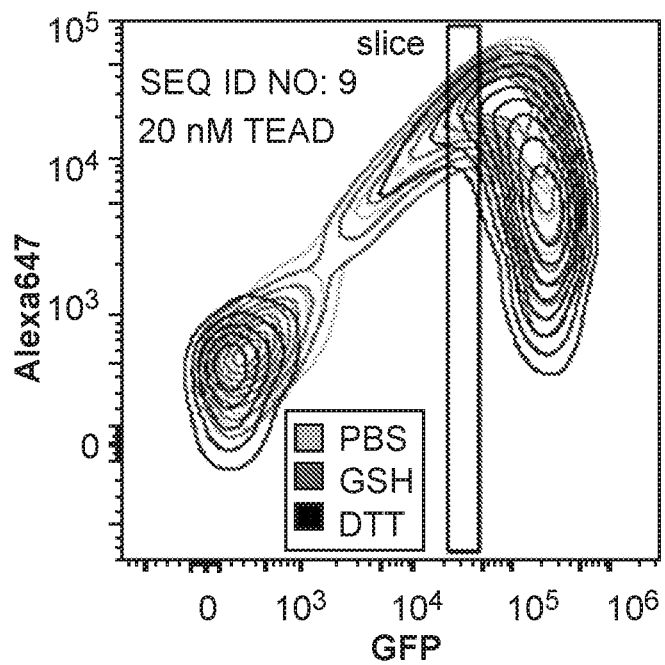
FIG. 13B illustrates a flow cytometry plot showing binding of HEK-293 suspension cells transfected with SDGF-SEQ ID NO: 9 (GFP) incubated for 5 minutes in PBS, 10 mM DTT, or 10 mM glutathione (GSH) before staining with 20 nM biotinylated TEAD, followed by a wash and then incubation with 20 nM AF647-streptavidin.
Figure 13C:
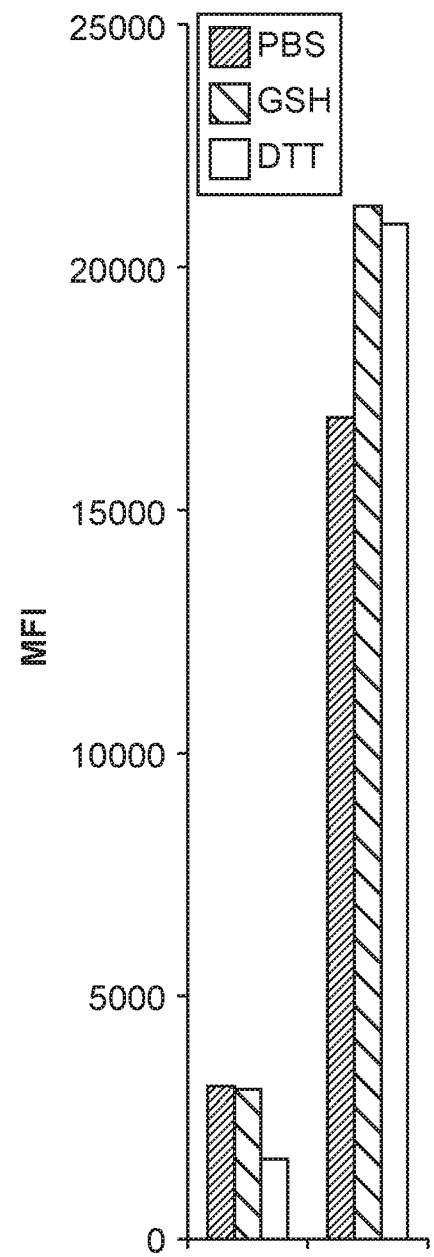
FIG. 13C illustrates quantification of the AF647 MFI of cells falling within the "slice" gate shown in FIG. 13A and FIG. 13B.

Peptides of this disclosure were also tested to evaluate if binding to TEAD was affected by exposure of peptide to reducing conditions. HEK-293T suspension cells were incubated with SDGF-SEQ ID NO: 1 or SDGF-SEQ ID NO: 9. Cultures were grown for two days followed by incubation in 10 mM GSH or 10 mM DTT. Finally, cells were stained with TEAD. FIG. 13 illustrates binding to TEAD after cells expressing SDGF-SEQ ID NO: 9 are exposed to a reducing agent. FIG. 13A illustrates a flow cytometry plot showing binding of HEK-293 suspension cells transfected with SDGF-SEQ ID NO: 1 (GFP) incubated for 5 minutes in PBS, 10 mM DTT, or 10 mM glutathione (GSH) before staining with 20 nM biotinylated TEAD and 20 nM AF647-streptavidin. FIG. 13B illustrates a flow cytometry plot showing binding of HEK-293 suspension cells transfected with SDGF-SEQ ID NO: 9 (GFP) incubated for 5 minutes in PBS, 10 mM DTT, or 10 mM glutathione (GSH) before staining with 20 nM biotinylated TEAD and 20 nM AF647-streptavidin. FIG. 13C illustrates quantification of the AF647 MFI of cells falling within the "slice" gate shown in FIG. 13A and FIG. 13B. The results of the binding assay indicated that cells displaying a peptide of SEQ ID NO: 1 showed partial loss in binding to TEAD after DTT treatment and no loss in binding to TEAD after GSH treatment. The results of the binding assay also indicated that cells displaying a peptide of SEQ ID NO: 9 showed no loss in binding to TEAD regardless of whether DTT or GSH was used as the reducing agent.

Example 12

Peptide Stability to Protease

This example illustrates stability of peptides of this disclosure to proteases. Tumor environments generally contain a high amount of proteases. Furthermore, resistance to proteolysis (degradation or cleaving by proteases) reduces the likelihood that a peptide will be degraded and then displayed to the immune system by MHC. In addition, resistance to proteolysis can increase peptide half-life in serum after administration prior to trafficking to a tumor. Thus, it is advantageous for peptides of the present disclosure to be resistant to degradation by proteases.

Soluble peptides were exposed to 500 U/mL porcine trypsin and analyzed by HPLC. Protease resistance was also assessed by using SDPR-displaying peptides. The SDPR vector is similar to the SDGF vector, but contains a C-terminal 6×His tag (SEQ ID NO: 284) and all basic or aromatic amino acid residues on the stalk removed. Protease resistance is then tested by incubation of cells displaying peptides with trypsin or chymotrypsin, followed by incubation in 10 mM DTT, and staining with an anti-6×His fluorophore-labeled antibody. If peptides are uncleaved, they retain the His tag and are stained with by the antibody. A control protease-sensitive knottin peptide (SK) was used as a positive control. Cells displaying peptides were treated with up to 40 µg/ml trypsin or chymotrypsin.

FIG. 14 illustrates protease resistance of a peptide of SEQ ID NO: 9. FIG. 14A illustrates HPLC chromatograms of a peptide of SEQ ID NO: 9 after incubation with 500 U trypsin (T), which was then quenched with trypsin inhibitor (I) and placed in non-reducing (NR) conditions or reducing (R) conditions with 10 mM DTT. The products were then run on HPLC. The chromatograms appear similar (though not identical) to those seen in experiments lacking trypsin. FIG. 14B illustrates a schematic of the SDPR vector, a variant of the SDGF vector shown in FIG. 2A, but with all basic or aromatic residues within the stalk removed to prevent trypsin/chymotrypsin cleavage, and with a 6×His (SEQ ID NO: 284) tag added to the C-terminus. In the schematic of FIG. 14B, the modified surface display vector was designed to be capable of assessment of protease or reduction resistance, which can be accomplished by staining for anti-6× His. In various embodiments, in experiments using this construct, cells expressing the constructs can be incubated with a protease, such as trypsin or chymotrypsin, followed by treatment with a reducing agent. After treatment with the protease and reducing agent, any linearized peptide product or degradation product resulting from reduction and/or proteolysis by treatment with a protease can be detected or analyzed by staining against the 6×His tag (SEQ ID NO: 284). For example, a peptide can become linearized in the presence of a reducing agent, which can make it more susceptible to proteolysis, or a reduction-resistant peptide can be cleaved by a protease. The presence of a single cleavage event in the peptide backbone can result in a linearized, displayed peptide, which can lose the 6×His tag (SEQ ID NO: 284) on the C-terminus, causing cells with such peptides to lose staining against 6×His (SEQ ID NO: 284).

Figure 14A:
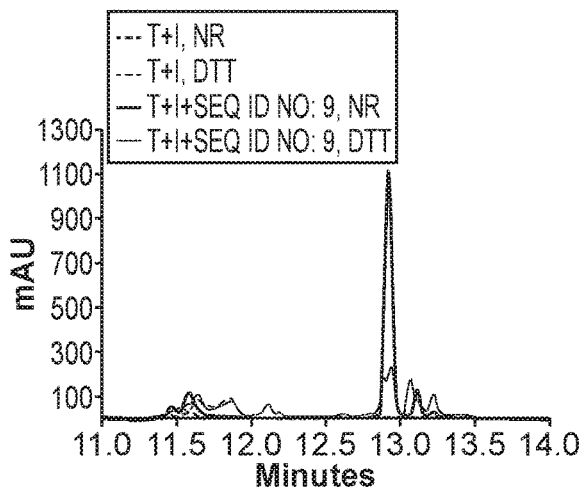
FIG. 14A illustrates HPLC chromatograms of a peptide of SEQ ID NO: 9 after incubation with 500 U trypsin (T), which was then quenched with trypsin inhibitor (I) and placed in non-reducing (NR) conditions or reducing (R) conditions with 10 mM DTT.
Figure 14B:
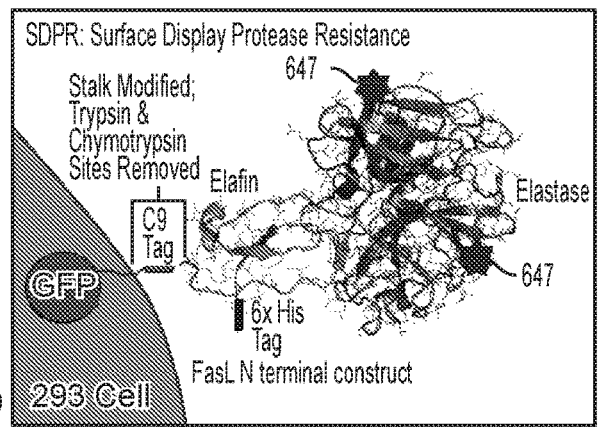
FIG. 14B illustrates a schematic of the SDPR vector, a variant of the SDGF vector shown in FIG. 2A, but with all basic and aromatic residues within the stalk removed to prevent trypsin/chymotrypsin cleavage, and with a 6×His tag (SEQ ID NO: 284) added to the C-terminus of the peptide. Elafin is shown as an example for illustrative purpose.
Figure 14C:
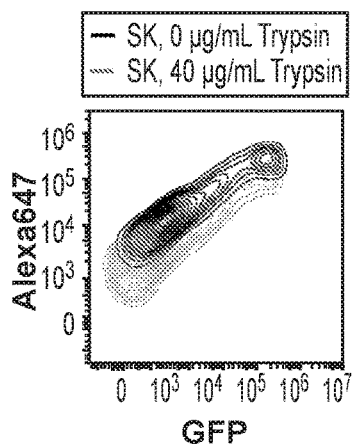
FIG. 14C illustrates a flow cytometry plot of HEK-293 suspension cells transfected with protease sensitive SDPR-SK peptide and 0 or 40 µg/ml trypsin for 20 minutes, and stained with an AF647 anti-6×HIS antibody.
Figure 14D:
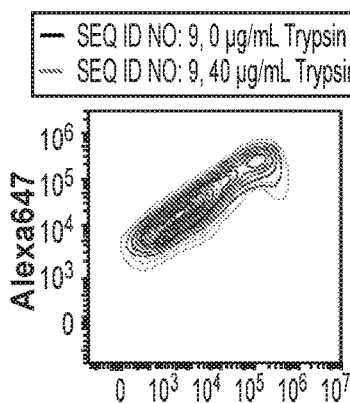
FIG. 14D illustrates a flow cytometry plot of HEK-293 suspension cells transfected with SDPR-SEQ ID NO: 9 peptide and 0 or 40 µg/ml trypsin for 20 minutes, and stained with an AF647 anti-6×HIS antibody.
Figure 14G:
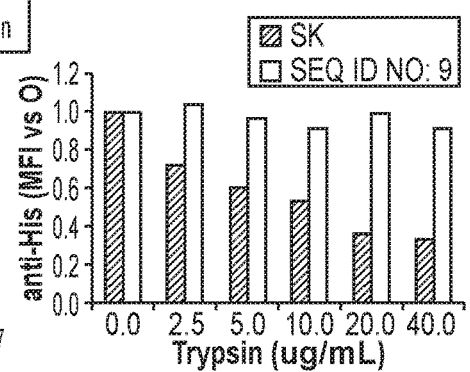
FIG. 14G illustrates quantification of flow cytometry data comparing SDPR-SK peptide transfected cells and SDPR-SEQ ID NO: 9 peptide transfected cells, both incubated with trypsin at various concentrations.
Figure 14E:
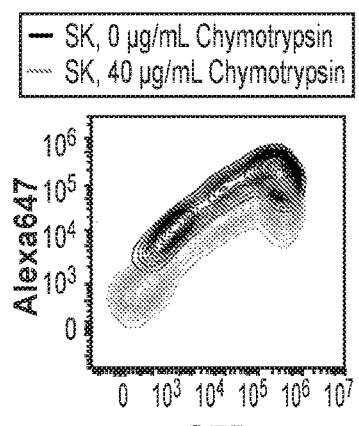
FIG. 14E illustrates a flow cytometry plot of HEK-293 suspension cells transfected with SDPR-SK peptide and 0 or 40 µg/ml chymotrypsin for 20 minutes, and stained with an AF647 anti-6×HIS antibody.
Figure 14F:
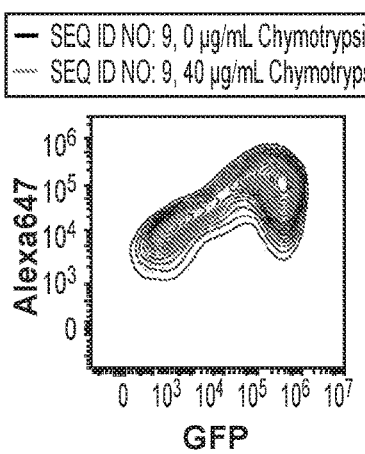
FIG. 14F illustrates a flow cytometry plot of HEK-293 suspension cells transfected with protease sensitive SDPR-SEQ ID NO: 9 peptide and 0 or 40 µg/ml chymotrypsin for 20 minutes, and stained with an AF647 anti-6×HIS antibody.
Figure 14H:
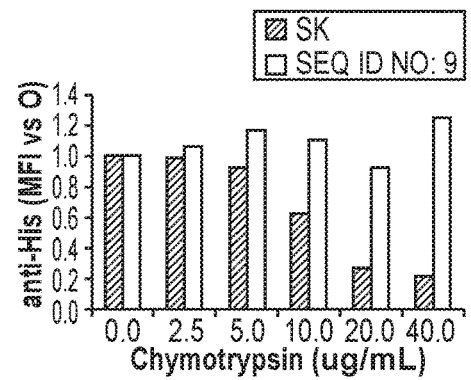
FIG. 14H illustrates quantification of flow cytometry data comparing SDPR-SK peptide transfected cells and SDPR-SEQ ID NO: 9 peptide transfected cells, both incubated with chymotrypsin at various concentrations.

FIG. 14C, FIG. 14D, FIG. 14E, and FIG. 14F illustrate the flow cytometry analyses of HEK-293 suspension cells transfected with either a protease sensitive knottin peptide SK cloned into the SDPR construct (SDPR-SK) or SEQ ID NO: 9 cloned into the SDPR construct, and treated with 0 or 40 µg/ml trypsin or chymotrypsin for 20 minutes, and then stained with an AF647 anti-6×HIS antibody. Loss of anti-6×HIS signal is indicative of peptide destabilization or degradation. FIG. 14C illustrates a flow cytometry plot of HEK-293 suspension cells transfected with protease sensitive SDPR-SK peptide and then treated with 0 or 40 µg/ml trypsin for 20 minutes, and stained with an AF647 anti-6× HIS antibody. In FIG. 14C, a knottin previously characterized as protease-sensitive (SK), displayed a loss of staining after treatment with trypsin or chymotrypsin (visualized as a reduction in APC signal when cells are stained with Alexa647-conjugated anti-6×His antibody. FIG. 14D illustrates a flow cytometry plot of HEK-293 suspension cells transfected with SDPR-SEQ ID NO: 9 peptide and then treated with 0 or 40 µg/ml trypsin for 20 minutes, and stained with an AF647 anti-6×HIS antibody. FIG. 14E illustrates a flow cytometry plot of HEK-293 suspension cells transfected with protease sensitive SDPR-SK peptide and then treated with 0 or 40 µg/ml chymotrypsin for 20 minutes, and stained with an AF647 anti-6×HIS antibody. FIG. 14F illustrates a flow cytometry plot of HEK-293 suspension cells transfected with SDPR-SEQ ID NO: 9 peptide and then treated with 0 or 40 µg/ml chymotrypsin for 20 minutes, and stained with an AF647 anti-6×HIS antibody. FIG. 14G illustrates quantification of flow cytometry data comparing SDPR-SK peptide transfected cells and SDPR-SEQ ID NO: 9 peptide transfected cells, both treated with trypsin at various concentrations. FIG. 14H illustrates quantification of flow cytometry data comparing SDPR-SK peptide transfected cells and SDPR-SEQ ID NO: 9 peptide transfected cells, both treated with chymotrypsin at various concentrations. The results of exposure to protease indicated that a peptide of SEQ ID NO: 9 was partially resistant to cleavage by proteases.

Example 13

Peptide Radiolabeling

This example describes the radiolabeling of peptides. Several peptides were radiolabeled by reductive methylation with $^{14}C$ formaldehyde and sodium cyanoborohydride with standard techniques (such as those described in Jentoft et al. J Biol Chem. 254(11):4359-65. 1979). The sequences were engineered to have the amino acids, "G" and "S" at the N terminus. See Methods in Enzymology V91:1983 p. 570 and JBC 254(11):1979 p. 4359. An excess of formaldehyde was used to drive complete methylation (dimethylation of every free amine). The labeled peptides were isolated via solid-phase extraction on Strata-X columns (Phenomenex 8B-S100-AAK), rinsed with water with 5% methanol, and recovered in methanol with 2% formic acid. Solvent was subsequently removed in a blowdown evaporator with gentle heat and a stream of nitrogen gas.

Example 14

Peptide Detectable Agent Conjugates

This example describes the dye labeling of peptides. A peptide of the disclosure is expressed recombinantly or chemically synthesized, and then the N-terminus of the peptide is conjugated to, linked to, or fused to a detectable agent via an NHS ester using DCC or EDC to produce a peptide-detectable agent conjugate. The detectable agent is the fluorophore dye is a cyanine dye, such as Cy5.5 or an Alexa fluorophore, such as Alexa647.

The peptide detectable agent conjugates are administered to a subject. The subject can be a human or a non-human animal. After administration, the peptide detectable agent conjugates home to the kidneys. The subject, or a biopsy from the subject, is imaged to visualize localization of the peptide detectable agent conjugates to the kidney. In some aspects, diagnosis of renal disorders is based on the visualization of the peptide detectable agent conjugates in kidneys after administration.

Example 15

Treatment of Cancer

This example illustrates treatment of cancer using peptides of the present disclosure. A peptide of the present disclosure is recombinantly expressed or chemically synthesized and used directly. The peptide is administered in a pharmaceutical composition to a subject in need thereof as a therapeutic for cancer. The peptide is selected from any one of the peptides of SEQ ID NO: 1-SEQ ID NO: 84. The peptide can be SEQ ID NO: 9. One or more peptides are administered to a subject. The subject can be a human or an animal. The pharmaceutical composition is administered intravenously, subcutaneously, intramuscularly, orally, or injected directly into the tumor microenvironment. The peptides disrupt YAP-TEAD interactions and TAZ-TEAD interactions by binding to TEAD, and precluding subsequent binding by YAP or TAZ. The peptides disrupt YAP-TEAD and TAZ-TEAD interactions by competing with bound YAP or TAZ, resulting in YAP or TAZ dissociation from TEAD and peptide binding to TEAD. The administered peptides, which disrupt YAP-TEAD and TAZ-TEAD interactions, treat a cancer condition in the subject. The cancer condition may be breast cancer, liver cancer, colon cancer, or brain cancer.

The same method can also be adapted for or used to treat diabetes Type I and II.

Example 16

Peptide Delivery by Gene Therapy-Modified Cells

This example illustrates peptide delivery by gene therapy-modified cells. Peptides of the present disclosure can be directed to the tumor microenvironment (e.g., immune infiltrates or a cancerous cell) by delivery mediated by gene therapy-modified cells. A gene therapy composition comprising a viral vector that selectively infects or targets cancer cells and carrying a gene encoding a peptide of the present disclosure can be administered to a subject to selectively express the peptide in cancer cells or a tumor. Alternatively, cells expressing the peptide of the present disclosure are modified ex vivo using gene therapy, followed by transplanting the modified cells back into the subject. The subject is a human or an animal. After transplantation, the modified cells migrate to a tumor microenvironment or cancer cells to disrupt TEAD binding in vivo. The pharmaceutical composition is administered intravenously, subcutaneously, or orally.

FIGS. 18A and 18B illustrate an example of SEQ ID NO: 1 and SEQ ID NO: 9 expression in target cells. FIG. 18A illustrates the relative luminescence units of SEQ ID NO: 1 or SEQ ID NO: 9 expressed directly into the cytosol as part of an mCherry-T2a-peptide fusion construct, co-transfected with YAP and 8×GTIIC (TEAD luciferase reporter). This was done in 24-well plate wells, in which 293F cells were transfected with 50 ng FLAG-YAP, 300 ng 8×GTIIC, and either 100 or 250 ng mCherry-T2a-peptide plasmids. *: P<0.05, : P<0.005 vs. YAP only. Reporter activity was reduced (P=0.003) when SEQ ID NO: 12 was expressed. FIG. 18B** illustrates the FLAG-tagged SEQ ID NO: 7, FLAG-tagged SEQ ID NO: 1, FLAG-tagged SEQ ID NO: 9, or FLAG-tagged SEQ ID NO: 184 in the mCherry-T2a-peptide construct SDS-PAGE gel mobility shift upon DTT reduction by Western blot (anti-FLAG M2 antibody). Shown are the bands corresponding to the size of the uncleaved fusion protein. SEQ ID NO: 184 is SEQ ID NO: 9-6×CS, in which all six cysteines were mutated to serines, simulating non-oxidizable sulfhydryls. While the FLAG-tagged, mCherry-fused versions showed a subtle, cysteine-dependent mobility shift in SDS-PAGE upon DTT reduction, the T2a-cleaved SEQ ID NO: 1 variants were not visible (FIG.

23). This suggests that the cysteines in SEQ ID NO: 1 and its variants can become oxidized to cystines in the cytosol, but its stability when directly expressed in the cytosol may be compromised without a fusion partner like mCherry.

Upon expression of the peptide, the peptide disrupts YAP/TAZ interactions with TEAD by binding to TEAD and precluding subsequent binding by YAP or TAZ, which downregulates oncogenes. The peptide disrupts YAP-TEAD and TAZ-TEAD interactions by competing with bound YAP or TAZ, resulting in YAP/TAZ dissociation from TEAD. The administered gene therapy encoding the peptide, which disrupts YAP/TAZ-TEAD interactions, is used to treat a cancer condition in the subject. The cancer condition may be breast cancer, liver cancer, colon cancer, or brain cancer.

The gene therapy can also be used to treat diabetes Type I and II using gene therapy vectors that selectively target pancreatic cells.

Example 17

Surface Plasmon Resonance (SPR) Analysis of Peptide Binding Interactions

This example illustrates surface plasmon resonance (SPR) analysis of peptide binding interactions. Various peptides of the present disclosure were analyzed for binding affinity to TEAD. Briefly, binding affinity was analyzed by SPR experiments, which were performed at 25° C. on a Biacore T100 instrument (GE Healthcare) with Series S SA chips. HBS-EP+ (10 mM HEPES, pH 7.4, 150 mM NaCl, 3 mM EDTA, 0.05% surfactant P20) was used as a running buffer in the experiments with 0.1 mg/mL bovine serum albumin (BSA). Biotinylated TEAD was injected over a flow cell at a concentration of 2 μg/mL and at a rate of 10 μL/min to capture TEAD corresponding to ~300 resonance units (RUs) on the SPR chip. A reference surface was generated by capturing a molar equivalent of biotinylated human transferrin receptor ectodomain. For peptides which were capable of reaching steady-state, serial two-fold dilutions of the peptides were prepared in the running buffer described above at concentration ranges which widely spanned and covered each peptide's $K_D$. Duplicate samples, interspersed with multiple buffer blanks, were randomly injected at 50 μL/minute with 2-5 minutes of association and 2-5 minutes of dissociation. Regeneration was accomplished by flowing buffer alone over the SPR chip. Double-referenced data were fit with either a 1:1 affinity or kinetics binding model using BIAevaluation 2.0.4 software (GE Healthcare). Two peptide samples (SEQ ID NO: 9 and SEQ ID NO: 10) were run using a single cycle kinetics protocol in the T100 Control 2.0.4 software. Serial three-fold dilutions (3.6 nM to 0.044 nM) of peptides of SEQ ID NO: 9 and SEQ ID NO: 10 were prepared in running buffer and injected at a rate of 50 μL/minute in increasing concentration order with 7 mins of injection time and 15 minutes dissociation time. Two buffer only blank cycles for referencing were run prior to peptide injection and one buffer only blank cycle followed which allowed time for complete peptide dissociation prior to the injection of the next peptide. Double-referenced data were fit with the 1:1 binding model for single cycle kinetics using BIAevaluation 2.0.4 software (GE Healthcare). TABLE 6 illustrates the SPR method conditions for assessing peptide binding to captured biotinylated TEAD.

TABLE 6

| | SPR Method Conditions | | | | | | | | |
|---|---|---|---|---|---|---|---|---|---|
| SEQ | Ligand: Captured Biotinylated TEAD Reference: Captured Biotinylated hTfR(ED) | | | | | Analyte: Peptide | | | |
| ID NO | Running Buffer | Flow Rate (μL/min) | Conc. (μg/mL) | Injection Time (s) | Capture Level (RU) | Flow Rate (μL/min) | Conc. | Injection Time (s) | Dissociation Time (s) | Analysis Model |
| 1 | HBS-EP + with 0.1 mg/mL BSA | 10 10 | 1.7 2 | 430 390 | 330 882 | 50 | 2 μM → 0.12 nM in duplicate serial 2x dilutions, random injections | 180 | 180 | Steady-State |
| 5 | HBS-EP + with 0.1 mg/mL BSA | 10 10 | 1.7 2 | 430 390 | 330 882 | 50 | 10 μM → 0.6 nM in duplicate serial 2x dilutions, random injections | 180 | 180 | Steady-State |
| 7 | HBS-EP + with 0.1 mg/mL BSA | 10 10 | 1.7 2 | 430 390 | 330 882 | 50 | 125 μM → 980 nM in duplicate serial 2x dilutions, random injections | 120 | 120 | Steady-State |
| 8 | HBS-EP + with 0.1 mg/mL BSA | 10 10 | 1.7 2 | 430 390 | 330 882 | 50 | 1 μM → 0.06 nM in duplicate serial 2x dilutions, random injections | 180 | 180 | Steady-State |

TABLE 6-continued

SPR Method Conditions

| | | Ligand: Captured Biotinylated TEAD Reference: Captured Biotinylated hTfR(ED) | | | | Analyte: Peptide | | | | |
|---|---|---|---|---|---|---|---|---|---|---|
| SEQ ID NO | Running Buffer | Flow Rate (μL/min) | Conc. (μg/mL) | Injection Time (s) | Capture Level (RU) | Flow Rate (μL/min) | Conc. | Injection Time (s) | Dissociation Time (s) | Analysis Model |
| 9 | HBS-EP + with 0.1 mg/mL BSA | 10 10 | 2 2 | 60 84 | 250 700 | 50 | 0.044, 0.133, 0.4, 1.2, 3.6 nM | 420 | 900 | Single Cycle Kinetics |
| 10 | HBS-EP + with 0.1 mg/mL BSA | 10 10 | 2 2 | 60 84 | 250 700 | 50 | 0.044, 0.133, 0.4, 1.2, 3.6 nM | 420 | 900 | Single Cycle Kinetics |
| 11 | HBS-EP+ with 0.1 mg/mL BSA | 10 10 | 2 2 | 60 84 | 250 700 | 50 | 200 nM → 49 pM in duplicate serial 2x dilutions, random injections | 300 | 300 | Steady-State |
| 11 | HBS-EP + with 0.1 mg/mL BSA | 10 10 | 2 2 | 60 84 | 250 700 | 50 | 50 nM → 390 pM in duplicate serial 2x dilutions, random injections | 300 | 300 | Kinetics 1:1 binding |

Figure 16A:
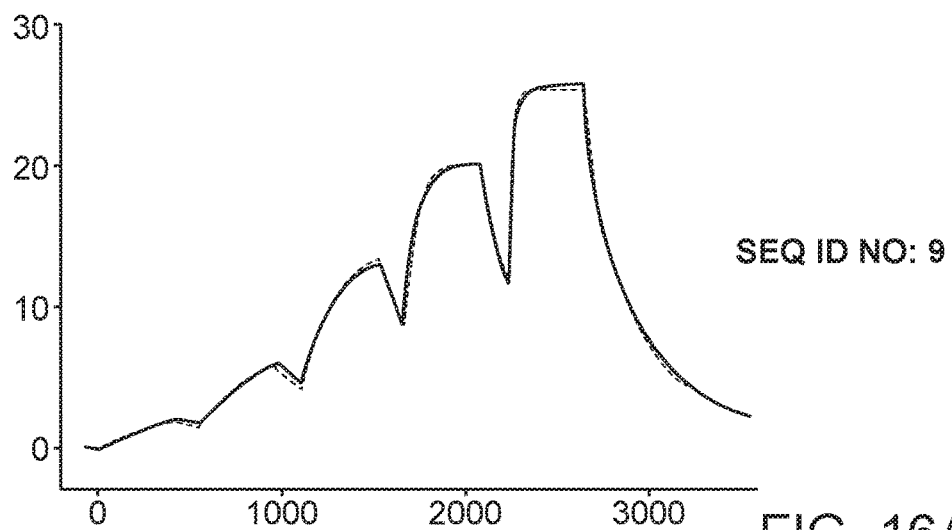
FIG. 16A illustrates binding of SEQ ID NO: 9 to TEAD using a single cycle kinetics protocol.
Figure 16B:
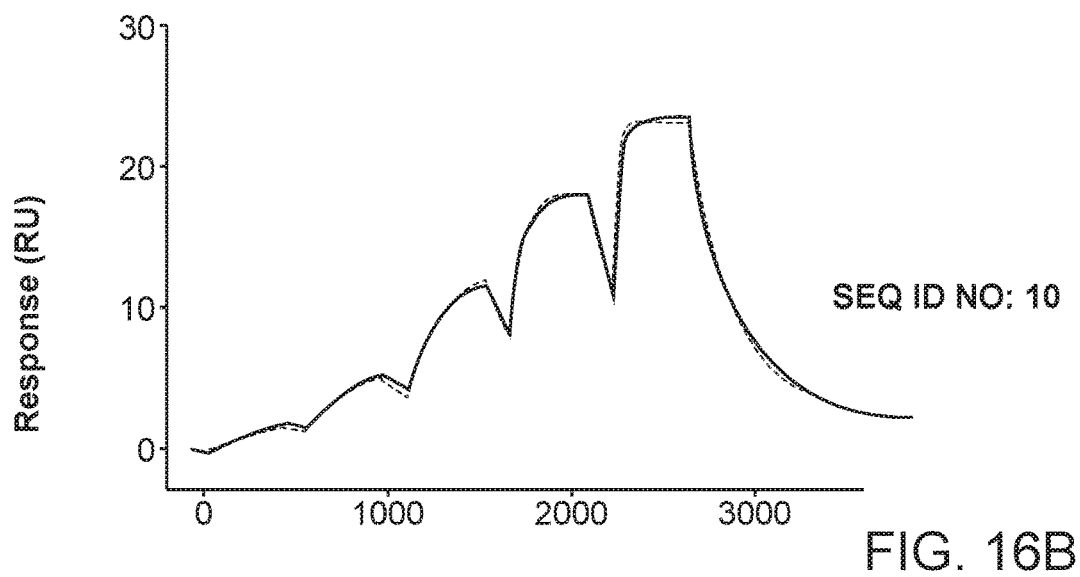
FIG. 16B illustrates binding of SEQ ID NO: 10 to TEAD using a single cycle kinetics protocol.
Figure 16C:
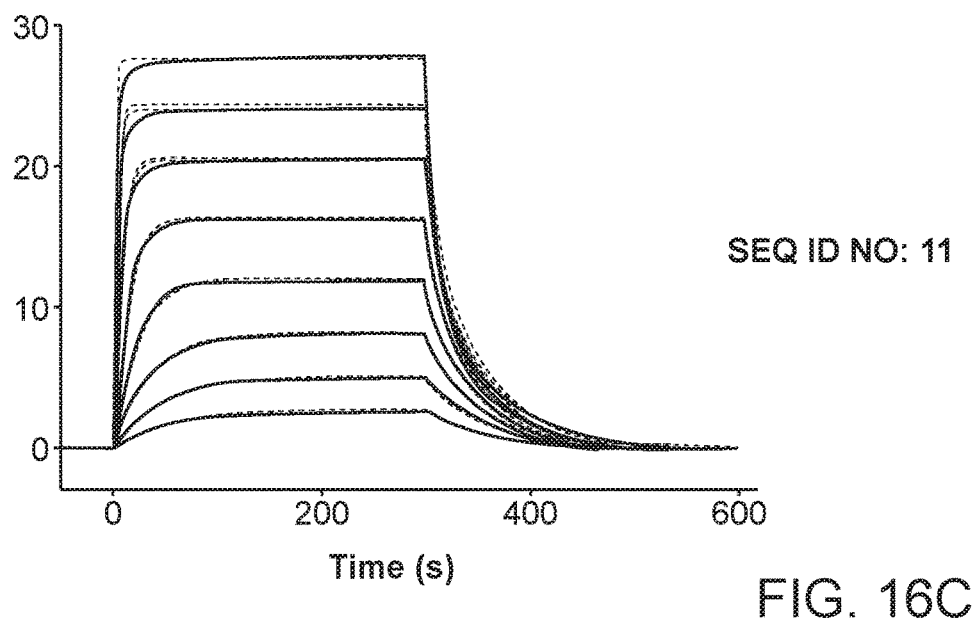
FIG. 16C illustrates binding of SEQ ID NO: 11 to TEAD using a steady-state kinetics protocol.

FIG. 15 shows the results of SPR experiments. FIG. 15A shows the raw data from SPR experiments illustrating binding of SEQ ID NO: 1 at various concentrations. FIG. 15B illustrates the data from SPR fit with the 1:1 binding model for single cycle kinetics. FIG. 15C shows the raw data from SPR experiments illustrating binding of SEQ ID NO: 5 at various concentrations. FIG. 15D illustrates the data from SPR fit with the 1:1 binding model for single cycle kinetics. FIG. 15E shows the raw data from SPR experiments illustrating binding of SEQ ID NO: 7 at various concentrations. FIG. 15F illustrates the data from SPR fit with the 1:1 binding model for single cycle kinetics. FIG. 15G shows the raw data from SPR experiments illustrating binding of SEQ ID NO: 8 at various concentrations. FIG. 15H illustrates the data from SPR fit with the 1:1 binding model for single cycle kinetics. FIG. 15I shows the raw data from SPR experiments illustrating binding of SEQ ID NO: 11 at various concentrations. FIG. 15J illustrates the data from SPR fit with the 1:1 binding model for single cycle kinetics. FIG. 16 illustrates data from SPR experiments illustrating binding of peptides of the present disclosure to TEAD. FIG. 16A illustrates binding of SEQ ID NO: 9 to TEAD using a single cycle kinetics protocol. FIG. 16B illustrates binding of SEQ ID NO: 10 to TEAD using a single cycle kinetics protocol. FIG. 16C illustrates binding of SEQ ID NO: 11 to TEAD using a steady-state kinetics protocol.

TABLE 7 shows the results of SPR experiments for each peptide tested, including quantification of association ($k_a$), dissociation ($k_d$) and the dissociation constant ($K_D$). A lower $K_D$ value indicates higher affinity and better binding.

TABLE 7

SPR Analysis Results

| SEQ ID NO | $k_a$ (M$^{-1}$ s$^{-1}$) | $k_d$ (s$^{-1}$) | $K_D$ (M) | Analysis Model |
|---|---|---|---|---|
| 1 | | | 3.1(2) × 10$^{-8}$ | Steady-State |
| 5 | | | 2.8(2) × 10$^{-7}$ | Steady-State |
| 7 | | | 2.28(5) × 10$^{-5}$ | Steady-State |
| 8 | | | 3.9(2) × 10$^{-8}$ | Steady-State |
| 9 | 2.21(2) × 10$^7$ | 8.14(6) × 10$^{-3}$ | 3.68(4) × 10$^{-10}$ | Single Cycle Kinetics |
| 10 | 2.06(2) × 10$^7$ | 7.67(7) × 10$^{-3}$ | 3.72(5) × 10$^{-10}$ | Single Cycle Kinetics |
| 11 | | | 6.3(4) × 10$^{-9}$ | Steady-State |
| 11 | 3.10(3) × 10$^7$ | 0.117(1) | 3.78(5) × 10$^{-9}$ | Kinetics 1:1 Binding |

* reported $k_a$ is approaching the limits that can be measured by the instrument Example 18

Cell-Penetrating Peptide Fusions

This example describes cell-penetrating peptide fusions. A TEAD-binding peptide of the present disclosure is recombinantly expressed as a fusion to a cell penetrating peptide moiety. The TEAD-binding peptide is selected from any one of the peptides of SEQ ID NO: 1-SEQ ID NO: 84. The cell penetrating peptide moiety is one or multiple Arg residues, such as an RRRRRRRR (SEQ ID NO: 146) sequence conjugated to, linked to, or fused at the N-terminus, or a Tat peptide with the sequence YGRKKRRQRRR (SEQ ID NO: 195) that is conjugated to, linked to, or fused to the N-terminus of any TEAD-binding peptide of the present disclosure. Alternatively, the cell penetrating peptide moiety is selected from maurocaline, imperatoxin, hadrucalcin, hemicalcin, oplicalin-1, opicalcin-2, midkine (62-104), MCoTI-II, or chlorotoxin, which is fused to the N-terminus of any TEAD-binding peptide of the present disclosure. Alternatively, the cell penetrating peptide moiety is selected from TAT (SEQ ID NO: 143), CysTAT (SEQ ID NO: 144), S19-TAT (SEQ ID NO: 145), R8 (SEQ ID NO: 146), pAntp (SEQ ID NO: 147), Pas-TAT (SEQ ID NO: 148), Pas-R8 (SEQ ID NO: 149), Pas-FHV (SEQ ID NO: 150), Pas-pAntP (SEQ ID NO: 151), F2R4 (SEQ ID NO: 152), B55 (SEQ ID NO: 153), azurin (SEQ ID NO: 154), IMT-P8 (SEQ ID NO: 155), BR2 (SEQ ID NO: 156), OMOTAG1 (SEQ ID NO: 157), OMOTAG2 (SEQ ID NO: 158), pVEC (SEQ ID NO: 159), SynB3 (SEQ ID NO: 160), DPV1047 (SEQ ID NO: 161), C105Y (SEQ ID NO: 162), transpotan (SEQ ID NO: 163), MTS (SEQ ID NO: 164), hLF (SEQ ID NO: 165), PFVYLI (SEQ ID NO: 166), or yBBR (SEQ ID NO: 167), which is fused to the N-terminus of any TEAD-binding peptide of the present disclosure. Alternatively, the cell penetrating peptide moiety is fused to the N-terminus of any TEAD-binding peptide of the present disclosure by a linker. The linker is selected from GGGSGGGSGGGS (SEQ ID NO: 210), KKYKPYVPVTTN (SEQ ID NO: 211) (linker from DkTx), or EPKSSDKTHT (SEQ ID NO: 212) (linker from human IgG3), any linker of SEQ ID NO: 203-SEQ ID NO: 212, or any other linker. Alternatively, the TEAD-binding peptide, the cell penetrating peptide moiety, and, optionally, the linker are joined by other means. For example, the other means includes, but is not limited to, chemical conjugation at any location, fusion of the cell penetrating peptide moiety and/or the linker to the C-terminus of the TEAD-binding peptide, co-formulation with liposomes, or other methods.

Cell-penetrating peptide fusions or conjugates are administered to a subject in need thereof. The subject is a human or animal and has a disease, such as cancer or diabetes (Type I or Type II). Upon administration, cell-penetrating peptide fusions traverse cellular membranes to access intracellular compartments and subsequently bind TEAD, preventing YAP association with TEAD.

Example 19

Peptide Fusions to Promote Nuclear Localization

This example describes peptide fusions to promote nuclear localization. A TEAD-binding peptide of the present disclosure is recombinantly expressed or chemically synthesized. The peptide is selected from any one of the peptides of SEQ ID NO: 1-SEQ ID NO: 84. TEAD-binding peptides are conjugated to, linked to, or fused to a nuclear localization signal, such as a four-residue sequence of K-K/R-X-K/R (SEQ ID NO: 202), wherein X can be any amino acid, or a variant thereof (Lange et al, J Biol Chem. 2007 Feb. 23; 282(8):5101-5). Peptide fusions are administered to a subject in need thereof. The subject is a human or animal and has a disease, such as cancer or diabetes (Type I or Type II). Upon administration, peptide fusions traffick to the nucleus, where they efficiently prevent YAP association with TEAD.

Example 20

Promotion of Cytosolic Delivery of a Peptide

This example describes the promotion of cytosolic delivery or cellular penetration of the peptide. A TEAD-binding peptide of the present disclosure is recombinantly expressed or chemically synthesized. The peptide is selected from any one of the peptides of SEQ ID NO: 1-SEQ ID NO: 84. TEAD-binding peptides are conjugated to, linked to, or fused to a dfTAT and/or co-delivered with dfTAT. A nuclear localization signal, such as a four-residue sequence of K-K/R-X-K/R (SEQ ID NO: 202), wherein X can be any amino acid, or a variant thereof (Lange et al, J Biol Chem. 2007 Feb. 23; 282(8):5101-5), can be further conjugated to, linked to, or fused to the TEAD-binding peptide. Peptide fusions are administered to a subject in need thereof. The subject is a human or animal and has a disease, such as cancer or diabetes (Type I or Type II). Upon administration, peptide fusions are expressed in the cytosol and interact with TEAD in the cytosol and nucleus to disrupt TEAD binding to transcription coactivators, such as YAP or TAZ.

For example, SEQ ID NO: 9 was co-administered with dfTAT, a small dimeric peptide that facilitates endosomal escape of cargoes up to 150 kDa without noticeable effects on viability or gene expression profiles. Using SEQ ID NO: 9 conjugated to DyLight 488 for visualization, co-incubation of HeLa cells with both SEQ ID NO: 9 and dfTAT yielded accumulation of SEQ ID NO: 9 in cells in a disperse pattern. More specifically, FIGS. 18-18I show that SEQ ID NO: 9 significantly reduces YAP:TEAD dimers in the nucleus. SEQ ID NO: 9-DyLight488 was introduced to the cytosol/nucleus of HeLa cells using 5 µM dfTAT, which induces endosomal leakage. dfTAT was visible in the TRITC channel (FIG. 18C), while SEQ ID NO: 9-DyLight488 was seen in the FITC channel (FIG. 18D). Proximity ligation assay (PLA) in HeLa cells was performed using primary antibodies against YAP and TEAD, in which speckles (APC channel) overlapping DAPI-stained nuclei (UV channel) were produced. FIG. 18E shows a representative image of cells treated with 5 µM dfTAT only. FIG. 18F shows a representative image of cells treated with 5 µM dfTAT and 5 µM SEQ ID NO: 9. FIG. 18G shows a representative image of a control proximity ligation assay (PLA) reaction with anti-YAP primary antibodies omitted in which some speckles were non-specific to YAP:TEAD dimers. FIG. 18H shows a representative image of a control PLA reaction with anti-TEAD primary antibodies omitted in which some speckles were non-specific to YAP:TEAD dimers. FIG. 18I illustrates a dot graph of automated counting of YAP:TEAD PLA speckles per nucleus of HeLa cells that were treated with 5 µM dfTAT and/or 5 µM TEAD-binding peptides. Each dot represents a single nucleus, with the bars representing the median ±95% confidence intervals. A line was drawn at the sum of the two antibody omission samples' average speckle counts, representing the approximate value attributable to non-specific speckles. ****: P<0.0001 vs. any other sample. All P-values were determined by two-tailed T-test. The speckles per nucleus were significantly reduced in cells that were treated with the peptide of SEQ ID NO: 9 combined with dfTAT, which is supportive that the treatment may have reduced the interactions of YAP and TEAD in the nucleus of the treated cells.

Example 21

Combination Treatment of Cancer

This example illustrates combination treatment of cancer using peptides of the present disclosure. A peptide of the present disclosure is recombinantly expressed or chemically synthesized and used directly. The peptide is administrated in a pharmaceutical composition to a subject in need thereof as a therapeutic for cancer. The peptide is selected from any one of the peptides of SEQ ID NO: 1-SEQ ID NO: 84. One or more peptides are administered to a subject along with a treatment regimen of standard small molecule or chemotherapy, such as cisplatin, methotrexate, docetaxel, and etoposide, among others. The subject is a human or an animal. The pharmaceutical composition is administered intravenously, subcutaneously, intramuscularly, orally, or injected directly into the tumor microenvironment. The peptides disrupt YAP-TEAD interactions by binding to TEAD, and precluding subsequent binding by YAP. The administered peptides with standard small molecule therapy, treats a cancer condition in the subject. The cancer condition may be breast cancer, liver cancer, colon cancer, or brain cancer.

Example 22

Analysis of Patient Cancer and Treatment with Peptides

This example illustrates analysis of a patient's cancer and treatment with peptides. Biopsies are taken from a subject in need thereof and are analyzed for mutations in the YAP/TAZ-TEAD pathway, such as mutations that result in YAP overexpression. A peptide of the present disclosure is recombinantly expressed or chemically synthesized and used directly. The peptide is administrated in a pharmaceutical composition to a subject in need thereof as a therapeutic for cancer. The peptide is selected from any one of the peptides of SEQ ID NO: 1-SEQ ID NO: 84. One or more peptides are administered to a subject. The subject is a human. The pharmaceutical composition is administered intravenously, subcutaneously, intramuscularly, orally, or injected directly into the tumor microenvironment. The peptides disrupt YAP/TAZ-TEAD interactions by binding to TEAD, and precluding subsequent binding by YAP or TAZ. The cancer condition may be breast cancer, liver cancer, colon cancer, or brain cancer.

Example 23

Mutation of Peptides to Improve Binding Affinity

This example illustrates mutation of peptides to decrease the off rate and/or increase the on rate. A peptide of the present disclosure is mutated using Site Saturation Mutagenesis (SSM) or any random mutagenesis method to decrease the off rate and/or increase the on rate, thereby increasing or improving the binding affinity. The peptide is selected from any one of the peptides of SEQ ID NO: 1-SEQ ID NO: 84. Alternatively, any one of the peptides of SEQ ID NO: 1-SEQ ID NO: 84 is mutated or grafted to comprise $LX_1X_2LF$ (SEQ ID NO: 217) sequence or motif to improve binding/antagonist activity on TEAD. The $LX_1X_2LF$ (SEQ ID NO: 217) is mutated or grafted on the peptide at any position along the sequence which allows for improve binding/antagonist activity on TEAD.

Example 24

Computational Design of a Peptide Library

The example illustrates a method for the computational design of a peptide library of scaffold peptides with three disulfide cross-links that bind to TEAD. Initial candidates were identified either by searching for specific peptide properties or through peptide design. The Rosetta software package was used for peptide design to identify de novo scaffold construction: candidate scaffold peptides with three disulfide cross-links were constructed by de novo fold design, optimizing only for folding and stability without regard to binding functionality. The input topology parameters used for scaffold construction were as follows: minimum and maximum sequence length: 30 and 41 residues, respectively; secondary structure types: helix, helix, helix; secondary structure length ranges: 6-18 residues; turn lengths: 2-4 residues; number of disulfides: 3; disulfide topology: H1-H2, H1-H3, and H2-H3. Several hundred thousand independent design simulations were performed to build a large library of candidate scaffolds, which was then be filtered by sequence-structure compatibility, packing, satisfaction of polar groups, and disulfide score. At the start of each design simulation, helix and turn lengths were sampled randomly from the corresponding length ranges, fixing the secondary structure of the design, which were then used to select backbone fragments for a low-resolution fragment assembly simulation. At the end of the low-resolution simulation, the protein backbone was scanned for residue pairs that could be linked by disulfide connections using a library of N—$C_\alpha$—C backbone transforms derived from disulfide bonds in the protein structure database. Backbones with matching residue pairs that satisfied the disulfide topology constraints were used to initiate an all-atom sequence design simulation consisting of two cycles of alternating fixed-backbone sequence design and fixed-sequence structure relaxation. Final designs were filtered for packing (sasapack score <0.5), satisfaction of buried polar groups (using a 1.0 Å probe radius), and sorted by energy per residue. The top 10% of the filtered designs were assessed for sequence-structure compatibility by an in silico refolding test in which the design sequence were used to initiate 3000 independent structure prediction simulations. Success was measured by assessing the fraction of low-energy structure prediction models within 2Å Cα-RMSD of the design model. Promising peptides identified by de novo scaffold construction, as well as 75 native knottin structures from the Protein Data Bank (PDB) of 30-50 residues in length, were then used as scaffolds for interface design targeting the YAP footprint on TEAD. Scaffold sequence redesign in the second stage targeted interface side chains while preserving the core amino acids and disulfide-forming residues. Additionally, the crystal structure of the YAP-TEAD complex (PDB ID 3KYS) was examined to identify binding patches on TEAD. Corresponding backbone elements on YAP were observed and selected to serve as templates for the interface design of each promising peptide in order to retain binding to TEAD. More specifically, the following backbone residue segments were selected as superposition targets for orienting design scaffolds: 3KYS/B/53-55, 3KYS/B/55-57, 3KYS/B/64-68, 3KYS/B/64-69, 3KYS/B/86-89, 3KYS/B/94-96 (given as: PDB ID/chain/residue numbers). For each peptide scaffold, 150 design simulations were conducted targeting each YAP backbone segment selected for superposition. Each design simulation consisted of the following steps: (1) superimposing the scaffold backbone onto the YAP backbone segment using a scaffold backbone element with matching secondary structure, (2) random small perturbations to generate diversity and relieve backbone clashes, and (3) all-atom sequence design alternating between fixed-backbone sequence selection and fixed-sequence structure relaxation. Final interface designs were filtered for satisfaction of polar groups (using a 1.0 Å probe radius), interface surface complementarity (sc score>0.5), and interface quality (predicted binding energy per 100 A of buried SASA <−1.1), and sorted by predicted binding energy. Top-scoring designs were assessed by an in silico redocking test in which the redesigned scaffold peptide was removed from TEAD, randomly reoriented, and redocked onto the TEAD protein structure. Success was measured as the fraction of low-energy redocking simulations that reached a final state close to the designed interface conformation. This process identified both SEQ ID NO: 1 and SEQ ID NO: 2 as potential soluble peptides with three disulfide cross-links that bind to TEAD, but only SEQ ID NO: 1 was found to be monodisperse and stable.

FIG. 17B illustrates the modeled TEAD interface for the YAP-TEAD structure from Protein Data Bank (PDB ID) 3KYS. FIG. 17C illustrates the modeled TEAD interface for SEQ ID NO: 1 modeled with the TEAD structure from FIG. 17A. FIG. 17D illustrates the modeled TEAD interface for SEQ ID NO: 2 modeled with the TEAD structure from FIG. 17A.

Example 25

Methods for Improving Cell Penetrance of a Peptide

This example illustrates methods for improving cell penetrance of a peptide. A peptide whose binding partner is located within a cell needs to enter/penetrate a cell in order to exert its activity.

One method to overcome this is to graft a binding interface of a designed peptide identified by the methods in EXAMPLE 24 onto a cell penetrating peptide scaffold. A naturally cell-penetrant peptide is used as the scaffold, such as a calcine or a modified cell-penetrant peptide (such as a modified calcine or calcine derivative). Some peptides that are used include, but are not limited to, imperatoxin, maurocalcine, hemicalcin, opiclacin 1, opicalcin 2, midkine (62-104), MCoTI-II, chlorotoxin, and hadrucalcin. Such scaffolds used are also modified derivatives of the foregoing calcines as described herein. As an example, the six amino acid portion of helix 3 (MLICLF; SEQ ID NO: 221), a major component of SEQ ID NO: 9 binding to TEAD, is transplanted onto a calcine scaffold and a bi-functional peptide that retains the cell penetration of the calcine with the novel SEQ ID NO: 9 TEAD binding function is produced. This method is used to improve the cell penetrance of any one of the peptides of SEQ ID NO: 1-SEQ ID NO: 84.

Alternatively, cis-acting elements, including inclusion of K/R-rich sequences like TAT or octa-arginine (SEQ ID NO: 146), intra-helical arginine patches, or fusion to larger fragments of proteins identified in cell penetration screening like penetratin or melittin are used to improve cell penetrance of a peptide. This method is used to improve the cell penetrance of any one of the peptides of SEQ ID NO: 1-SEQ ID NO: 84.

Alternately, site saturation mutagenesis is used to improve the binding of a calcine based-TEAD binding peptide. Alternatively, peptides that are not calcines but that have similar surface charge distributions to calcines are designed, containing a TEAD binding pharmacophore. As an additional alternative, selenocysteine is substituted for some or all cysteine residues in the peptides to result in bridges that are more stable to cytosolic reducing conditions than disulfide bonds. As a further alternative, activity on ryanoride receptors is mutated out of the peptide.

Example 26

Computational Design of a Cell Penetrating Peptide Library

The example illustrates a method for the computational design of a peptide library of scaffold cell penetrating peptides. Initial candidates are identified either by searching for specific peptide properties (such as cell penetration) or through peptide design. The Rosetta software package is used for peptide design to identify de novo scaffold construction: candidate cell-penetrating scaffold peptides with are constructed by de novo fold design, optimizing only for folding and stability without regard to binding functionality. Promising peptides identified by de novo scaffold construction, as well as known cell-penetrating peptides of 30-50 residues in length, are then used as scaffolds for interface design targeting the SEQ ID NO: 9 footprint on TEAD. Interface side chains of the scaffold peptide redesign sequence are targeted in the second stage preserving the core amino acids and disulfide-forming residues. Additionally, the crystal structure of the SEQ ID NO: 9-TEAD complex is examined to identify binding patches on TEAD. Corresponding backbone elements on SEQ ID NO: 9 are observed and are selected to serve as templates for the interface design of the peptide in order to retain binding to TEAD. From this, specific backbone residue segments are selected as superposition targets for orienting design scaffolds. For each peptide scaffold, multiple design simulations are conducted targeting each SEQ ID NO: 9 backbone segment selected for superposition. The following steps are followed for each design simulation: (1) superimposing the scaffold backbone onto the SEQ ID NO: 9 backbone segment using a scaffold backbone element with matching secondary structure, (2) random small perturbations to generate diversity and relieve backbone clashes, and (3) all-atom sequence design alternating between fixed-backbone sequence selection and fixed-sequence structure relaxation. Final interface designs are filtered for satisfaction of polar groups (using a 1.0 A probe radius), interface surface complementarity (sc score>0.5), and interface quality (predicted binding energy per 100 Å of buried SASA <−1.1), and sorted by predicted binding energy. Top-scoring designs are assessed by an in silico redocking test in which the redesigned scaffold peptide was removed from TEAD, randomly reoriented, and redocked onto the TEAD protein structure. Success is measured as the fraction of low-energy redocking simulations that reached a final state close to the designed interface conformation. Cell-penetrating peptides that bind to TEAD are identified.

Example 27

Peptide Stability at High Temperatures

This example shows peptides of this disclosure are stable in extreme heat. Protein secondary structures were assessed using Circular Dichroism (CD). CD spectra were measured with a Jasco J-720W spectropolarimeter using a 1.0 mm path length cell. Protein samples in 10 mM phosphate buffer (pH=7.4) were at 25-30 μM protein concentration. Samples were analyzed at wavelength ranges of 260-190 nM. Data were expressed in terms of relative ellipticity [Θ]; (mdeg). To determine thermal stability of proteins, samples were subjected to incremental increase in temperature at a ramp of 2° C./min from 20° C. to 95° C. Stability and protein unfolding were monitored at 220 and 215 for α-helix and β-sheet secondary structures, respectively. Data are expressed in terms of relative ellipticity [0], reported in mdeg. For SEQ ID NO: 9 and its point mutant variants, no changes to the α-helix-dominated structure were observed upon heating up to 95° C. FIG. 20A illustrates that the CD spectra of SEQ ID NO: 9 demonstrated that the structure was dominated by α-helical elements, and that this secondary structure signature was identical before (Pre) and after (Post) incubation at 95° C. The inset shows relative ellipticity at 220 nm during heating from 20° C. to 95° C. FIG. 20B illustrates that the circular dichroism spectra of SEQ ID NO: 10 demonstrated the structure is dominated by α-helical elements, and that this secondary structure signature was identical before (Pre) and after (Post) incubation at 95° C. This inset also shows relative ellipticity at 220 nm during heating from 20° C. to 95° C. FIG. 20C illustrates that the circular dichroism spectra of SEQ ID NO: 11 demonstrated the structure was dominated by α-helical elements, and that this secondary structure signature was identical before (Pre) and after (Post) incubation at 95° C. Again, the inset shows relative ellipticity at 220 nm during heating from 20° C. to 95° C. Additionally, protein melting temperature (Tm) determination was performed by monitoring protein unfolding using SYPRO Orange dye (Molecular Probes). In brief, 0.1 mg/mL protein sample in 20 μL total volume PBS buffer were mixed with 2 μL of 10×SYPRO Orange dye. Dye intercalation into the hydrophobic protein core following protein unfolding was assayed using the C1000 Touch Thermal Cycler with CFX96 Deep Well Real-Time System (BioRad). Samples were heated from 20° C. to 95° C. with stepwise increments of 0.5° C. per minute and a 5 sec hold step for every point, followed by fluorescence reading. Tm was calculated by analyzing the derivatives of Relative florescence Units (RFU). FIG. 20D illustrates this SYPRO Orange melting assay of peptides. Human siderocalin (HuScn) demonstrated an expected melting temperature of 79° C., as interpreted by the peak of its RFU vs. temperature slope. Conversely, no melting temperature could be determined for the three peptides tested (SEQ ID NO: 9, SEQ ID NO: 10, and SEQ ID NO: 11). Thus, the SYPRO Orange thermal shift assay showed no evidence of protein unfolding, and therefore, SEQ ID NO: 9 and its point variants were shown to be stable at high temperatures.

Example 28

Peptide Conjugates to Promote Cell Penetrance

This example describes peptide conjugates to promote cellular penetration of the peptide. A TEAD-binding peptide of the present disclosure is recombinantly expressed or chemically synthesized. The peptide is selected from any one of the peptides of SEQ ID NO: 1-SEQ ID NO: 84. TEAD-binding peptides are conjugated to maurocaline (SEQ ID NO: 168), imperatoxin (SEQ ID NO: 169), hadrucalcin (SEQ ID NO: 170), hemicalcin (SEQ ID NO: 171), oplicalin-1 (SEQ ID NO: 172), opicalcin-2 (SEQ ID NO: 173), midkine (62-104) (SEQ ID NO: 174), MCoTI-II (SEQ ID NO: 175), chlorotoxin (SEQ ID NO: 176), DRI-TAT31 (rrrqrrkkrgy, wherein the lowercase notation indicates D-amino acids; SEQ ID NO: 280), cyclic heptapeptide cyclo (cFΦR4) (FΦRRRRQ, where Φ is 1-2-naphthylalanine, the entire moiety is cyclized, and Gln serves as a conjugation handle and can be substituted for other functional groups such as Lys (for amine coupling) or Cys (for sulfhydryl coupling); SEQ ID NO: 281), or myristate. In some cases, the peptide is linked to the cell penetrating moiety by a linker, in which amine coupling is used to attach the linker/functional group to amines on a TEAD-binding peptide of the present disclosure. Any or all Lys residues of a TEAD-binding peptide of the present disclosure may be mutated to Arg to homogenize chemical conjugation and/or enhance cell penetration.

Cell penetration of peptide conjugates are tested for functional impairment of TEAD signaling in 293T cells transfected with a luciferase reporter responsive to YAP: TEAD signaling (8×GTIIC), and for inhibition of YAP: TEAD dimerization in HeLa cells by proximity ligation assay (PLA). Liposomal formulation of successful peptide conjugates is investigated. Additionally, in some peptide conjugates, a disulfide bridge, a furin cleavage site (RX[K/R]R), and/or a cathepsin cleavage site is introduced into the linker.

A peptide conjugate is administered to a subject in need thereof. The subject is a human or animal and has a disease, such as cancer or diabetes (Type I or Type II). Upon administration, target cells are penetrated by peptide conjugates and interact with TEAD to disrupt TEAD binding to transcription coactivators, such as YAP or TAZ.

Example 29

Extension of Peptide Serum Half Life

This example shows a method of extending the serum half life of a peptide as disclosed herein. A peptide of any one of SEQ ID NO: 1-SEQ ID NO: 142 and SEQ ID NO: 222-SEQ ID NO: 279 is modified in order to increase its serum half life. Conjugation of the peptide to a near infrared dye, such as Cy5.5 is used to extend serum half life of the peptide conjugate. Alternatively, conjugation of the peptide to an albumin binder, such as Albu-tag, is used to extend serum half-life. Optionally, serum half-life is extended as a result of reduced immunogenicity by using minimal non-human protein sequences.

Example 30

Small Scale and Large Scale Production of CPP Fusions and Tandem-CDPs

This example describes small scale and large scale production of TEAD Binder-Cell Penetrating Peptide fusions (CPP fusions) and Tandem-Cysteine Dense Peptides (Tandem-CDPs). CPP fusions and Tandem-CDPs were cloned in a Daedalus vector, which is a lentivector that drives secretion of siderocalin-tagged proteins. The siderocalin produced by this vector is 6×His-tagged (SEQ ID NO: 284) and contains the linker that has a TEV cleavage site, leaving only "GS" behind on the peptide's N-terminus after cleavage. The cloned vector sequence was verified using Sanger sequencing (Genewiz), and the verified vectors were then purified at small (1 mL in 96-well deep well blocks) volumes or large (400 mL) volumes. VSV-G pseudotyped lentivirus was then produced through standard methods. Suspension 293F cells were transduced with the VSV-G pseudotyped lentivirus and were grown in FreeStyle (ThermoFisher) expression media. For small scale production, 1×10$^6$ cells were then transduced in 1 mL with 100 μL viral supernatant and shaken at 1,000 rpm until harvest (~7 days). 3 mM valproic acid was added after 5 days. For large scale production, 1×10$^7$ cells were transduced with VSV-G pseudotyped lentivirus in 10 mL with 1 mL viral supernatant (target multiplicity of infection is ~10), after which the culture (shaken at 125 rpm) was expanded over the course of 8-10 days to 400 mL final volume. CPP fusions and Tandem-CDPs were collected from culture media after pelleting cells and 0.22 µm filtration of debris, followed by nickel resin purification and TEV protease cleavage. For large scale production, an additional SEC purification was performed and monitored at wavelengths of 205, 214, and 280 nm. For both small scale production and large scale production, quality control was performed by SDS-PAGE followed by Coomassie staining. Protein concentrations were determined by UV spectral absorption at 214 or 280 nm.

FIG. 25 illustrates SDS-PAGE gels of CPP fusions and Tandem-CDPs under non-reduced (NR) and reduced (R) conditions. The tested CPP fusions were SEQ ID NO: 96, SEQ ID NO: 95, SEQ ID NO: 85, SEQ ID NO: 97, SEQ ID NO: 105, SEQ ID NO: 111, SEQ ID NO: 100, SEQ ID NO: 94, SEQ ID NO: 109, SEQ ID NO: 99, and SEQ ID NO: 108. The tested Tandem-CDPs were SEQ ID NO: 134, SEQ ID NO: 124, SEQ ID NO: 117, SEQ ID NO: 125, SEQ ID NO: 132, SEQ ID NO: 119, SEQ ID NO: 141, SEQ ID NO: 130, and SEQ ID NO: 138. The CPP fusions and Tandem-CDPs were produced at small scale in 1 mL cultures and TEV-cleaved to separate the peptide (lower band(s) in FIG. 25) from the siderocalin carrier (middle band(s) in FIG. 25). Uncleaved fusion proteins appear as the top-most band (s). Molecular weight markers (MWMs) are shown in kiloDalton (kDa) in the lane immediately to the right of the (non-reduced) NR and (reduced) R lanes for each sequence.

FIG. 26 illustrates non-reduced SDS-PAGE gels of CPP fusions and Tandem-CDPs. From left to right, FIG. 26 shows four controls including hadrucalcin (SEQ ID NO: 170), imperatoxin (SEQ ID NO: 169), opicalcin-2 (SEQ ID NO: 173), and chlorotoxin (SEQ ID NO: 176) were tested. FIG. 26 additionally shows the TEAD Binder of (SEQ ID NO: 9), CPP fusions of SEQ ID NO: 95 and SEQ ID NO: 96, and Tandem-CDPs of SEQ ID NO: 117, SEQ ID NO: 119, SEQ ID NO: 124, SEQ ID NO: 125, and SEQ ID NO: 134. Molecular weight markers (MWMs) are shown in kiloDalton (kDa) in the left most lane.

Example 31

Determination of Cell Penetrating Peptides Using a Chloroalkane Penetration Assay (CAPA)

This example shows the use of a chloroalkane penetration assay (CAPA) to determine cell penetration and cytosolic access of the Tandem CDP of SEQ ID NO: 124.

HeLa cells expressing the HaloEnzyme (a modified bacterial haloalkane dehalogenase, further modified to target to the cytosol-facing side of the outer mitochondrial membrane) were grown in 24 well dishes until ~60% confluent. Cells were rinsed with PBS and then incubated with solutions comprising no HaloTag (HT) or 1 µM HT, or with 1 µM HT-SEQ ID NO: 176, HT-SEQ ID NO: 9, HT-SEQ ID NO: 232, or HT-SEQ ID NO: 124 in Opti-MEM serum free buffer for 4 hours. After incubation, cells were rinsed and incubated with Opti-MEM for 30 minutes, and were then incubated with 5 µM HT-TAMRA ligand (Promega G8251) for 30 minutes. An additional control with no HT-TAMRA was tested. After this incubation, cells were rinsed with PBS and then imaged on a fluorescent microscope in FITC/green (all cells) and TRITC/red (HT-TAMRA accumulation) channels. Cells without color indicated that the intracellular HaloEnzyme was occupied by HT, and thus, the tested HT-ligand-labeled peptide comprises a peptide that was cell penetrating. Cells with color indicated that the HaloEnzyme was unoccupied and HT-TAMRA was able to accumulate in cells, and thus the tested HT-ligand-labeled peptide was not cell penetrating.

FIG. 27 illustrates microscopy images of HeLa cells evaluated for cell penetration with a Halo assay. The top left image shows the fluorescence of cells treated with a test solution with 1 µM HT (no protein). The top right image shows the fluorescence of cells treated with buffer only. The bottom left image shows the fluorescence of cells treated with 1 µM HT-SEQ ID NO: 9 (bottom left). The bottom right image shows the fluorescence of cells treated with 1 µM HT-SEQ ID NO: 124 (bottom right). The peptide of SEQ ID NO: 124 (bottom right) exhibited high cell penetration.

FIG. 28 illustrates cell-by-cell quantitation of average fluorescence in the red channel of cells in a CAPA. Cells were incubated with no HaloTag (HT) (not shown in figure; used for calibration as 0 cell penetration score (CPS) indicating no cell penetration), 1 µM HT (not shown in graph; used for calibration as 1 CPS indicating total cell penetration), 1 µM HT-SEQ ID NO: 9 (a control TEAD binder), 1 µM SEQ ID NO: 94, 1 µM HT-SEQ ID NO: 95, 1 µM HT-SEQ ID NO: 96, 1 µM HT-SEQ ID NO: 119, 1 µM HT-SEQ ID NO: 124, 1 µM HT-SEQ ID NO: 125, or 1 µM HT-SEQ ID NO: 134. A high CPS (the inverse of the cells' fluorescence, calibrated to the no HT (0 CPS) and 1 µM HT (1 CPS) controls) indicated that the intracellular HaloEnzyme was occupied by HT, and thus, the tested HT-ligand-labeled peptide comprised a peptide that was cell penetrating. A low CPS indicated that the intracellular HaloEnzyme was unoccupied allowing for accumulation of HT-TAMRA in cells, and that, therefore, the tested HT-ligand-labeled peptide was not cell penetrating. A CPS above the original TEAD binder (SEQ ID NO: 9) suggests an improvement in cell penetration.

While preferred embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A composition comprising a non-naturally occurring transcriptional enhanced associate domain (TEAD)-binding peptide, wherein the TEAD-binding peptide comprises:
   a $LX_1X_2LF$ (SEQ ID NO: 217) motif, wherein $X_1$ is E, I, M, or V and $X_2$ is C;
   at least six cysteine amino acid residues, wherein
      a first cysteine amino acid residue of the at least six cysteine amino acid residues is positioned 25 residues N-terminal of Xz;
      a second cysteine amino acid residue of the at least six cysteine amino acid residues is positioned 24 residues N-terminal of $X_2$;
      a third cysteine amino acid residue of the at least six cysteine amino acid residues is positioned 17 residues N-terminal of $X_2$;
      a fourth cysteine amino acid residue of the at least six cysteine amino acid residues is positioned 16 residues N-terminal of $X_2$;
      a fifth cysteine amino acid residue of the at least six cysteine amino acid residues corresponds to $X_2$; and
      a sixth cysteine amino acid residue of the at least six cysteine amino acid residues is positioned 3 residues C-terminal of $X_2$; and
   two or more disulfide bridges formed between the at least six cysteine amino acid residues.

2. The composition of claim 1, wherein the TEAD-binding peptide is a knotted peptide.

3. The composition of claim 1, wherein the $X_1X_2$ in the $LX_1X_2LF$ (SEQ ID NO: 217) motif is selected from the group consisting of IC, EC, MC, and VC.

4. The composition of claim 1, wherein the TEAD-binding peptide has an amino acid sequence length of 20 to 55 amino acid residues.

5. The composition of claim 1, wherein the TEAD-binding peptide comprises a sequence of any one of SEQ ID NO: 51, SEQ ID NO: 9, SEQ ID NO: 43, SEQ ID NO: 1, SEQ ID NO: 52, SEQ ID NO: 10, SEQ ID NO: 53, or SEQ ID NO: 11.

6. The composition of claim 1, wherein the TEAD-binding peptide has a $K_D$ of less than 40 nM for binding to a TEAD.

7. The composition of claim 1, further comprising a pharmaceutically acceptable carrier.

8. A composition comprising:
   i) a transcriptional enhanced associate domain (TEAD)-binding peptide, wherein the TEAD-binding peptide comprises: a $LX_1X_2LF$ (SEQ ID NO: 217) motif, wherein $X_1$ is E, I, M, or V and $X_2$ is C; at least six cysteine amino acid residues, wherein
      a first cysteine amino acid residue of the at least six cysteine amino acid residues is positioned 25 residues N-terminal of $X_2$;
      a second cysteine amino acid residue of the at least six cysteine amino acid residues is positioned 24 residues N-terminal of $X_2$;
      a third cysteine amino acid residue of the at least six cysteine amino acid residues is positioned 17 residues N-terminal of $X_2$;
      a fourth cysteine amino acid residue of the at least six cysteine amino acid residues is positioned 16 residues N-terminal of $X_2$;
      a fifth cysteine amino acid residue of the at least six cysteine amino acid residues corresponds to $X_2$; and
      a sixth cysteine amino acid residue of the at least six cysteine amino acid residues is positioned 3 residues C-terminal of $X_2$; and
   two or more disulfide bridges formed between the at least six cysteine amino acid residues, and
   ii) a cell-penetrating moiety,
   wherein the TEAD-binding peptide is fused to or conjugated to the cell-penetrating moiety.

9. The composition of claim 8, wherein the TEAD-binding peptide is a knotted peptide.

10. The composition of claim 8, wherein the $X_1X_2$ in the $LX_1X_2LF$ (SEQ ID NO: 217) motif is selected from the group consisting of IC, EC, MC, and VC.

11. The composition of claim 8, wherein the TEAD-binding peptide has an amino acid sequence length of 20 to 55 amino acid residues.

12. The composition of claim 8, wherein the TEAD-binding peptide comprises a sequence of any one of SEQ ID NO: 51, SEQ ID NO: 9, SEQ ID NO: 43, SEQ ID NO: 1, SEQ ID NO: 52, SEQ ID NO: 10, SEQ ID NO: 53, or SEQ ID NO: 11.

13. The composition of claim 8, wherein the cell-penetrating moiety is selected from the group consisting of polycations, polyorganic acids, endosomal releasing polymers, poly(2-propylacrylic acid), poly(2-ethylacrylic acid), Tat peptide, Arg patch, a knotted peptide, CysTAT, S19-TAT, R8, pAntp, Pas-TAT, Pas-R8, Pas-FHV, Pas-pAntP, F2R4 (SEQ ID NO: 152), B55, aurin, IMT-P8, BR2, OMOTAG1, OMOTAG2, pVEC, SynB3, DPV1047, C105Y, Transportan, MTS, hLF, PFVYLI, DRI-TAT, cFΦR$_4$, myristate, yBBR, maurocalcin, imperatoxin, hadrucalcin, hemicalcin, opicalcin-1, opicalcin-2, SEQ ID NO: 174, MCoTI-II, and chlorotoxin, or any combination thereof.

14. The composition of claim 8, wherein the cell-penetrating moiety is a cell-penetrating peptide having at least 90% sequence identity with any sequence of SEQ ID NO: 143-SEQ ID NO: 176, SEQ ID NO: 280, SEQ ID NO: 281, SEQ ID NO: 286, or SEQ ID NO: 287.

15. The composition of claim 8, wherein the TEAD-binding peptide fused to the cell-penetrating moiety is a fusion peptide.

16. The composition of claim 15, wherein the fusion peptide comprises a sequence of any one of SEQ ID NO: 222, SEQ ID NO: 85, SEQ ID NO: 231, SEQ ID NO: 94, SEQ ID NO: 232, SEQ ID NO: 95, SEQ ID NO: 256, SEQ ID NO: 119, SEQ ID NO: 257, SEQ ID NO: 120, SEQ ID NO: 258, SEQ ID NO: 121, SEQ ID NO: 259, SEQ ID NO: 122, SEQ ID NO: 260, SEQ ID NO: 123, SEQ ID NO: 261, or SEQ ID NO: 124.

17. A composition comprising:
i) a transcriptional enhanced associate domain (TEAD)-binding peptide, wherein the TEAD-binding peptide comprises: a LX$_1$X$_2$LF (SEQ ID NO: 217) motif, wherein X$_1$ is E, I, M, or V and X$_2$ is C; at least six cysteine amino acid residues, wherein
  a first cysteine amino acid residue of the at least six cysteine amino acid residues is positioned 25 residues N-terminal of X$_2$;
  a second cysteine amino acid residue of the at least six cysteine amino acid residues is positioned 24 residues N-terminal of X$_2$;
  a third cysteine amino acid residue of the at least six cysteine amino acid residues is positioned 17 residues N-terminal of X$_2$;
  a fourth cysteine amino acid residue of the at least six cysteine amino acid residues is positioned 16 residues N-terminal of X$_2$;
  a fifth cysteine amino acid residue of the at least six cysteine amino acid residues corresponds to X$_2$; and
  a sixth cysteine amino acid residue of the at least six cysteine amino acid residues is positioned 3 residues C-terminal of X$_2$; and
two or more disulfide bridges formed between the at least six cysteine amino acid residues, and
ii) a nuclear localization signal peptide,
wherein the TEAD-binding peptide is fused to or conjugated to the nuclear localization signal peptide.

18. The composition of claim 17, wherein the nuclear localization signal peptide has at least 90% sequence identity with any sequence of SEQ ID NO: 195-SEQ ID NO: 202 or SEQ ID NO: 288.

19. The composition of claim 8, further comprising a pharmaceutically acceptable carrier.

20. The composition of claim 17, further comprising a pharmaceutically acceptable carrier.

21. A method of treating a subject having a condition with a dysregulated HIPPO signaling pathway, the method comprising:
administering to the subject a composition comprising a transcriptional enhanced associate domain (TEAD)-binding peptide, wherein the TEAD-binding peptide comprises: a LX$_1$X$_2$LF (SEQ ID NO: 217) motif, wherein X$_1$ is E, I, M, or V and X$_2$ is C; at least six cysteine amino acid residues, wherein
  a first cysteine amino acid residue of the at least six cysteine amino acid residues is positioned 25 residues N-terminal of X$_2$;
  a second cysteine amino acid residue of the at least six cysteine amino acid residues is positioned 24 residues N-terminal of X$_2$;
  a third cysteine amino acid residue of the at least six cysteine amino acid residues is positioned 17 residues N-terminal of X$_2$;
  a fourth cysteine amino acid residue of the at least six cysteine amino acid residues is positioned 16 residues N-terminal of X$_2$;
  a fifth cysteine amino acid residue of the at least six cysteine amino acid residues corresponds to X$_2$; and
  a sixth cysteine amino acid residue of the at least six cysteine amino acid residues is positioned 3 residues C-terminal of X$_2$; and
two or more disulfide bridges formed between the at least six cysteine amino acid residues;
thereby treating the subject.

22. The method of claim 21, further comprising delivering the TEAD-binding peptide into a cell of the subject.

23. The method of claim 21, wherein the TEAD-binding peptide binds to a TEAD with a K$_D$ of less than 40 nM.

24. The method of claim 21, further comprising inhibiting yes-associated protein (YAP) binding to a TEAD and tafazzin (TAZ) binding to the TEAD by the binding of the TEAD-binding peptide to the TEAD.

25. The method of claim 21, further comprising inhibiting an oncogene in a HIPPO signaling pathway.

26. The method of claim 21, wherein the condition with a dysregulated HIPPO pathway is a tumor.

27. The method of claim 21, wherein the condition with a dysregulated HIPPO pathway is lung cancer, breast cancer, liver cancer, kidney cancer, colon cancer, stomach cancer, osteosarcoma, brain cancer, leukemia, prostate cancer, or melanoma.

28. The method of claim 1, wherein the X$_1$X$_2$ in the LX$_1$X$_2$LF (SEQ ID NO: 217) motif is selected from the group consisting of IC, EC, MC, and VC.

29. The method of claim 21, wherein the TEAD-binding peptide has an amino acid sequence length of 20 to 55 amino acid residues.

30. The method of claim 21, wherein the TEAD-binding peptide comprises a sequence of any one of SEQ ID NO: 51, SEQ ID NO: 9, SEQ ID NO: 43, SEQ ID NO: 1, SEQ ID NO: 52, SEQ ID NO: 10, SEQ ID NO: 53, or SEQ ID NO: 11.

31. The method of claim 21, wherein the TEAD-binding peptide is fused to or conjugated to a cell-penetrating moiety.

32. The method of claim 31, wherein the cell penetrating moiety is a cell penetrating peptide having at least 90% sequence identity with any sequence of SEQ ID NO: 143-SEQ ID NO: 176 or SEQ ID NO: 280, SEQ ID NO: 281, SEQ ID NO: 286, or SEQ ID NO: 287.

33. The method of claim 21, wherein the TEAD-binding peptide is a fusion peptide further comprising a cell-penetrating peptide, and wherein the fusion peptide comprises a sequence of any one of SEQ ID NO: 222, SEQ ID NO: 85, SEQ ID NO: 231, SEQ ID NO: 94, SEQ ID NO: 232, SEQ ID NO: 95, SEQ ID NO: 256, SEQ ID NO: 119, SEQ ID NO: 257, SEQ ID NO: 120, SEQ ID NO: 258, SEQ ID NO:

121, SEQ ID NO: 259, SEQ ID NO: 122, SEQ ID NO: 260, SEQ ID NO: 123, SEQ ID NO: 261, or SEQ ID NO: 124.

34. The composition of claim 1, wherein $X_1$ is I and $X_2$ is C.

35. The composition of claim 1, wherein the TEAD-binding peptide comprises MLICLF (SEQ ID NO: 221).

36. The composition of claim 1, wherein the TEAD-binding peptide comprises an E or a D amino acid residue positioned toward the N-terminus of the peptide relative to the $LX_1X_2LF$.

37. The composition of claim 1, wherein the TEAD-binding peptide comprises an E or a D amino acid residue positioned toward the N-terminus of the peptide relative to the $LX_1X_2LF$ motif and separated from the $LX_1X_2LF$ motif by 8 amino acid residues.

38. The composition of claim 1, wherein the TEAD-binding peptide comprises:
  a G or Q amino acid residue positioned toward the N-terminus of the peptide relative to the $LX_1X_2LF$ motif and separated from the $LX_1X_2LF$ motif by 18 amino acid residues;
  a Y or I amino acid residue positioned toward the N-terminus of the peptide relative to the $LX_1X_2LF$ motif and separated from the $LX_1X_2LF$ motif by 10 amino acid residues;
  an E or a D amino acid residue positioned toward the N-terminus of the peptide relative to the $LX_1X_2LF$ motif and separated from the $LX_1X_2LF$ motif by 8 amino acid residues;
  a G or K amino acid residue positioned toward the N-terminus of the peptide relative to the $LX_1X_2LF$ motif and separated from the $LX_1X_2LF$ motif by 5 amino acid residues; and
  a P or W amino acid residue positioned toward the C-terminus of the peptide relative to the $LX_1X_2LF$ motif and separated from the $LX_1X_2LF$ motif by 1 amino acid residue.

39. The composition of claim 1, wherein the first cysteine amino acid residue is positioned at residue 11 of the TEAD-binding peptide, the second cysteine amino acid residue is positioned at residue 12 of the TEAD-binding peptide, the third cysteine amino acid residue is positioned at residue 19 of the TEAD-binding peptide, the fourth cysteine amino acid residue is positioned at residue 20 of the TEAD-binding peptide, the fifth cysteine amino acid residue is positioned at residue 36 of the TEAD-binding peptide, and the sixth cysteine amino acid residue is positioned at residue 39 of the TEAD-binding peptide.

* * * * *

UNITED STATES PATENT AND TRADEMARK OFFICE
CERTIFICATE OF CORRECTION

| | |
|---|---|
| PATENT NO. | : 11,548,923 B2 |
| APPLICATION NO. | : 16/478672 |
| DATED | : January 10, 2023 |
| INVENTOR(S) | : James M. Olson, Zachary Crook and Philip H. Bradley |

It is certified that error appears in the above-identified patent and that said Letters Patent is hereby corrected as shown below:

In the Claims

Claim 1, Column 285, Line 33, replace "XZ" with --X2--

Claim 28, Column 288, Line 42, replace "1" with --21--

Signed and Sealed this
Fifth Day of December, 2023

Katherine Kelly Vidal
*Director of the United States Patent and Trademark Office*